US008952037B2

(12) United States Patent
Allen et al.

(10) Patent No.: US 8,952,037 B2
(45) Date of Patent: Feb. 10, 2015

(54) HETEROARYLOXYCARBOCYCLYL COMPOUNDS AS PDE10 INHIBITORS

(75) Inventors: Jennifer R. Allen, Newbury Park, CA (US); Michael J. Frohn, Thousand Oaks, CA (US); Paul E. Harrington, Camarillo, CA (US); Essa Hu, Camarillo, CA (US); Alexander J. Pickrell, Westlake Village, CA (US); Robert M. Rzasa, Ventura, CA (US); Kelvin K. C. Sham, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 217 days.

(21) Appl. No.: 13/105,873

(22) Filed: May 11, 2011

(65) Prior Publication Data

US 2011/0306591 A1   Dec. 15, 2011

Related U.S. Application Data

(60) Provisional application No. 61/334,514, filed on May 13, 2010.

(51) Int. Cl.

| | |
|---|---|
| *C07D 401/12* | (2006.01) |
| *C07D 405/14* | (2006.01) |
| *A61K 31/4433* | (2006.01) |
| *A61K 31/4439* | (2006.01) |
| *C07D 471/04* | (2006.01) |
| *C07D 401/14* | (2006.01) |
| *C07D 403/14* | (2006.01) |
| *C07D 413/14* | (2006.01) |
| *C07D 417/12* | (2006.01) |
| *C07D 417/14* | (2006.01) |
| *C07D 487/04* | (2006.01) |

(52) U.S. Cl.
CPC ............ *C07D 471/04* (2013.01); *C07D 401/14* (2013.01); *C07D 403/14* (2013.01); *C07D 405/14* (2013.01); *C07D 413/14* (2013.01); *C07D 417/12* (2013.01); *C07D 417/14* (2013.01); *C07D 487/04* (2013.01)
USPC ...................................... 514/338; 546/273.4

(58) Field of Classification Search
CPC ............... C07D 401/12; C07D 405/14; A61K 31/4433; A61K 31/4439
USPC ....................................... 546/273.4; 514/338
See application file for complete search history.

(56) References Cited

U.S. PATENT DOCUMENTS

| | | |
|---|---|---|
| 4,107,288 A | 8/1978 | Oppenheim et al. |
| 5,145,684 A | 9/1992 | Liversidge et al. |
| 2006/0019975 A1 | 1/2006 | Humphrey et al. |
| 2011/0306587 A1 | 12/2011 | Allen et al. |
| 2011/0306588 A1 | 12/2011 | Allen et al. |
| 2011/0306590 A1 | 12/2011 | Allen et al. |

FOREIGN PATENT DOCUMENTS

| | | |
|---|---|---|
| EP | 0 039 051 | 4/1981 |
| WO | WO 99/31072 A1 | 6/1999 |
| WO | WO 2005/012485 A2 | 2/2005 |
| WO | WO 2007/100880 A1 | 9/2007 |
| WO | WO 2008/151957 A1 | 12/2008 |
| WO | WO 2009/024821 A2 | 2/2009 |
| WO | WO 2010/060836 A2 | 6/2010 |

OTHER PUBLICATIONS

Dorwald, Side Reactions in Organic Synthesis, 2005, Wiley: VCH Weinheim Preface, pp. 1-15 & Chapter 8, pp. 279-308.*
Berge, et al., "Pharmaceutical Salts", *JPharmaSciences*, 66:1 (1977).
Bundgaard, et al., "A Novel Solution-Stable, Water-Soluble Prodrug Type for Drugs Containing a Hydroxyl or an NH-Acidic Group", *JMedChem*, 32:12, 2503-2507, (1989).
Celen, et al., "Preclinical Evaluation of $^{18}$F-JNJ41510417 as a Radioligand for PET Imaging of Phosphodiesterase-10A in the Brain," J Nuclear Med., 51(10):1584-1591, (2010).
Fujishige, et al., "Cloning and Characterization of a Novel Human Phosphodiesterase That Hydrolyzes Both cAMP and cGMP ((PDE10A)", *Jour Biol Chem*, 274:26, 18438-18445, (1999).
Giedd, et al., "MRI Assessment of Children With Obsessive-Compulsive Disorder or Tics Associated with Streptococcal Infection", *AmJPsych*, 157:281-283, (2000).
Loughney, et al., "Isolation and characterization of PDE10A, a novel human 3', 5'-cyclic nucleotide phosphodiesterase", *Gene*, 234: 109-117, (1999).
Obeso, et al., "The origin of motor fluctuations in Parkinson's disease", Neurology, 62(Suppl 1): S17-S30 (2004).
Saxena, et al., "Neuroimaging and frontal-subcortical circuitry in obsessive-compulsive disorder", *Br. JPsych. Suppl.*, 35:26-37, (1998).
Solderling, et al., "Isolation and characterization of a dual-substrate phosphodiesterase gene family: PDE10A", *Proc. Natl. Acad. Sci.*, 96: 7071-7076, (1999).
Svensson, et al., "The Design and Bioactivation of Presystemically Stable Prodrugs", *Drug Metabolism Rev.*, 19(2), 165-194 (1988).

* cited by examiner

*Primary Examiner* — Patricia L Morris
(74) *Attorney, Agent, or Firm* — Elsa D. LeMoine

(57) ABSTRACT

Heteroaryloxycarbocyclyl compounds, and compositions containing them, and processes for preparing such compounds. Provided herein also are methods of treating disorders or diseases treatable by inhibition of PDE10, such as obesity, non-insulin dependent diabetes, schizophrenia, Huntington's Disease, bipolar disorder, obsessive-compulsive disorder, and the like.

13 Claims, No Drawings

HETEROARYLOXYCARBOCYCLYL COMPOUNDS AS PDE10 INHIBITORS

CROSS-REFERENCE TO RELATED APPLICATIONS

This application claims the benefit of U.S. Provisional Application No. 61/334,514, filed May 13, 2010 which is hereby incorporated by reference.

FIELD OF THE INVENTION

Provided herein are certain heteroaryloxycarbocyclyl compounds that are PDE10 inhibitors, pharmaceutical compositions containing such compounds, and processes for preparing such compounds. Provided herein also are methods of treating disorders or diseases treatable by inhibition of PDE10, such as obesity, non-insulin dependent diabetes, schizophrenia, bipolar disorder, obsessive-compulsive disorder, and the like.

BACKGROUND

Neurotransmitters and hormones, as well as other types of extracellular signals such as light and odors, create intracellular signals by altering the amounts of cyclic nucleotide monophosphates (cAMP and cGMP) within cells. These intracellular messengers alter the functions of many intracellular proteins. Cyclic AMP regulates the activity of cAMP-dependent protein kinase (PKA). PKA phosphorylates and regulates the function of many types of proteins, including ion channels, enzymes, and transcription factors. Downstream mediators of cGMP signaling also include kinases and ion channels. In addition to actions mediated by kinases, cAMP and cGMP bind directly to some cell proteins and directly regulate their activities.

Cyclic nucleotides are produced from the actions of adenylyl cyclase and guanylyl cyclase, which convert ATP to cAMP and GTP to cGMP. Extracellular signals, often through the actions of G protein-coupled receptors, regulate the activities of the cyclases. Alternatively, the amount of cAMP and cGMP may be altered by regulating the activities of the enzymes that degrade cyclic nucleotides. Cell homeostasis is maintained by the rapid degradation of cyclic nucleotides after stimulus-induced increases. The enzymes that degrade cyclic nucleotides are called 3',5'-cyclic nucleotide-specific phosphodiesterases (PDEs).

Eleven PDE gene families (PDE1-PDE11) have been identified based on their distinct amino acid sequences, catalytic and regulatory characteristics, and sensitivity to small molecule inhibitors. These families are coded for by 21 genes; and further multiple splice variants are transcribed from many of these genes. Expression patterns of each of the gene families are distinct. PDEs differ with respect to their affinity for cAMP and cGMP. Activities of different PDEs are regulated by different signals. For example, PDE1 is stimulated by $Ca^{2+}$/calmodulin. PDE2 activity is stimulated by cGMP. PDE3 is inhibited by cGMP. PDE4 is cAMP specific and is specifically inhibited by rolipram. PDE5 is cGMP-specific. PDE6 is expressed in retina.

PDE10 sequences were identified by using bioinformatics and sequence information from other PDE gene families (Fujishige et al., *J. Biol. Chem.* 274:18438-18445, 1999; Loughney et al., *Gene* 234:109-117, 1999; Soderling et al., *Proc. Natl. Acad. Sci. USA* 96:7071-7076, 1999). The PDE10 gene family is distinguished based on its amino acid sequence, functional properties and tissue distribution. The human PDE10 gene is large, over 200 kilobases, with up to 24 exons coding for each of the splice variants. The amino acid sequence is characterized by two GAF domains (which bind cGMP), a catalytic region, and alternatively spliced N and C termini. Numerous splice variants are possible because at least three alternative exons encode N termini and two exons encode C-termini. PDE10A1 is a 779 amino acid protein that hydrolyzes both cAMP and cGMP. The $K_m$ values for cAMP and cGMP are 0.05 and 3.0 micromolar, respectively. In addition to human variants, several variants with high homology have been isolated from both rat and mouse tissues and sequence banks.

PDE10 RNA transcripts were initially detected in human testis and brain. Subsequent immunohistochemical analysis revealed that the highest levels of PDE10 are expressed in the basal ganglia. Specifically, striatal neurons in the olfactory tubercle, caudate nucleus and nucleus accumbens are enriched in PDE10. Western blots did not reveal the expression of PDE10 in other brain tissues, although immunoprecipitation of the PDE10 complex was possible in hippocampal and cortical tissues. This suggests that the expression level of PDE10 in these other tissues is 100-fold less than in striatal neurons. Expression in hippocampus is limited to the cell bodies, whereas PDE10 is expressed in terminals, dendrites and axons of striatal neurons.

The tissue distribution of PDE10 indicates that PDE10 inhibitors can be used to raise levels of cAMP and/or cGMP within cells that express the PDE10 enzyme, for example, in neurons that comprise the basal ganglia and therefore would be useful in treating a variety of neuropsychiatric conditions involving the basal ganglia such as obesity, non-insulin dependent diabetes, schizophrenia, bipolar disorder, obsessive compulsive disorder, and the like.

Noninvasive, nuclear imaging techniques can be used to obtain basic and diagnostic information about the physiology and biochemistry of a variety of living subjects including experimental animals, normal humans and patients. These techniques rely on the use of sophisticated imaging instrumentation that is capable of detecting radiation emitted from radiotracers administered to such living subjects. The information obtained can be reconstructed to provide planar and tomographic images that reveal distribution of the radiotracer as a function of time. Use of appropriately designed radiotracers can result in images which contain information on the structure, function and most importantly, the physiology and biochemistry of the subject. Much of this information cannot be obtained by other means. The radiotracers used in these studies are designed to have defined behaviors in vivo which permit the determination of specific information concerning the physiology or biochemistry of the subject or the effects that various diseases or drugs have on the physiology or biochemistry of the subject. Currently, radiotracers are available for obtaining useful information concerning such things as cardiac function, myocardial blood flow, lung perfusion, liver function, brain blood flow, regional brain glucose and oxygen metabolism.

Compounds of the invention can be labeled with either positron or gamma emitting radionuclides. For imaging, the most commonly used positron emitting (PET) $^{11}C$, $^{18}F$, $^{15}O$, $^{13}N$, $^{76}Br$, $^{77}Br$, $^{123}I$, or $^{125}I$, wherein $^{11}C$, $^{18}F$, $^{123}I$, or $^{125}I$ are preferred, all of which are accelerator produced. In the last two decades, one of the most active areas of nuclear medicine research has been the development of receptor imaging radiotracers. These tracers bind with high affinity and specificity to selective receptors and neuroreceptors. For example, Johnson and Johnson has synthesized and evaluated $^{18}F$-JNJ41510417 as a selective and high-affinity radioligand for in vivo brain imaging of PDE10A using PET (The Journal Of Nuclear Medicine; Vol. 51; No. 10; October 2010).

SUMMARY OF THE INVENTION

The present invention comprises a new class of heteroaryloxycarbocyclyl compounds useful in the treatment of diseases, such as PDE10-mediated diseases and other maladies, such as schizophrenia, Huntington's disease, bipolar disorder, or obsessive-compulsive disorder. Accordingly, the invention also comprises pharmaceutical compositions comprising the compounds, methods for the treatment of PDE10-mediated diseases and other maladies, such as schizophrenia, Huntington's disease, bipolar disorder, or obsessive-compulsive disorder, using the compounds and compositions of the invention, and intermediates and processes useful for the preparation of the compounds of the invention.

Another aspect of the invention comprises a new class of heteroaryloxycarbocyclyl compounds radiolabeled with a positron emitting radionuclide selected from $^{18}C$, $^{18}F$, $^{15}O$, $^{13}N$, $^{76}Br$, $^{123}I$, or $^{125}I$, a radiopharmaceutical composition comprising the radiolabelled compound, a method for the diagnostic imaging of PDE10 receptors in a mammal, including human, or tissues bearing PDE10 receptors in a mammal, including human brain, which comprises administering to a mammal in need of such diagnostic imaging an effective amount of the radiolabeled compound, and a method for the detection or quantification of PDE10 receptors in mammalian tissue, including human tissue, which comprises contacting such mammalian tissue in which such detection or quantification is desired with an effective amount of the radiolabeled compound.

The compounds of the invention are represented by the following general structure:

(I)

or a pharmaceutically acceptable salt thereof, wherein m, p, q, $R^1$, $R^2$, $R^{4a}$, $R^{4b}$, $R^{4c}$, $X^1$, $X^2$, $X^3$, and $X^4$ are defined below.

Other compounds of the invention are represented by the following general structure:

(II)

or a pharmaceutically acceptable salt thereof, wherein m, p, q, Ring D, $R^2$, $R^{4a}$, $R^{4b}$, $R^{4c}$, $X^1$, $X^2$, $X^3$, and $X^4$ are defined below.

DETAILED DESCRIPTION OF THE INVENTION

One aspect of the current invention relates to compounds having the general structure of formula (I):

(I)

a stereoisomer, or a pharmaceutically-acceptable salt thereof, wherein:

each of $X^1$, $X^2$, and $X^3$ is independently N or $CR^3$; and $X^4$ is N; wherein no more than one of $X^1$, $X^2$, and $X^3$ are N;

optionally, the ring containing $X^1$, $X^2$, $X^3$, and $X^4$ may be fused to a saturated, partially saturated, or unsaturated 3-, 4-, 5-, or 6-membered monocyclic ring containing 0, 1, 2 or 3 N atoms and 0, 1, or 2 atoms selected from O and S; wherein said monocyclic ring is independently substituted by 0, 1, 2, 3, or 4 $R^3$ groups;

m is 1, 2, 3, or 4;

each of p and q is independently 0, 1, 2, 3, 4, 5, or 6; wherein the sum of p and q is 2 to 6;

the ring containing p and q is in cis or trans configuration;

$R^1$ is F, Cl, Br, I, $C_{1-8}$alk, $C_{1-4}$haloalk, —$OR^a$, —$NR^aR^a$, —$N(R^a)C(=O)R^b$, —$C(=O)R^a$, —$C(=O)R^c$, —$C(=O)$—O—$R^a$, —$OR^c$, —$NR^aR^c$, —$N(R^c)C(=O)R^b$, —$N(R^a)C(=O)R^c$, —$C(=O)NR^aR^b$, —$C(=O)NR^aR^c$, or $C_{0-4}$alk-$L^1$; wherein said $C_{1-8}$alk group is substituted by 0, 1, 2 or 3 groups selected from halo, $C_{1-3}$haloalk, —OH, —$OC_{1-4}$alk, —$NH_2$, —$NHC_{1-4}$alk, —$OC(=O)C_{1-4}$alk, or —$N(C_{1-4}alk)C_{1-4}alk$;

$R^2$ is —$C(=O)R^5$, —$C(=O)OR^5$, —$C(=O)NR^5R^6$, or a group —Y-$L^2$;

Y is a $C_{0-4}$alk, O, $NR^7$, S, SO, or $SO_2$;

$R^3$ is H, F, Cl, Br, CN, OH, $OC_{1-4}$alk, $C_{1-4}$alk, or $C_{1-4}$haloalk;

$R^{4a}$ is H, $C_{1-4}$alk, or $C_{1-4}$haloalk;

each $R^{4b}$ is independently H, F, Cl, Br, CN, OH, $OC_{1-4}$alk, $C_{1-4}$alk, or $C_{1-4}$haloalk;

$R^{4c}$ is $R^{4b}$ when $R^2$ is —$C(=O)R^5$, —$C(=O)OR^5$, —$C(=O)NR^5R^6$, or said group —Y-$L^2$;

wherein Y is $C_{0-4}$alk, SO, or $SO_2$;

$R^{4a}$ is $R^{4a}$ when $R^2$ is said group —Y-$L^2$, wherein Y is O, $NR^7$, or S;

each of $R^5$ and $R^6$ is independently H, $C_{1-8}$alk, or $C_{0-8}$alk-$L^3$;

$R^7$ is independently H or $R^b$;

$R^a$ is independently H or $R^b$;

$R^b$ is independently phenyl, benzyl, or $C_{1-6}$alk, wherein said phenyl, benzyl, and $C_{1-6}$alk are being substituted by 0, 1, 2 or 3 substituents selected from halo, $C_{1-4}$alk, $C_{1-3}$haloalk, —OH, —$OC_{1-4}$alk, —$NH_2$, —$NHC_{1-4}$alk, —$OC(=O)C_{1-4}$alk, or —$N(C_{1-4}alk)C_{1-4}alk$;

$R^c$ is $C_{0-4}$alk-$L^4$; and each of $L^1$, $L^2$, $L^3$, and $L^4$ is independently a carbon-linked or nitrogen-linked saturated, partially-saturated or unsaturated 3-, 4-, 5-, 6-, or 7-membered monocyclic ring or a saturated, partially-saturated or unsaturated 8-, 9-, 10-, 11-, or 12-membered bicyclic ring, wherein each said ring contains 0, 1, 2, 3, or 4 N atoms and 0, 1, or 2 atoms selected from O or S; wherein each $L^1$, $L^2$, $L^3$, and $L^4$ is independently substituted by 0, 1, 2 or 3 $R^8$ groups selected from F, Cl, Br, $C_{1-6}$alk, $C_{1-4}$haloalk, —$OR^a$, —$OC_{1-4}$haloalk, CN, —$C(=O)R^b$, —$C(=O)OR^a$, —$C(=O)NR^aR^a$, —$C(=NR^a)NR^aR^a$, —$OC(=O)R^b$, —$OC(=O)NR^aR^a$, —$OC_{2-6}$alk$NR^aR^a$, —$OC_{2-6}$alk$OR^a$, —$SR^a$, —$S(=O)R^b$, —$S(=O)_2R^b$, —$S(=O)_2NR^aR^a$, —$NR^aR^a$, —$N(R^a)C(=O)R^b$, —$N(R^a)C$ (=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkNR$^a$R$^a$, —NR$^a$C$_{2-6}$alkOR$^a$, —C$_{1-6}$alkNR$^a$R$^a$, —C$_{1-6}$alkOR$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$ and oxo.

In another embodiment, the group

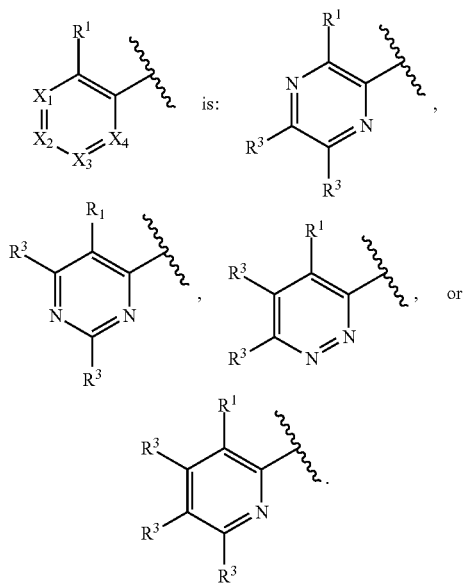

is:

In another embodiment, the ring containing X$^1$, X$^2$, X$^3$, and X$^4$ is fused to a saturated, partially saturated, or unsaturated 3-, 4-, 5-, or 6-membered monocyclic ring containing 0, 1, 2 or 3 N atoms and 0, 1, or 2 atoms selected from O and S; wherein said monocyclic ring is independently substituted by 0, 1, 2, 3, or 4 R$^3$ groups.

In another embodiment, said monocyclic ring is selected from fused phenyl, cyclobutyl, cyclopentyl, cyclohexyl, furanyl, thiophenyl, pyrrolyl, pyrrolinyl, pyrrolidinyl, dioxolanyl, oxazolyl, thiazolyl, isothiazolyl, imidazolyl, imidazolinyl, imidazolidinyl, pyrazolyl, pyrazolinyl, pyrazolidinyl, isoxazolyl, isothiazolyl, pyranyl, pyridinyl, piperidinyl, dioxanyl, morpholinyl, dithianyl, thiomorpholinyl, pyridazinyl, pyrazinyl, and piperazinyl.

In another embodiment, Y is a bond, NH, or N—CH$_3$.

In another embodiment, Y is NH.

In another embodiment, R$^{4b}$ is H.

In another embodiment, p is 1 and q is 1.

In another embodiment, wherein the ring containing p and q is in cis configuration.

In another embodiment, R$^1$ is F, Cl, Br, I, —OR$^a$, —NR$^a$R$^c$, —C(=O)—O—R$^a$, —C(=O)NR$^a$R$^b$, —OR$^a$, or —C(=O)NR$^a$R$^b$.

In another embodiment, R$^1$ is C$_{0-4}$alk-L$^1$; wherein said L$^1$ is a carbon-linked or nitrogen-linked saturated, partially-saturated or unsaturated 4-, 5-, 6-, or 7-membered monocyclic ring, wherein each said ring contains 0, 1, 2, or 3 N atoms and 0, 1 or 2 O atoms, and wherein each said ring is substituted by 0, 1, 2 or 3 R$^8$ groups selected from F, Cl, Br, C$_{1-6}$alk, C$_{1-4}$haloalk, —OR$^a$, —OC$_{1-4}$haloalk, CN, —C(=O)R$^b$, —C(=O)OR$^a$, —NR$^a$R$^a$, —C(=O)NR$^a$R$^a$, —SR$^a$, and —C$_{1-6}$alkOR$^a$.

In another embodiment, R$^1$ is C$_{0-4}$alk-L$^1$; wherein said L$^1$ is a carbon-linked or nitrogen-linked saturated, partially-saturated or unsaturated 8-, 9-, 10-, 11-, or 12-membered bicyclic ring, wherein each said ring contains 0, 1, 2, or 3 N atoms and 0, 1, or 2 O atoms, and wherein each said ring is substituted by 0, 1, 2 or 3 R$^8$ groups selected from F, Cl, Br, C$_{1-6}$alk, C$_{1-4}$haloalk, —OR$^a$, —OC$_{1-4}$haloalk, CN, —C(=O)R$^b$, —C(=O)OR$^a$, —NR$^a$R$^a$, —C(=O)NR$^a$R$^a$, —SR$^a$, and —C$_{1-6}$alkO$^a$.

In another embodiment, R$^1$ is C$_{0-4}$alk-L$^1$; wherein said L$^1$ is cyclobutyl, cyclohexyl, cyclopentyl, cyclopentenyl, cyclohexenyl, cycloheptyl, azetidinyl, phenyl, 2-pyridyl, 3-pyridyl, 4-pyridyl, pyrazolyl, morpholinyl, pyrimidyl, piperazinyl, piperidinyl, dihydropyranyl, tetrahydropyranyl, tetrahydrofuranyl, tetrahydropyridinyl, tetrahydrothiopyranyl, oxaspiro[3.5]nonyl, azepanyl, oxepanyl, or quinolinyl, all of which are substituted by 0, 1, 2 or 3 R$^8$ groups selected from F, Cl, Br, C$_{1-6}$alk, C$_{1-4}$haloalk, —OR$^a$, —OC$_{1-4}$haloalk, CN, —C(=O)R$^b$, —C(=O)OR$^a$, —NR$^a$R$^a$, —C(=O)NR$^a$R$^a$, —SR$^a$, and —C$_{1-6}$alkOR$^a$.

In another embodiment, R$^1$ is C$_{0-4}$alk-L$^1$; wherein said L$^1$ is 3-pyridyl, 4-pyridyl, tetrahydropyranyl, tetrahydrofuranyl, piperidinyl, pyrimidyl, dihydropyranyl, or piperazinyl, all of which are substituted by 0, 1, 2 or 3 R$^8$ groups selected from F, Cl, Br, C$_{1-6}$alk, C$_{1-4}$haloalk, —OR$^a$, —OC$_{1-4}$haloalk, CN, —C(=O)R$^b$, —C(=O)OR$^a$, —NR$^a$R$^a$, —C(=O)NR$^a$R$^a$, —SR$^a$, and —C$_{1-6}$alkOR$^a$.

In another embodiment, R$^1$ is not methyl.

In another embodiment, R$^1$ is:

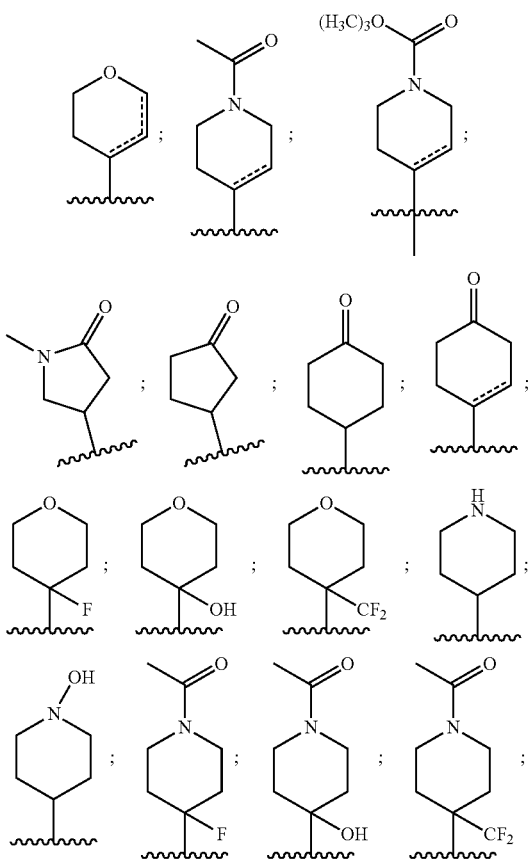

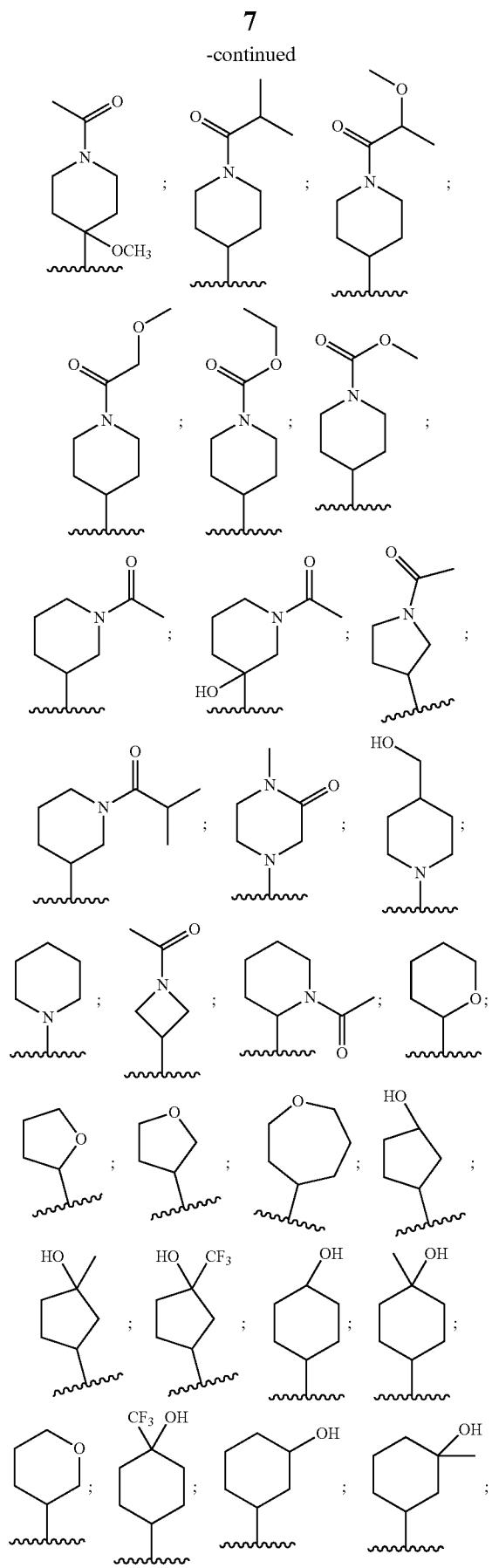
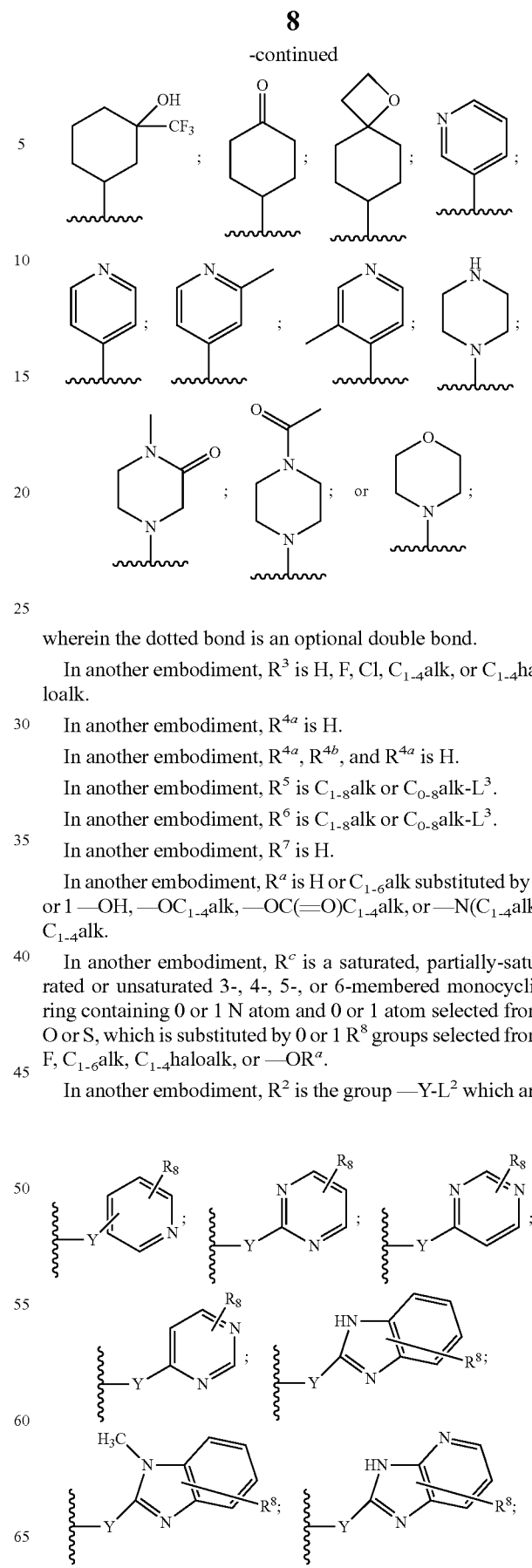

wherein the dotted bond is an optional double bond.

In another embodiment, $R^3$ is H, F, Cl, $C_{1-4}$alk, or $C_{1-4}$haloalk.

In another embodiment, $R^{4a}$ is H.

In another embodiment, $R^{4a}$, $R^{4b}$, and $R^{4a}$ is H.

In another embodiment, $R^5$ is $C_{1-8}$alk or $C_{0-8}$alk-$L^3$.

In another embodiment, $R^6$ is $C_{1-8}$alk or $C_{0-8}$alk-$L^3$.

In another embodiment, $R^7$ is H.

In another embodiment, $R^a$ is H or $C_{1-6}$alk substituted by 0 or 1 —OH, —OC$_{1-4}$alk, —OC(=O)C$_{1-4}$alk, or —N(C$_{1-4}$alk)C$_{1-4}$alk.

In another embodiment, $R^c$ is a saturated, partially-saturated or unsaturated 3-, 4-, 5-, or 6-membered monocyclic ring containing 0 or 1 N atom and 0 or 1 atom selected from O or S, which is substituted by 0 or 1 $R^8$ groups selected from F, $C_{1-6}$alk, $C_{1-4}$haloalk, or —OR$^a$.

In another embodiment, $R^2$ is the group —Y-$L^2$ which are wherein Y is a NH.

In another embodiment, $R^2$ is —C(=O)$R^5$, —C(=O)O$R^5$, or —C(=O)N$R^5R^6$.

In another embodiment, each $R^2$ is the group —Y-$L^2$ which are

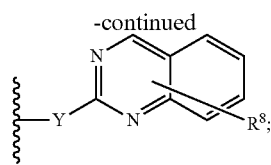

wherein Y is NH; and $L^2$ is independently substituted by 0, 1, or 2 $R^8$ groups which are F, Br, $C_1$, $CF_3$, methyl, methoxy, or CN.

Another aspect of the current invention relates to compounds having the general structure of formula (II):

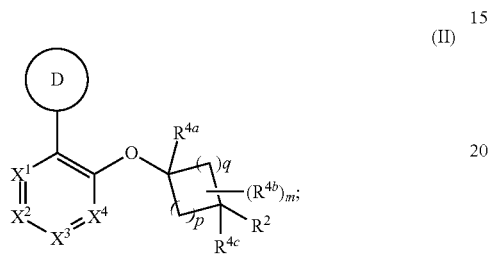

or any pharmaceutically-acceptable salt thereof, wherein:
each of $X^1$, $X^2$, and $X^3$ is independently N or $CR^3$; and $X^4$ is N; wherein no more than one of $X^1$, $X^2$, and $X^3$ are N; and wherein any adjacent $X^1$, $X^2$, and $X^3$ may optionally form an optionally substituted-saturated, -partially saturated, or -unsaturated-heterocyclic or -heteroaryl ring fused to the ring containing $X^1$, $X^2$, $X^3$, and $X^4$;
m is 1, 2, 3, or 4;
each of p and q is independently 0, 1, 2, 3, 4, 5, or 6; wherein the sum of p and q is 2 to 6;
the ring containing p and q is in cis or trans configuration;
Ring D is $L^1$;
$R^2$ is —C(=O)$R^5$, —C(=O)O$R^5$, —C(=O)N$R^5R^6$, or a group —Y-$L^2$;
Y is a $C_{0-4}$alk, O, $NR^7$, S, SO, or $SO_2$;
$R^3$ is H, F, Cl, Br, CN, OH, O$C_{1-4}$alk, $C_{1-4}$alk, or $C_{1-4}$haloalk;
$R^{4a}$ is H, $C_{1-4}$alk, or $C_{1-4}$haloalk;
each $R^{4b}$ is independently H, F, Cl, Br, CN, OH, O$C_{1-4}$alk, $C_{1-4}$alk, or $C_{1-4}$haloalk;
$R^{4c}$ is $R^{4b}$ if $R^2$ is —C(=O)$R^5$, —C(=O)O$R^5$, —C(=O)N$R^5R^6$, or said group —Y-$L^2$; wherein Y is $C_{0-4}$alk, SO, or $SO_2$;
$R^{4c}$ is $R^{4a}$ if $R^2$ is said group —Y-$L^2$, wherein Y is O, $NR^7$, or S;
each of $R^5$ and $R^6$ is independently H, $C_{1-8}$alk, or $C_{0-8}$alk-$L^3$;
$R^7$ is independently H or $R^b$;
$R^a$ is independently H or $R^b$;
$R^b$ is independently phenyl, benzyl, or $C_{1-6}$alk, wherein said phenyl, benzyl, and $C_{1-6}$alk are being substituted by 0, 1, 2 or 3 substituents selected from halo, $C_{1-4}$alk, $C_{1-3}$haloalk, —OH, —O$C_{1-4}$alk, —$NH_2$, —NH$C_{1-4}$alk, —OC(=O)$C_{1-4}$alk, and —N($C_{1-4}$alk)$C_{1-4}$alk; and
each of $L^1$, $L^2$, $L^3$, and $L^4$ is independently a carbon-linked or nitrogen-linked saturated, partially-saturated or unsaturated 3-, 4-, 5-, 6-, or 7-membered monocyclic ring or a saturated, partially-saturated or unsaturated 8-, 9-, 10-, 11-, or 12-membered bicyclic ring, wherein each said ring contains 0, 1, 2, 3, or 4 N atoms and 0, 1, or 2 atoms selected from O or S; wherein each $L^1$, $L^2$, $L^3$, and $L^4$ is independently substituted by 0, 1, 2 or 3 $R^8$ groups selected from F, Cl, Br, $C_{1-6}$alk, $C_{1-4}$haloalk, —O$R^a$, —O$C_{1-4}$haloalk, CN, —C(=O)$R^b$, —C(=O)O$R^a$, —C(=O)N$R^aR^a$, —C(=N$R^a$)N$R^aR^a$, —OC(=O)$R^b$, —OC(=O)N$R^aR^a$, —O$C_{2-6}$alkN$R^aR^a$, —O$C_{2-6}$alkO$R^a$, —S$R^a$, —S(=O)$R^b$, —S(=O)$_2R^b$, —S(=O)$_2$N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkN$R^aR^a$, —N$R^aC_{2-6}$alkO$R^a$, —$C_{1-6}$alkN$R^aR^a$, —$C_{1-6}$ alkO$R^a$, —$C_{1-6}$ alkN($R^a$)C(=O)$R^b$, —$C_{1-6}$ alkOC(=O)$R^b$, —$C_{1-6}$alkC(=O)N$R^aR^a$, —$C_{1-6}$alkC(=O)O$R^a$ and oxo.

In another embodiment, the group

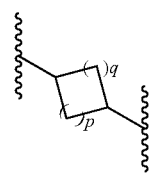

is cyclobutyl, cyclopentyl, cylohexyl, or cycloheptyl.

In another embodiment, the group

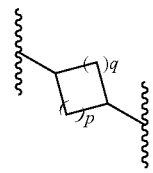

is cyclobutyl.

In another embodiment, the group

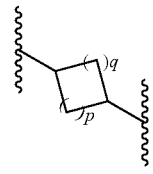

is cyclopentyl.

In another embodiment, the group

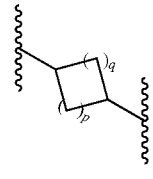

is cyclohexyl.

In another embodiment, the group

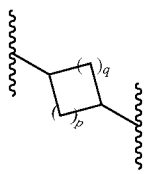

is in trans configuration.
In another embodiment, the group

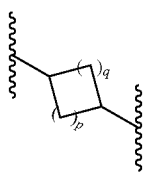

is in cis configuration.

In another embodiment, $R^3$ is H, $C_{1-4}$alk, or $C_{1-4}$haloalk.
In another embodiment, $R^{4a}$ is H or $C_{1-4}$alk.
In another embodiment, $R^5$ is $C_{1-8}$alk or $C_{0-8}$alk-$L^3$.
In another embodiment, $R^6$ is $C_{1-8}$alk or $C_{0-8}$alk-$L^3$.
In another embodiment, $R^7$ is H.
In another embodiment, $R^a$ is H or $C_{1-6}$alk substituted by 0 or 1 —OH, —O$C_{1-4}$alk, —OC(=O)$C_{1-4}$alk, or —N($C_{1-4}$alk)$C_{1-4}$alk.
In another embodiment, $R^c$ is a carbon-linked saturated, partially-saturated or unsaturated 3-, 4-, 5-, or 6-membered monocyclic ring containing 0 or 1 N atom and 0 or 1 atom selected from O or S, which is substituted by 0 or 1 $R^8$ groups selected from F, $C_{1-6}$alk, $C_{1-4}$haloalk, or —O$R^a$.
In another embodiment, $R^c$ is a nitrogen-linked saturated, partially-saturated, or unsaturated 4-, 5-, 6- or 7-membered ring heterocycle containing the linking nitrogen and 0, 1 or 2 additional nitrogen atoms and containing 0 or 1 sulfur or oxygen atom, the heterocycle being substituted by 0, 1, 2 or 3 $R^8$ groups selected from F, Cl, Br, $C_1$, $C_{1-4}$alk, $C_{1-4}$haloalk, —O$C_{1-4}$alk, —NH$_2$, —NH$C_{1-4}$alk, —N($C_{1-4}$alk)$C_{1-4}$alk, or oxo.
In another embodiment, $R^c$ is a $C_{0-4}$alk-linked saturated, partially-saturated or unsaturated 3-, 5-, or 6-membered monocyclic ring containing 0 or 1 N atom and 0 or 1 atom selected from O and S, which is substituted by 0 or 1 $R^8$ groups selected from F, $C_{1-6}$alk, $C_{1-4}$haloalk, or —O$R^a$.
In another embodiment, $R^2$ is —C(=O)$R^5$, —C(=O)O$R^5$, or —C(=O)N$R^5R^6$.

Another aspect of the invention relates to a method of treating conditions that may be treated with PDE10 inhibitors comprising the step of administering to a patient in need thereof a therapeutically effective amount of any one of the above compounds, or a pharmaceutically acceptable salt thereof.

In one embodiment of the method, said conditions is psychoses, Parkinson's disease, dementias, obsessive compulsive disorder, tardive dyskinesia, choreas, depression, mood disorders, impulsivity, drug addiction, attention deficit/hyperactivity disorder (ADHD), depression with parkinsonian states, personality changes with caudate or putamen disease, dementia and mania with caudate and pallidal diseases, or compulsions with pallidal disease.

In another embodiment of the method, said condition is schizophrenia, Huntington's disease, bipolar disorder, or obsessive-compulsive disorder.

In another embodiment of the method, said condition is schizophrenia.

Another aspect of the invention relates to a pharmaceutical composition comprising any one of the above compounds, or a pharmaceutically acceptable salt thereof, and a pharmaceutically-acceptable excipient.

Another aspect of the invention relates to the use of any one of the above compounds, or a pharmaceutically acceptable salt thereof, as a medicament.

Another aspect of the invention relates to the use of any one of the above compounds, or a pharmaceutically acceptable salt thereof in the manufacture of a medicament for the treatment of schizophrenia, bipolar disorder, or obsessive-compulsive disorder.

Another aspect of the invention relates to a compound, or a pharmaceutically acceptable salt thereof, which is listed below:

N-(3-((3-(tetrahydro-2H-pyran-4-yl)pyridin-2-yl)oxy)cyclobutyl)benzo[d]thiazol-2-amine;
N-((1S,3S)-3-((3-(tetrahydro-2H-pyran-4-yl)pyridin-2-yl)oxy)cyclobutyl)benzo[d]thiazol-2-amine;
N-((1R,3R)-3-((3-(tetrahydro-2H-pyran-4-yl)pyridin-2-yl)oxy)cyclobutyl)benzo[d]thiazol-2-amine;
5-methyl-N-((1R,3R)-3-((3-(tetrahydro-2H-pyran-4-yl)pyridin-2-yl)oxy)cyclobutyl)pyridin-2-amine;
5-methyl-N-((1S,3S)-3-((3-(tetrahydro-2H-pyran-4-yl)pyridin-2-yl)oxy)cyclobutyl)pyridin-2-amine;
1-(4-(2-((1S,3S)-3-(benzo[d]thiazol-2-ylamino)cyclobutoxy)pyridin-3-yl)piperidin-1-yl)ethanone;
1-(4-(3-((1S,3S)-3-(benzo[d]thiazol-2-ylamino)cyclobutoxy)pyrazin-2-yl)piperidin-1-yl)ethanone;
N-((1S,3S)-3-((3-(tetrahydro-2H-pyran-4-yl)pyridin-2-yl)oxy)cyclobutyl)-1H-benzo[d]imidazol-2-amine;
N-((1R,3R)-3-((3-(tetrahydro-2H-pyran-4-yl)pyridin-2-yl)oxy)cyclobutyl)-1H-benzo[d]imidazol-2-amine;
1-(4-(3-((1R,3R)-3-(quinolin-2-ylamino)cyclobutoxy)pyrazin-2-yl)piperidin-1-yl)ethanone;
N-((1S,3S)-3-((5-fluoro-3-(tetrahydro-2H-pyran-4-yl)pyridin-2-yl)oxy)cyclobutyl)benzo[d]thiazol-2-amine;
N-((1R,3R)-3-((5-fluoro-3-(tetrahydro-2H-pyran-4-yl)pyridin-2-yl)oxy)cyclobutyl)benzo[d]thiazol-2-amine;
1-(4-(3-((1S,3S)-3-((5-methylpyridin-2-yl)amino)cyclobutoxy)pyrazin-2-yl)piperidin-1-yl)ethanone;
1-(4-(3-((1R,3R)-3-((5-methylpyridin-2-yl)amino)cyclobutoxy)pyrazin-2-yl)piperidin-1-yl)ethanone;
N-((1S,3S)-3-((3-(tetrahydro-2H-pyran-4-yl)pyridin-2-yl)oxy)cyclobutyl)-5-(trifluoromethyl)pyridin-2-amine;
N-((1R,3R)-3-((3-(tetrahydro-2H-pyran-4-yl)pyridin-2-yl)oxy)cyclobutyl)-5-(trifluoromethyl)pyridin-2-amine;
6-(((1S,3S)-3-((3-(tetrahydro-2H-pyran-4-yl)pyridin-2-yl)oxy)cyclobutyl)amino)nicotinonitrile;
6-(((1R,3R)-3-((3-(tetrahydro-2H-pyran-4-yl)pyridin-2-yl)oxy)cyclobutyl)amino)nicotinonitrile;
5-chloro-N-((1R,3R)-3-((3-(tetrahydro-2H-pyran-4-yl)pyridin-2-yl)oxy)cyclobutyl)pyridin-2-amine;
5-chloro-N-((1S,3S)-3-((3-(tetrahydro-2H-pyran-4-yl)pyridin-2-yl)oxy)cyclobutyl)pyridin-2-amine;
N-((1S,3S)-3-((3-(2-methylpyridin-4-yl)pyrazin-2-yl)oxy)cyclobutyl)benzo[d]thiazol-2-amine;
5-fluoro-N-((1S,3S)-3-((3-(tetrahydro-2H-pyran-4-yl)pyrazin-2-yl)oxy)cyclobutyl)benzo[d]thiazol-2-amine;
6-fluoro-N-((1S,3S)-3-((3-(tetrahydro-2H-pyran-4-yl)pyrazin-2-yl)oxy)cyclobutyl)benzo[d]thiazol-2-amine;

4-fluoro-N-((1S,3S)-3-((3-(tetrahydro-2H-pyran-4-yl)
pyrazin-2-yl)oxy)cyclobutyl)benzo[d]thiazol-2-amine;
N-((1S,3S)-3-((3-(2-methoxypyridin-3-yl)pyrazin-2-yl)oxy)
cyclobutyl)benzo[d]thiazol-2-amine;
7-fluoro-N-((1S,3S)-3-((3-(tetrahydro-2H-pyran-4-yl)
pyrazin-2-yl)oxy)cyclobutyl)benzo[d]thiazol-2-amine;
(1-(3-((1S,3S)-3-(benzo[d]thiazol-2-ylamino)cyclobutoxy)
pyrazin-2-yl)piperidin-4-yl)methanol;
1-(4-(3-((1S,3S)-3-(benzo[d]thiazol-2-ylamino)cyclobu-
toxy)pyrazin-2-yl)piperazin-1-yl)ethanone;
N-((1S,3S)-3-((3-(3-methylpyridin-4-yl)pyrazin-2-yl)oxy)
cyclobutyl)benzo[d]thiazol-2-amine;
1-(3-((1S,3S)-3-(benzo[d]thiazol-2-ylamino)cyclobutoxy)
pyrazin-2-yl)piperidin-4-one;
N-((1S,3S)-3-((3-(6-methylpyridin-3-yl)pyrazin-2-yl)oxy)
cyclobutyl)benzo[d]thiazol-2-amine;
6-fluoro-N-((1S,3S)-3-((5-fluoro-3-(tetrahydro-2H-pyran-
4-yl)pyridin-2-yl)oxy)cyclobutyl)benzo[d]thiazol-2-
amine;
4-fluoro-N-((1S,3S)-3-((5-fluoro-3-(tetrahydro-2H-pyran-
4-yl)pyridin-2-yl)oxy)cyclobutyl)benzo[d]thiazol-2-
amine;
4-(3-(1S,3S)-3-(benzo[d]thiazol-2-ylamino)cyclobutoxy)
pyrazin-2-yl)piperidine-1-carboxylate;
5-fluoro-N-((1S,3S)-3-((5-fluoro-3-(tetrahydro-2H-pyran-
4-yl)pyridin-2-yl)oxy)cyclobutyl)benzo[d]thiazol-2-
amine;
7-fluoro-N-((1S,3S)-3-((5-fluoro-3-(tetrahydro-2H-pyran-
4-yl)pyridin-2-yl)oxy)cyclobutyl)benzo[d]thiazol-2-
amine;
methyl 3-(3-((1S,3S)-3-(benzo[d]thiazol-2-ylamino)cy-
clobutoxy)pyrazin-2-yl)azetidine-1-carboxylate;
N-((1S,3S)-3-((3-(3-fluoro-4-methylphenyl)pyrazin-2-yl)
oxy)cyclobutyl)benzo[d]thiazol-2-amine;
N-((1R,3R)-3-((5-(tetrahydro-2H-pyran-4-yl)pyrimidin-4-
yl)oxy)cyclobutyl)-5-(trifluoromethyl)pyridin-2-amine;
N-((1S,3S)-3-((5-(tetrahydro-2H-pyran-4-yl)pyrimidin-4-
yl)oxy)cyclobutyl)-5-(trifluoromethyl)pyridin-2-amine;
N-((1R,3R)-3-((3-(1-acetylpiperidin-4-yl)pyridin-2-yl)oxy)
cyclobutyl)-4-methylbenzenesulfonamide;
N-((1S,3S)-3-((3-(1-acetylpiperidin-4-yl)pyridin-2-yl)oxy)
cyclobutyl)-4-methylbenzenesulfonamide;
N-((1R,3R)-3-((3-(3-fluoro-4-methylphenyl)pyrazin-2-yl)
oxy)cyclobutyl)benzo[d]thiazol-2-amine;
2'-((1S,3S)-3-(benzo[d]thiazol-2-ylamino)cyclobutoxy)-[3,
3'-bipyridine]-6-carbonitrile;
N-(3-((3-(3-methylpyrrolidin-1-yl)pyrazin-2-yl)oxy)cy-
clobutyl)benzo[d]thiazol-2-amine;
(1-(3-(3-(benzo[d]thiazol-2-ylamino)cyclobutoxy)pyrazin-
2-yl)piperidin-3-yl)methanol;
2'-((1R,3R)-3-(benzo[d]thiazol-2-ylamino)cyclobutoxy)-[3,
3'-bipyridine]-6-carbonitrile;
N-((1S,3S)-3-((3-(4,4-difluoropiperidin-1-yl)pyrazin-2-yl)
oxy)cyclobutyl)benzo[d]thiazol-2-amine;
tert-butyl 4-(2-((1S,3S)-3-(quinolin-2-ylamino)cyclobu-
toxy)pyridin-3-yl)piperidine-1-carboxylate;
tert-butyl 2-((1S,3S)-3-(quinolin-2-ylamino)cyclobutoxy)-
5',6'-dihydro-[3,4'-bipyridine]-1'(2'H)-carboxylate;
1-(3-(3-(benzo[d]thiazol-2-ylamino)cyclobutoxy)pyrazin-2-
yl)pyrrolidine-3-carbonitrile;
N-((1S,3S)-3-((3-(2-methylpyrimidin-5-yl)pyrazin-2-yl)
oxy)cyclobutyl)benzo[d]thiazol-2-amine;
N-((1S,3S)-3-((3-(6-chloropyridin-3-yl)pyrazin-2-yl)oxy)
cyclobutyl)benzo[d]thiazol-2-amine;
N-((1S,3S)-3-((3-(6-fluoropyridin-3-yl)pyrazin-2-yl)oxy)
cyclobutyl)benzo[d]thiazol-2-amine;
5-(3-((1S,3S)-3-(benzo[d]thiazol-2-ylamino)cyclobutoxy)
pyrazin-2-yl)picolinonitrile;
1-(4-(2-((1S,3S)-3-(quinolin-2-ylamino)cyclobutoxy)pyri-
din-3-yl)piperidin-1-yl)ethanone;
5-(3-((1S,3S)-3-(quinolin-2-ylamino)cyclobutoxy)pyrazin-
2-yl)picolinonitrile;
(1-(3-((1S,3S)-3-(quinolin-2-ylamino)cyclobutoxy)pyrazin-
2-yl)piperidin-4-yl)methanol;
methyl 4-(2-((1S,3S)-3-(benzo[d]thiazol-2-ylamino)cy-
clobutoxy)pyridin-3-yl)piperidine-1-carboxylate;
2-methoxy-1-(4-(2-((1S,3S)-3-(quinolin-2-ylamino)cy-
clobutoxy)pyridin-3-yl)piperidin-1-yl)ethanone;
N-((1S,3S)-3-((3-(tetrahydro-2H-pyran-4-yl)pyrazin-2-yl)
oxy)cyclobutyl)quinolin-2-amine;
1-(4-(2-((1S,3S)-3-(benzo[d]thiazol-2-ylamino)cyclobu-
toxy)pyridin-3-yl)piperidin-1-yl)-2-methoxyethanone;
((R)-1-(3-((1S,3S)-3-(benzo[d]thiazol-2-ylamino)cyclobu-
toxy)pyrazin-2-yl)piperidin-3-yl)methanol;
((S)-1-(3-((1S,3R)-3-(benzo[d]thiazol-2-ylamino)cyclobu-
toxy)pyrazin-2-yl)piperidin-3-yl)methanol;
2'-((1S,3S)-3-(quinolin-2-ylamino)cyclobutoxy)-[3,3'-bipy-
ridine]-6-carbonitrile;
1-(4-(3-((1S,3S)-3-(quinolin-2-ylamino)cyclobutoxy)
pyrazin-2-yl)piperazin-1-yl)ethanone;
2-methoxy-1-(4-(3-((1S,3S)-3-(quinolin-2-ylamino)cy-
clobutoxy)pyrazin-2-yl)piperidin-1-yl)ethanone;
N-((1S,3S)-3-((3-(tetrahydro-2H-pyran-4-yl)pyridin-2-yl)
oxy)cyclobutyl)quinolin-2-amine;
N-((1S,3S)-3-((3-morpholinopyrazin-2-yl)oxy)cyclobutyl)
benzo[d]thiazol-2-amine;
(R)-1-(3-((1S,3S)-3-(benzo[d]thiazol-2-ylamino)cyclobu-
toxy)pyrazin-2-yl)pyrrolidin-3-ol;
1-(1-(3-((1S,3S)-3-(benzo[d]thiazol-2-ylamino)cyclobu-
toxy)pyrazin-2-yl)piperidin-4-yl)ethanol;
1-(4-3-((1S,3S)-3-(quinolin-2-ylamino)cyclobutoxy)
pyrazin-2-yl)piperidin-1-yl)ethanone;
(S)-1-(3-((1S,3R)-3-(benzo[d]thiazol-2-ylamino)cyclobu-
toxy)pyrazin-2-yl)pyrrolidin-3-ol;
N-(3-((3-(3-methylpiperidin-1-yl)pyrazin-2-yl)oxy)cy-
clobutyl)benzo[d]thiazol-2-amine;
N-((1S,3S)-3-((3-((R)-3-methylpyrrolidin-1-yl)pyrazin-2-
yl)oxy)cyclobutyl)benzo[d]thiazol-2-amine;
N-((1R,3S)-3-((3-((S)-3-methylpyrrolidin-1-yl)pyrazin-2-
yl)oxy)cyclobutyl)benzo[d]thiazol-2-amine;
1-(3-((1S,3S)-3-(benzo[d]thiazol-2-ylamino)cyclobutoxy)
pyrazin-2-yl)piperidine-4-carbonitrile;
1-(3-((1S,3S)-3-(quinolin-2-ylamino)cyclobutoxy)pyrazin-
2-yl)piperidine-4-carbonitrile;
N-((1S,3S)-3-((6-chloro-3-(3,6-dihydro-2H-pyran-4-yl)py-
ridin-2-yl)oxy)cyclobutyl)benzo[d]thiazol-2-amine;
5-(3-((1S,3S)-3-(benzo[d]thiazol-2-ylamino)cyclobutoxy)
pyrazin-2-yl)picolinamide;
(R)-1-(3-((1S,3S)-3-(benzo[d]thiazol-2-ylamino)cyclobu-
toxy)pyrazin-2-yl)pyrrolidine-3-carbonitrile;
(S)-1-(3-((1S,3R)-3-(benzo[d]thiazol-2-ylamino)cyclobu-
toxy)pyrazin-2-yl)pyrrolidine-3-carbonitrile;
5-(3-((1S,3S)-3-(quinolin-2-ylamino)cyclobutoxy)pyrazin-
2-yl)picolinamide;
1-(4-(3-((1S,3S)-3-(benzo[d]thiazol-2-ylamino)cyclobu-
toxy)pyrazin-2-yl)piperidin-1-yl)-2-hydroxyethanone;
N-((1S,3S)-3-((3-(3,3-difluoropyrrolidin-1-yl)pyrazin-2-yl)
oxy)cyclobutyl)benzo[d]thiazol-2-amine;
N-(3-((3-(3-fluoropyrrolidin-1-yl)pyrazin-2-yl)oxy)cy-
clobutyl)benzo[d]thiazol-2-amine;
2'-((1S,3S)-3-(quinolin-2-ylamino)cyclobutoxy)-[3,3'-bipy-
ridine]-6-carboxamide;

N-((1S,3S)-3-((3-(4-methylpiperazin-1-yl)pyrazin-2-yl)oxy)cyclobutyl)benzo[d]thiazol-2-amine;

5-fluoro-N-((1S,3S)-3-((3-(6-methylpyridin-3-yl)pyrazin-2-yl)oxy)cyclobutyl)benzo[d]thiazol-2-amine;

1-(4-(3-((1S,3S)-3-(benzo[d]thiazol-2-ylamino)cyclobutoxy)pyrazin-2-yl)piperidin-1-yl)-2-methoxyethanone;

N-((1S,3S)-3-((6-fluoro-5-iodopyridin-2-yl)oxy)cyclobutyl)benzo[d]thiazol-2-amine;

4-(3-((1S,3S)-3-(benzo[d]thiazol-2-ylamino)cyclobutoxy)pyrazin-2-yl)thiomorpholine 1,1-dioxidecyclobutyl}-amine;

2'-((1S,3S)-3-(benzo[d]thiazol-2-ylamino)cyclobutoxy)-[3,3'-bipyridine]-6-carboxamide;

N-((1S,3S)-3-((3-(6-methylpyridin-3-yl)pyrazin-2-yl)oxy)cyclobutyl)quinazolin-2-amine;

N-((1S,3S)-3-((6-fluoro-3-(tetrahydro-2H-pyran-4-yl)pyridin-2-yl)oxy)cyclobutyl)benzo[d]thiazol-2-amine;

5-(3-((1S,3S)-3-(quinazolin-2-ylamino)cyclobutoxy)pyrazin-2-yl)picolinonitrile;

N-((1S,3S)-3-((3-(2-methylpyridin-3-yl)pyrazin-2-yl)oxy)cyclobutyl)benzo[d]thiazol-2-amine;

1-(2-((1S,3S)-3-(benzo[d]thiazol-2-ylamino)cyclobutoxy)pyridin-3-yl)piperidine-4-carbonitrile;

1-(5-(3-((1S,3S)-3-(benzo[d]thiazol-2-ylamino)cyclobutoxy)pyrazin-2-yl)pyridin-2-yl)ethanone;

N-((1S,3S)-3-((3-(1-methylpiperidin-4-yl)pyrazin-2-yl)oxy)cyclobutyl)benzo[d]thiazol-2-amine;

N-((1S,3S)-3-((3-(5,6-dihydroimidazo[1,5-a]pyrazin-7(8H)-yl)pyrazin-2-yl)oxy)cyclobutyl)benzo[d]thiazol-2-amine;

N-((1S,3S)-3-((3-(4-methylpiperazin-1-yl)pyrazin-2-yl)oxy)cyclobutyl)quinazolin-2-amine; or (1-(3-((1S,3S)-3-(quinazolin-2-ylamino)cyclobutoxy)pyrazin-2-yl)piperidin-4-yl)methanol.

Another aspect of the invention relates to the compounds of Examples 118 to 127 as listed in Table 13 below, or a pharmaceutically acceptable salt thereof.

Yet another aspect of the current invention relates to any compound of the present invention, or a pharmaceutically-acceptable salt thereof, radiolabeled with a positron emitting radionuclide selected from $^{11}$C, $^{18}$F, $^{15}$O, $^{13}$N, $^{76}$Br, $^{77}$Br, $^{123}$I, or $^{125}$I.

Yet another aspect of the current invention relates to a radiopharmaceutical composition comprising any compound of the present invention, or a pharmaceutically-acceptable salt thereof, radiolabeled with a positron emitting radionuclide selected from $^{11}$C, $^{15}$O, $^{13}$N, $^{76}$Br, $^{77}$Br, $^{123}$I, or $^{125}$I, and at least one pharmaceutically acceptable carrier or excipient.

Yet another aspect of the current invention relates to a method for the diagnostic imaging of PDE10 receptors in a mammal, including human, or tissues bearing PDE10 receptors in a mammal, including human brain, which comprises administering to a mammal in need of such diagnostic imaging an effective amount of any compound of the present invention, or a pharmaceutically-acceptable salt thereof, radiolabeled with a positron emitting radionuclide selected from $^{11}$C, $^{18}$F, $^{15}$O, $^{13}$N, $^{76}$Br, $^{77}$Br, $^{123}$I, or $^{125}$I.

Yet another aspect of the current invention relates to a method for the diagnostic imaging of PDE10 receptors in a mammal, including human, or tissues bearing PDE10 receptors in a mammal, including human brain, which comprises administering to a mammal in need of such diagnostic imaging an effective amount of any compound of the present invention, or a pharmaceutically-acceptable salt thereof, radiolabeled with a positron emitting radionuclide selected from $^{11}$C, $^{18}$F, $^{15}$O, $^{13}$N, $^{76}$Br, $^{77}$Br, $^{123}$I, or $^{125}$I.

Yet another aspect of the current invention relates to a method for the detection or quantification of PDE10 receptors in mammalian tissue, including human tissue, which comprises contacting such mammalian tissue in which such detection or quantification is desired with an effective amount of any compound of the present invention, or a pharmaceutically-acceptable salt thereof, radiolabeled with a positron emitting radionuclide selected from $^{11}$C, $^{18}$F, $^{15}$O, $^{13}$N, $^{76}$Br, $^{77}$Br, $^{123}$I, or $^{125}$I.

The compounds of this invention may have in general several asymmetric centers and are typically depicted in the form of racemic mixtures. This invention is intended to encompass racemic mixtures, other racemic mixtures and separate enantiomers and diastereomers.

The present invention includes all pharmaceutically acceptable isotopically-labelled compounds of the present invention wherein one or more atoms are replaced by atoms having the same atomic number, but an atomic mass or mass number different from the atomic mass or mass number which predominates in nature.

Examples of isotopes suitable for inclusion in the compounds of the invention include, but are not limited to, isotopes of hydrogen, such as $^2$H and $^3$H, carbon, such as $^{11}$C, $^{13}$C and $^{14}$C, chlorine, such as $^{38}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labelled compounds of the present invention, for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of the present invention can generally be prepared by conventional techniques known to those skilled in the art or by processes analogous to those described in the accompanying Examples and Preparations using an appropriate isotopically-labeled reagent in place of the non-labeled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

Specific embodiments of the present invention include the compounds exemplified in the Examples below and their pharmaceutically acceptable salts, complexes, solvates, polymorphs, stereoisomers, metabolites, prodrugs, and other derivatives thereof, Unless otherwise specified, the following definitions apply to terms found in the specification and claims:

Heteroaryloxycarbocyclyl compounds of the invention may possess one or more asymmetric carbon atoms. Rotation about carbon-carbon bonds in carbocyclic compounds is limited by the ring structure and therefore the compounds can exist as multiple diastereomers. When two substituent groups of a carbocyclic compound are oriented in the same direction, the diastereomer is referred to as cis, whereas, when the substituents are oriented in opposing directions, the diastereomer is referred to as trans. For example, there are two different 1,2-dichloro-cyclohexane diastereomers, one with the two chloros on the same side (cis) of the ring and one with the chloros on opposite sides (trans). Below are the structures of trans and cis diastereoisomers of 1,2-dichloro-cyclobutane; 1,2-dichloro-cyclopentane, and 1,2-dichloro-cyclohexane, respectively:

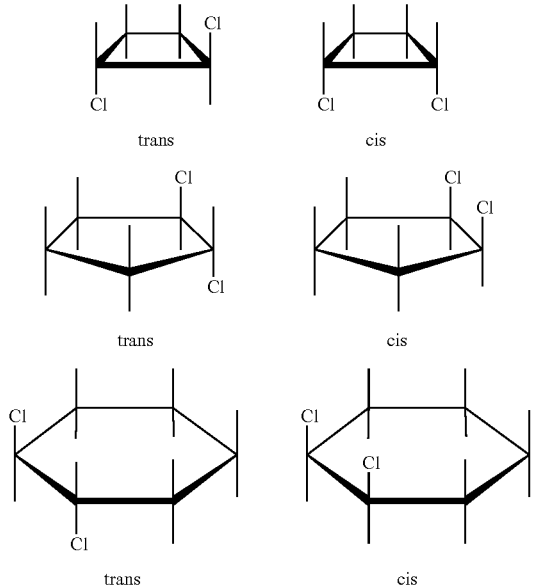

Similarly, a compound of formula (I):

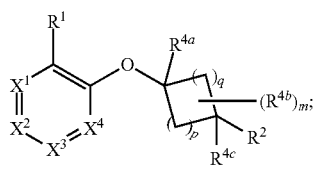

(I)

may exist in the following four stereoisomeric forms:

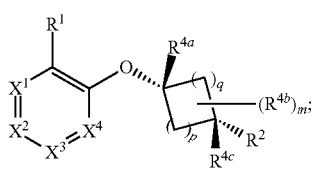

(a)

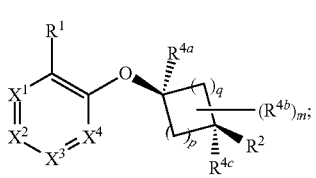

(b)

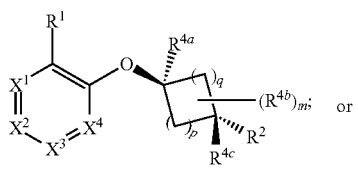

(c)

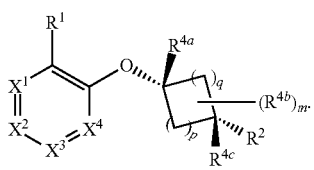

(d)

It will be appreciated that in the compound of formula (I), where m is not 0, all compounds of formula (a), (b), (c), and (d) exist as 4 different stereoisomers, and each of which is contemplated to be within the claimed invention. It will also be appreciated that in the compound of formula (I), where m is 0, and the sum of p and q is an odd number (3 or 5), all compounds of formula (a), (b), (c), and (d) exist as 4 different stereoisomers, and each of which is contemplated to be within the claimed invention.

It will also be appreciated that the compound of formula (I), where m is 0, and the sum of p and q is an even number (2, 4, or 6), are symmetrical, and in the absence of any other stereocenter elsewhere in the molecule, accordingly the compound of formula (a) is identical to (b), and the compound of formula (c) is identical to (d). Therefore said compound exists as 2 different stereoisomers, and each of which is contemplated to be within the claimed invention.

More specifically, for example, in the compound of Example 22, m is 0, and the sum of p and q is an even number (2); and the compound is symmetrical. Therefore said compound may exist as two different stereoisomers, cis and trans, as follows:

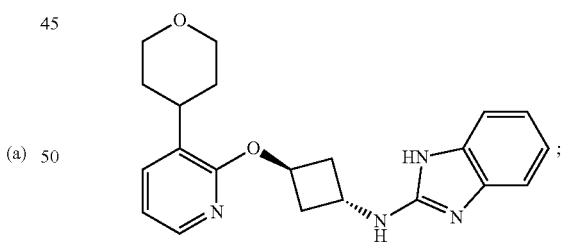

(a)

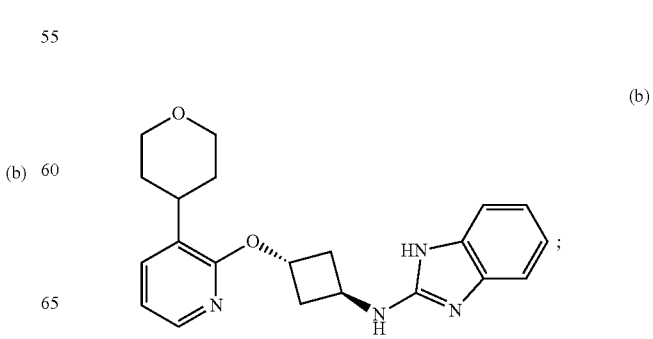

(b)

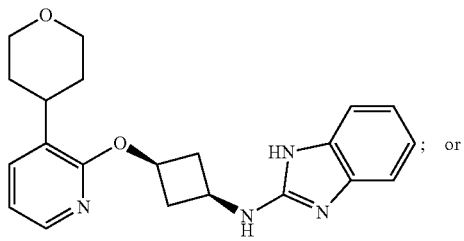

(c)

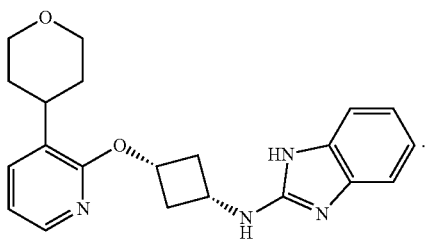

(d)

Compounds (a) and (b) are called trans stereoisomers because the substituents of the middle carbocyclic ring are oriented in the same directions. Compounds (c) and (d) are called cis stereoisomers because the substituents of the middle carbocyclic ring are oriented in the opposite directions. Because the compound is symmetrical, compound (a) is identical to compound (b) (trans stereoisomers) and compound (c) is identical to compound (d) (cis stereoisomers); each of which is contemplated to be within the claimed invention.

The term "$C_{\alpha-\beta}$alk" means an alkyl group comprising a minimum of α and a maximum of β carbon atoms in a branched, cyclical or linear relationship or any combination of the three, wherein α and β represent integers. The alkyl groups described in this section may also contain one or two double or triple bonds. A designation of $C_0$alk indicates a direct bond. Examples of $C_{1-6}$alkyl include, but are not limited to the following:

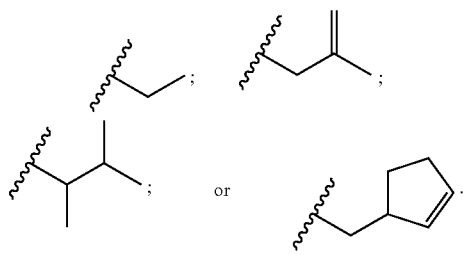

The term "benzo group", alone or in combination, means the divalent radical $C_4H_4$=, one representation of which is —CH=CH—CH=CH—, that when vicinally attached to another ring forms a benzene-like ring—for example tetrahydronaphthylene, indole and the like.

The terms "oxo" and "thioxo" represent the groups =O (as in carbonyl) and =S (as in thiocarbonyl), respectively.

The term "halo" or "halogen" means a halogen atom selected from F, Cl, Br or I.

The term "$C_{\alpha-\beta}$haloalk" means an alk group, as described above, wherein one or more hydrogen atom of the alk group is replaced by F, Cl, Br or I.

The term "carbon-linked" means a substituent is linked to another group through a carbon atom. Examples of "carbon-linked" substituents include, but are not limited to the following:

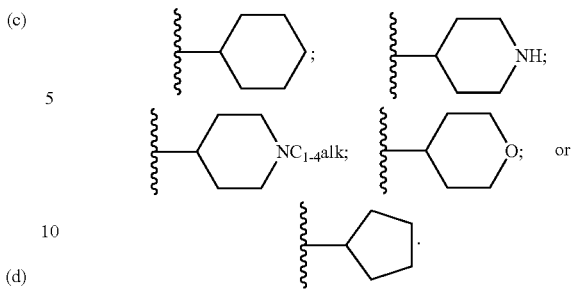

The term "nitrogen-linked" means a substituent is linked to another group through a nitrogen atom. Examples of "nitrogen-linked" substituents include, but are not limited to the following:

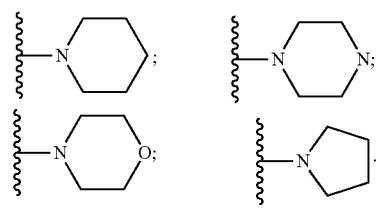

The group $N(R^a)R^a$ and the like include substituents where the two $R^a$ groups together form a ring, optionally including a N, O or S atom, and include groups such as:

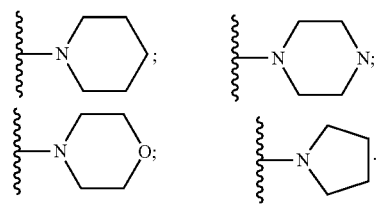

The group $N(C_{\alpha-\beta}$alk) $C_{\alpha-\beta}$alk, wherein α and β are as defined above, include substituents where the two $C_{\alpha-\beta}$alk groups together form a ring, optionally including a N, O or S atom, and include groups such as:

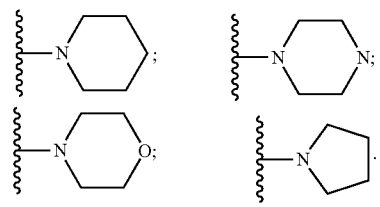

The term "carbocyclyl" means a ring comprising by itself or in combination with other terms, represents, unless otherwise stated, cyclic version of "$C_{\alpha-\beta}$alk". Thus, the term "carbocyclyl" is meant to be included in the terms "$C_{\alpha-\beta}$alk". Examples of carbocycle include cyclopentyl, cyclohexyl, or partially unsaturated ring such as 1-cyclohexenyl, 3-cyclohexenyl, cycloheptyl, cyclobutylene, cyclohexylene and the like. Unless otherwise stated, carbocycle can include fully saturated ring such as phenyl or naphthyl.

The term "heteroatom" means N, O and S.

The term "heterocyclyl" means a ring comprising at least one carbon atom and at least one other atom selected from N, O and S. "Heterocyclyl" includes aromatic heterocyclic ring which is commonly known as heteroaryl. Thus, the term "heteroaryl" is meant to be included in the terms "heterocyclyl". Examples of heterocycles that may be found in the claims include, but are not limited to, the following:

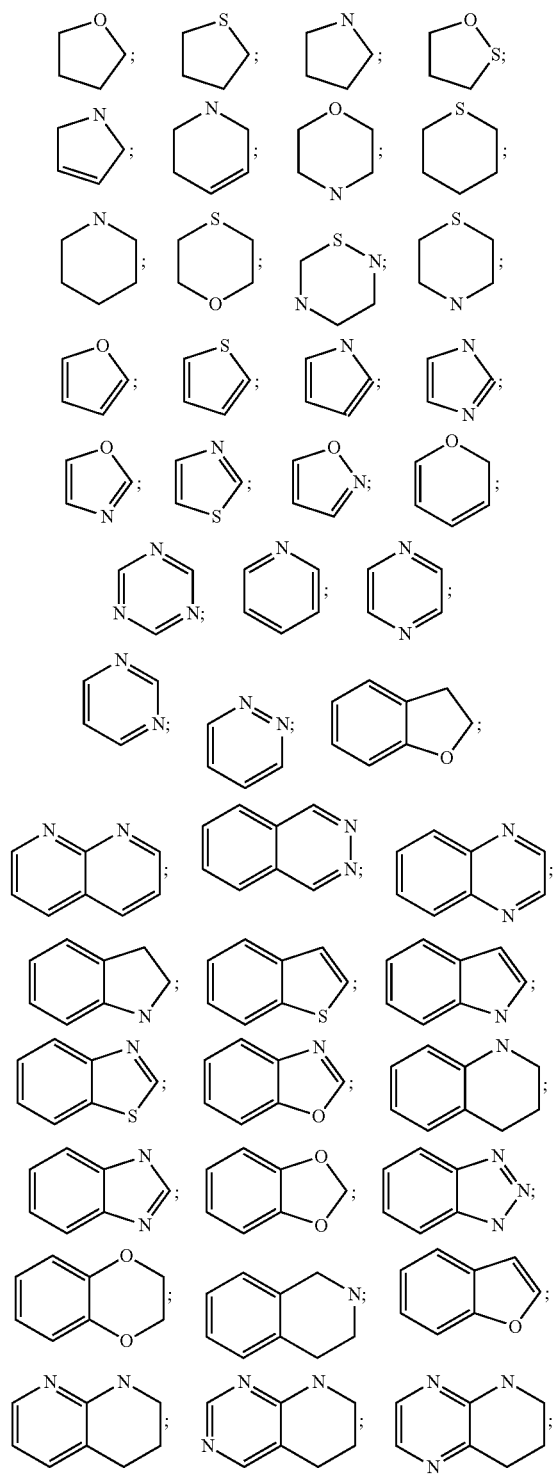

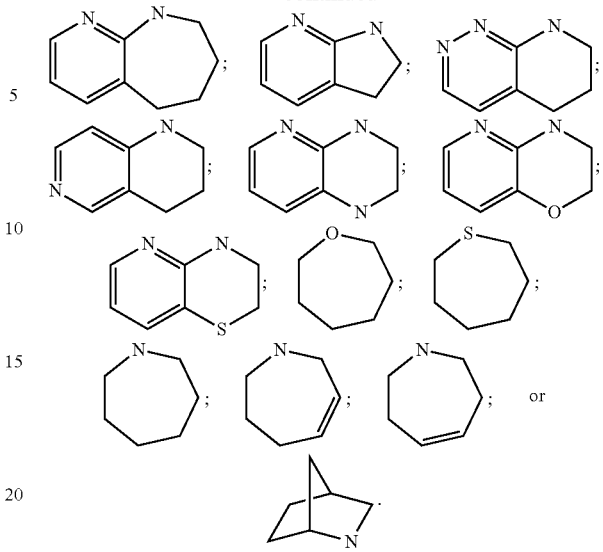

The term "pharmaceutically acceptable salt" means a salt prepared by conventional means, and are well known by those skilled in the art. The "pharmacologically acceptable salts" include basic salts of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. When compounds of the invention include an acidic function such as a carboxy group, then suitable pharmaceutically acceptable cation pairs for the carboxy group are well known to those skilled in the art and include alkaline, alkaline earth, ammonium, quaternary ammonium cations and the like. For additional examples of "pharmacologically acceptable salts," and Berge et al., J. Pharm. Sci. 66:1 (1977).

The term "saturated, partially-saturated or unsaturated" includes substituents saturated with hydrogens, substituents completely unsaturated with hydrogens and substituents partially saturated with hydrogens.

Representative examples of "saturated, partially-saturated or unsaturated" five to eight membered rings, optionally having one to three heteroatoms, are cyclopentyl, cyclohexyl, cycloheptyl, cyclooctyl and phenyl. Further exemplary five membered rings are furyl, thienyl, pyrrolyl, 2-pyrrolinyl, 3-pyrrolinyl, pyrrolidinyl, 1,3-dioxolanyl, oxazolyl, thiazolyl, imidazolyl, 2H-imidazolyl, 2-imidazolinyl, imidazolidinyl, pyrazolyl, 2-pyrazolinyl, pyrazolidinyl, isoxazolyl, isothiazolyl, 1,2-dithiolyl, 1,3-dithiolyl, 3H-1,2-oxathiolyl, 1,2,3-oxadizaolyl, 1,2,4-oxadiazolyl, 1,2,5-oxadiazolyl, 1,3,4oxadiazolyl, 1,2,3-triazolyl, 1,2,4-trizaolyl, 1,3,4-thiadiazolyl, 3H-1,2,3-dioxazolyl, 1,2,4-dioxazolyl, 1,3,2-dioxazolyl, 1,3,4-dioxazolyl, 5H-1,2,5-oxathiazolyl, and 1,3-oxathiolyl.

Further exemplary six membered rings are 2H-pyranyl, 4H-pyranyl, pyridinyl, piperidinyl, 1,2-dioxinyl, 1,3-dioxinyl, 1,4-dioxanyl, morpholinyl, 1,4-dithianyl, thiomorpholinyl, pyndazinyl, pyrimidinyl, pyrazinyl, piperazinyl, 1,3,5-triazinyl, 1,2,4-triazinyl, 1,2,3-triazinyl, 1,3,5-trithianyl, 4H-1,2-oxazinyl, 2H-1,3-oxazinyl, 6H-1,3-oxazinyl, 6H-1,2-oxazinyl, 1,4-oxazinyl, 2H-1,2-oxazinyl, 4H-1,4-oxazinyl, 1,2,5-oxathiazinyl, 1,4-oxazinyl, o-isoxazinyl, p-isoxazinyl, 1,2,5-oxathiazinyl, 1,2,6-(3 oxathiazinyl, and 1,4,2-oxadiazinyl.

Further exemplary seven membered rings are azepinyl, oxepinyl, thiepinyl and 1,2,4-triazepinyl.

Further exemplary eight membered rings are cyclooctyl, cyclooctenyl and cyclooctadienyl.

The term "monocyclic" means a group having a single saturated, partially-saturated, or unsaturated ring system. Typically a monocyclic ring system can have from 3- to 8 atoms in the ring system. The term includes, but is not limited to, cyclopropyl, cyclopropyl, cyclobutyl, cyclopentyl, cyclohexyl, cycloheptyl, phenyl, and the like.

The term "bicyclic" means a group having two interconnected saturated, partially-saturated, or unsaturated rings that include stable bridged, fused, or spiro rings. The bicyclic ring may be attached at any carbon or heteroatom which affords a stable group. Typically a bicyclic ring system can have from 6- to 14 atoms in the ring system. The term includes, but is not limited to, benzimidazole, naphthyl, bicyclo[3.1.0]hexane, bicyclo[4.1.0]heptane, spiro[2.4]heptane, spiro[2.5]octane, bicyclo[4.4.0]decane, bicyclo[4.3.0]nonane, bicyclo[3.3.1]nonane, bicyclo[3.2.1]octane, spiro[4.5]decane, spiro[3.5]nonane, norbornane, bicyclo[2.1.0]pentane, bicyclo[3.3.0]octane, bicyclo[2.2.2]octane, bicyclo[3.3.3]undecane, and the like.

The term "tricyclic" means a group having three interconnected saturated, partially-saturated, or unsaturated rings that include stable bridged, fused, or spiro rings. Typically a tricyclic ring system can have from 11 to 18 ring atoms in the ring system. The term includes, but is not limited to, adamantyl, tricyclo[5.2.1.0.sup.2,6]decane, and the like.

Exemplary bicyclic rings consisting of two fused partially saturated, fully saturated or fully unsaturated five and/or six membered rings, optionally having one to four heteroatoms, are indolizinyl, indolyl, isoindolyl, indolinyl, cyclopenta(b)pyridinyl, pyrano(3,4-b)pyrrolyl, benzofuryl, isobenzofuryl, benzo[b]thienyl, benzo[c]thienyl, 1H-indazolyl, indoxazinyl, benzoxazolyl, anthranilyl, benzimidazolyl, benzthiazolyl, purinyl, quinolinyl, isoquinolinyl, cinnolinyl, phthalazinyl, quinazolinyl, quinoxalinyl, 1,8-naphthyridinyl, pteridinyl, indenyl, isoindenyl, naphthyl, tetralinyl, decalinyl, 2H-1-benzopyranyl, pyrido(3,4-b)pyridinyl, pyrido(3,2-b)pyridinyl, pyrido(4,3-b)-pyridinyl, 2H-1,3-benzoxazinyl, 2H-1,4-benzoxazinyl, 1H-2,3-benzoxazinyl, 4H-3,1-benzoxazinyl, 2H-1,2-benzoxazinyl and 4H-1,4-benzoxazinyl.

A cyclic ring group may be bonded to another group in more than one way. If no particular bonding arrangement is specified, then all possible arrangements are intended. For example, the term "pyridyl" includes 2-, 3-, or 4-pyridyl, and the term "thienyl" includes 2-, or 3-thienyl.

The term "substituted" means that a hydrogen atom on a molecule or group is replaced with a group or atom. Typical substitutents include: halogen, $C_{1-8}$alkyl, hydroxyl, $C_{1-8}$alkoxy, $-NR^xR^x$, nitro, cyano, halo or perhalo$C_{1-8}$alkyl, $C_{2-8}$alkenyl, $C_{2-8}$alkynyl, $-SR^x$, $-S(=O)_2R^x$, $-C(=O)OR^x$, $-C(=O)R^x$, wherein each $R^x$ is independently hydrogen or $C_1$-$C_8$ alkyl. It is noted that when the substituent is $-NR^xR^x$, the $R^x$ groups may be joined together with the nitrogen atom to form a ring.

A group or atom that replaces a hydrogen atom is also called a substituent.

Any particular molecule or group can have one or more substituent depending on the number of hydrogen atoms that can be replaced.

The symbol "—" represents a covalent bond and can also be used in a radical group to indicate the point of attachment to another group. In chemical structures, the symbol is commonly used to represent a methyl group in a molecule.

The term "leaving group" generally refers to groups readily displaceable by a nucleophile, such as an amine, a thiol or an alcohol nucleophile. Such leaving groups are well known in the art. Examples of such leaving groups include, but are not limited to, N-hydroxysuccinimide, N-hydroxybenzotriazole, halides, triflates, tosylates and the like. Preferred leaving groups are indicated herein where appropriate.

The term "protecting group" generally refers to groups well known in the art which are used to prevent selected reactive groups, such as carboxy, amino, hydroxy, mercapto and the like, from undergoing undesired reactions, such as nucleophilic, electrophilic, oxidation, reduction and the like. Preferred protecting groups are indicated herein where appropriate. Examples of amino protecting groups include, but are not limited to, aralkyl, substituted aralkyl, cycloalkenylalkyl and substituted cycloalkenyl alkyl, allyl, substituted allyl, acyl, alkoxycarbonyl, aralkoxycarbonyl, silyl and the like. Examples of aralkyl include, but are not limited to, benzyl, ortho-methylbenzyl, trityl and benzhydryl, which can be optionally substituted with halogen, alkyl, alkoxy, hydroxy, nitro, acylamino, acyl and the like, and salts, such as phosphonium and ammonium salts. Examples of aryl groups include phenyl, naphthyl, indanyl, anthracenyl, 9-(9-phenylfluorenyl), phenanthrenyl, durenyl and the like. Examples of cycloalkenylalkyl or substituted cycloalkylenylalkyl radicals, preferably have 6-10 carbon atoms, include, but are not limited to, cyclohexenyl methyl and the like. Suitable acyl, alkoxycarbonyl and aralkoxycarbonyl groups include benzyloxycarbonyl, t-butoxycarbonyl, iso-butoxycarbonyl, benzoyl, substituted benzoyl, butyryl, acetyl, trifluoroacetyl, trichloro acetyl, phthaloyl and the like. A mixture of protecting groups can be used to protect the same amino group, such as a primary amino group can be protected by both an aralkyl group and an aralkoxycarbonyl group. Amino protecting groups can also form a heterocyclic ring with the nitrogen to which they are attached, for example, 1,2-bis(methylene)benzene, phthalimidyl, succinimidyl, maleimidyl and the like and where these heterocyclic groups can further include adjoining aryl and cycloalkyl rings. In addition, the heterocyclic groups can be mono-, di- or tri-substituted, such as nitrophthalimidyl. Amino groups may also be protected against undesired reactions, such as oxidation, through the formation of an addition salt, such as hydrochloride, toluenesulfonic acid, trifluoroacetic acid and the like. Many of the amino protecting groups are also suitable for protecting carboxy, hydroxy and mercapto groups. For example, aralkyl groups. Alkyl groups are also suitable groups for protecting hydroxy and mercapto groups, such as tert-butyl.

The term "silyl protecting groups" means silicon atoms optionally substituted by one or more alkyl, aryl and aralkyl groups. Suitable silyl protecting groups include, but are not limited to, trimethylsilyl, triethylsilyl, triisopropylsilyl, tert-butyldimethylsilyl, dimethylphenylsilyl, 1,2-bis(dimethylsilyl)benzene, 1,2-bis(dimethylsilyl)ethane and diphenylmethylsilyl. Silylation of an amino groups provide mono- or di-silylamino groups. Silylation of aminoalcohol compounds can lead to a N,N,O-trisilyl derivative. Removal of the silyl function from a silyl ether function is readily accomplished by treatment with, for example, a metal hydroxide or ammonium fluoride reagent, either as a discrete reaction step or in situ during a reaction with the alcohol group. Suitable silylating agents are, for example, trimethylsilyl chloride, tert-butyl-dimethylsilyl chloride, phenyldimethylsilyl chloride, diphenylmethyl silyl chloride or their combination products with imidazole or DMF. Methods for silylation of amines and removal of silyl protecting groups are well known to those skilled in the art. Methods of preparation of these amine derivatives from corresponding amino acids, amino acid amides or amino acid esters are also well known to those skilled in the art of organic chemistry including amino acid/amino acid ester or aminoalcohol chemistry.

Protecting groups are removed under conditions which will not affect the remaining portion of the molecule. These methods are well known in the art and include acid hydrolysis, hydrogenolysis and the like. A preferred method involves removal of a protecting group, such as removal of a benzyloxycarbonyl group by hydrogenolysis utilizing palladium on carbon in a suitable solvent system such as an alcohol, acetic acid, and the like or mixtures thereof. A t-butoxycarbonyl protecting group can be removed utilizing an inorganic or organic acid, such as HCl or trifluoroacetic acid, in a suitable solvent system, such as dioxane or methylene chloride. The resulting amino salt can readily be neutralized to yield the free amine. Carboxy protecting group, such as methyl, ethyl, benzyl, tert-butyl, 4-methoxyphenylmethyl and the like, can be removed under hydrolysis and hydrogenolysis conditions well known to those skilled in the art.

It should be noted that compounds of the invention may contain groups that may exist in tautomeric forms, such as cyclic and acyclic amidine and guanidine groups, heteroatom substituted aromatic heterocyclyl groups (Y'=O, S, NR), and the like, which are illustrated in the following examples:

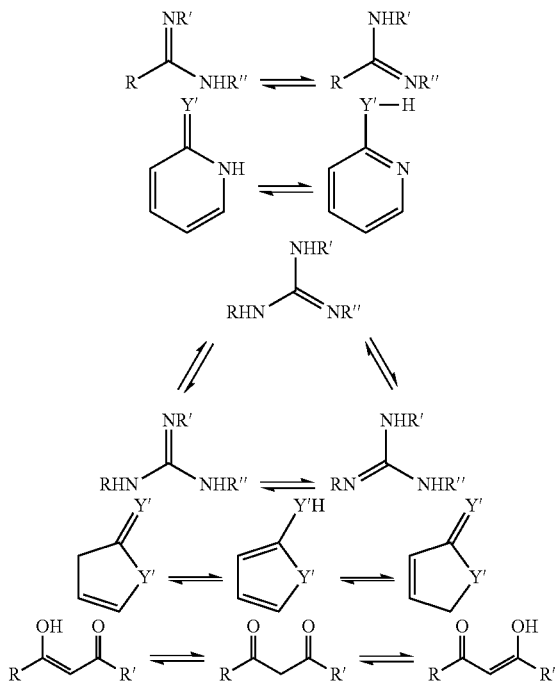

and though one form is named, described, displayed and/or claimed herein, all the tautomeric forms are intended to be inherently included in such name, description, display and/or claim.

Prodrugs of the compounds of this invention are also contemplated by this invention. A prodrug is an active or inactive compound that is modified chemically through in vivo physiological action, such as hydrolysis, metabolism and the like, into a compound of this invention following administration of the prodrug to a patient. The suitability and techniques involved in making and using prodrugs are well known by those skilled in the art. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use.

The term "therapeutically effective amount" means an amount of a compound that ameliorates, attenuates or eliminates one or more symptom of a particular disease or condition, or prevents or delays the onset of one of more symptom of a particular disease or condition.

The term "patient" means animals, such as dogs, cats, cows, horses, sheep and humans. Particular patients are mammals. The term patient includes males and females.

The term "pharmaceutically acceptable" means that the referenced substance, such as a compound of Formula I, or a salt of a compound of Formula I, or a formulation containing a compound of Formula I, or a particular excipient, are suitable for administration to a patient.

The terms "treating", "treat" or "treatment" and the like include preventative (e.g., prophylactic) and palliative treatment.

The term "excipient" means any pharmaceutically acceptable additive, carrier, diluent, adjuvant, or other ingredient, other than the active pharmaceutical ingredient (API), which is typically included for formulation and/or administration to a patient.

Utility and Methods of Use

Provided herein are methods for treating a disorder or disease by inhibiting PDE10 enzyme. The methods, in general, comprises the step of administering a therapeutically effective amount of a compounds of the present invention, or an individual stereoisomer, a mixture of stereoisomers, or a pharmaceutically acceptable salt or solvate thereof, to a patient in need thereof to treat the disorder or disease.

In certain embodiments, this invention provides a use of a compound as described herein in the manufacture of a medicament for treating a disorder or disease treatable by inhibition of PDE10.

The compounds of the present invention inhibit PDE10 enzyme activity, and hence raise the levels of cAMP or cGMP within cells that express PDE10. Accordingly, inhibition of PDE10 enzyme activity would be useful in the treatment of diseases caused by deficient amounts of cAMP or cGMP in cells. PDE10 inhibitors would also be of benefit in cases wherein raising the amount of cAMP or cGMP above normal levels results in a therapeutic effect. Inhibitors of PDE10 may be used to treat disorders of the peripheral and central nervous system, cardiovascular diseases, cancer, gastro-enterological diseases, endocrinological diseases and urological diseases.

Indications that may be treated with PDE10 inhibitors, either alone or in combination with other drugs, include, but are not limited to, those diseases thought to be mediated in part by the basal ganglia, prefrontal cortex, and hippocampus. These indications include psychoses, Parkinson's disease, dementias, obsessive compulsive disorder, tardive dyskinesia, choreas, depression, mood disorders, impulsivity, drug addiction, attention deficit/hyperactivity disorder (ADHD), depression with parkinsonian states, personality changes with caudate or putamen disease, dementia and mania with caudate and pallidal diseases, and compulsions with pallidal disease.

Psychoses are disorders that affect an individual's perception of reality. Psychoses are characterized by delusions and hallucinations. The compounds of the present invention are suitable for use in treating patients suffering from all forms of psychoses, including, but not limited to, schizophrenia, late-onset schizophrenia, schizoaffective disorders, prodromal schizophrenia, and bipolar disorders. Treatment can be for the positive symptoms of schizophrenia as well as for the cognitive deficits and negative symptoms. Other indications for PDE10 inhibitors include psychoses resulting from drug abuse (including amphetamines and PCP), encephalitis, alcoholism, epilepsy, Lupus, sarcoidosis, brain tumors, multiple sclerosis, dementia with Lewy bodies, or hypoglycemia. Other psychiatric disorders, like posttraumatic stress disorder (PTSD), and schizoid personality can also be treated with PDE10 inhibitors.

Obsessive-compulsive disorder (OCD) has been linked to deficits in the frontal-striatal neuronal pathways (Saxena et al., Br. J. Psychiatry Suppl, 35:26-37, 1998). Neurons in these pathways project to striatal neurons that express PDE10. PDE10 inhibitors cause cAMP to be elevated in these neurons; elevations in cAMP result in an increase in CREB phosphorylation and thereby improve the functional state of these neurons. The compounds of the present invention are therefore suitable for use in the indication of OCD. OCD may result, in some cases, from streptococcal infections that cause autoimmune reactions in the basal ganglia (Giedd et al., Am J Psychiatry. 157:281-283, 2000). Because PDE10 inhibitors may serve a neuroprotective role, administration of PDE10 inhibitors may prevent the damage to the basal ganglia after repeated streptococcal infections and thereby prevent the development of OCD.

In the brain, the level of cAMP or cGMP within neurons is believed to be related to the quality of memory, especially long term memory. Without wishing to be bound to any particular mechanism, it is proposed that, since PDE10 degrades cAMP or cGMP, the level of this enzyme affects memory in animals, for example, in humans. A compound that inhibits cAMP phosphodiesterase (PDE) can thereby increase intracellular levels of cAMP, which in turn activate a protein kinase that phosphorylates a transcription factor (cAMP response binding protein). The phosphorylated transcription factor then binds to a DNA promoter sequence to activate genes that are important in long term memory. The more active such genes are, the better is long-term memory. Thus, by inhibiting a phosphodiesterase, long term memory can be enhanced.

Dementias are diseases that include memory loss and additional intellectual impairment separate from memory. The compounds of the present invention are suitable for use in treating patients suffering from memory impairment in all forms of dementia. Dementias are classified according to their cause and include: neurodegenerative dementias (e.g., Alzheimer's, Parkinson's disease, Huntington's disease, Pick's disease), vascular (e.g., infarcts, hemorrhage, cardiac disorders), mixed vascular and Alzheimer's, bacterial meningitis, Creutzfeld-Jacob Disease, multiple sclerosis, traumatic (e.g., subdural hematoma or traumatic brain injury), infectious (e.g., HIV), genetic (down syndrome), toxic (e.g., heavy metals, alcohol, some medications), metabolic (e.g., vitamin B12 or folate deficiency), CNS hypoxia, Cushing's disease, psychiatric (e.g., depression and schizophrenia), and hydrocephalus.

The condition of memory impairment is manifested by impairment of the ability to learn new information and/or the inability to recall previously learned information. The present invention includes methods for dealing with memory loss separate from dementia, including mild cognitive impairment (MCI) and age-related cognitive decline. The present invention includes methods of treatment for memory impairment as a result of disease. Memory impairment is a primary symptom of dementia and can also be a symptom associated with such diseases as Alzheimer's disease, schizophrenia, Parkinson's disease, Huntington's disease, Pick's disease, Creutzfeld-Jakob disease, HIV, cardiovascular disease, and head trauma as well as age-related cognitive decline. The compounds of the present invention are suitable for use in the treatment of memory impairment due to, for example, Alzheimer's disease, multiple sclerosis, amylolaterosclerosis (ALS), multiple systems atrophy (MSA), schizophrenia, Parkinson's disease, Huntington's disease, Pick's disease, Creutzfeld-Jakob disease, depression, aging, head trauma, stroke, spinal cord injury, CNS hypoxia, cerebral senility, diabetes associated cognitive impairment, memory deficits from early exposure of anesthetic agents, multiinfarct dementia and other neurological conditions including acute neuronal diseases, as well as HIV and cardiovascular diseases.

The compounds of the present invention are also suitable for use in the treatment of a class of disorders known as polyglutamine-repeat diseases. These diseases share a common pathogenic mutation. The expansion of a CAG repeat, which encodes the amino acid glutamine, within the genome leads to production of a mutant protein having an expanded polyglutamine region. For example, Huntington's disease has been linked to a mutation of the protein huntingtin. In individuals who do not have Huntington's disease, huntingtin has a polyglutamine region containing about 8 to 31 glutamine residues. For individuals who have Huntington's disease, huntingtin has a polyglutamine region with over 37 glutamine residues. Aside from Huntington's disease (HD), other known polyglutamine-repeat diseases and the associated proteins include dentatorubral-pallidoluysian atrophy, DRPLA (atrophin-1); spinocerebellar ataxia type-1 (ataxin-1); spinocerebellar ataxia type-2 (ataxin-2); spinocerebellar ataxia type-3 (also called Machado-Joseph disease or MJD) (ataxin-3); spinocerebellar ataxia type-6 (alpha 1a-voltage dependent calcium channel); spinocerebellar ataxia type-7 (ataxin-7); and spinal and bulbar muscular atrophy (SBMA, also know as Kennedy disease).

The basal ganglia are important for regulating the function of motor neurons; disorders of the basal ganglia result in movement disorders. Most prominent among the movement disorders related to basal ganglia function is Parkinson's disease (Obeso et al., Neurology. 62(1 Suppl 1):517-30, 2004). Other movement disorders related to dysfunction of the basal ganglia include tardive dyskinesia, progressive supranuclear palsy and cerebral palsy, corticobasal degeneration, multiple system atrophy, Wilson disease, dystonia, tics, and chorea. The compounds of the invention are also suitable for use to treat movement disorders related to dysfunction of basal ganglia neurons.

PDE10 inhibitors are useful in raising cAMP or cGMP levels and prevent neurons from undergoing apoptosis. PDE10 inhibitors may be anti-inflammatory by raising cAMP in glial cells. The combination of anti-apoptotic and anti-inflammatory properties, as well as positive effects on synaptic plasticity and neurogenesis, make these compounds useful to treat neurodegeneration resulting from any disease or injury, including stroke, spinal cord injury, Alzheimer's disease, multiple sclerosis, amylolaterosclerosis (ALS), and multiple systems atrophy (MSA).

Autoimmune diseases or infectious diseases that affect the basal ganglia may result in disorders of the basal ganglia including ADHD, OCD, tics, Tourette's disease, Sydenham chorea. In addition, any insult to the brain can potentially damage the basal ganglia including strokes, metabolic abnormalities, liver disease, multiple sclerosis, infections, tumors, drug overdoses or side effects, and head trauma. Accordingly, the compounds of the invention can be used to stop disease progression or restore damaged circuits in the brain by a combination of effects including increased synaptic plasticity, neurogenesis, anti-inflammatory, nerve cell regeneration and decreased apoptosis.

The growth of some cancer cells is inhibited by cAMP and cGMP. Upon transformation, cells may become cancerous by expressing PDE10 and reducing the amount of cAMP or cGMP within cells. In these types of cancer cells, inhibition of PDE10 activity inhibits cell growth by raising cAMP. In some cases, PDE10 may be expressed in the transformed, cancerous cell but not in the parent cell line. In transformed renal carcinoma cells, PDE10 is expressed and PDE10 inhibitors reduce the growth rate of the cells in culture. Similarly, breast cancer cells are inhibited by administration of PDE10 inhibitors. Many other types of cancer cells may also be sensitive to growth arrest by inhibition of PDE10. Therefore, compounds disclosed in this invention can be used to stop the growth of cancer cells that express PDE10.

The compounds of the invention are also suitable for use in the treatment of diabetes and related disorders such as obesity, by focusing on regulation of the cAMP signaling system. By inhibiting PDE-10, especially PDE-10A, intracellular levels of cAMP are increased, thereby increasing the release of insulin-containing secretory granules and, therefore, increasing insulin secretion. See, for example, WO 2005/012485. The compounds of Formula (I) can also be used to treat diseases disclosed in US Patent application publication No. 2006/019975.

Testing

The PDE10 inhibitory activities of the compounds of the present invention can be tested, for example, using the in vitro and in vivo assays described in the Biological Examples below.

Administration and Pharmaceutical Compositions

In general, the compounds of this invention can be administered in a therapeutically effective amount by any of the accepted modes of administration for agents that serve similar utilities. The actual amount of a compound of this invention, i.e., the active ingredient, depends upon numerous factors, such as the severity of the disease to be treated, the age and relative health of the subject, the potency of the compound used, the route and form of administration, and other factors.

Therapeutically effective amounts of compounds of formula (I) may range from approximately 0.1-1000 mg per day; preferably 0.5 to 250 mg/day, more preferably 3.5 mg to 70 mg per day.

In general, compounds of this invention can be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen, which can be adjusted according to the degree of affliction. Compositions can take the form of tablets, pills, capsules, semisolids, powders, sustained release formulations, solutions, suspensions, elixirs, aerosols, or any other appropriate compositions.

The choice of formulation depends on various factors, such as the mode of drug administration (e.g., for oral administration, formulations in the form of tablets, pills or capsules are preferred) and the bioavailability of the drug substance. Recently, pharmaceutical formulations have been developed especially for drugs that show poor bioavailability based upon the principle that bioavailability can be increased by increasing the surface area, i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of, in general, a compounds of the present invention in combination with at least one pharmaceutically acceptable excipient. Acceptable excipients are non-toxic, aid administration, and do not adversely affect the therapeutic benefit of the compounds of the present invention. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this invention in aerosol form. Inert gases suitable for this purpose are nitrogen, carbon dioxide, etc.

Other suitable pharmaceutical excipients and their formulations are described in Remington's Pharmaceutical Sciences, Gennaro, A. R. (Mack Publishing Company, 18th ed., 1995).

The level of the compound in a formulation can vary within the full range employed by those skilled in the art. Typically, the formulation contains, on a weight percent (wt %) basis, from about 0.01-99.99 wt % of a compounds of the present invention based on the total formulation, with the balance being one or more suitable pharmaceutical excipients. Preferably, the compound is present at a level of about 1-80 wt %.

The compounds can be administered as the sole active agent or in combination with other pharmaceutical agents such as other agents used in the treatment of psychoses, especially schizophrenia and bipolar disorder, obsessive-compulsive disorder, Parkinson's disease, Alzheimer's disease, cognitive impairment and/or memory loss, e.g., nicotinic α-7 agonists, PDE4 inhibitors, other PDE10 inhibitors, calcium channel blockers, muscarinic m1 and m2 modulators, adenosine receptor modulators, ampakines, NMDA-R modulators, mGluR modulators, dopamine modulators, serotonin modulators, canabinoid modulators, and cholinesterase inhibitors (e.g., donepezil, rivastigimine, and galanthanamine). In such combinations, each active ingredient can be administered either in accordance with their usual dosage range or a dose below their usual dosage range, and can be administered either simultaneously or sequentially.

Drugs suitable in combination with the compounds of the present invention include, but are not limited to, other suitable schizophrenia drugs such as Clozaril, Zyprexa, Risperidone, and Seroquel; bipolar disorder drugs, including, but not limited to, Lithium, Zyprexa, and Depakote; Parkinson's disease drugs, including, but not limited to, Levodopa, Parlodel, Permax, Mirapex, Tasmar, Contan, Kemadin, Artane, and Cogentin; agents used in the treatment of Alzheimer's disease, including, but not limited to, Reminyl, Cognex, Aricept, Exelon, Akatinol, Neotropin, Eldepryl, Estrogen and Cliquinol; agents used in the treatment of dementia, including, but not limited to, Thioridazine, Haloperidol, Risperidone, Cognex, Aricept, and Exelon; agents used in the treatment of epilepsy, including, but not limited to, Dilantin, Luminol, Tegretol, Depakote, Depakene, Zarontin, Neurontin, Barbita, Solfeton, and Felbatol; agents used in the treatment of multiple sclerosis, including, but not limited to, Detrol, Ditropan XL, OxyContin, Betaseron, Avonex, Azothioprine, Methotrexate, and Copaxone; agents used in the treatment of Huntington's disease, including, but not limited to, Amitriptyline, Imipramine, Despiramine, Nortriptyline, Paroxetine, Fluoxetine, Setraline, Terabenazine, Haloperidol, Chloropromazine, Thioridazine, Sulpride, Quetiapine, Clozapine, and Risperidone; agents useful in the treatment of diabetes, including, but not limited to, PPAR ligands (e.g. agonists, antagonists, such as Rosiglitazone, Troglitazone and Pioglitazone), insulin secretagogues (e.g., sulfonylurea drugs, such as Glyburide, Glimepiride, Chlorpropamide, Tolbutamide, and Glipizide, and non-sulfonyl secretagogues), α-glucosidase inhibitors (such as Acarbose, Miglitol, and Voglibose), insulin sensitizers (such as the PPAR-γ agonists, e.g., the glitazones; biguanides, PTP-1B inhibitors, DPP-IV inhibitors, and 11beta-HSD inhibitors), hepatic glucose output lowering compounds (such as glucagon antagonists and metaformin, e.g., Glucophage and Glucophage XR), insulin and insulin derivatives (both long and short acting forms and formulations of insulin); and anti-obesity drugs, including, but not limited to, β-3 agonists, CB-1 agonists, neuropeptide Y5 inhibitors, Ciliary Neurotrophic Factor and derivatives (e.g., Axokine), appetite suppressants (e.g., Sibutramine), and lipase inhibitors (e.g., Orlistat).

EXPERIMENTAL

Unless otherwise noted, all materials were purchased from Sinopharm Chemical Reagent Co., Ltd and used without further purification. All microwave assisted reactions were conducted with a Initiator Synthesizer® from Biotage®. All compounds showed NMR spectra consistent with their assigned structures. Melting points were determined on a Buchi apparatus and are uncorrected. Mass spectral data was determined by electrospray ionization technique. All examples were purified to >90% purity as determined by high-performance liquid chromatography. Unless otherwise stated, reactions were run at room temperature.

The following abbreviations are commonly used:
Ac the group $CH_3$—(CO)—
AcOH or HOAc acetic acid
$Ac_2O$ acetic anhydride
BINAP 2,2'-bis(diphenylphosphino)-1,1'-binaphthalene
BnO Benzyloxy
$Boc_2O$ di-tert-butyl dicarbonate
BTEA-Cl benzyltriethylammonium chloride
Bz Benzyl group
Cbz carboxylic acid benzyl ester
CDI 1,1'-carbonyldiimidazole
d Day
DCM Dichloromethane
DIAD $(CH_3)_2CHOOCN$=$NCOOCH(CH_3)_2$
DIEA N,N-diisopropylethylamine
Diox Dioxane
DIPEA diisopropylethyl amine
DMA Dimethylamine
DMAP 4-(dimethylamino)pyridine
DME Dimethoxyethane
DMF N,N-dimethylformamide
Dess martin Periodinane 1,1,1-Tris(acetyloxy)-1,1-dihydro-1,2-benziodoxol-3-(1H)-one
DMSO dimethyl sulfoxide
DPPA diphenyl phosphoryl azide
EDCI N-(3-Dimethylaminopropyl)-N'-ethylcarbodiimide hydrochloride
ESI-MS electrospray ionization mass spectrometry
$Et_2O$ diethyl ether
EtOAc ethyl acetate
EtOH ethyl alcohol
$Et_3N$ triethyl amine
g Grams
h hour or hours
HATU O-(7-Azobenzotriazol-1-yl)-1,1,3,3-tetramethyluronium hexafluorophosphate
HBTU 2-(1H-Benzotriazole-1-yl)-1,1,3,3-tetramethylaminium hexafluorophosphate
HCl Hydrochloric acid
HPLC high pressure liquid chromatography
IPA isopropyl alcohol
i $Pr_2NEt$ diisopropylethylamine
i PrOH Isopropyl alcohol
ISCO in-situ chemical oxidation
Lawesson reagent 4-Methoxyphenylthiophosphoric cyclic di(thioanhydride), LR, 2,4-Bis(4-methoxyphenyl)-2,4-dithioxo-1,3,2,4-dithiadiphosphetane, 2,4-Bis-(4-methoxyphenyl)-1,3-dithia-2,4-diphosphetane 2,4-disulfide
LCMS liquid chromatography mass spectrometry
LDA Lithium diisopropyl amide
LiHMDS Lithium bis(trimethylsilyl)amide
Me Methyl
MeCN Acetonitrile
MeI Iodomethane
MeOH methyl alcohol
MeOD deuteurated methyl alcohol
mg Milligrams
min Min
mL Milliliters
Mo—$(CO)_6$ molybdenum hexacarbonyl
MTBE methyl tert-butyl ether
NBS N-bromosuccinimide
NMP 1-methyl-2-pyrrolidinone
NMR nuclear magnetic resonance
NOESY nuclear Overhauser effect spectroscopy
Pd(dppf)$Cl_2$ [1,1'-Bis(diphenylphosphino)ferrocene]dichloropalladium(II), complex with dichloromethane
PMBCl 1-(chloromethyl)-4-methoxybenzene
PTSA p-toluenesulfonic acid
Py pyridine
RT RT
sat. saturated
t-bu tert-butyl group
TFA trifluoroacetic acid
THF tetrahydrofuran
TLC thin layer chromatography TMSCl Trimethylsilyl chloride
TBDPS Tert-Butylchlorodiphenyl
Tol Toluene
TsCl 4-toluenesulfonyl chloride ($CH_3C_6H_4SO_2Cl$)
Xantphos 4,5-bis(diphenylphosphino)-9,9-dimethylxanthene General Synthetic Methodology:

The compounds of the present invention can be prepared from commercially available starting materials and by using general synthetic techniques known to those of skill in the art. Outlined below are general reaction schemes suitable for preparing the compounds of the invention claimed herein. Further exemplification is found in the specific examples provided. One skilled in the art will understand that similar or related methods can be used for the synthesis of the compounds. One skilled in the art will also appreciate that in several instances it is possible to change the order of the steps used in the preparation of these compounds and obtain similar results.

GENERAL SCHEME 1

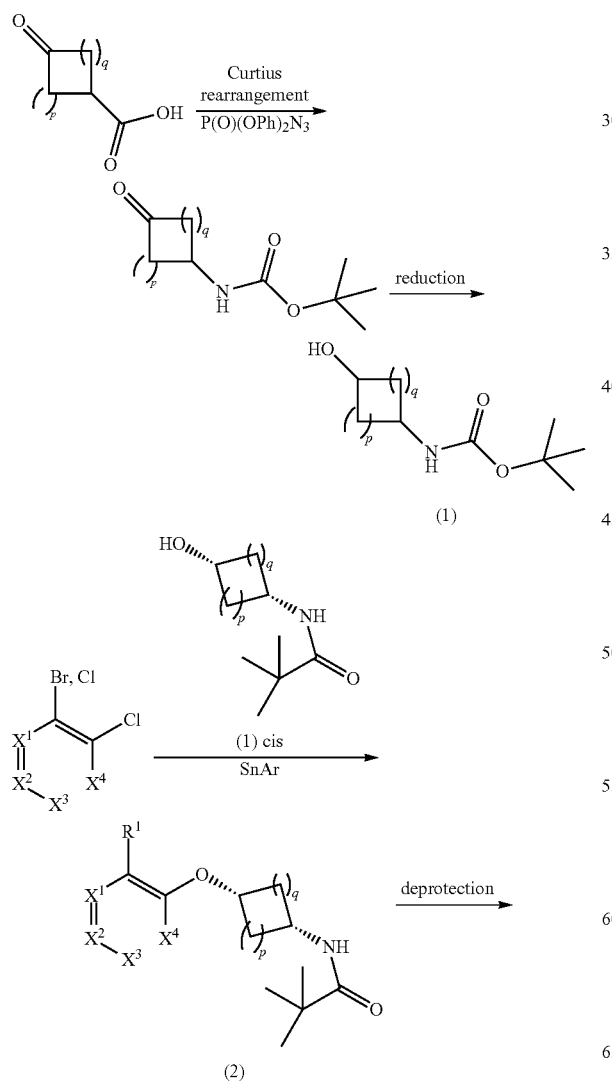

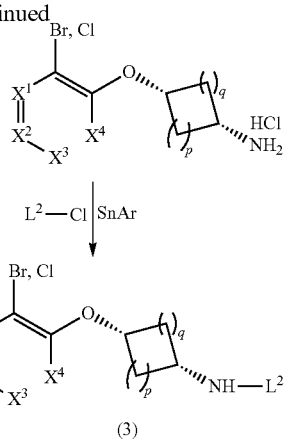

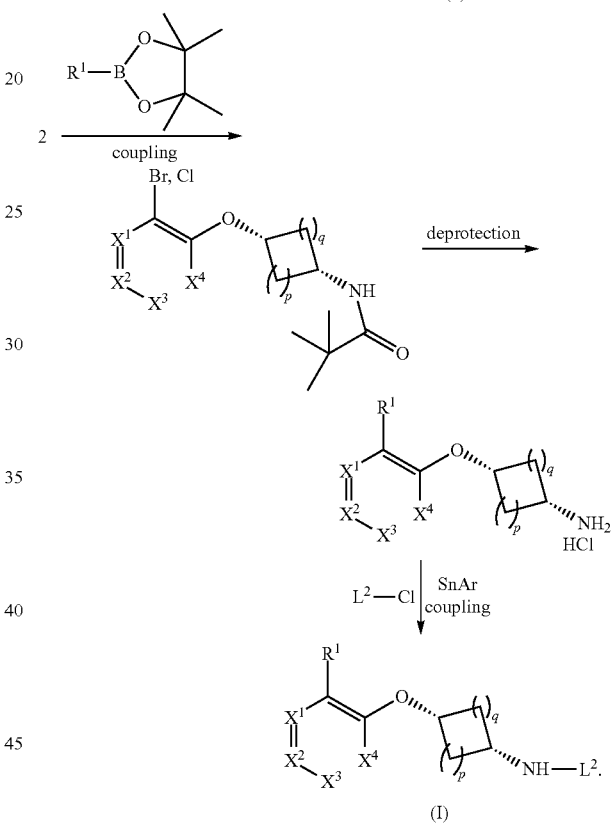

Alternatively, compounds of formula (I) can be prepared as follows:

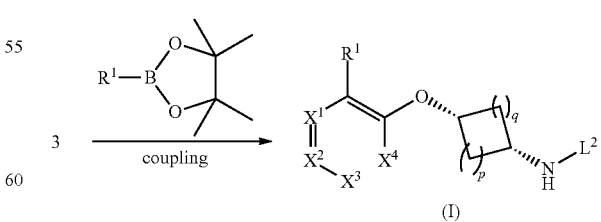

General Scheme 1 above shows a general method for preparing compounds of formula (I) of the invention, for example wherein $R^2$ is $NH-L^2$, as defined herein, via key intermediate compounds (1) and (2), which include the cis and trans isomers. A cis isomer of compound (I) is depicted in the above scheme to obtain the cis compound of formula (I). However, those skilled in the art would appreciate that the trans isomer of (1) can produce the trans isomer compound of formula (I) thereof.

In the general schemes that follow, while the cis isomer is specified, it can be appreciated that the trans isomers can be produced by using the trans isomer starting material.

More specific examples of General Scheme 1 are depicted below in General Schemes 1A-1B.

GENERAL SCHEMES 1A-1B:

1A.

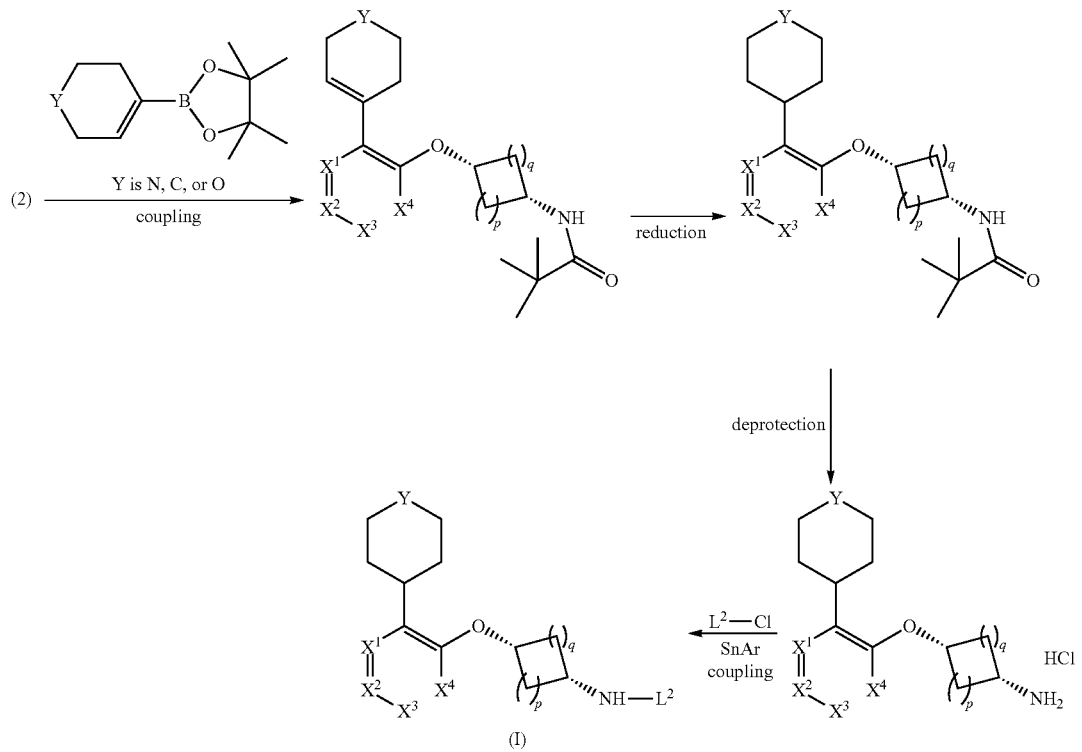

1B.

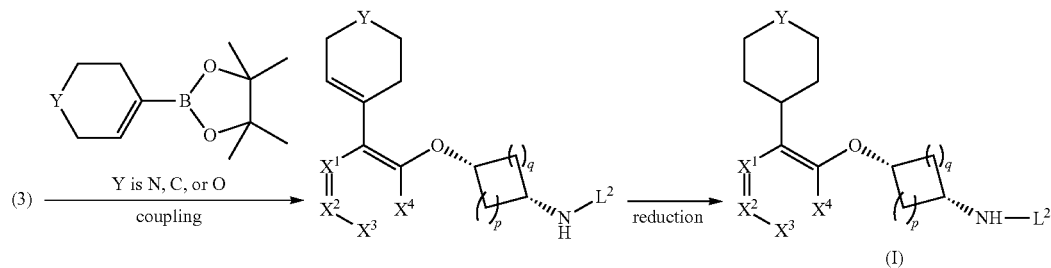

Preparation 1

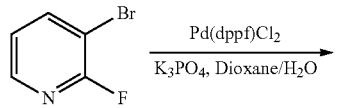

Preparation 1A:
2-Fluoro-3-(Tetrahydro-Pyran-4-YL)-Pyridine

Step 1. 3-(3,6-DIHYDRO-2H-PYRAN-4-YL)-2-FLUORO-PYRIDINE

A mixture of 3-bromo-2-fluoro-pyridine (500 mg, 2.84 mmol), 4-(4,4,5,5-Tetramethyl-[1,3]dioxolan-2-yl)-3,6-dihydro-2H-pyran (656 mg, 3.12 mmol), $K_3PO_4$ (1.2 g, 5.68 mmol), and Pd (dppf)$Cl_2$ (208 mg, 0.284 mmol) in 1,4-Dioxane/$H_2O$ (5:1) (30 mL) was heated to reflux overnight under N₂ atmosphere. The reaction mixture was filtered and the filtrate was concentrated and purification by prep-TLC to give 2-fluoro-3-(tetrahydro-pyran-4-yl)-pyridine (260 mg, 1.45 mmol, 51.2%).

Step 2.
2-FLUORO-3-(TETRAHYDRO-PYRAN-4-YL)-PYRIDINE

To a solution of 3-(3,6-dihydro-2H-pyran-4-yl)-2-fluoropyridine (260 mg, 1.45 mmol) in MeOH (20 mL) was added Pd/C (0.1 g), bubbled with H₂ and stirred at RT overnight. The reaction mixture was filtered and the filtrate was concentrated to give 2-fluoro-3-(tetrahydro-pyran-4-yl)-pyridine (250 mg, 1.38 mmol, 95.3% yield).

Preparation 1B:
2-FLUORO-3-(2-METHYLPYRIDIN-4-YL)PYRIDINE

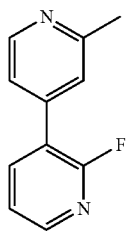

Step 1. 2-FLUORO-3-(2-METHYLPYRIDIN-4-YL)PYRIDINE

A mixture of 4-bromo-2-methylpyridine (25.0 g, 145 mmol), 2-fluoropyridin-3-ylboronic acid (22.5 g, 160 mmol), Pd(PPh₃)₂Cl₂ (5.10 g, 7.27 mmol), and sodium carbonate (46.2 g, 436 mmol) in 1,2-dimethoxyethane:ethanol:water (7:2:0.75, 292.5 ml total volume) was heated to 80° C. for 4 h. After cooling to room temperature, the mixture was diluted with saturated aqueous sodium bicarbonate solution and water, then extracted with dichloromethane (3×). The combined organic extracts were then extracted with 2 N aqueous HCl solution (4×). The combined aqueous layers were washed with dichloromethane, then the pH was raised to 10 with 10 N NaOH. The resulting suspension was extracted with dichloromethane (3×). The combined extracts were concentrated in vacuo to give 2-fluoro-3-(2-methylpyridin-4-yl)pyridine (22.14 g, 118 mmol, 81% yield).

Preparation 2:
3-(BENZYLOXY)CYCLOBUTANAMINE

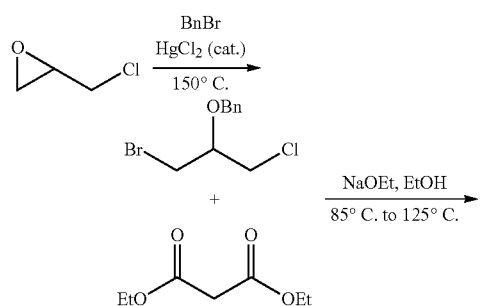

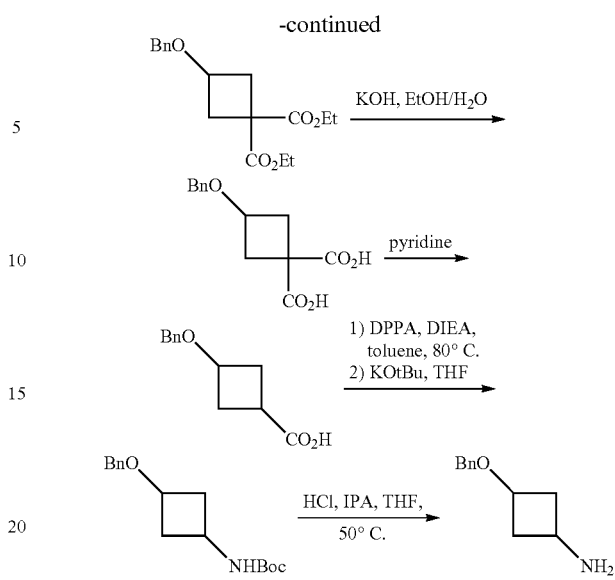

Step 1.
((1-BROMO-3-CHLOROPROPAN-2-YLOXY)METHYL)BENZENE

A mixture of mercury (II) chloride (0.05 g, 0.18 mmol), epichlorohydrin (34.0 g, 367 mmol), and benzyl bromide (64.7 g, 378 mmol) in a 500 mL two necked flask with a reflux condenser and thermometer (to measure internal temperature), under nitrogen atmosphere, was slowly heated to 150° C. internal temperature over 6 h. Heating at that temperature continued for 12 h, and then the mixture was cooled to RT. Vacuum distillation gave product as a colorless oil. (55.6 g, 57%). (BP=125-130° C. at <5 mmHg).

Step 2. DIETHYL
3-(BENZYLOXY)CYCLOBUTANE-1,1-DICARBOXYLATE

A solution of NaOEt in EtOH was prepared by dissolving sodium (1.75 g, 76 mmol) in EtOH (30 mL) under nitrogen atmosphere. This solution was added slowly to a solution of ((1-bromo-3-chloropropan-2-yloxy)methyl)benzene (8.0 g, 30.4 mmol) and diethyl malonate (11.58 mL, 76 mmol) in EtOH (20 mL) under nitrogen via addition funnel. This mixture was heated to reflux for 3 h, then cooled to RT. The resulting suspension was filtered and the filtrate was concentrated by distillation. The resulting mixture was heated to 125° C. for 2 h, cooled to RT, and filtered to remove the resulting solid, the solid was washed with EtOH and the filtrate was concentrated in vacuo to give diester. This material was taken to the next step without further purification.

Step 3.
3-(BENZYLOXY)CYCLOBUTANE-1,1-DICARBOXYLIC ACID

An aqueous solution of potassium hydroxide was prepared by dissolving potassium hydroxide (8.52 g, 152 mmol) in water (11 mL). This solution was added slowly to a solution of diethyl 3-(benzyloxy)cyclobutane-1,1-dicarboxylate (obtained in step 2) in EtOH (30 mL) under nitrogen atmosphere and the mixture was then heated to reflux for 45 min, then cooled to RT. The organic solvent was removed in vacuo and water (20 mL) was added. The aqueous suspension was then taken to pH 2-3 with conc. HCl (about 6 mL). MeOtBu (35 mL) was added, the resulting biphasic mixture was stirred vigorously for 10 minutes, and the layers were separated. The aqueous layer was extracted with MeOtBu again, the combined extracts were dried (MgSO$_4$), filtered, and concentrated in vacuo to give a yellow oil. Toluene (35 mL) was added and the solution was concentrated in vacuo, during which time a solid precipitated. After all the toluene had been removed, toluene (30 mL) was again added. The resulting suspension was heated to 90° C. for 45 minutes, then cooled back to 15° C. with an ice bath. The suspension was filtered and the collected solid was washed with cyclohexane and dried to give product as a white solid (3.51 g, 46% for 2 steps).

Step 4. 3-(BENZYLOXY)CYCLOBUTANECARBOXYLIC ACID

A solution of 3-(benzyloxy)cyclobutane-1,1-dicarboxylic acid (1.5 g, 5.99 mmol) in pyridine (3 mL) was heated in a 120° C. oil bath for 12 h. The mixture was cooled to RT and the pyridine was removed under vacuum. Toluene (10 mL) was added and the solution was washed with 1N HCl (3×), dried (MgSO$_4$), filtered, and concentrated in vacuo to give product as a brown oil (1.17 g, 95%).

Step 5. TERT-BUTYL 3-(BENZYLOXY)CYCLOBUTYLCARBAMATE

A solution of 3-(benzyloxy)cyclobutanecarboxylic acid (3.40 g, 16.49 mmol), DPPA (4.62 mL, 21.43 mmol), and diisopropylethylamine (3.73 mL, 21.43 mmol) in toluene (35 mL) under argon was warmed to 80° C. and stirred for 7 h, then cooled to RT. The mixture was cooled to 0° C. and then added slowly via canula to a suspension of potassium tert butoxide (3.70 g, 33.0 mmol) in THF (50 mL) under argon held at RT. The mixture was then stirred for 1 h and EtOAc and water were then added. The layers were separated, and the organic layer was dried (MgSO$_4$), filtered, and concentrated to give an oil. The oil was purified by silica gel chromatography (0 to 50% EtOAc/hexane gradient) to give product as a white solid (3.42 g, 75%).

Step 6. 3-(BENZYLOXY)CYCLOBUTANAMINE

HCl (5-6 N in IPA, 3 mL) was added to a solution of tert-butyl 3-(benzyloxy)cyclobutylcarbamate (1.07 g, 3.86 mmol) in THF (10 mL). The mixture was stirred at 50° C. for 3 h, then cooled to RT. The solvent was removed in vacuo and EtOAc (10 mL) was added. The resulting suspension was cooled to 0° C. for 1 h, then the solid was collected by filtration to give the amine as a white solid (601 mg, 73%).

Preparation 3: 1-(4-(3-CHLOROPYRAZIN-2-YL) PIPERIDIN-1-YL)ETHANONE

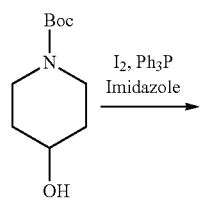

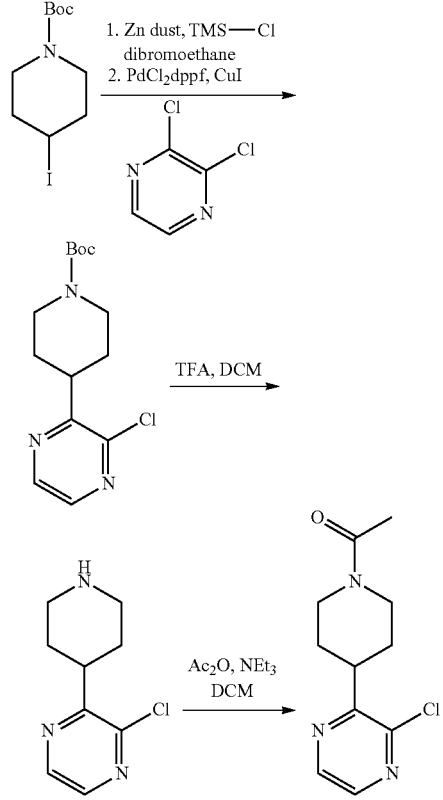

Step 1. TERT-BUTYL 4-IODOPIPERIDINE-1-CARBOXYLATE

A solution of N-Boc-4-hydroxypiperidine (246 g, 1.224 mol), imidazole (100 g, 1.469 mol, 1.2 eq.) and triphenylphosphine (385 g, 1.469 mol, 1.2 eq.) in THF (750 mL) was cooled using an ice bath. Then a solution of iodine (373 g, 1.469 mol, 1.2 eq.) in THF (750 mL) was added slowly over a period of 1 h keeping the internal temperature below 18° C. The resulting mixture was allowed to stir at room temperature for 5 h and the mixture was diluted with ethyl acetate (2 L), brine (1 L) and water (500 mL). The organic layer was separated and the aqueous layer was extracted with ethyl acetate (1 L×2). The organic layers were combined, washed with 15% aqueous sodium sulfite (1 L), brine (1 L), dried and concentrated. The resulting residue was stirred with hexanes (2 L) and the solid was removed by filtration. The solid was stirred with hexanes (2 L×2) and filtered. The filtrate was concentrated to give 363 g of crude oil which was purified by column chromatography (eluting with hexanes/ethyl acetate=50:1 to 20:1) to afford 319 g tert-butyl 4-iodopiperidine-1-carboxylate Yield: 84%.

Step 2. TERT-BUTYL 4-(3-CHLOROPYRAZIN-2-YL)PIPERIDINE-1-CARBOXYLATE

To a suspension of activated zinc dust (84.4 g, 1.29 mol, 1.94 eq.) in anhydrous DMA (270 mL) was added 1,2-dibromoethane (9.1 mL, 0.106 mol, 0.16 eq.), followed by the slow addition of chlorotrimethylsilane (13.5 mL, 0.106 mol, 0.16 eq.) over a period of 5 min. The resulting mixture was stirred for 15 min under nitrogen. Then a solution of tert-butyl 4-(3-chloropyrazin-2-yl)piperidine-1-carboxylate (329 g, 1.06 mol, 1.59 eq.) in anhydrous DMA (670 mL) was added to the above suspension over a period of 45 min keeping the internal temperature below 65° C. The resulting mixture was stirred for 1 h while cooling back to room temperature. The prepared zinc reagent was allowed to stand and the upper clear solution was transferred to a degassed and well stirred solution of 2,3-dichloropyrazine (99 g, 0.664 mol, 1 eq.), PdCl$_2$(dppf) CH$_2$Cl$_2$ (16.3 g, 19.9 mmol, 0.03 eq.) and CuI (7.8 g, 41.2 mmol, 0.062 eq.) in anhydrous DMA (670 mL) using a cannula. DMA (400 mL) was used to rinse the remaining zinc dust and added to the above mixture. The resulting mixture was heated to 80° C. under nitrogen and stirred overnight (19 h). The mixture was cooled to room temperature and diluted with brine (1 L) and ethyl acetate (6 L). The aqueous phase was extracted with ethyl acetate (4 L) and organic extracts were combined, washed with brine (1 L), dried and concentrated. The resulting residue was purified by column chromatography (eluting with hexanes/ethyl acetate=9:1 to 6:1) to give 92 g tert-butyl 4-(3-chloropyrazin-2-yl)piperidine-1-carboxylate. Yield: 47%.

Step 3. 2-CHLORO-3-(PIPERIDIN-4-YL)PYRAZINE

To a well stirred solution of tert-butyl 4-(3-chloropyrazin-2-yl)piperidine-1-carboxylate (92 g, 0.309 mol, 1 eq.) in dichloromethane (1 L) was added trifluoroacetic acid (119 mL, 1.545 mol, 5 eq.). The resulting mixture was heated to reflux overnight (16 h). The mixture was concentrated and the resulting TFA salt was dried with toluene (500 mL) azetropically to give 150 g 2-chloro-3-(piperidin-4-yl)pyrazine. This was used in the next step without further purification.

Step 4. 1-(4-(3-CHLOROPYRAZIN-2-YL)PIPERIDIN-1-YL)ETHANONE

To an ice cooled solution of 2-chloro-3-(piperidin-4-yl)pyrazine-3TFA (150 g, 0.278 mol) in anhydrous dichloromethane (1.5 L) kept under nitrogen was added triethylamine (194 mL, 1.39 mol, 5 eq.) over a period of 15 min., followed by acetic anhydride (53 mL, 0.556 mol, 2 eq.) over a period of 10 min. The resulting mixture was allowed to stir at room temperature for 2 h and quenched with 500 mL of water. After separation, the organic phase was further washed with water (500 mL) and brine (500 mL). The aqueous phases were combined and back extracted with dichloromethane (1 L). Organic extracts were combined, dried and concentrated. The resulting residue was purified by column chromatography (eluting with hexanes/ethyl acetate=2:3 to 100% ethyl acetate) to give 70 g 1-(4-(3-chloropyrazin-2-yl)piperidin-1-yl)ethanone. Yield: 94% for two steps.

Preparation 4A: TERT-BUTYL ((1S,3S)-3-HYDROXYCYCLOBUTYL)CARBAMATE

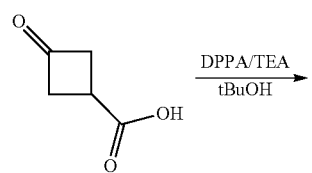

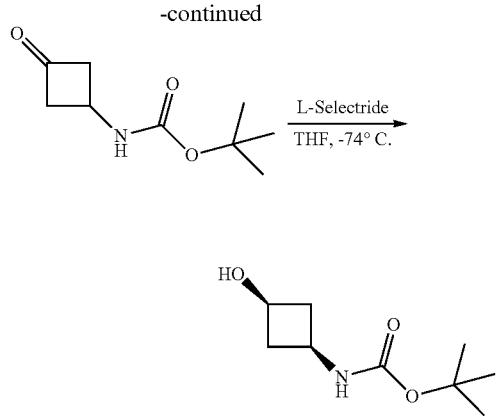

Step 1. TERT-BUTYL (3-OXOCYCLOBUTYL)CARBAMATE

A 22 L three neck flask was charged with 3-oxocyclobutanecarboxylic acid (630 g, 5.52 mol, 1.0 equiv), toluene (12 L), and triethylamine (850 mL, 6.07 mol, 1.1 equiv). The acid dissolved in toluene after the addition of triethylamine. The solution was cooled below 10° C. and diphenylphosphoryl azide (DPPA) (1.32 L, 6.07 mol, 1.1 equiv) was added dropwise over 15 minutes under N$_2$. The solution was then warmed up to RT and stirred overnight. The reaction mixture was then transferred to 22 L separatory funnel, washed with aqueous NaHCO$_3$ (2×4 L), water (4 L), brine (2 L), dried over MgSO$_4$ and filtered. The filtrate was then transferred to a 22 L three neck flask and to it was added tert-butanol (1260 mL, 13.2 mol, 2.4 equiv). The resultant reaction mixture was then heated at reflux overnight. Upon completion, the reaction mixture was cooled to RT and concentrated under reduced pressure. Another 70 g batch was combined prior to the column purification. The crude residue thus obtained was then purified using column chromatography eluting with ethyl acetate/hexanes (25:75 to 40:60) to afford 350 g of tert-butyl (3-oxocyclobutyl)carbamate (30% yield).

Step 2. TERT-BUTYL ((1S,3S)-3-HYDROXYCYCLOBUTYL)CARBAMATE

Tert-butyl (3-oxocyclobutyl)carbamate (280 g, 1.51 mol, 1.0 equiv) was dissolved in anhydrous THF (6.0 L). To this solution under N$_2$ atmosphere at −74° C. (acetone/dry ice bath) was added L-selectride (1 M in THF, 1.82 L, 1.82 mol, 1.2 equiv) drop-wise over 30 min. Upon completion of the addition, the reaction mixture was stirred at −74° C. for 2 h and allowed to warm up to RT and stirred overnight. Disappearance of starting material was monitored in LCMS. Upon completion, the reaction mixture was cooled to −40° C. and quenched with ice-cold water (4.0 L). The crude reaction mixture was then extracted with ethyl acetate (2×8.0 L) and the combined organic extracts was washed with brine (4.0 L), dried over Na$_2$SO$_4$, and concentrated under reduced pressure. The crude residue thus obtained was then purified using column chromatography eluting with ethyl acetate/hexanes (20: 80) to ethyl acetate/MeOH (98:02) to afford 201 g of the tert-butyl ((1S,3S)-3-hydroxycyclobutyl)carbamate (71% yield). $^1$H NMR (300 MHz, CDCl$_3$): δ 1.44 (s, 9H), 1.80-1.75

(m, 2H), 2.26 (bs, 1H), 2.80-2.72 (m, 2H), 3.67-3.64 (m, 1H), 4.05-3.98 (m, 1H), 4.69 (bs, 1H).

Preparation 4B: TERT-BUTYL (3-HYDROXYCYCLOBUTYL)CARBAMATE

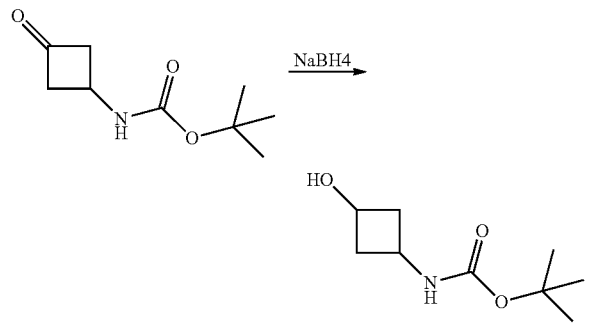

To tert-butyl (3-oxocyclobutyl)carbamate (see PREPARATION 4A, STEP 1; 110 g, 0.594 mol, 1 eq) in ethanol (600 mL) was slowly added sodium borohydride (11.23 g, 0.297 mol, 0.5 eq) at 0° C. Reaction mixture was warmed to RT and stirred at this temperature for 2 h. It was quenched with water (1 L). Solvent was removed under reduced pressure. Water layer was extracted with EtOAc (3×2 L). Combined organic layer was washed with brine, dried over magnesium sulfate, filtered and concentrated. Residue was purified by column chromatography with aluminum oxide (Eluent: 20% EtOAc in hexane to 10% MeOH in DCM) to get 64 g of tert-butyl (3-hydroxycyclobutyl)carbamate as a white solid in 58% yield.

Preparation 5A: (1S,3S)-3-((3-CHLOROPYRAZIN-2-YL)OXY)CYCLOBUTANAMINE HYDROCHLORIDE

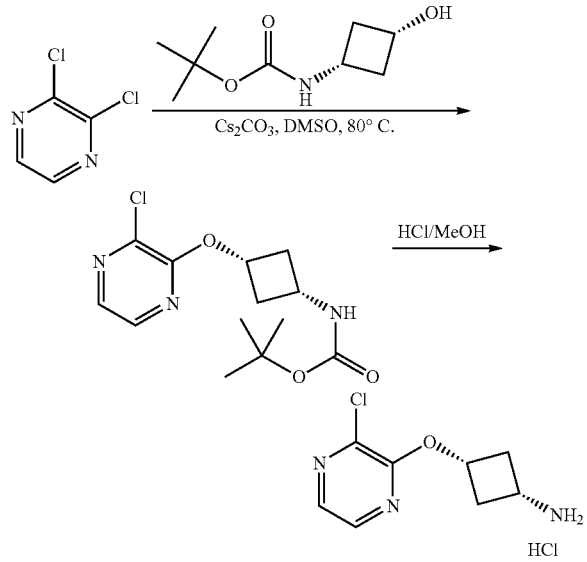

Step 1. TERT-BUTYL ((1S,3S)-3-((3-CHLOROPYRAZIN-2-YL)OXY)CYCLOBUTYL)CARBAMATE

To a mixture of 2,3-dichloro-pyrazine (3.0 g, 20 mmol) and tert-butyl ((1S,3S)-3-hydroxycyclobutyl)carbamate (see PREPARATION 4A; 3.65 g, 20 mmol) in DMSO (50 mL) was added $Cs_2CO_3$ (13.2 g, 40 mmol), and then the mixture was stirred at 80° C. overnight. The reaction mixture was diluted with water and filtered. The filter cake was washed with water, and dried to give tert-butyl ((1S,3S)-3-((3-chloropyrazin-2-yl)oxy)cyclobutyl)carbamate (5.7 g, 19.0 mmol, 96.6%). ESI-MS (M+1): 300 calc. for $C_{13}H_{18}ClN_3O_3$ 299.

Step 2. (1S,3S)-3-((3-CHLOROPYRAZIN-2-YL)OXY)CYCLOBUTANAMINE HYDROCHLORIDE

To a mixture of tert-butyl ((1S,3S)-3-((3-chloropyrazin-2-yl)oxy)cyclobutyl)carbamate (2.8 g, 9.3 mmol) in MeOH (20 mL) was added HCl/MeOH (20 mL, saturated with HCl gas), and then stirred at RT for 1 hour. The reaction mixture was concentrated to give (1S,3S)-3-((3-chloropyrazin-2-yl)oxy)cyclobutanamine hydrochloride (2.18 g, 9.3 mmol, yield 100%). ESI-MS (M+1): 200 calc. for $C_8H_{10}ClN_3O$ 199.

Preparation 5B: N-((1S,3S)-3-((3-CHLOROPYRAZIN-2-YL)OXY)CYCLOBUTYL)BENZO[D]THIAZOL-2-AMINE

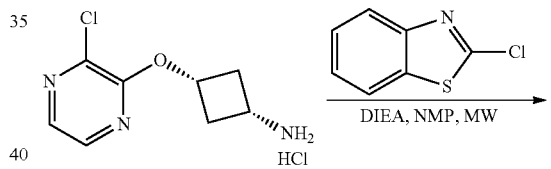

A mixture of (1S,3S)-3-((3-chloropyrazin-2-yl)oxy)cyclobutanamine hydrochloride (see PREPARATION 5A; 1.42 g, 6.0 mmol), 2-chloro-benzothiazole (purchased from ALDRICH™) (1.07 g, 6.0 mmol) and DIEA (1.6 g, 12.0 mmol) in NMP (12 mL) was heated to 180° C. for 2 hours in microwave. The reaction mixture was diluted with water, extracted with EtOAc (2×30 mL). The combined organic extracts were washed with water (30 mL) and brine (30 mL), dried over $Na_2SO_4$ and filtered. The filtrate was evaporated in vacuo and the residue was purified by flash column chromatography on silica gel to give N-((1S,3S)-3-((3-chloropyrazin-2-yl)oxy)

cyclobutyl)benzo[d]thiazol-2-amine (1.80 g, 5.4 mmol, yield 90%). ESI-MS (M+1): 333 calc. for $C_{15}H_{13}ClN_4OS$ 332.

Preparation 5C: N-(3-((3-CHLOROPYRAZIN-2-YL)OXY)CYCLOBUTYL) BENZO[D]THIAZOL-2-AMINE

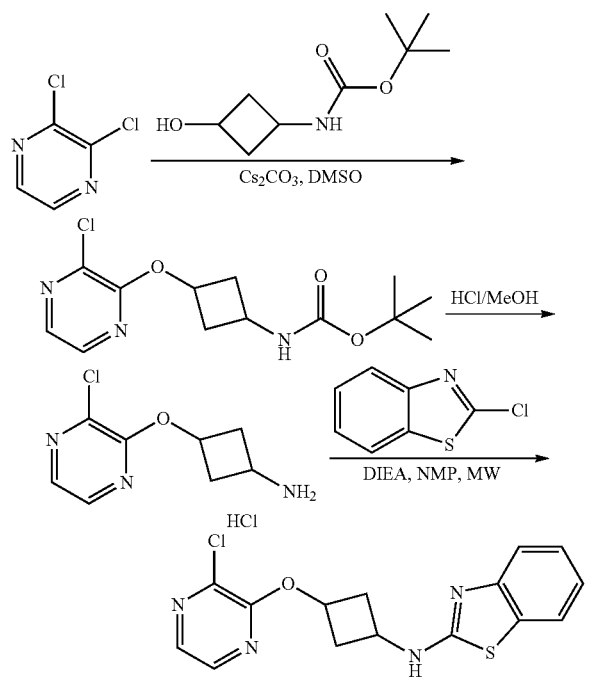

Step 1. TERT-BUTYL (3-((3-CHLOROPYRAZIN-2-YL)OXY)CYCLOBUTYL)CARBAMATE

To a mixture of 2,3-dichloro-pyrazine (3.0 g, 20 mmol) and tert-butyl (3-hydroxycyclobutyl)carbamate (see PREPARATION 4B; 3.65 g, 20 mmol) in DMSO (50 mL) was added $Cs_2CO_3$ (13.2 g, 40 mmol), and then the mixture was stirred at 80° C. overnight. The reaction mixture was diluted with water and filtered. The filtrate cake was washed with water, and dried to give tert-butyl (3-((3-chloropyrazin-2-yl)oxy) cyclobutyl)carbamate (4.5 g, 15.2 mmol, 76%). ESI-MS (M+1): 300 calc. for $C_{13}H_{18}ClN_3O_3$ 299.

Step 2. 3-((3-CHLOROPYRAZIN-2-YL)OXY)CYCL OBUTANAMINE HYDROCHLORIDE

To a mixture of tert-butyl (3-((3-chloropyrazin-2-yl)oxy) cyclobutyl)carbamate (2.8 g, 9.61 mmol) in MeOH (20 mL) was added HCl/MeOH (20 mL, saturated with HCl gas), and then stirred at RT for 1 hour. The reaction mixture was concentrated to give 3-((3-chloropyrazin-2-yl)oxy)cyclobutanamine hydrochloride (2.2 g, 9.61 mmol, 100%). ESI-MS (M+1): 200 calc. for $C_8H_{10}ClN_3O$ 199.

Step 3. N-(3-((3-CHLOROPYRAZIN-2-YL)OXY) CYCLOBUTYL)BENZO[D]THIAZOL-2-AMINE

A mixture of 3-(3-chloro-pyrazin-2-yloxy)-cyclobutylamine hydrochloride (1.2 g, 6.28 mmol), 2-chloro-benzothiazole (purchased from ALDRICH™) (1.07 g, 6.28 mmol) and DIEA (1.8 g, 12.56 mmol) in NMP (12 mL) was heated to 180° C. for 2 hours in microwave. The reaction mixture was extracted with EtOAc (40 mL) and water, the organic phase was washed with brine and dried over $Na_2SO_4$. The organic layers were concentrated and purified by column chromatography on silica gel to give N-(3-((3-chloropyrazin-2-yl)oxy)cyclobutyl)benzo[d]thiazol-2-amine (3.0 g, 6 mmol, 95.5%). ESI-MS (M+1): 333 calc. for $C_{15}H_{13}ClN_4OS$ 332.

Preparation 5D: (1S,3S)-3-((3-(TETRAHYDRO-2H-PYRAN-4-YL)PYRAZIN-2-YL)OXY)CYCLOBUTANAMINE HYDROCHLORIDE

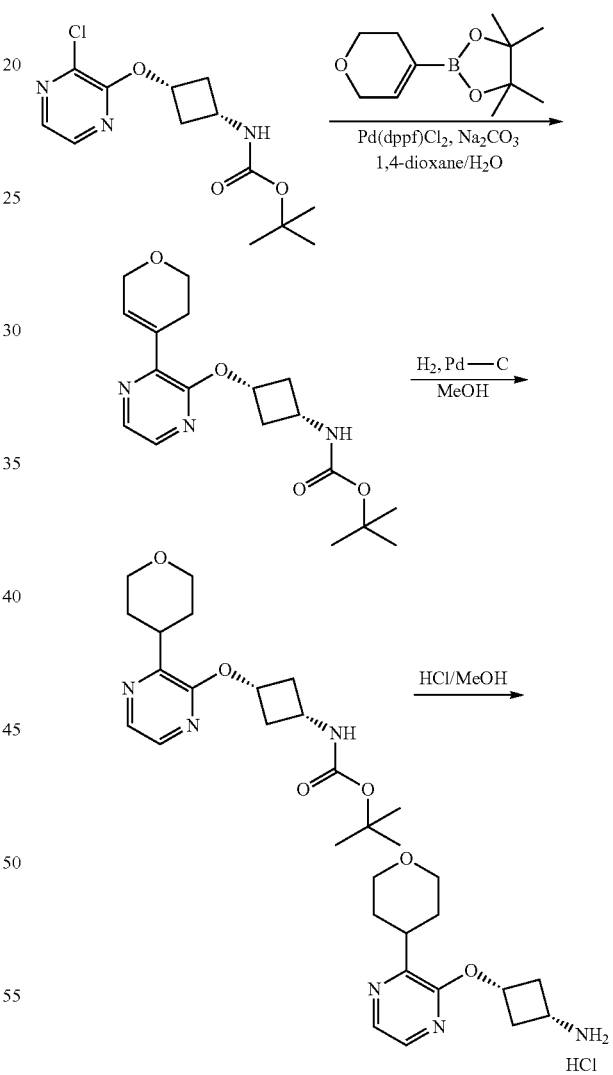

Step 1. TERT-BUTYL ((1S,3S)-3-((3-(3,6-DIHYDRO-2H-PYRAN-4-YL)PYRAZIN-2-YL)OXY) CYCLOBUTYL)CARBAMATE To a solution of tert-butyl ((1S,3S)-3-((3-chloropyrazin-2-yl)oxy)cyclobutyl)carbamate (see PREPARATION 5A, step 1; 4 g, 11.2 mmol), 4-(3,3,4,4-tetramethyl-borolan-1-yl)-3,6- dihydro-2H-pyran (2.58 g, 12.4 mmol) and Na$_2$CO$_3$ (2.38 g, 22.4 mmol) in 1,4-dioxane (60 mL) and water (6 mL) was added Pd(dppf)Cl$_2$ (410 mg, 0.56 mmol). The reaction mixture was stirred at 110° C. under N$_2$ overnight. The reaction mixture was filtered through CELITE® and washed with CH$_2$Cl$_2$ (50 mL). The organic layer was concentrated and the crude product was purified by silica gel column chromatography to give tert-butyl ((1S,3S)-3-((3-(3,6-dihydro-2H-pyran-4-yl)pyrazin-2-yl)oxy)cyclobutyl)carbamate (3.5 g, 8.7 mmol, 70%). ESI-MS (M+1): 348 calc. for C$_{18}$H$_{25}$N$_3$O$_4$ 347.

Step 2. TERT-BUTYL ((1S,3S)-3-((3-(TETRAHY-DRO-2H-PYRAN-4-YL)PYRAZIN-2-YL)OXY) CYCLOBUTYL)CARBAMATE A mixture of tert-butyl ((1S,3S)-3-((3-(3,6-dihydro-2H-pyran-4-yl)pyrazin-2-yl)oxy)cyclobutyl)carbamate (3.5 g, 9.6 mmol) and wet Pd—C (50%, 1.0 g) in MeOH (100 mL) was stirred under H$_2$ atmosphere (40 psi) at 30° C. overnight. The reaction mixture was filtered through CELITE® and washed with MeOH (100 mL). The filtrate was concentrated to give tert-butyl ((1S,3S)-3-((3-(tetrahydro-2H-pyran-4-yl)pyrazin-2-yl)oxy)cyclobutyl)carbamate (3.2 g, 8.1 mmol, 91%). ESI-MS (M+1): 350 calc. for C$_{18}$H$_{27}$N$_3$O$_4$ 349

Step 3. (1S,3S)-3-((3-(TETRAHYDRO-2H-PYRAN-4-YL)PYRAZIN-2-YL)OXY)CYCLOBU-TANAMINE HYDROCHLORIDE To tert-butyl ((1S,3S)-3-((3-(tetrahydro-2H-pyran-4-yl)pyrazin-2-yl)oxy)cyclobutyl)carbamate (3.2 g, 8.8 mmol) was added 4 M HCl in MeOH (100 mL). The solution was stirred at RT for 2 hours. The solvent was removed under reduced pressure to give (1S,3S)-3-((3-(tetrahydro-2H-pyran-4-yl)pyrazin-2-yl)oxy)cyclobutanamine hydrochloride (2 g, 9.8 mmol, 95%). ESI-MS (M+1): 250 calc. for C$_{13}$H$_{19}$N$_3$O$_2$ 249.

Preparation 5E: N-((1S,3S)-3-((3-(PIPERIDIN-4-YL)PYRAZIN-2-YL)OXY)CYCLOBUTYL) BENZO[D]THIAZOL-2-AMINE HYDROCHLO-RIDE

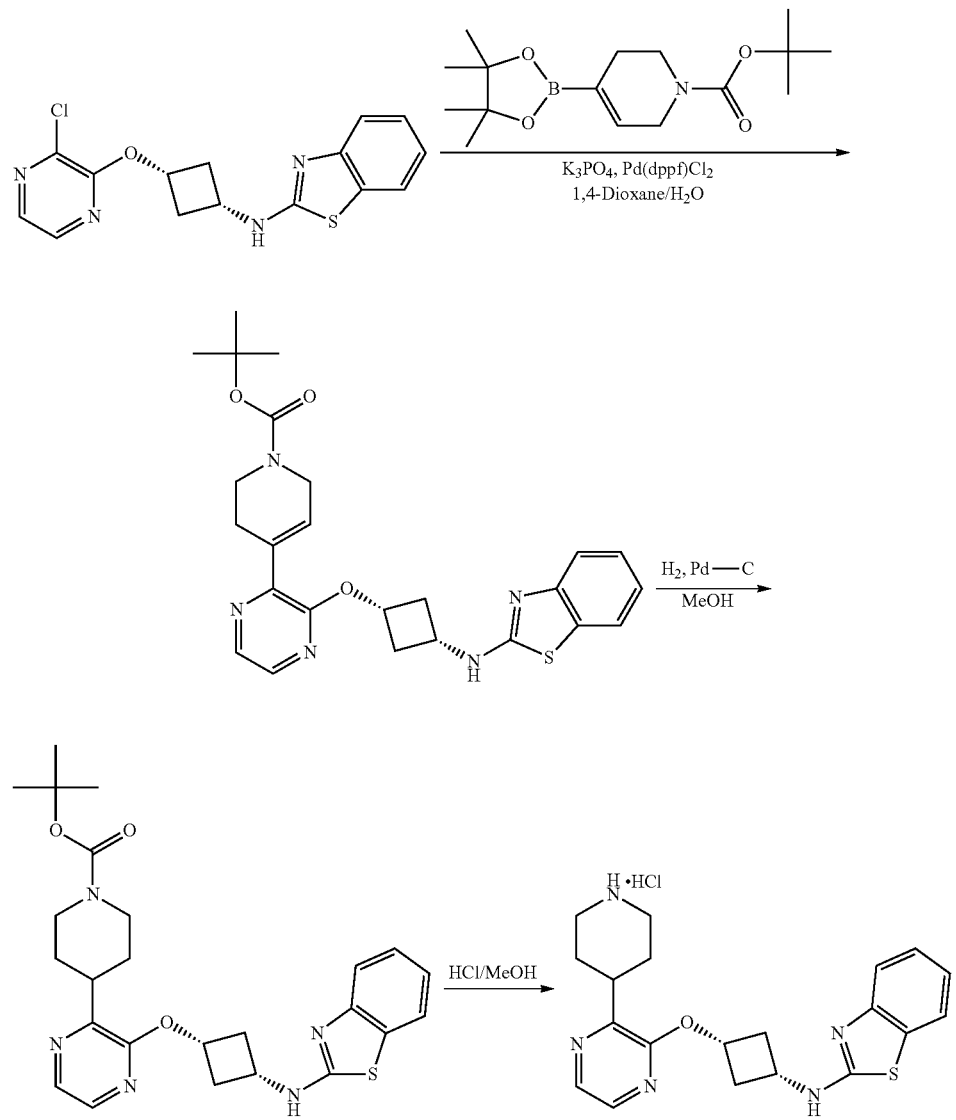

Step 1. TERT-BUTYL 4-(3-((1S,3S)-3-(BENZO[D]THIAZOL-2-YLAMINO)CYCLOBUTOXY)PYRAZIN-2-YL)-5,6-DIHYDROPYRIDINE-1(2H)-CARBOXYLATE To a mixture of N-((1S,3S)-3-((3-chloropyrazin-2-yl)oxy)cyclobutyl)benzo[d]thiazol-2-amine (see PREPARATION 5B; 150 mg, 0.6 mmol) in 1,4-Dioxane/water (5:1, 12 mL) was added 4-(4,4,5,5-Tetramethyl-[1,3,2]dioxaborolan-2-yl)-3,6-dihydro-2H-pyridine-1-carboxylic acid tert-butyl ester (278 mg, 0.9 mmol), $K_3PO_4$ (254 mg, 1.2 mmol) and Pd(dppf)Cl$_2$ (44 mg, 0.06 mmol). The mixture was refluxed overnight. The reaction mixture was filtered and concentrated. The residue was purification by prep-HPLC to give tert-butyl 4-(3-((1S,3S)-3-(benzo[d]thiazol-2-ylamino)cyclobutoxy)pyrazin-2-yl)-5,6-dihydropyridine-1(2H)-carboxylate (86 mg, 0.18 mmol, yield 30%). ESI-MS (M+1): 480 calc. for $C_{25}H_{29}N_5O_3S$ 479.

Step 2. TERT-BUTYL 4-(3-((1S,3S)-3-(BENZO[D]THIAZOL-2-YLAMINO)CYCLOBUTOXY)PYRAZIN-2-YL)PIPERIDINE-1-CARBOXYLATE A mixture of tert-butyl 4-(3-((1S,3S)-3-(benzo[d]thiazol-2-ylamino)cyclobutoxy)pyrazin-2-yl)-5,6-dihydropyridine-1(2H)-carboxylate (479 mg, 1 mmol) and wet Pd—C (50%, 500 mg) in MeOH (100 mL) was stirred under $H_2$ (40 psi) at 30° C. overnight then the reaction mixture was filtered through CELITE® and washed with MeOH. The filtrate was concentrated to give the tert-butyl 4-(3-((1S,3S)-3-(benzo[d]thiazol-2-ylamino)cyclobutoxy)pyrazin-2-yl)piperidine-1-carboxylate (438 mg, 0.91 mmol, yield 91%). ESI-MS (M+1): 482 calc. for $C_{25}H_{31}N_5O_3S$ 481.

Step 3. N-((1S,3S)-3-((3-(PIPERIDIN-4-YL)PYRAZIN-2-YL)OXY)CYCLOBUTYL)BENZO[D]THIAZOL-2-AMINE HYDROCHLORIDE To tert-butyl 4-(3-((1S,3S)-3-(benzo[d]thiazol-2-ylamino)cyclobutoxy)pyrazin-2-yl)piperidine-1-carboxylate (481 mg, 1 mmol) was added 4 M HCl in MeOH (100 mL). The solution was stirred at RT for 2 hours. The solvent was removed under reduced pressure to give N-((1S,3S)-3-((3-(piperidin-4-yl)pyrazin-2-yl)oxy)cyclobutyl)benzo[d]thiazol-2-amine hydrochloride (362 mg, 0.95 mmol, yield 95%). ESI-MS (M+1): 382 calc. for $C_{20}H_{23}N_5OS$ 381.

Preparation 5F: N-((1S,3S)-3-((3-(AZETIDIN-3-YL)PYRAZIN-2-YL)OXY)CYCLOBUTYL)BENZO[D]THIAZOL-2-AMINE HYDROCHLORIDE

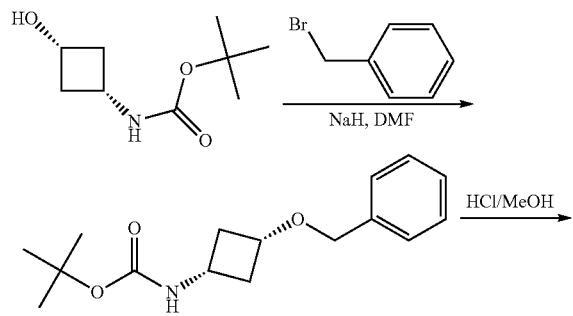

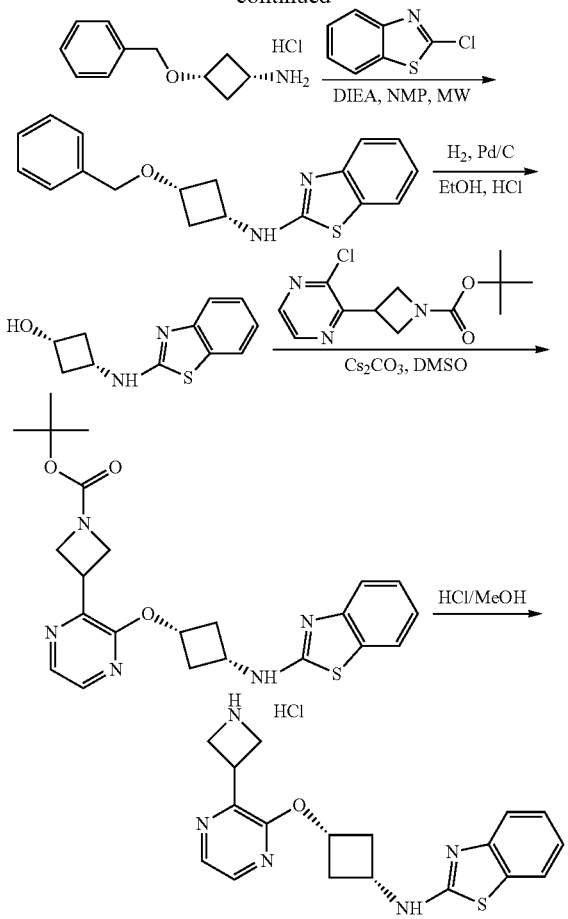

Step 1. TERT-BUTYL ((1S,3S)-3-(BENZYLOXY)CYCLOBUTYL)CARBAMATE

To a solution of tert-butyl ((1S,3S)-3-hydroxycyclobutyl)carbamate (see PREPARATION 4A; 187 mg, 1 mmol) in DMF (20 mL) at RT was added sodium hydride (60% wt in mineral oil) (48 mg, 2 mmol). The mixture was stirred at RT for 10 mins and then bromomethyl-benzene (171 mg, 1 mmol) was added. The reaction mixture was stirred at RT for 1 h and then diluted with water (20 mL) and extracted with EtOAc (2×30 mL). The combined organic extracts were washed with water (10 mL) and brine (10 mL), dried over $Na_2SO_4$, and filtered. The filtrate was evaporated in vacuo and the residue was purified by flash column chromatography on silica gel (5% to 30% EtOAc in hexanes) to give tert-butyl ((1S,3S)-3-(benzyloxy)cyclobutyl)carbamate (146 mg, 0.5 mmol, 50% yield). ESI-MS (M+1): 278 calc. for $C_{16}H_{23}NO_3$ 277.

Step 2. (1S,3S)-3-(BENZYLOXY)CYCLOBUTANAMINE HYDROCHLORIDE

To tert-butyl ((1S,3S)-3-(benzyloxy)cyclobutyl)carbamate (277 mg, 1 mmol) was added 4 M HCl in MeOH (50 mL). The solution was stirred at RT for 2 hours. The solvent was removed under reduced pressure to give (1S,3S)-3-(benzyloxy)cyclobutanamine hydrochloride (168 mg, 0.95 mmol, yield 95%). ESI-MS (M+1): 178 calc. for $C_{11}H_{15}NO$ 177.

Step 3. N-((1S,3S)-3-(BENZYLOXY)CYCLOBU-TYL)BENZO[D]THIAZOL-2-AMINE

A mixture of (1S,3S)-3-(benzyloxy)cyclobutanamine hydrochloride (242 mg, 1 mmol), 2-chloro-benzothiazole (purchased from ALDRICH) (169 mg, 1 mmol) and DIEA (286 mg, 2 mmol) in NMP (10 mL) was heated to 180° C. for 2 hours in microwave. To the reaction mixture was added water, and the residue was extracted with EtOAc (40 mL). The combined organic phase was washed with brine and dried over $Na_2SO_4$. The organic layers were concentrated and purified by column chromatography on silica gel to give N-((1S, 3S)-3-(benzyloxy)cyclobutyl)benzo[d]thiazol-2-amine (225 mg, 0.6 mmol, yield 60%). ESI-MS (M+1): 311 calc. for $C_{18}H_{18}N_2OS$ 310.

Step 4. (1S,3S)-3-(BENZO[D]THIAZOL-2-YLAMINO) CYCLOBUTANOL

A mixture of N-((1S,3S)-3-(benzyloxy)cyclobutyl)benzo[d]thiazol-2-amine (310 mg, 1 mmol) and wet Pd—C (50%, 300 mg) in 2 M HCl in EtOH (100 mL) was stirred under $H_2$ (40 psi) at 30° C. overnight then the reaction mixture was filtered through CELITE® and washed with EtOH. The filtrate was concentrated to give (1S,3S)-3-(benzo[d]thiazol-2-ylamino)cyclobutanol (198 mg, 0.90 mmol, yield 90%). ESI-MS (M+1): 221 calc. for $C_{11}H_{12}N_2OS$ 220.

Step 5. TERT-BUTYL 3-(3-((1S,3S)-3-(BENZO[D]THIAZOL-2-YLAMINO)CYCLOBUTOXY) PYRAZIN-2-YL)AZETIDINE-1-CARBOXYLATE To a mixture of (1S,3S)-3-(benzo[d]thiazol-2-ylamino)cyclobutanol (220 mg, 1 mmol) and tert-butyl 3-(3-chloropyrazin-2-yl)azetidine-1-carboxylate (see PREPARATION 10; 269 mg, 1 mmol) in DMSO (50 mL) was added $Cs_2CO_3$ (652 mg, 2 mmol). The mixture was stirred at 80° C. overnight. The reaction mixture was diluted with water and filtered. The filtrate cake was washed with water, and dried to give tert-butyl 3-(3-((1S,3S)-3-(benzo[d]thiazol-2-ylamino)cyclobutoxy)pyrazin-2-yl)azetidine-1-carboxylate (272 mg, 0.6 mmol, yield 60%). ESI-MS (M+1): 454 calc. for $C_{23}H_{27}N_5O_3S$ 453.

Step 6. N-((1S,3S)-3-((3-(AZETIDIN-3-YL)PYRAZIN-2-YL)OXY)CYCLOBUTYL)BENZO[D]THIAZOL-2-AMINE HYDROCHLORIDE To tert-butyl 3-(3-((1S,3S)-3-(benzo[d]thiazol-2-ylamino)cyclobutoxy)pyrazin-2-yl)azetidine-1-carboxylate (481 mg, 1 mmol) was added 4 M HCl in MeOH (100 mL). The solution was stirred at RT for 2 hours. The solvent was removed under reduced pressure to give N-((1S,3S)-3-((3-(azetidin-3-yl)pyrazin-2-yl)oxy)cyclobutyl)benzo[d]thiazol-2-amine hydrochloride (362 mg, 0.95 mmol, yield 95%). ESI-MS (M+1): 354 calc. for $C_{18}H_{19}N_5OS$ 353.

Preparation 5G: N-((1S,3S)-3-((3-CHLOROPYRAZIN-2-YL)OXY)CYCLOBUTYL)QUINOLIN-2-AMINE

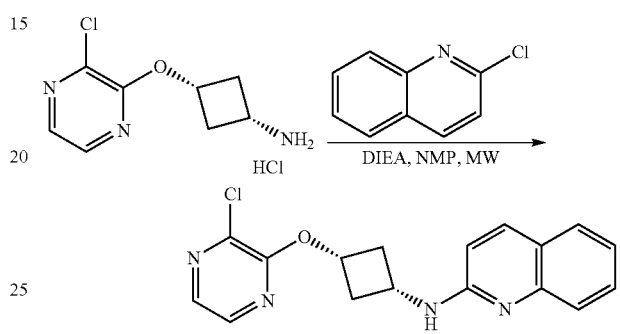

A mixture of (1S,3S)-3-((3-chloropyrazin-2-yl)oxy)cyclobutanamine hydrochloride (see PREPARATION 5A; 1.2 g, 6.28 mmol), 2-chloro-quinoline (purchased from Alfa Aesar™) (1.02 g, 6.28 mmol) and DIEA (1.8 g, 12.56 mmol) in NMP (12 mL) was heated to 200° C. for 2 hours in microwave. The reaction mixture was poured into water, and extracted with EtOAc (40 mL). The organic phase was collected, washed with brine and dried over $Na_2SO_4$. The organic layers were concentrated and purified by column chromatography on silica gel to give N-((1S,3S)-3-((3-chloropyrazin-2-yl)oxy)cyclobutyl)quinolin-2-amine (921 mg, 2.83 mmol, 45%). ESI-MS (M+1): 327 calc. for $C_{17}H_{15}ClN_4O$ 326.

Preparation 5H: N-((1S,3S)-3-((3-(PIPERIDIN-4-YL)PYRAZIN-2-YL)OXY)CYCLOBUTYL)QUINOLIN-2-AMINE HYDROCHLORIDE

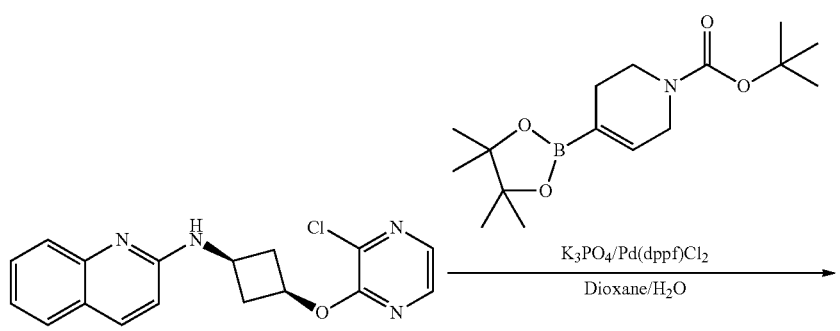

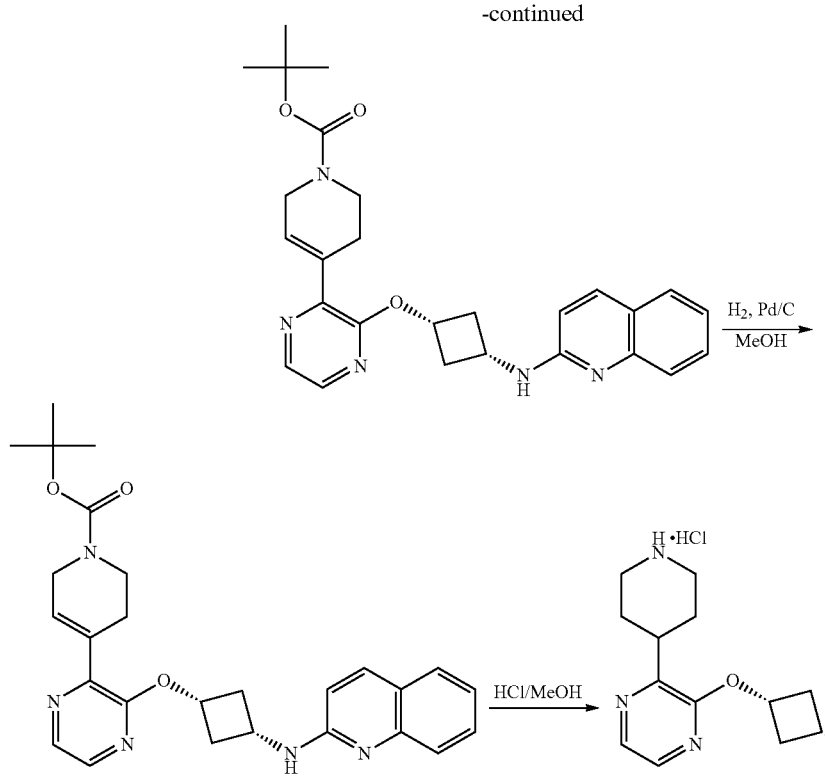

Step 1. TERT-BUTYL 4-(3-((1S,3S)-3-(QUINOLIN-2-YLAMINO)CYCLOBUTOXY)PYRAZIN-2-YL)-5,6-DIHYDROPYRIDINE-1(2H)-CARBOXYLATE To a mixture of N-((1S,3S)-3-((3-chloropyrazin-2-yl)oxy)cyclobutyl)quinolin-2-amine (see PREPARATION 5G; 326 mg, 1 mmol) in 1,4-dioxane/$H_2O$ (5:1, 12 mL) was added tert-butyl 4-(4,4,5,5-tetramethyl-1,3,2-dioxaborolan-2-yl)-5,6-dihydropyridine-1(2H)-carboxylate (340 mg, 1.1 mmol), $K_3PO_4$ (424 mg, 2 mmol) and Pd(dppf)$Cl_2$ (37 mg, 0.05 mmol). The reaction mixture was stirred at 110° C. under $N_2$ overnight. The reaction mixture was filtered and concentrated. The residue was purified by flash chromatography on silica gel (5% to 30% EtOAc in hexanes) to give tert-butyl 4-(3-((1S,3S)-3-(quinolin-2-ylamino)cyclobutoxy)pyrazin-2-yl)-5,6-dihydropyridine-1(2H)-carboxylate (237 mg, 0.5 mmol, yield 50%).

Step 2: TERT-BUTYL 4-(3-((1S,3S)-3-(QUINOLIN-2-YLAMINO)CYCLOBUTOXY) PYRAZIN-2-YL)PIPERIDINE-1-CARBOXYLATE A mixture of tert-butyl 4-(3-((1S,3S)-3-(quinolin-2-ylamino)cyclobutoxy)pyrazin-2-yl)-5,6-dihydropyridine-1(2H)-carboxylate (473 mg, 1 mmol) and wet Pd—C (50%, 500 mg) in MeOH (100 mL) was stirred under $H_2$ (40 psi) at 30° C. overnight then the reaction mixture was filtered through CELITE® and washed with MeOH. The filtrate was concentrated to give tert-butyl 4-(3-((1S,3S)-3-(quinolin-2-ylamino)cyclobutoxy)pyrazin-2-yl)piperidine-1-carboxylate (432 mg, 0.91 mmol, yield 91%). ESI-MS (M+1): 476 calc. for $C_{27}H_{33}N_5O_3$ 475.

Step 3: N-((1S,3S)-3-((3-(PIPERIDIN-4-YL)PYRAZIN-2-YL)OXY)CYCLOBUTYL)QUINOLIN-2-AMINE HYDROCHLORIDE To tert-butyl 4-(3-((1S,3S)-3-(quinolin-2-ylamino)cyclobutoxy)pyrazin-2-yl)piperidine-1-carboxylate (475 mg, 1 mmol) was added 4 M HCl in MeOH (100 mL). The solution was stirred at RT for 2 hours. The solvent was removed under reduced pressure to give N-((1S,3S)-3-((3-(piperidin-4-yl)pyrazin-2-yl)oxy)cyclobutyl)quinolin-2-amine hydrochloride (356 mg, 0.95 mmol, yield 95%). ESI-MS (M+1): 376 calc. for $C_{22}H_{25}N_5O$ 375.

Preparation 5I: N-((1S,3S)-3-((3-CHLOROPYRAZIN-2-YL)OXY)CYCLOBUTYL)-5-FLUOROBENZO[D]THIAZOL-2-AMINE

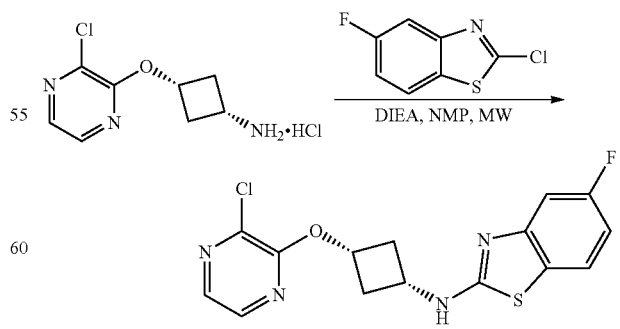

A mixture of (1S,3S)-3-((3-chloropyrazin-2-yl)oxy)cyclobutanamine hydrochloride (see PREPARATION 5A; 470 mg, 2 mmol), 2-chloro-5-fluorobenzo[d]thiazole (see PREPARATION 6; 374 mg, 2 mmol) and DIEA (570 mg, 4 mmol) in NMP (2 mL) was heated to 180° C. for 2 hours in microwave. The reaction mixture was extracted with EtOAc (40 mL) and water, the organic phase was washed with brine and dried over $Na_2SO_4$. The organic layers were concentrated and purified by silica gel column chromatography to give N-((1S,3S)-3-((3-chloropyrazin-2-yl)oxy)cyclobutyl)-5-fluorobenzo[d]thiazol-2-amine (450 mg, 1.28 mmol, 64% yield). ESI-MS (M+1): 351 calc. for $C_{15}H_{12}ClFN_4OS$ 350.

Preparation 5J: N-((1S,3S)-3-((3-CHLOROPY-RAZIN-2-YL)OXY)CYCLOBUTYL)QUINAZO-LIN-2-AMINE

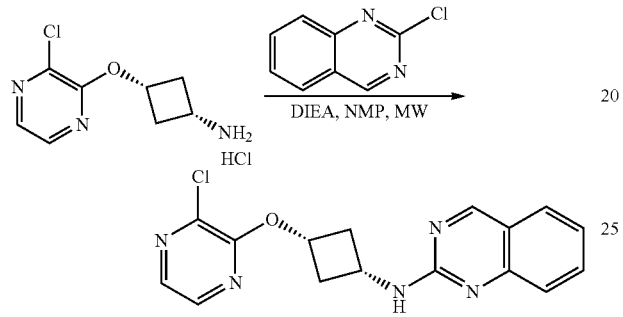

A mixture of (1S,3S)-3-((3-chloropyrazin-2-yl)oxy)cyclobutanamine hydrochloride (see PREPARATION 5A; 1.2 g, 6.28 mmol), 2-chloroquinazoline (1.03 g, 6.28 mmol) and DIEA (1.8 g, 12.56 mmol) in NMP (12 mL) was heated to 200° C. for 2 hours in microwave. The reaction mixture was poured into water, and extracted with EtOAc (40 mL). The organic phase was collected, washed with brine and dried over $Na_2SO_4$. The organic layers were concentrated and purified by column chromatography on silica gel to give N-((1S,3S)-3-((3-chloropyrazin-2-yl)oxy)cyclobutyl)quinazolin-2-amine (925 mg, 2.83 mmol, 45%). ESI-MS (M+1): 328 calc. for $C_{16}H_{14}ClN_5O$ 327.

Preparation 6:
2-CHLORO-5-FLUOROBENZO[D]THIAZOLE

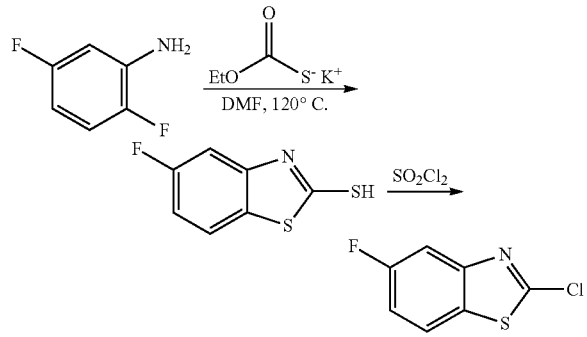

Step 1.
5-FLUOROBENZO[D]THIAZOLE-2-THIOL

A mixture of 2,5-difluoro-phenylamine (129 mg, 1 mmol) and potassium o-ethyl dithiocarbonate (352 mg, 2.2 mmol) in DMF (5 mL) was heated to 120° C. for 15 min in microwave. The reaction mixture was cooled, diluted with 10 mL of ice water, and acidified with 3 mL of HCl solution (1 mol/L). Then the mixture was extracted with EtOAc (3×50 mL), washed with brine and dried over $Na_2SO_4$. The dried organic layers were concentrated to give 5-fluorobenzo[d]thiazole-2-thiol (120 mg, 0.67 mmol, 67%). ESI-MS (M+1): 185 calc. for $C_7H_4FN_4S_2$ 184.

Step 2.
2-CHLORO-5-FLUOROBENZO[D]THIAZOLE

Sulfuryl chloride (0.3 mL, 4.41 mmol) was added neat to 5-fluoro-benzothiazole-2-thiol (680 mg, 3.67 mmol). The mixture was stirred at RT for 1 hour, and then heated to 60° C. for 40 mins. The resulting solution was cooled to room temperature, and poured onto ice, extracted with EtOAc (3×50 mL), washed with brine and dried over $Na_2SO_4$. The dried organic layers were concentrated to give 2-chloro-5-fluorobenzo[d]thiazole (520 mg, 2.75 mmol, 75%). ESI-MS (M+1): 187 calc. for $C_7H_5ClFN_4S$ 186.

Preparation 7A: TERT-BUTYL ((1S,3S)-3-((3-BROMO-5-FLUOROPYRIDIN-2-YL)OXY)CY-CLOBUTYL)CARBAMATE

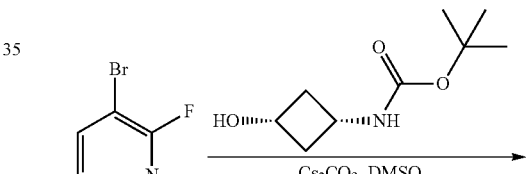

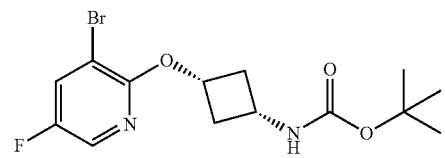

To a mixture of 3-bromo-2,5-difluoro-pyridine (500 mg, 2.58 mmol) and tert-butyl ((1S,3S)-3-hydroxycyclobutyl)carbamate (see PREPARATION 4A; 485 mg, 2.58 mmol) in DMSO (20 mL) was added $Cs_2CO_3$ (1.68 g, 5.16 mmol), and then the mixture was stirred at 80° C. overnight. The reaction mixture was diluted with water and extracted with EtOAc (3×50 mL), washed with brine and dried over $Na_2SO_4$. The dried organic layers were concentrated to tert-butyl ((1S,3S)-

3-((3-bromo-5-fluoropyridin-2-yl)oxy)cyclobutyl)carbamate (380 mg, 1.06 mmol, 41%). ESI-MS (M+1): 361 calc. for $C_{14}H_{18}BrFN_2O_3$ 360.

Preparation 7B: TERT-BUTYL (3-((3-BROMOPYRIDIN-2-YL)OXY)CYCLOBUTYL)CARBAMATE

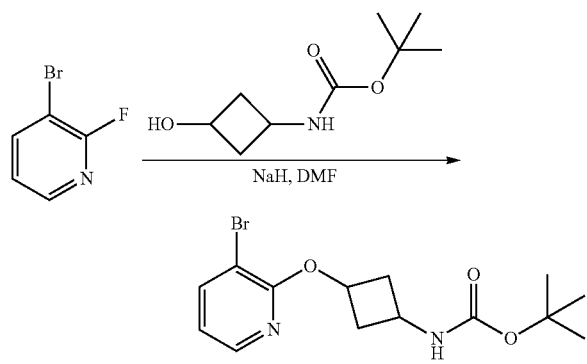

To a solution of tert-butyl (3-hydroxycyclobutyl)carbamate (see PREPARATION 4B; 1.08 g, 3.8 mmol) in DMF (20 mL) at RT was added sodium hydride (60% wt in mineral oil) (0.18 g, 7.6 mmol). The mixture was stirred at RT for 10 min and then 3-Bromo-2-fluoro-pyridine (665 mg, 3.8 mmol) was added. The reaction mixture was stirred at RT for 1 h and then diluted with water (20 mL) and extracted with EtOAc (2×30 mL). The combined organic extracts were washed with water (10 mL) and brine (10 mL), dried over $Na_2SO_4$, and filtered. The filtrate was evaporated in vacuo and the residue was purified by flash column chromatography on silica gel (5% to 30% EtOAc in hexanes) to give tert-butyl ((1S,3S)-3-((3-bromopyridin-2-yl)oxy)cyclobutyl)carbamate (391 mg, 1.14 mmol, 30% yield) as white solid. ESI-MS (M+1): 343 calc. for $C_{14}H_{19}BrN_2O_3$ 342.

Preparation 7C: 3-((3-(TETRAHYDRO-2H-PYRAN-4-YL)PYRIDIN-2-YL)OXY)CYCLOBUTANAMINE HYDROCHLORIDE

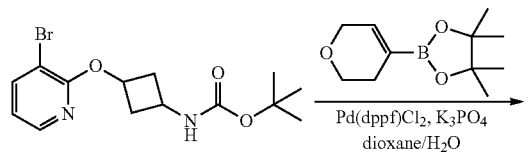

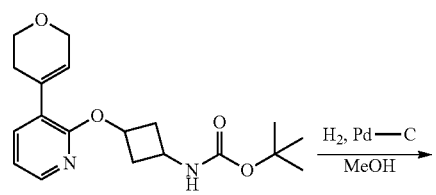

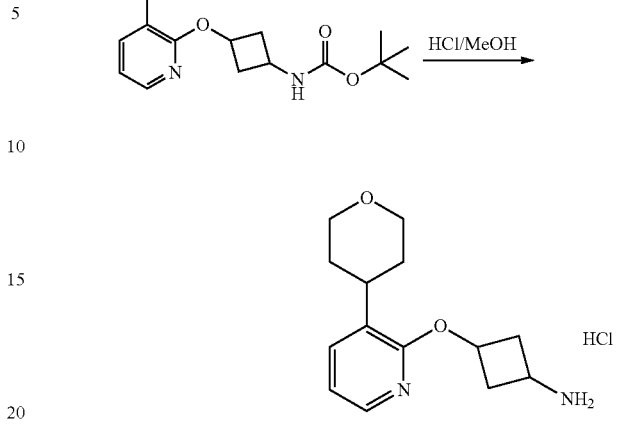

Step 1: TERT-BUTYL (3-((3-(3,6-DIHYDRO-2H-PYRAN-4-YL)PYRIDIN-2-YL)OXY)CYCLOBUTYL)CARBAMATE To a solution of tert-butyl (3-((3-bromopyridin-2-yl)oxy)cyclobutyl)carbamate (see PREPARATION 7B; 343 mg, 1 mmol), 4-(3,3,4,4-tetramethyl-borolan-1-yl)-3,6-dihydro-2H-pyran (2.27 mg, 1.1 mmol) and $K_3PO_4$ (424 mg, 2 mmol) in 1,4-dioxane (60 mL) and $H_2O$ (6 mL) was added Pd(dppf)$Cl_2$ (36.6 mg, 0.05 mmol) then the reaction mixture was stirred at 110° C. under $N_2$ for overnight. The reaction mixture was filtered through CELITE® and washed with $CH_2Cl_2$. The organic layer was concentrated and the crude product was purified by silica gel column to give tert-butyl (3-((3-(3,6-dihydro-2H-pyran-4-yl)pyridin-2-yl)oxy)cyclobutyl)carbamate (242 mg, 0.7 mmol, yield 70%). ESI-MS (M+1): 347 calc. for $C_{19}H_{26}N_2O_4$ 346

Step 2: TERT-BUTYL (3-((3-(TETRAHYDRO-2H-PYRAN-4-YL)PYRIDIN-2-YL)OXY)CYCLOBUTYL)CARBAMATE A mixture of tert-butyl (3-((3-(3,6-dihydro-2H-pyran-4-yl)pyridin-2-yl)oxy)cyclobutyl)carbamate (346 mg, 1 mmol) and wet Pd—C (50%, 200 mg) in MeOH (100 mL) was stirred under $H_2$ (40 psi) at 30° C. overnight then the reaction mixture was filtered through CELITE® and washed with MeOH. The filtrate was concentrated to give tert-butyl (3-((3-(tetrahydro-2H-pyran-4-yl)pyridin-2-yl)oxy)cyclobutyl)carbamate (331 mg, 0.95 mmol, yield 95%). ESI-MS (M+1): 349 calc. for $C_{19}H_{28}N_2O_4$ 348.

Step 3: 3-((3-(TETRAHYDRO-2H-PYRAN-4-YL)PYRIDIN-2-YL)OXY)CYCLOBUTANAMINE HYDROCHLORIDE To tert-butyl (3-((3-(tetrahydro-2H-pyran-4-yl)pyridin-2-yl)oxy)cyclobutyl)carbamate (348 mg, 1 mmol) was added 4 M HCl in MeOH (100 mL). The solution was stirred at RT for 2 hours. The solvent was removed under reduced pressure to give 3-((3-(tetrahydro-2H-pyran-4-yl)pyridin-2-yl)oxy)cyclobutanamine hydrochloride (248 mg, 0.95 mmol, yield 95%). ESI-MS (M+1): 249 calc. for $C_{19}H_{28}N_2O_4$ 248.

Preparation 7D: (1S,3S)-3-((5-FLUORO-3-(TETRAHYDRO-2H-PYRAN-4-YL)PYRIDIN-2-YL)OXY)CYCLOBUTANAMINE HYDROCHLORIDE

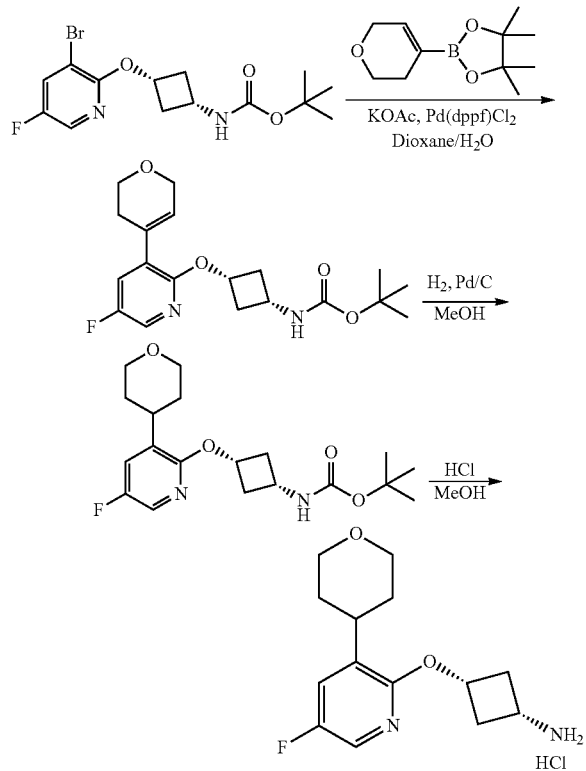

Step 1: TERT-BUTYL ((1S,3S)-3-((3-(3,6-DIHYDRO-2H-PYRAN-4-YL)-5-FLUOROPYRIDIN-2-YL)OXY)CYCLOBUTYL)CARBAMATE To a solution of tert-butyl ((1S,3S)-3-((3-bromo-5-fluoropyridin-2-yl)oxy)cyclobutyl)carbamate (see PREPARATION 7A; 430 mg, 1.19 mmol), 4-(3,3,4,4-tetramethyl-borolan-1-yl)-3,6-dihydro-2H-pyran (372 mg, 1.79 mmol) and $K_3PO_4$ (505 mg, 2.38 mmol) in 1,4-dioxane (30 mL) and $H_2O$ (6 mL) was added Pd(dppf)Cl$_2$ (87 mg, 0.12 mmol), then the reaction mixture was stirred at 110° C. under $N_2$ overnight. The reaction mixture was filtered through CELITE® and washed with $CH_2Cl_2$. The organic layer was concentrated and the crude product was purified by silica gel column to give tert-butyl ((1S,3S)-3-((3-(3,6-dihydro-2H-pyran-4-yl)-5-fluoropyridin-2-yl)oxy)cyclobutyl)carbamate (200 mg, 0.55 mmol, yield 46%). ESI-MS (M+1): 365 calc. for $C_{19}H_{25}FN_2O_4$ 364.

Step 2: TERT-BUTYL ((1S,3S)-3-((5-FLUORO-3-(TETRAHYDRO-2H-PYRAN-4-YL)PYRIDIN-2-YL)OXY)CYCLOBUTYL)CARBAMATE A mixture of tert-butyl ((1S,3S)-3-((3-(3,6-dihydro-2H-pyran-4-yl)-5-fluoropyridin-2-yl)oxy)cyclobutyl)carbamate (100 mg, 0.275 mmol) and wet Pd—C (50%, 80 mg) in MeOH (10 mL) was stirred under $H_2$ (40 psi) at 30° C. overnight. The reaction mixture was filtered through CELITE® and the filtrate was concentrated to give the desired compound (80 mg, 0.22 mmol, yield 80%). ESI-MS (M+1): 367 calc. for $C_{19}H_{27}FN_2O_4$ 366.

Step 3: (1S,3S)-3-((5-FLUORO-3-(TETRAHYDRO-2H-PYRAN-4-YL)PYRIDIN-2-YL)OXY)CYCLOBUTANAMINE HYDROCHLORIDE To tert-butyl ((1S,3S)-3-((5-fluoro-3-(tetrahydro-2H-pyran-4-yl)pyridin-2-yl)oxy)cyclobutyl)carbamate (200 mg, 0.546 mmol) in MeOH (10 mL) was added MeOH (10 mL, saturated with HCl gas), and then stirred at RT for 2 hour. The reaction mixture was concentrated to give (1S,3S)-3-((5-fluoro-3-(tetrahydro-2H-pyran-4-yl)pyridin-2-yl)oxy)cyclobutanamine hydrochloride (180 g, 0.535 mmol, 98%). ESI-MS (M+1): 267 calc. for $C_{14}H_{19}FN_2O_2$ 266.

Preparation 7E: N-(3-((3-BROMOPYRIDIN-2-YL)OXY)CYCLOBUTYL) BENZO[D]THIAZOL-2-AMINE

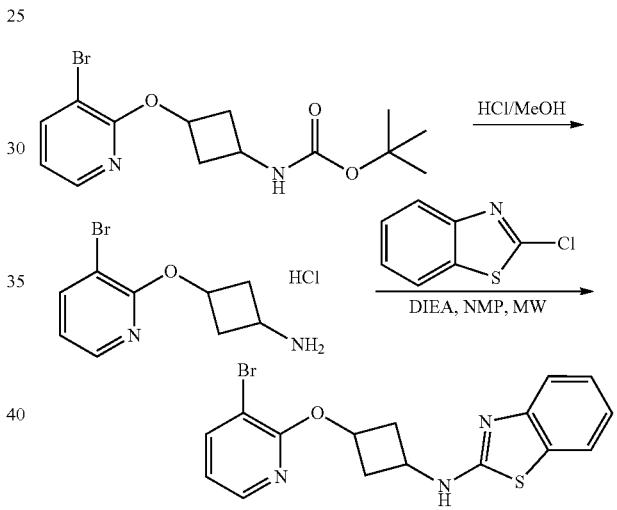

Step 1: 3-((3-BROMOPYRIDIN-2-YL)OXY)CYCLOBUTANAMINE HYDROCHLORIDE

To tert-butyl (3-((3-bromopyridin-2-yl)oxy)cyclobutyl)carbamate (see PREPARATION 7B; 342 mg, 1 mmol) was added 4 M HCl in MeOH (50 mL). The solution was stirred at RT for 2 hours. The solvent was removed under reduced pressure to give 3-((3-bromopyridin-2-yl)oxy)cyclobutanamine hydrochloride (223 mg, 0.95 mmol, yield 95%). ESI-MS (M+1): 243 calc. for $C_9H_{11}BrN_2O$ 242.

Step 2: N-(3-((3-BROMOPYRIDIN-2-YL)OXY)CYCLOBUTYL)BENZO[D]THIAZOL-2-AMINE

A mixture of 3-((3-bromopyridin-2-yl)oxy)cyclobutanamine hydrochloride (242 mg, 1 mmol), 2-chloro-benzothiazole (169 mg, 1 mmol) and DIEA (286 mg, 2 mmol) in NMP (10 mL) was heated to 180° C. for 2 hours in microwave. The reaction mixture was added water, extracted with EtOAc (40 mL), washed with brine and dried over $Na_2SO_4$. The organic layers were concentrated and purified by column chromatography to give N-(3-((3-bromopyridin-2-yl)oxy)cyclobutyl)benzo[d]thiazol-2-amine (225 mg, 0.6 mmol, yield 60%). ESI-MS (M+1): 376 calc. for $C_{16}H_{14}BrN_3OS$ 375.

Preparation 7F: (1S,3S)-3-((3-BROMOPYRIDIN-2-YL)OXY)CYCLOBUTANAMINE HYDROCHLORIDE

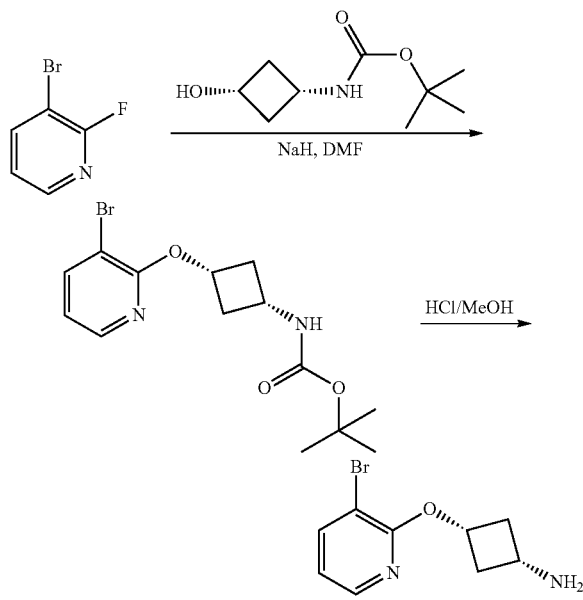

Step 1: TERT-BUTYL ((1S,3S)-3-((3-BROMOPYRIDIN-2-YL)OXY)CYCLOBUTYL) CARBAMATE

To a solution of tert-butyl ((1S,3S)-3-((3-bromopyridin-2-yl)oxy)cyclobutyl)carbamate (see PREPARATION 4A; 1.08 g, 3.8 mmol) in DMF (20 mL) at RT was added sodium hydride (60% wt in mineral oil) (0.18 g, 7.6 mmol). The mixture was stirred at RT for 10 min and then 3-bromo-2-fluoro-pyridine (665 mg, 3.8 mmol) was added. The reaction mixture was stirred at RT for 1 h and then diluted with water (20 mL) and extracted with EtOAc (2×30 mL). The combined organic phases were washed with water (10 mL) and brine (10 mL), dried over $Na_2SO_4$, and filtered. The filtrate was evaporated in vacuo and the residue was purified by flash chromatography on silica gel (5% to 30% EtOAc in hexanes) to give tert-butyl ((1S,3S)-3-((3-bromopyridin-2-yl)oxy)cyclobutyl)carbamate (391 mg, 1.14 mmol, 30%) as white solid. ESI-MS (M+1): 343 calc. for $C_{14}H_{19}BrN_2O_3$ 342.

Step 2: (1S,3S)-3-((3-BROMOPYRIDIN-2-YL)OXY)CYCLOBUTANAMINE HYDROCHLORIDE

To a solution of tert-butyl ((1S,3S)-3-((3-bromopyridin-2-yl)oxy)cyclobutyl)carbamate (342 mg, 1 mmol) was added 4 M HCl in MeOH (50 mL). The solution was stirred at RT for 2 hours. The solvent was removed under reduced pressure to give (1S,3S)-3-((3-bromopyridin-2-yl)oxy)cyclobutanamine hydrochloride (223 mg, 0.95 mmol, yield 95%). ESI-MS (M+1): 243 calc. for $C_9H_{11}BrN_2O$ 242.

Preparation 7G: N-((1S,3S)-3-((3-BROMOPYRIDIN-2-YL)OXY)CYCLOBUTYL)QUINOLIN-2-AMINE

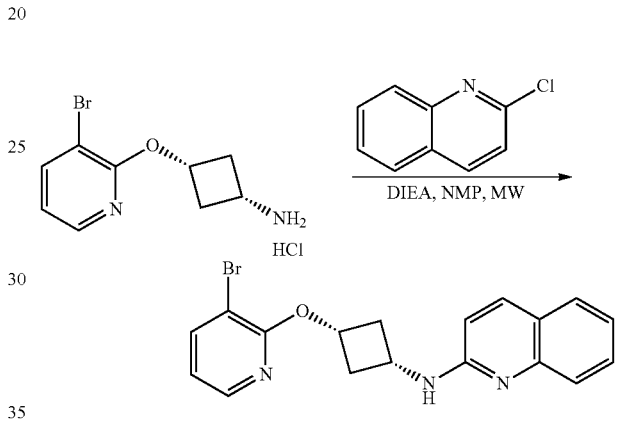

A mixture of (1S,3S)-3-((3-bromopyridin-2-yl)oxy)cyclobutanamine hydrochloride (1.52 g, 6.28 mmol), 2-chloroquinoline (purchased from AlfaAesar™) (1.02 g, 6.28 mmol) and DIEA (1.8 g, 12.56 mmol) in NMP (12 mL) was heated to 200° C. for 2 hours in microwave. The reaction mixture was added water, extracted with EtOAc (40 mL), washed with brine and dried over $Na_2SO_4$. The organic layers were concentrated and purified by column chromatography on silica gel to give N-((1S,3S)-3-((3-bromopyridin-2-yl)oxy)cyclobutyl)quinolin-2-amine (1.04 g, 2.83 mmol, 45%). ESI-MS (M+1): 370 calc. for $C_{18}H_{16}BrN_3O$ 369.

Preparation 7H: N-((1S,3S)-3-((3-(PIPERIDIN-4-YL)PYRIDIN-2-YL)OXY)CYCLOBUTYL)QUINOLIN-2-AMINE HYDROCHLORIDE

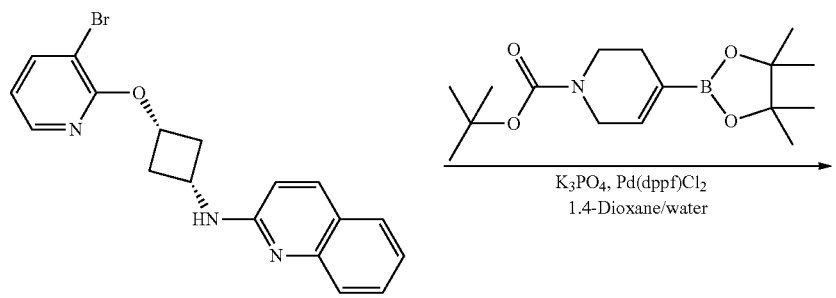

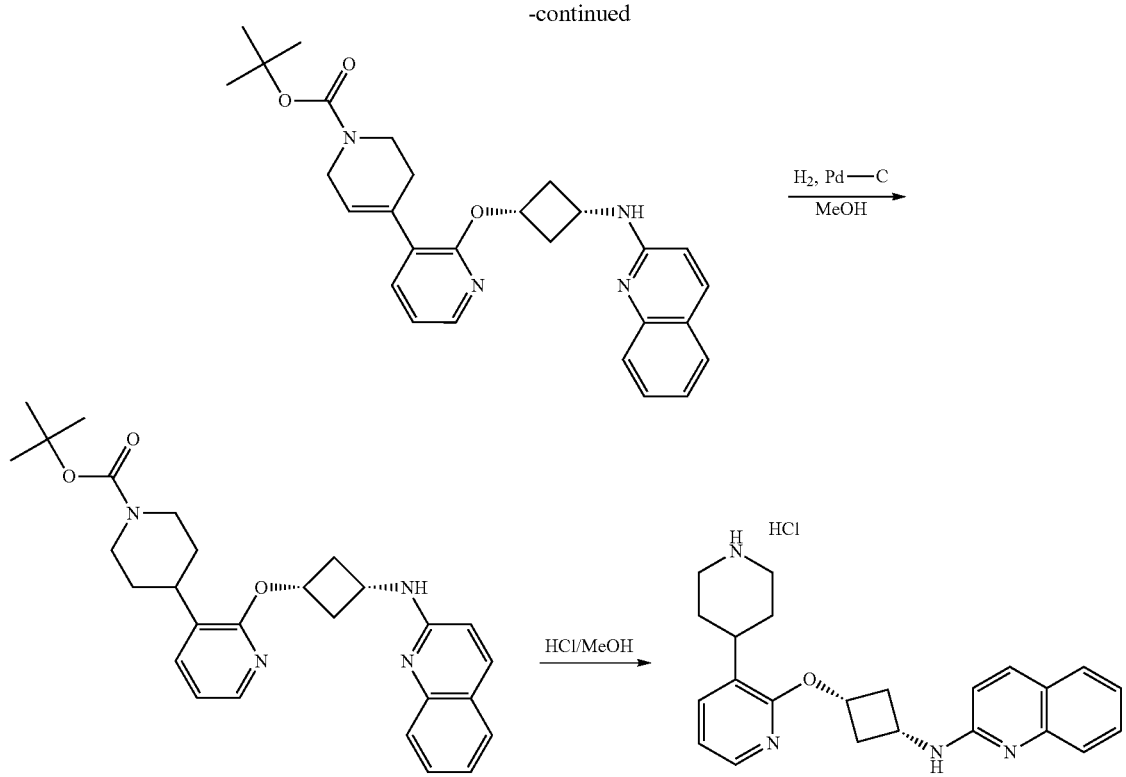

Step 1: TERT-BUTYL 2-((1S,3S)-3-(QUINOLIN-2-YLAMINO)CYCLOBUTOXY)-5',6'-DIHYDRO-[3,4'-BIPYRIDINE]-1'(2'H)-CARBOXYLATE To a mixture of N-((1S,3S)-3-((3-bromopyridin-2-yl)oxy)cyclobutyl)quinolin-2-amine (see PREPARATION 7G; 222 mg, 0.6 mmol) in 1,4-dioxane/H$_2$O (5:1, 12 mL) was added tert-butyl 4-(4,4,5,5-tetramethyl-1,3,2-dioxaborolan-2-yl)-5,6-dihydropyridine-1(2H)-carboxylate (278 mg, 0.9 mmol), K$_3$PO$_4$ (254 mg, 1.2 mmol) and Pd(dppf)Cl$_2$ (44 mg, 0.06 mmol). The mixture was refluxed overnight. The reaction mixture was filtered and concentrated. The residue was purification by prep-HPLC to give tert-butyl 2-((1S,3S)-3-(quinolin-2-ylamino)cyclobutoxy)-5',6'-dihydro-[3,4'-bipyridine]-1'(2'H)-carboxylate (86 mg, 0.18 mmol, yield 30%). ESI-MS (M+1): 473 calc. for C$_{28}$H$_{32}$N$_4$O$_3$ 472.

Step 2: TERT-BUTYL 4-(2-((1S,3S)-3-(QUINOLIN-2-YLAMINO)CYCLOBUTOXY)PYRIDIN-3-YL)PIPERIDINE-1-CARBOXYLATE A mixture of tert-butyl 2-((1S,3S)-3-(quinolin-2-ylamino)cyclobutoxy)-5',6'-dihydro-[3,4'-bipyridine]-1'(2'H)-carboxylate (472 mg, 1 mmol) and wet Pd—C (50%, 500 mg) in MeOH (100 mL) was stirred under H$_2$ (40 psi) at 30° C. overnight then the reaction mixture was filtered through CELITE® and washed with MeOH. The filtrate was concentrated to give tert-butyl 4-(2-((1S,3S)-3-(quinolin-2-ylamino)cyclobutoxy)pyridin-3-yl)piperidine-1-carboxylate (431 mg, 0.91 mmol, yield 91%). ESI-MS (M+1): 475 calc. for C$_{27}$H$_{33}$N$_5$O$_3$ 474.

Step 3: N-((1S,3S)-3-((3-(PIPERIDIN-4-YL)PYRIDIN-2-YL)OXY)CYCLOBUTYL)QUINOLIN-2-AMINE HYDROCHLORIDE To tert-butyl 4-(2-(1S,3S)-3-(quinolin-2-ylamino)cyclobutoxy)pyridine-1-carboxylate (474 mg, 1 mmol) was added 4 M HCl in MeOH (100 mL). The solution was stirred at RT for 2 hours. The solvent was removed under reduced pressure to give N-((1S,3S)-3-((3-(piperidin-4-yl)pyridin-2-yl)oxy)cyclobutyl)quinolin-2-amine hydrochloride (356 mg, 0.95 mmol, yield 95%). ESI-MS (M+1): 375 calc. for C$_{22}$H$_{25}$N$_5$O 374.

Preparation 71: N-((1S,3S)-3-((3-BROMOPYRIDIN-2-YL)OXY)CYCLOBUTYL)BENZO[D]THIAZOL-2-AMINE

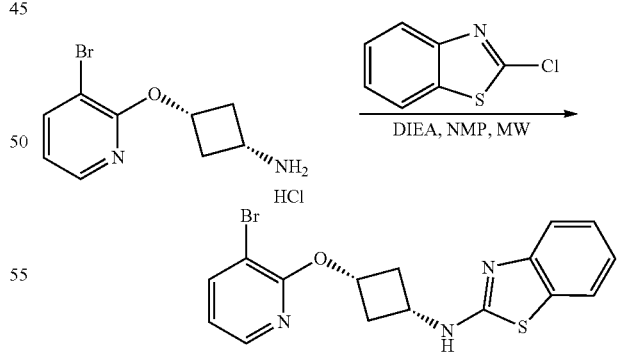

A mixture of (1S,3S)-3-((3-bromopyridin-2-yl)oxy)cyclobutanamine hydrochloride (see PREPARATION 7F) (242 mg, 1 mmol), 2-chloro-benzothiazole (169 mg, 1 mmol) and DIEA (286 mg, 2 mmol) in NMP (10 mL) was heated to 180° C. for 2 hours in microwave. The reaction mixture was extracted with EtOAc (40 mL) and water. The organic phase was collected, washed with brine and dried over Na$_2$SO$_4$. The organic layers were concentrated and purified by column chromatography on silica gel to give N-((1S,3S)-3-((3-bromopyridin-2-yl)oxy)cyclobutyl)benzo[d]thiazol-2-amine (225 mg, 0.6 mmol, yield 60%). ESI-MS (M+1): 376 calc. for $C_{16}H_{14}BrN_3OS$ 375.

Preparation 7J: N-((1S,3S)-3-((3-(PIPERIDIN-4-YL)PYRIDIN-2-YL)OXY)CYCLOBUTYL)BENZO[D]THIAZOL-2-AMINE HYDROCHLORIDE

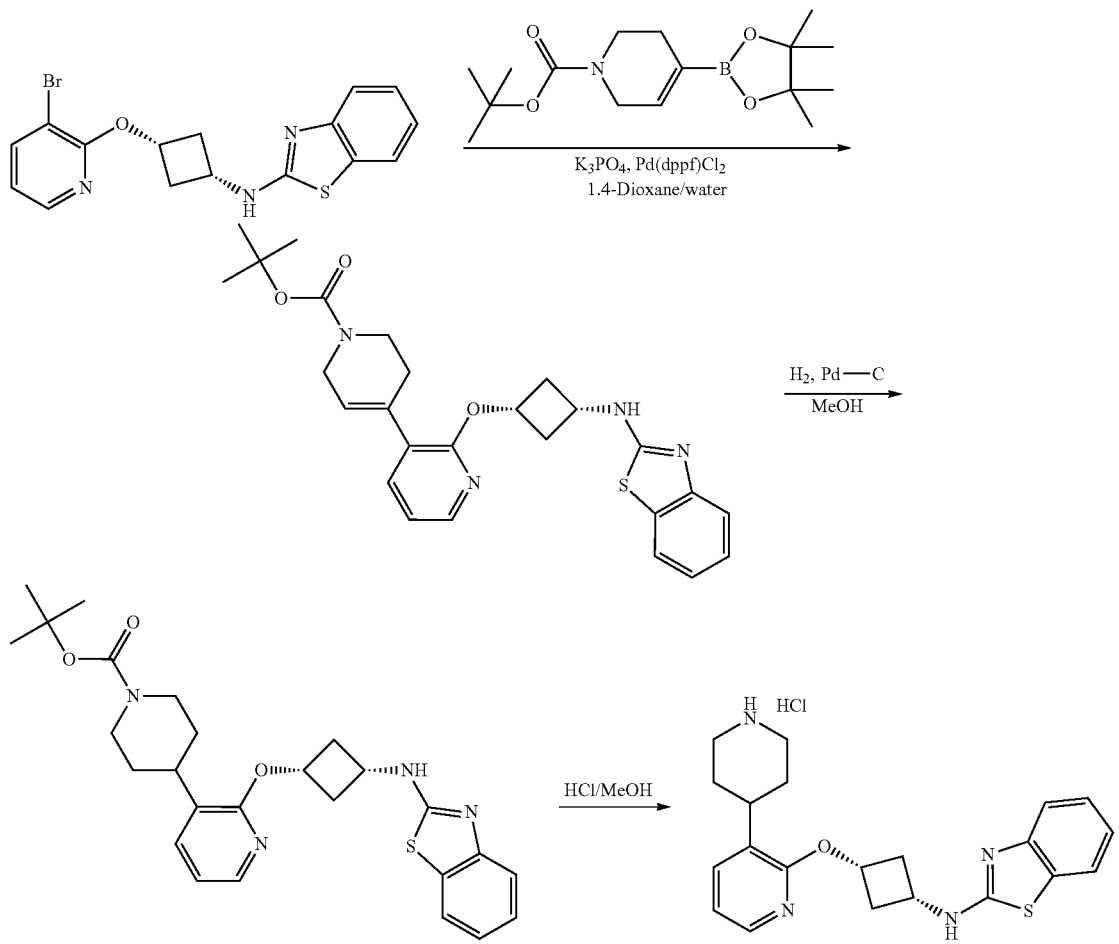

Step 1: TERT-BUTYL 2-((1S,3S)-3-(BENZO[D]THIAZOL-2-YLAMINO)CYCLOBUTOXY)-5',6'-DIHYDRO-[3,4'-BIPYRIDINE]-1'(2'H)-CARBOXYLATE To a mixture of N-((1S,3S)-3-((3-bromopyridin-2-yl)oxy)cyclobutyl)benzo[d]thiazol-2-amine (see PREPARATION 7I; 225 mg, 0.6 mmol) in 1,4-dioxane/H₂O (5:1, 12 mL) was added tert-butyl 4-(4,4,5,5-tetramethyl-1,3,2-dioxaborolan-2-yl)-5,6-dihydropyridine-1(2H)-carboxylate (278 mg, 0.9 mmol), K₃PO₄ (254 mg, 1.2 mmol) and Pd(dppf)Cl₂ (44 mg, 0.06 mmol). The mixture was refluxed overnight. The reaction mixture was filtered and concentrated. The residue was purification by flash chromatography on silica gel (5% to 30% EtOAc in hexanes) to give tert-butyl 2-((1S,3S)-3-(benzo[d]thiazol-2-ylamino)cyclobutoxy)-5',6'-dihydro-[3, 4'-bipyridine]-1'(2'H)-carboxylate (86 mg, 0.18 mmol, yield 30%). ESI-MS (M+1): 479 calc. for $C_{26}H_{30}N_4O_3S$ 478.

Step 2: TERT-BUTYL 4-(2-((1S,3S)-3-(BENZO[D]THIAZOL-2-YLAMINO)CYCLOBUTOXY)PYRIDIN-3-YL)PIPERIDINE-1-CARBOXYLATE A mixture of tert-butyl 2-((1S,3S)-3-(benzo[d]thiazol-2-ylamino)cyclobutoxy)-5',6'-dihydro-[3,4'-bipyridine]-1'(2'H)-carboxylate (478 mg, 1 mmol) and wet Pd—C (50%, 500 mg) in MeOH (100 mL) was stirred under H₂ (40 psi) at 30° C. overnight then the reaction mixture was filtered through CELITE® and washed with MeOH. The filtrate was concentrated to give tert-butyl 4-(2-((1S,3S)-3-(benzo[d]thiazol-2-ylamino)cyclobutoxy)pyridin-3-yl)piperidine-1-carboxylate (437 mg, 0.91 mmol, yield 91%). ESI-MS (M+1): 481 calc. for $C_{26}H_{32}N_4O_3S$ 480.

Step 3: N-((1S,3S)-3-((3-(PIPERIDIN-4-YL)PYRIDIN-2-YL)OXY)CYCLOBUTYL)BENZO[D]THIAZOL-2-AMINE HYDROCHLORIDE To tert-butyl 4-(2-((1S,3S)-3-(benzo[d]thiazol-2-ylamino)cyclobutoxy)pyridin-3-yl)piperidine-1-carboxylate (480 mg, 1 mmol) was added 4 M HCl in MeOH (100 mL). The solution was stirred at RT for 2 hours. The solvent was removed under reduced pressure to give N-((1S,3S)-3-((3-(piperidin-4-yl)pyridin-2-yl)oxy)cyclobutyl)benzo[d]thiazol-2-amine hydrochloride (361 mg, 0.95 mmol, yield 95%). ESI-MS (M+1): 381 calc. for $C_{21}H_{24}N_4OS$ 380.

Preparation 7K: (1S,3S)-3-((6-CHLORO-3-(3,6-DIHYDRO-2H-PYRAN-4-YL)PYRIDIN-2-YL)OXY)CYCLOBUTANAMINE HYDROCHLORIDE

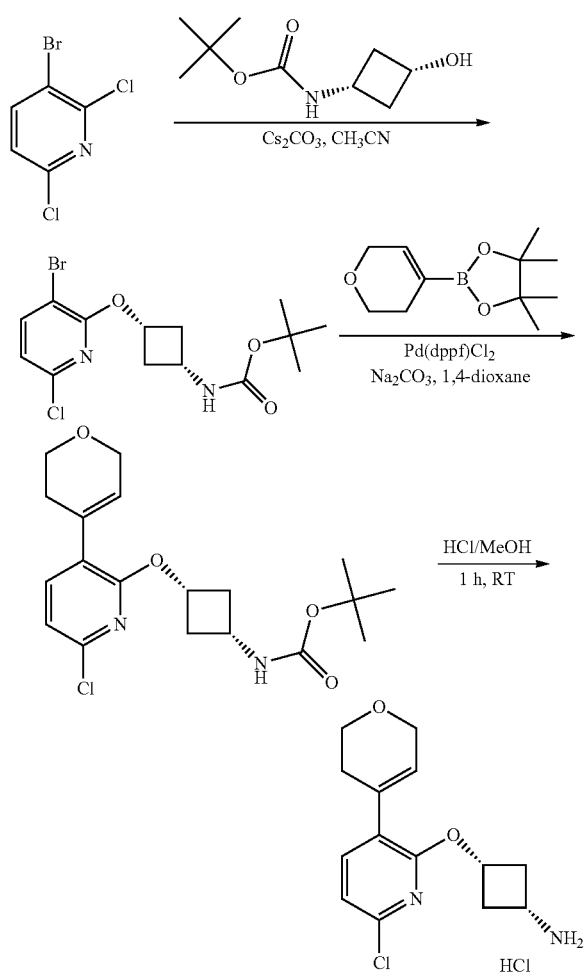

Step 1. TERT-BUTYL ((1S,3S)-3-((3-BROMO-6-CHLOROPYRIDIN-2-YL)OXY)CYCLOBUTYL)CARBAMATE To a mixture of 3-bromo-2,6-dichloropyridine (4.5 g, 20 mmol) and tert-butyl ((1S,3S)-3-hydroxycyclobutyl)carbamate (see PREPARATION 4A; 3.65 g, 20 mmol) in acetonitrile (50 mL) was added $Cs_2CO_3$ (13.2 g, 40 mmol), and then the mixture was stirred at RT overnight. The reaction mixture was filtered and concentrated under vacuum to give tert-butyl ((1S,3S)-3-((3-bromo-6-chloropyridin-2-yl)oxy)cyclobutyl)carbamate (4.2 g, 11.2 mmol, 56%). ESI-MS (M+1): 377 calc. for $C_{14}H_{18}BrClN_2O_3$ 376.

Step 2. TERT-BUTYL ((1S,3S)-3-((6-CHLORO-3-(3,6-DIHYDRO-2H-PYRAN-4-YL)PYRIDIN-2-YL)OXY)CYCLOBUTYL)CARBAMATE To a solution of tert-butyl ((1S,3S)-3-((3-bromo-6-chloropyridin-2-yl)oxy)cyclobutyl)carbamate (375 mg, 1 mmol), 2-(3,6-dihydro-2H-pyran-4-yl)-4,4,5,5-tetramethyl-1,3,2-dioxaborolane (250 mg, 1.2 mmol) and $Na_2CO_3$ (212 mg, 2 mmol) in 1,4-dioxane (60 mL) and $H_2O$ (6 mL) was added $Pd(dppf)Cl_2$ (36.6 mg, 0.05 mmol) then the reaction mixture was stirred at 110° C. under $N_2$ overnight. The reaction mixture was filtered through CELITE® and washed with $CH_2Cl_2$ (50 mL). The organic layer was concentrated and the crude product was purified by silica gel column to give tert-butyl ((1S,3S)-3-((6-chloro-3-(3,6-dihydro-2H-pyran-4-yl)pyridin-2-yl)oxy)cyclobutyl)carbamate (265 mg, 0.7 mmol, yield 70%). ESI-MS (M+1): 381 calc. for $C_{19}H_{25}ClN_2O_4$ 380.

Step 3. (1S,3S)-3-((6-CHLORO-3-(3,6-DIHYDRO-2H-PYRAN-4-YL)PYRIDIN-2-YL)OXY)CYCLOBUTANAMINE HYDROCHLORIDE To tert-butyl ((1S,3S)-3-((6-chloro-3-(3,6-dihydro-2H-pyran-4-yl)pyridin-2-yl)oxy)cyclobutyl)carbamate (379 mg, 1 mmol) was added 4 M HCl in MeOH (100 mL). The solution was stirred at RT for 2 hours. The solvent was removed under reduced pressure to give (1S,3S)-3-((6-chloro-3-(3,6-dihydro-2H-pyran-4-yl)pyridin-2-yl)oxy)cyclobutanamine hydrochloride (265 mg, 0.95 mmol, yield 95%). ESI-MS (M+1): 281 calc. for $C_{14}H_{17}ClN_2O_2$ 280.

Preparation 7 L: 1-(2-((1S,3S)-3-AMINOCYCLOBUTOXY)PYRIDIN-3-YL)PIPERIDINE-4-CARBONITRILE HYDROCHLORIDE

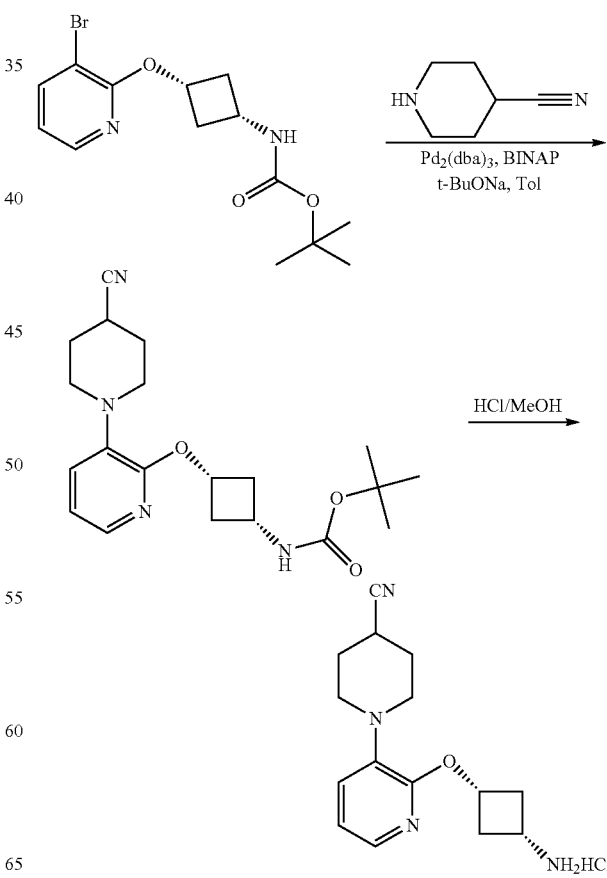

Step 1. TERT-BUTYL ((1S,3S)-3-((3-(4-CYANOPIPERIDIN-1-YL)PYRIDIN-2-YL)OXY)CYCLOBUTYL)CARBAMATE The mixture of tert-butyl ((1S,3S)-3-((3-bromopyridin-2-yl)oxy)cyclobutyl)carbamate (see PREPARATION 7F, step 1; 684 mg, 2 mmol, 1.0 eqv), piperidine-4-carbonitrile (220 mg, 2 mmol, 1.0 eqv), Pd$_2$(dba)$_3$ (91 mg, 0.1 mmol), 2,2'-bis(diphenylphosphino)-1,1'-binaphthalene (BINAP) (248 mg, 0.4 mmol), potassium tert-butoxide (224 mg, 2 mmol) and toluene (10 ml) was stirred at 100° C. overnight. The mixture was concentrated and purified by silica gel chromatography to give the title compound (420 mg, 1.1 mmol, 55% yield) ESI-MS (M+1): 373 calc. for C$_{20}$H$_{28}$N$_4$O$_3$ 372.

Step 2. 1-(2-((1S,3S)-3-aminocyclobutoxy)pyridin-3-yl)piperidine-4-carbonitrile hydrochloride The mixture of tert-butyl ((1S,3S)-3-((3-(4-cyanopiperidin-1-yl)pyridin-2-yl)oxy)cyclobutyl)carbamate (420 mg, 1.1 mmol, 1.0 eqv) in HCl/methanol 4N (20 ml) was stirred at RT overnight. The mixture was concentrated to give the title compound (320 mg, 1.04 mmol, 95% yield) ESI-MS (M+1): 273 calc. for C$_{15}$H$_{20}$N$_4$O 272

Preparation 8: 2,6-DIFLUORO-3-IODOPYRIDINE

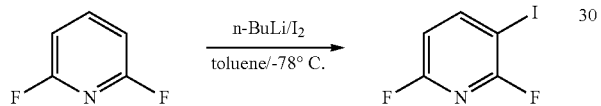

To a mixture of 2,6-difluoropyridine (1.15 g, 10 mmol, 10. eqv) in toluene (300 ml) was added n-BuLi (4.8 ml, 12 mmol, 1.2 eqv) at −78° C. under nitrogen and the mixture was stirred at the same temperature for 4 hrs. Iodine (2.53 g, 10 mmol) was added with the temperature still below −70° C. The mixture was allowed to warm up to RT and quenched with 10 ml water. The organic solvent was removed under vacuum and the product was collected by filtration. Chromatography by silica gel (petroleum ether: EtOAc=50:1 to 5:1) to give 2,6-difluoro-3-iodopyridine as solid (1.49 g, 6.1 mmol, 61% yield) ESI-MS (M+1): 242 calc. for C$_5$H$_2$F$_2$IN 241.

Preparation 9: 1-(5-(4,4,5,5-TETRAMETHYL-1,3,2-DIOXABOROLAN-2-YL)PYRIDIN-2-YL)ETHANONE

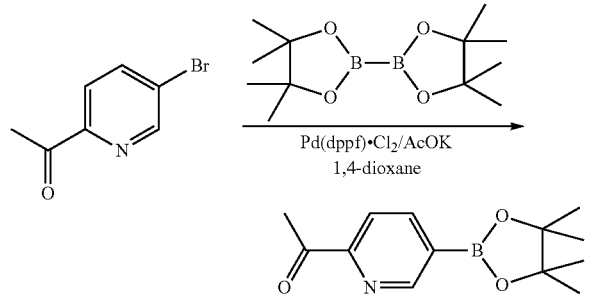

The a mixture of 1-(5-bromo-pyridin-2-yl)-ethanone (199 mg, 1 mmol), 4,4,4',4',5,5,5',5'-octamethyl-2,2'-bi(1,3,2-dioxaborolane) (254 mg, 1 mmol), potassium acetate (AcOK) (196 mg, 2 mmol), Pd(dppf)Cl$_2$ (73 mg, 0.1 mmol) in 1,4-dioxane (2 ml) was stirred at 100° C. for 2.5 h. The mixture was used in the next step without purification.

Preparation 10: TERT-BUTYL 3-(3-CHLOROPYRAZIN-2-YL)AZETIDINE-1-CARBOXYLATE

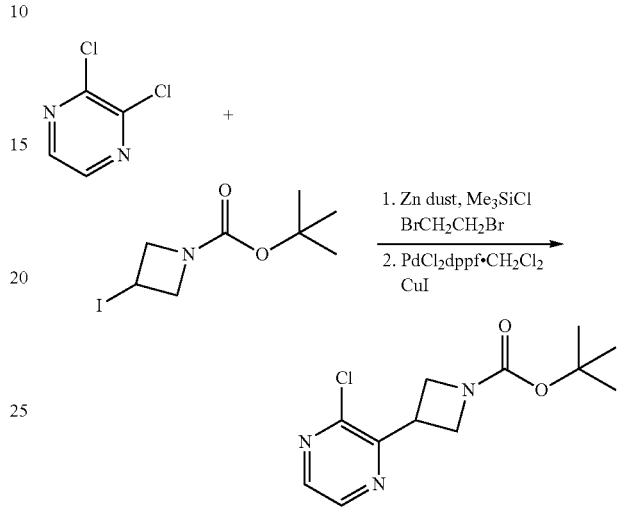

Preparation of TERT-BUTYL 3-(3-CHLOROPYRAZIN-2-YL)AZETIDINE-1-CARBOXYLATE

A 12 L 3-neck round bottom flask fitted with a magnetic stirrer under nitrogen was charged with zinc dust (745 g, pre-activated, 11.4 mol, 2 eq.) and DMA (2 L, anhydrous). 1,2-dibromoethane (71 mL, 0.855 mol, 0.15 eq, Aldrich) was then added over 10 minutes, followed by TMSCl (108 mL, 0.855 mol, 0.15 eq, Acros) over 20 minutes. The reaction mixture was stirred for 25 minutes at room temperature. A solution of N-Boc-3-iodoazetidine (2420 g, 8.55 mol, 1.5 eq, CNH Technologies) in DMA (5 L, anhydrous) was added via a 2 L addition funnel over 2 h keeping the internal temperature below 65° C. using a water bath. The suspension was stirred for 1 hour at RT at which point it was degassed with nitrogen. Stirring was stopped and the suspension was allowed to stand. A 22 L 3-neck round bottom flask fitted with a mechanical stirrer was charged with 2,3-dichloropyrazine (850 g, 5.70 mol, 1.0 eq, AK Scientific), PdCl$_2$dppf.CH$_2$Cl$_2$ (140 g, 171 mmol, 0.03 eq, Aldrich), CuI (67.3 g, 353 mmol, 0.062 eq, Aldrich), and DMA (5 L, anhydrous). The solution was degassed with nitrogen. The clear zinc reagent solution above the residual solid zinc was poured into the 22 L flask under nitrogen. The brown solution was degassed with nitrogen and heated to 80° C. for 16 hours at which point LCMS indicated complete conversion of 2,3-dichloropyrazine. The reaction mixture was transferred to brine (8 L) in 50 L reparatory funnel. Water (8 L) and EtOAc (15 L) were added and the layers were separated. The aqueous layer was extracted with EtOAc (2×10 L). The combined organics were washed with water (3×10 L) and brine (5 L), dried over sodium sulfate and evaporated. The resulting residue was purified by column chromatography (eluting with hexanes/ethyl acetate=10:1) to get 536 g of pure tert-butyl 3-(3-chloropyrazin-2-yl)azetidine-1-carboxylate and 121 g of mixed fractions. The impure material was distilled under high vacuum to remove the impurity (N-Boc-azetidine) to give 81 g of pure tert-butyl 3-(3-chloropyrazin-2-yl)azetidine-1-carboxylate.

Total: 617 g, Yield: 40%.

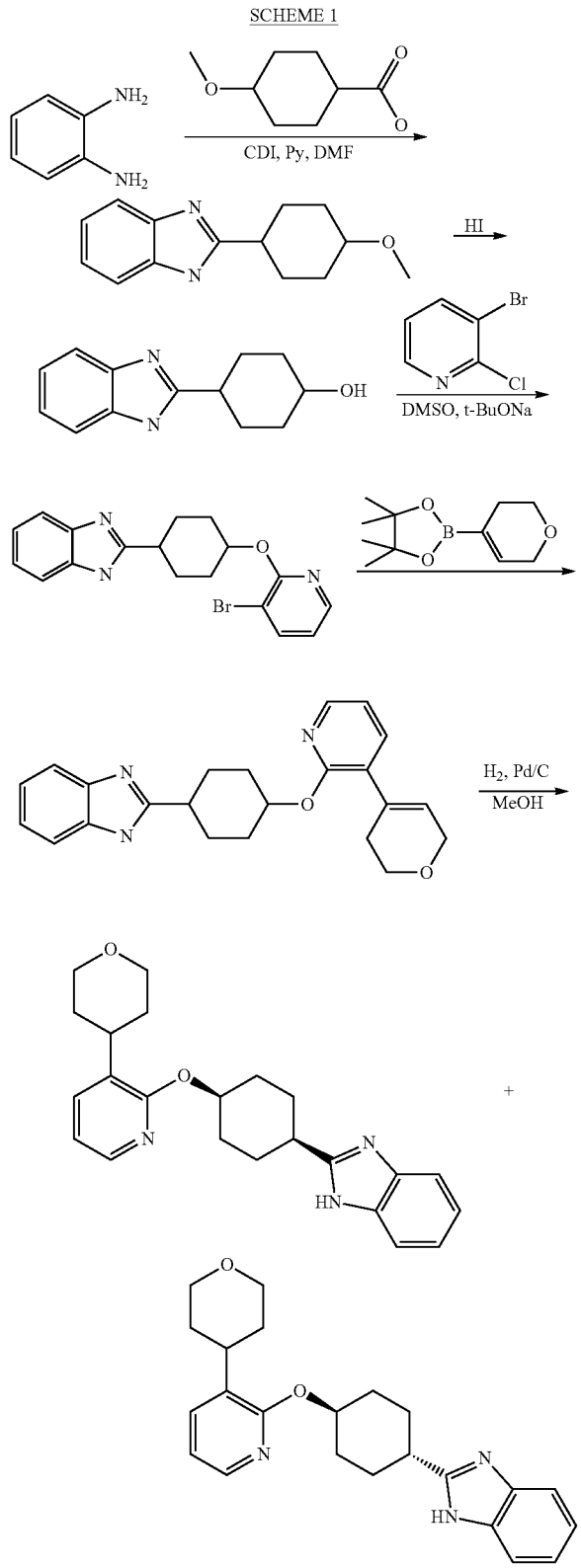

Example 1

TRANS/CIS-2-{4-[3-(TETRAHYDRO-PYRAN-4-YL)-PYRIDIN-2-YLOXY]-CYCLOHEXYL}-1H-BENZOIMIDAZOLE

Step 1. 2-(4-METHOXY-CYCLOHEXYL)-1H-BENZOIMIDAZOLE

4-Hydroxy-cyclohexanecarboxylic acid (2 g, 13.8 mmol) in a mixture of DMF (4 mL) and pyridine (4 mL) was treated with 1,1-carbonyldiimidazole (2.26 g, 213.8 mmol) at RT and the resulting solution was stirred at 45° C. for 2 h. The mixture was treated with benzene-1,2-diamine (1.5 g, 13.8 mmol) and stirred at RT overnight. After completion, the mixture was concentrated and the obtained residue was treated with glacial acetic acid (20 mL) and heated at 110° C. for 0.5 h. The solution was allowed to cool to RT and concentrated to get a residue, which was purified by flash chromatography on silica gel to provide the title compound (3.0 g, 13.0 mmol, 71% yield) as yellow solid.

Step 2. 4-(1H-BENZOIMIDAZOL-2-YL)-CYCLOHEXANOL

A solution of 2-(4-methoxy-cyclohexyl)-1H-benzoimidazole (500 mg, 2.17 mmol) in HI (35%) (5 mL) was heated to 90° C. for 1 h. The reaction mixture was diluted with water (20 mL) and extracted with EtOAc (2×10 mL); the organic layers was combined and washed with brine (2×10 mL), dried over $Na_2SO_4$, and concentrated to give the desired product (400 mg, 1.85 mmol, 85% yield) as brown solid.

Step 3. 2-[4-(3-BROMO-PYRIDIN-2-YLOXY)-CYCLOHEXYL]-1H-BENZOIMIDAZOLE

The mixture of 4-(1H-benzoimidazol-2-yl)-cyclohexanol (0.36 g, 1.67 mmol), 3-bromo-2-chloro-pyridine (0.64 g, 3.34 mmol), t-BuONa (0.37 g, 3.34 mmol) and DMSO (5 mL) was heated at 60° C. for 2 days under $N_2$ atmosphere. Then the mixture was concentrated under vacuum and the obtained residue was purified by silica gel chromatograph (DCM:MeOH=10:1) to give 2-[4-(3-bromo-pyridin-2-yloxy)-cyclohexyl]-1H-benzoimidazole (0.15 g, 0.403 mmol, 36% yield) as white solid.

Step 4. 2-{4-[3-(3,6-DIHYDRO-2H-PYRAN-4-YL)-PYRIDIN-2-YLOXY]-CYCLOHEXYL}-1H-BENZOIMIDAZOLE The mixture of 2-[4-(3-bromo-pyridin-2-yloxy)-cyclohexyl]-1H-benzoimidazole (0.15 g, 0.40 mmol), 4-(4,4,5,5-Tetramethyl-[1,3,2]dioxaborolan-2-yl)-3,6-dihydro-2H-pyran (0.09, 0.40 mmol), $Pd(dppf)Cl_2$, $Na_2CO_3$, dioxane and $H_2O$ was heated at 90° C. for 10 h under $N_2$ atmosphere. Then the mixture was concentrated and the obtained residue was purified by silica gel chromatography (DCM:MeOH=10:1) to give 2-{4-[3-(3,6-dihydro-2H-pyran-4-yl)-pyridin-2-yloxy]-cyclohexyl}-1H-benzoimidazole (0.10 g, 0.267 mmol, 75% yield) as light yellow oil.

Step 5. TRANS/CIS 2-{4-[3-(TETRAHYDRO-PYRAN-4-YL)-PYRIDIN-2-YLOXY]-CYCLOHEXYL}-1H-BENZOIMIDAZOLE The mixture of 2-{4-[3-(3,6-dihydro-2H-pyran-4-yl)-pyridin-2-yloxy]-cyclohexyl}-1H-benzoimidazole (0.15 g, 0.45 mmol), Pd/C (0.5 g) in MeOH (50 mL) was stirred under H$_2$ atmosphere at 40° C. for 24 h. Then the reaction mixture was filtrated and the filtrate was concentrated and purified by prep-HPLC to give trans-2-{4-[3-(Tetrahydro-pyran-4-yl)-pyridin-2-yloxy]-cyclohexyl}-1H-benzoimidazole (0.11 g, 0.292 mmol, 65% yield) and cis-2-{4-[3-(Tetrahydro-pyran-4-yl)-pyridin-2-yloxy]-cyclohexyl}-1H-benzoimidazole (0.1 g, 0.265 mmol, 60% yield) as white solid. [M+1] 378 each. IC50 (uM): (trans) 0.023 and (cis) 0.025.

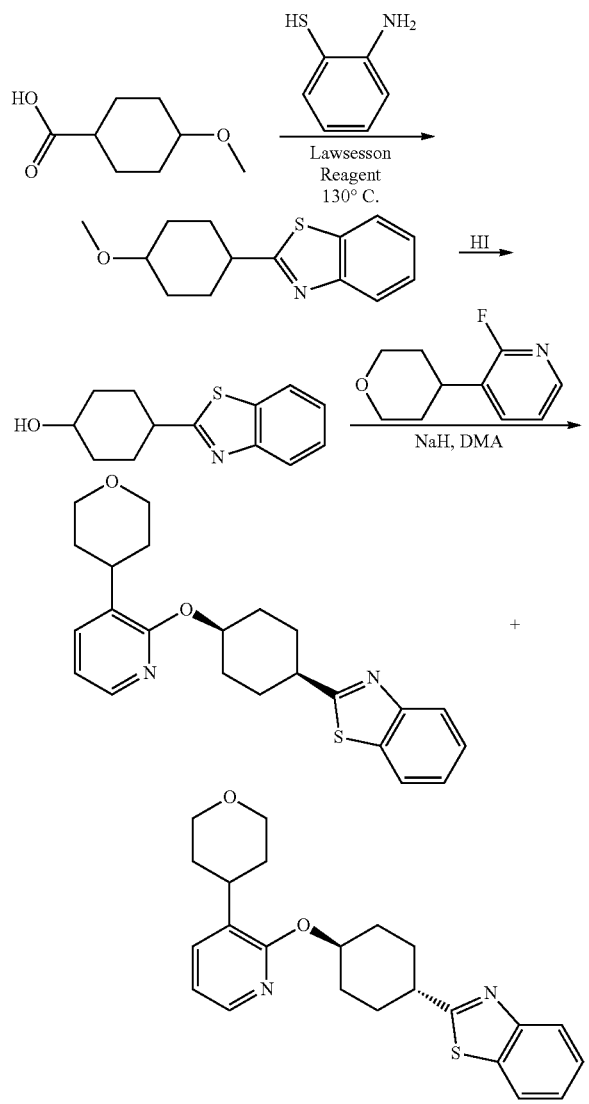

Example 2

TRANS/CIS 2-{4-[3-(TETRAHYDRO-PYRAN-4-YL)-PYRIDIN-2-YLOXY]-CYCLOHEXYL}-BENZOTHIAZOLE

Step 1.
2-(4-METHOXY-CYCLOHEXYL)-BENZOTHIAZOLE

A mixture of 2-amino-benzenethiol (796 mg, 6.32 mmol), 4-methoxy-cyclohexanecarboxylic acid (1.0 g, 6.32 mmol) and Lawesson reagent (889 mg, 2.2 mmol) was heated to 160~190° C. for 1 h. Then the mixture was diluted with DCM (100 ml) and washed with 10% aqueous NaOH solution (2×10 mL), brine, and dried over Na$_2$SO$_4$. The organic layer was concentrated and purified by flash column chromatography to give 2-(4-methoxy-cyclohexyl)-benzothiazole which was used in the next step without further purification.

Step 2.
4-BENZOTHIAZOL-2-YL-CYCLOHEXANOL

A solution of 2-(4-methoxy-cyclohexyl)-benzothiazole (1.2 g, 5.15 mmol) in HI (35%)(12 mL) was heated to 90° C. for 1 h. Then the reaction mixture was diluted with water (20 mL), extracted with EtOAc (2×) and the separated organic layer was washed with brine (2×), dried over Na$_2$SO$_4$, and concentrated to give the desired product (960 mg, 4.12 mmol, 85% yield) as brown solid.

Step 3. TRANS/CIS 2-{4-[3-(TETRAHYDRO-PYRAN-4-YL)-PYRIDIN-2-YLOXY]-CYCLOHEXYL}-BENZOTHIAZOLE A mixture of 2-fluoro-3-(tetrahydro-pyran-4-yl)-pyridine, as prepared in preparation 1a, (200 mg, 1.1 mmol), 4-benzothiazol-2-yl-cyclohexanol (257 mg, 1.1 mmol) and NaH (60%) (53 mg, 2.2 mmol) in DMA (4 mL) was heated to 120° C. for 2 h. Then the reaction mixture was diluted with water (10 mL) and extracted with EtOAc (3×15 mL), washed with brine, dried over Na$_2$SO$_4$. After concentration, the residue was purified by Prep-TLC and then Prep-HPLC to give trans-2-{4-[3-(Tetrahydro-pyran-4-yl)-pyridin-2-yloxy]-cyclohexyl}-benzothiazole (14 mg, 0.036 mmol, 3.2% yield) and cis-2-{4-[3-(Tetrahydro-pyran-4-yl)-pyridin-2-yloxy]-cyclohexyl}-benzothiazole (15 mg, 0.038 mmol, 3.5%). [M+1] 395 each. IC$_{50}$ (uM): (trans) 0.408 and (cis) 0.584.

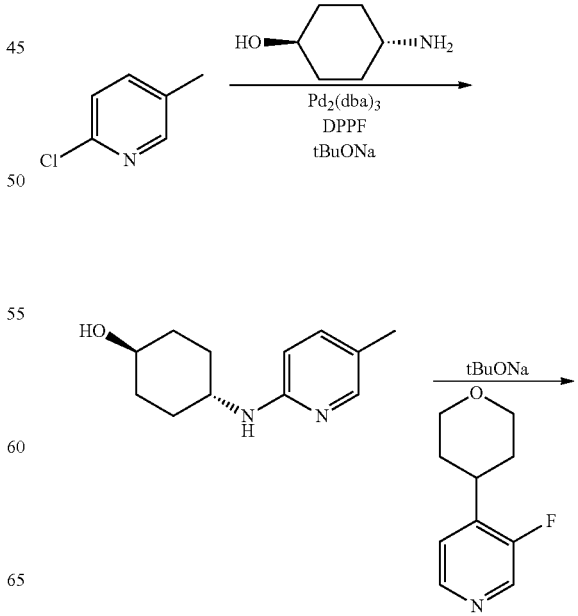

Example 3A

TRANS (5-METHYL-PYRIDIN-2-YL)-{4-[3-(TETRAHYDRO-PYRAN-4-YL)-PYRIDIN-2-YLOXY]-CYCLOHEXYL}-AMINE

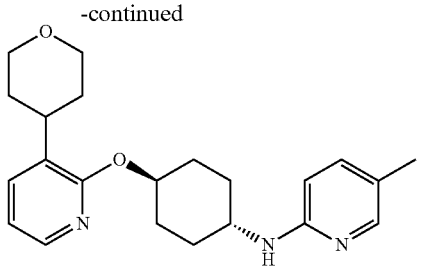

Step 1. Trans 4-(5-METHYL-PYRIDIN-2-YLAMINO)-CYCLOHEXANOL

A mixture of 2-Chloro-5-methyl-pyridine (0.1 g, 0.78 mmol), 4-amino-cyclohexanol (0.117 g, 0.78 mmol), $Pd_2(dba)_3$ (0.057 g, 0.0624 mmol), t-BuONa (0.262 g, 2.73 mmol) and Binap (0.076 g, 0.1248 mmol) in toluene (10 mL) was stirred at 85° C. until TLC analysis confirmed the absence of starting materials. Then the mixture was diluted with water (10 mL), and extracted with EtOAc (3×20 mL). The combined organic extracts were washed with water (5 mL) and brine (10 mL), dried over $Na_2SO_4$, and filtered. The filtrate was evaporated in vacuo and the residue was purified by column chromatography (EtOAc:Petrol ether=1:2) to provide 4-(5-methyl-pyridin-2-ylamino)-cyclohexanol (0.06 g, yield 60%) as a solid.

Step 2. Trans (5-METHYL-PYRIDIN-2-YL)-{4-[3-(TETRAHYDRO-PYRAN-4-YL)-PYRIDIN-2-YLOXY]-CYCLOHEXYL}-AMINE 4-(5-methyl-pyridin-2-ylamino)-cyclohexanol (50 mg) was added to a solution of 2-fluoro-3-(tetrahydro-pyran-4-yl)-pyridine, as prepared in preparation 1a, (50 mg) in DMSO (15 mL) and the reaction mixture was stirred until TLC analysis confirmed the absence of starting materials. Then the mixture was diluted with water (10 mL), and extracted with EtOAc (3×20 mL). The combined organic extracts were washed with water (5 mL) and brine (10 mL), dried over $Na_2SO_4$, and filtered. The filtrate was evaporated in vacuo and the residue was purified by column chromatography (EtOAc:Petrol ether=1:1) to provide (5-methyl-pyridin-2-yl)-{4-[3-(tetrahydro-pyran-4-yl)-pyridin-2-yloxy]-cyclohexyl}-amine (0.03 g, yield 60%) as a solid. [M+1] 368. $IC_{50}$ (uM): 0.057.

Examples 3B and 3C

N-(TRANS-4-(3-(3,6-DIHYDRO-2H-PYRAN-4-YL)PYRIDIN-2-YLOXY)CYCLOHEXYL)BENZO[D]THIAZOL-2-AMINE AND N-(TRANS-4-(3-(3,4-DIHYDRO-2H-PYRAN-4-YL)PYRIDIN-2-YLOXY)CYCLOHEXYL)BENZO[D]THIAZOL-2-AMINE

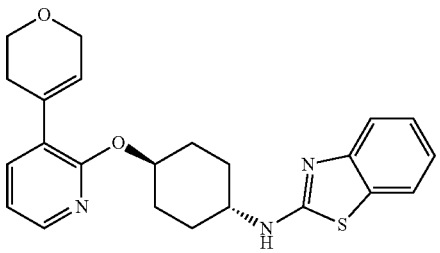

and

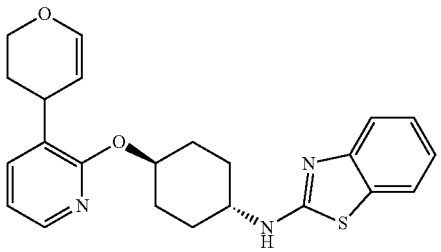

Step 1. N-(TRANS-4-(3-(3,6-DIHYDRO-2H-PYRAN-4-YL)PYRIDIN-2-YLOXY)CYCLOHEXYL)BENZO[D]THIAZOL-2-AMINE AND N-(TRANS-4-(3-(3,4-DIHYDRO-2H-PYRAN-4-YL)PYRIDIN-2-YLOXY)CYCLOHEXYL)BENZO[D]THIAZOL-2-AMINE Sodium hydride (0.054 g, 1.3 mmol, 60% dispersion in mineral oil) was added to a mixture of trans-4-(benzo[d]thiazol-2-ylamino)cyclohexanol (0.17 g, 0.67 mmol) in NMP (1.5 mL) in a microwave tube. The tube was sealed and placed under an argon atmosphere. The mixture was stirred at RT for 45 min before 3-(3,6-dihydro-2H-pyran-4-yl)-2-fluoropyridine, as prepared in preparation 1a, step 1, (0.10 g, 0.56 mmol) was added via syringe. The reaction mixture was warmed to 120° C. and stirred for 1 h. Water was added, and the aqueous mixture was extracted with EtOAc (2×). The organic extracts were combined, washed with saturated sodium chloride, dried over magnesium sulfate, filtered, and concentrated. The resulting crude product was purified via silica gel chromatography to give both N-(trans-4-(3-(3,6-dihydro-2H-pyran-4-yl)pyridin-2-yloxy)cyclohexyl)benzo[c/]thiazol-2-amine and N-(trans-4-(3-(3,4-dihydro-2H-pyran-4-yl)pyridin-2-yloxy)cyclohexyl)benzo[d]thiazol-2-amine as white solids. [M+1] 408.1 each. $IC_{50}$ (uM): 0.007281 (Example 3b) and 0.9154 (Example 3c).

SCHEME 4

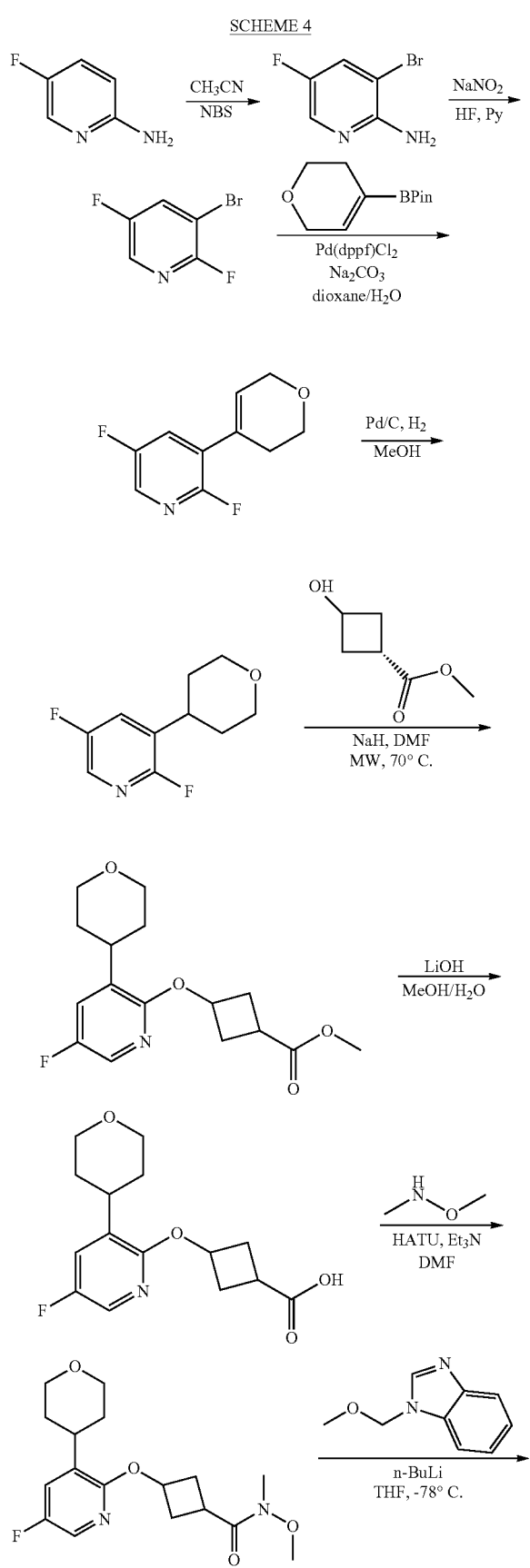

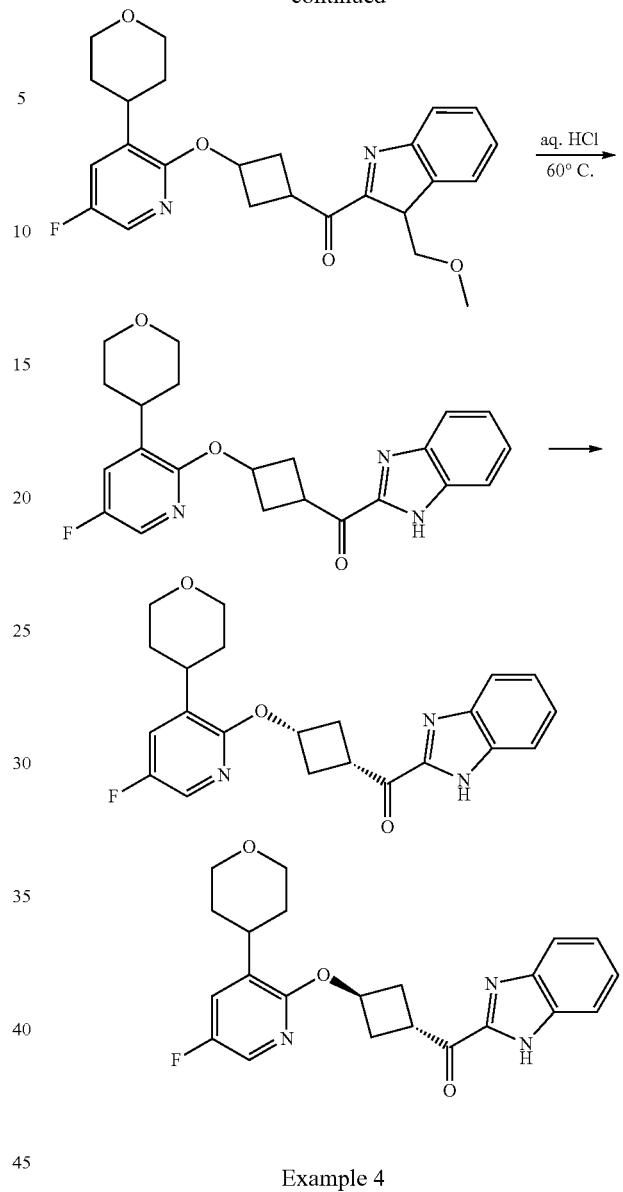

Example 4

TRANS/CIS-(1H-BENZOIMIDAZOL-2-YL)-{3-[5-FLUORO-3-(TETRAHYDRO-PYRAN-4-YL)-PYRIDIN-2-YLOXY]-CYCLOBUTYL}-METHANONE

Step 1.
3-BROMO-5-FLUORO-PYRIDIN-2-YLAMINE

NBS (10 g, 56.2 mmol) was added slowly to a solution of 5-fluoro-pyridin-2-ylamine (12.4 g, 56.2 mmol) in MeCN (200 mL). The reaction mixture was stirred at RT overnight. After completion, the solution was filtered and the filtrate was concentrated to get a residue, which was purified by silica gel chromatography to give the product (5.2 g, 31%) as a yellow solid.

Step 2. 3-BROMO-2,5-DIFLUORO-PYRIDINE

NaNO₂ (1.4 g, 14.4 mmol) was added in portions to a solution of 3-bromo-5-fluoro-pyridin-2-ylamine (5.2 g, 17.3 mmol) in a HF/pyridine mixture (40 mL) in a polyethylene reaction vessel. The resulting mixture was stirred at 0° C. for 0.5 h, then heated to 50° C. and stirred for 1 h. The reaction mixture was poured onto crushed ice, partially neutralized with $Na_2CO_3$, and extracted with EtOAc. The organic phase was washed with brine, dried over $Na_2SO_4$, filtered and concentrated to give the product (4.1 g, 68%) as a white solid.

Step 3. 3-(3,6-DIHYDRO-2H-PYRAN-4-YL)-2,5-DIFLUORO-PYRIDINE

To a solution of 3-bromo-2,5-difluoro-pyridine (4.1 g, 20.8 mmol) in dioxane (60 mL) was treated with $Na_2CO_3$ (4.4 g, 41.6 mmol) in 20 mL of $H_2O$ as a solution, followed by additional of 4-(4,4,5,5-Tetramethyl-[1,3,2]dioxaborolan-2-yl)-3,6-dihydro-2H-pyran (4.8 g 22.9 mmol) and Pd(dppf)$Cl_2$ (761 mg). The resulting mixture was heated at refluxing overnight under $N_2$ atmosphere. TLC showed that most of the staring materials were consumed. The solution was filtered and the filtrate was concentrated to get a residue, which was purified by silica gel chromatography to give the product (3.7 g).

Step 4. 2,5-DIFLUORO-3-(TETRAHYDRO-PYRAN-4-YL)-PYRIDINE

To a solution of 3-(3,6-dihydro-2H-pyran-4-yl)-2,5-difluoro-pyridine (3.7 g, 18.8 mmol) in MeOH (40 mL) was added Pd/C (1.0 g). The reaction solution was stirred at RT overnight under $H_2$ atmosphere until LCMS showed that the starting material was consumed completely. The mixture was filtered and the filtrate was concentrated to give the product (2.9 g, 78%).

Step 5. 3-[5-FLUORO-3-(TETRAHYDRO-PYRAN-4-YL)-PYRIDIN-2-YLOXY]-CYCLOBUTAN-ECARBOXYLIC ACID METHYL ESTER To a solution of methyl 3-hydroxycyclobutanecarboxylate (1.2 g, 9.0 mmol) in DMF (20 mL) was added sodium hydride (60% wt in mineral oil) (1.8 g, 45 mmol) at RT. The mixture was stirred for 1 h and then 2,5-difluoro-3-(tetrahydro-pyran-4-yl)-pyridine (1.8 g, 9.0 mmol) was added. The reaction mixture was heated to 60° C. for 3 h and then quenched with saturated $NH_4Cl$. The solution was diluted with EtOAc and water and extracted with EtOAc (2×10 mL). The organic extracts were combined, washed with brine (10 mL), dried over $MgSO_4$, filtered, and concentrated to get a residue, which was purified by flash column chromatography on silica gel (5% to 30% EtOAc in hexanes) to give the product (3.2 g) as yellow oil.

Step 6. 3-[5-FLUORO-3-(TETRAHYDRO-PYRAN-4-YL)-PYRIDIN-2-YLOXY]-CYCLOBUTAN-ECARBOXYLIC ACID To a solution of 3-[5-fluoro-3-(tetrahydro-pyran-4-yl)-pyridin-2-yloxy]-cyclobutanecarboxylic acid methyl ester (3.2 g) in MeOH (60 mL) and water (15 mL) at RT was added lithium hydroxide (1.0 g, 41.6 mmol). The reaction mixture was heated to 50° C. for 2 h and then additional LiOH (400 mg) was added. Stirring was continued at 50° C. for 1 h. The reaction was neutralized with 5 M HCl and concentrated. The concentrated solution was extracted with EtOAc (50 mL) and the organic layer was washed with water (10 mL), brine (10 mL), dried over $MgSO_4$ and concentrated to give the product (1.5 g), which was used in the next step without further purification.

Step 7. 3-[5-FLUORO-3-(TETRAHYDRO-PYRAN-4-YL)-PYRIDIN-2-YLOXY]-CYCLOBUTAN-ECARBOXYLIC ACID METHOXY-METHYL-AMIDE To a solution of 3-[5-fluoro-3-(tetrahydro-pyran-4-yl)-pyridin-2-yloxy]-cyclobutanecarboxylic acid (1.5 g, 4.68 mmol) was added DMF (20 mL), triethylamine (1 mL, 7.02 mmol), and 2-(1H-benzo[d][1,2,3]triazol-1-yl)-1,1,3,3-tetramethylisouronium hexafluorophosphate(V) (2.24 g, 5.90 mmol). The reaction mixture was stirred at RT for 1d. Then it was diluted with water and EtOAc. The organic layer was separated and the aqueous phase was extracted with EtOAc (2×10 mL). All the organic layers were combined and washed with brine (1×10 mL), dried over $MgSO_4$, filtered, and concentrated to get a crude, which was purified by flash column chromatography on silica gel (30% to 70% EtOAc in hexanes) to give the product (2.2 g) as yellow oil.

Step 8. {3-[5-FLUORO-3-(TETRAHYDRO-PYRAN-4-YL)-PYRIDIN-2-YLOXY]-CYCLOBUTYL}-(1-METHOXYMETHYL-1H-BENZOIMI-DAZOL-2-YL)-METHANONE To a solution of 1-(methoxymethyl)-1H-benzo[d]imidazole (1.5 g, 9.04 mmol) in THF (20 mL) at −78° C. was added butyllithium (2.5 M in hexane) (3.7 mL, 9.16 mmol). The solution was stirred at −78° C. for 30 min and a solution of 3-[5-fluoro-3-(tetrahydro-pyran-4-yl)-pyridin-2-yloxy]-cyclobutanecarboxylic acid methoxy-methyl-amide (2.2 g, 6.87 mmol) in THF (20 mL) was added dropwise via cannula. The reaction mixture was stirred at −78° C. for 30 min and then warmed to RT and quenched with water. The reaction mixture was extracted with EtOAc (3×25 mL) and the organic phases were combined and washed with water (1×10 mL), brine (1×10 mL), dried over $MgSO_4$, filtered, and concentrated to get a residue, which was purified by flash column chromatography on silica gel (10% to 60% EtOAc in hexanes) to give the product (1.2 g) as yellow oil.

Step 9. TRANS/CIS-(1H-BENZOIMIDAZOL-2-YL)-{3-[5-FLUORO-3-(TETRAHYDRO-PYRAN-4-YL)-PYRIDIN-2-YLOXY]-CYCLOBUTYL}-METHANONE To a solution of {3-[5-fluoro-3-(tetrahydro-pyran-4-yl)-pyridin-2-yloxy]-cyclobutyl}-(1-methoxymethyl-1H-benzoimidazol-2-yl)-methanone (1.2 g) in THF (20 mL) at RT was added concentrated HCl (20 mL). The reaction mixture was stirred at RT for 1 h and then heated to 60° C. for 6 h. The mixture was partially concentrated, neutralized with saturated $NaHCO_3$ and diluted with EtOAc. The aqueous phase was extracted with EtOAc (2×10 mL) and the combined organic extracts were washed with brine (10 mL), dried over $MgSO_4$, filtered, and concentrated to get a residue, which was purified by flash column chromatography on silica gel (5% to 30% EtOAc in DCM) gave cis-(1H-benzoimidazol-2-yl)-{3-[5-fluoro-3-(tetrahydro-pyran-4-yl)-pyridin-2-yloxy]-cyclobutyl}-methanone and trans-(1H-benzoimidazol-2-yl)-{3-[5-fluoro-3-(tetrahydro-pyran-4-yl)-pyridin-2-yloxy]-cyclobutyl}-methanone (196 mg) as white solid. [M+1] 396 each. $IC_{50}$ (uM) 0.00003 (cis) and 0.0005 (trans).

SCHEME 5A

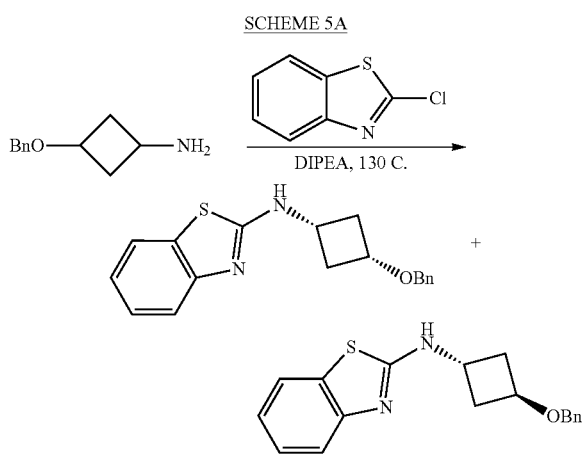

SCHEME 5B

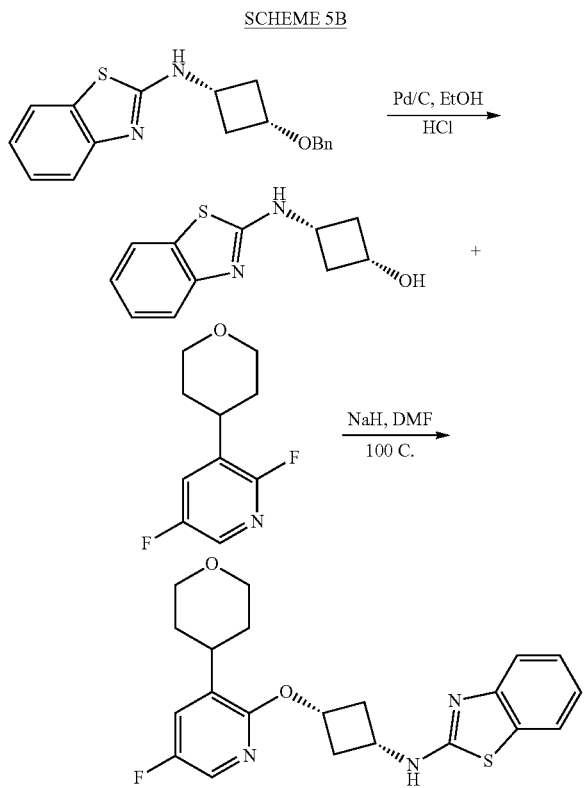

Example 5A

Cis-BENZOTHIAZOL-2-YL-{3-[5-FLUORO-3-(TETRAHYDRO-PYRAN-4-YL)-PYRIDIN-2-YL]-CYCLOBUTYL}-AMINE

Step 1. TRANS/CIS BENZOTHIAZOL-2-YL-(3-BENZYLOXY-CYCLOBUTYL)-AMINE

A mixture of N-ethyl-N-isopropylpropan-2-amine (3 g, 24 mmol), 2-chlorobenzo[d]thiazole (2.0 g, 12 mmol), and 3-benzyloxy-cyclobutylamine (2.08 g, 12 mmol) in DMA (20 mL) was heated to 130° C. for 20 h. Then it was cooled to RT and diluted with EtOAc (50 mL). The mixture was washed with water (2×25 mL), brine (25 mL), dried over MgSO$_4$, filtered, and concentrated in vacuo to give an oil. The oil was purified by silica gel chromatography (0 to 30% EtOAc/hexane gradient) to give two products as a white solid.

Top spot on TLC is cis stereoeisomer according to NOESY. LC-MS (102289-80-1X). ESI-MS (M+1) 311, calc. for $C_{18}H_{18}N_2OS$ MW: 310; (102289-80-1) $^1$H NMR (CD$_3$OD, 400 MHz): δ (ppm) 7.57 (t, 2H, J=8.4 Hz), 7.34-7.26 (m, 6H), 7.08 (t, 1H, J=7.2 Hz), 6.06 (s, 1H), 4.44 (s, 2H), 3.88-3.81 (m, 2H), 2.90 (d, 2H, J=5.2 Hz), 2.01 (d, 2H, J=7.2 Hz).

Bottom spot on TLC is trans stereoeisomer according to NOESY. LC-MS (102289-80-1X) ESI-MS (M+1) 311, calc. for $C_{18}H_{18}N_2OS$ MW: 310; (102289-80-2) $^1$H NMR (CD$_3$OD, 400 MHz): δ (ppm) 7.52 (d, 1H, J=8.0 Hz), 7.45 (d, 1H, J=8.0 Hz), 7.29-7.17 (m, 6H), 7.01 (t, 1H, J=6.4 Hz), 6.22 (br, 1H), 4.35 (s, 2H), 4.21-4.16 (m, 2H), 2.53-2.47 (m, 2H), 2.25-2.19 (m, 2H).

Step 2. Cis-3-(BENZOTHIAZOL-2-YLAMINO)-CYCLOBUTANOL

A mixture of hydrogen chloride (5-6 N) in isopropyl alcohol (5 mL, 25 mmol), cis-benzothiazol-2-yl-(3-benzyloxy-cyclobutyl)-amine (500 mg, 1.6 mmol), and palladium black (250 mg, 50% wt percent) in EtOH (20 mL) under hydrogen atmosphere (balloon) was heated to 70° C. for 20 h. Then it was cooled to RT and solid NaHCO$_3$ (500 mg) was added. The mixture was stirred until gas evolution ceased. The palladium was filtered off using Celite® and the filtrate was concentrated in vacuo to give oil (400 mg), which was used for next step without further purification.

Step 3. CIS-BENZOTHIAZOL-2-YL-{3-[5-FLUORO-3-(TETRAHYDRO-PYRAN-4-YL)-PYRIDIN-2-YL]-CYCLOBUTYL}-AMINE Sodium hydride (81.8 mg, 2.0 mmol) was added to a solution of cis-3-(benzothiazol-2-ylamino)-cyclobutanol (150 mg, 0.68 mmol) in DMF (3 mL) under argon and the mixture was stirred for 1 h at RT. Then 2,5-difluoro-3-(tetrahydro-pyran-4-yl)-pyridine, as prepared in Example 4, steps 1-4, (162 mg, 0.82 mmol) was added and the resulting mixture was heated to 100° C. for 2 h. It was cooled to RT and EtOAc and saturated NH$_4$Cl were added. The organic layer was separated, washed with water (2×25 mL), brine (25 mL), dried over MgSO$_4$, filtered and concentrated in vacuo to give oil, which was purified by prep-HPLC to give product (20 mg). [M+1] 400. IC$_{50}$ (uM) 0.0002.

Example 5B

TRANS-BENZOTHIAZOL-2-YL-{3-[5-FLUORO-3-(TETRAHYDRO-PYRAN-4-YL)-PYRIDIN-2-YL]-CYCLOBUTYL}-AMINE

Step 1. Trans-3-(BENZOTHIAZOL-2-YLAMINO)-CYCLOBUTANOL

A mixture of hydrogen chloride (5-6N) in isopropyl alcohol (5 mL, 25 mmol), trans-benzothiazol-2-yl-(3-benzyloxy-cyclobutyl)amine (500 mg, 1.6 mmol), and palladium black (250 mg, 50% wt percent) in EtOH (20 mL) under hydrogen atmosphere (balloon) was heated to 70° C. for 20 h. Then it was cooled to RT and solid NaHCO$_3$ (500 mg) was added. The mixture was stirred until gas evolution ceased. The palladium was filtered off using Celite® and the filtrate was concentrated in vacuo to give an oil (400 mg), which was used to next step without further purification.

Step 2. Trans-BENZOTHIAZOL-2-YL-{3-[5-FLUORO-3-(TETRAHYDRO-PYRAN-4-YL)-PYRIDIN-2-YL]-CYCLOBUTYL}-AMINE Sodium hydride (81.8 mg, 2.0 mmol) was added to a solution of cis-3-(benzothiazol-2-ylamino)-cyclobutanol (150 mg, 0.68 mmol) in DMF (3 mL) under argon and the mixture was stirred for 1 h at RT. Then 2,5-difluoro-3-(tetrahydro-pyran-4-yl)-pyridine (162 mg, 0.82 mmol) was added and the mixture was heated to 100° C. for 2 h. It was cooled to RT and EtOAc (25 mL) and saturated $NH_4Cl$ (15 mL) were added. The organic layer was separated, washed with water (2×25 mL), brine (25 mL), dried over $MgSO_4$, filtered and concentrated in vacuo to give an oil, which was purified by prep-HPLC to give trans-benzothiazol-2-yl-{3-[5-fluoro-3-(tetrahydro-pyran-4-yl)-pyridin-2-yl]-cyclobutyl}-amine (30 mg, yield 10%). [M+1] 400. $IC_{50}$ (uM) 0.0001.

TABLE 1A

EXAMPLES 6-26 PREPARED ANALOGOUS TO SCHEMES 3-5.

| Example No. | Chemical Structure | Chemical Name | M + 1 | $IC_{50}$ (uM) |
|---|---|---|---|---|
| 6 | 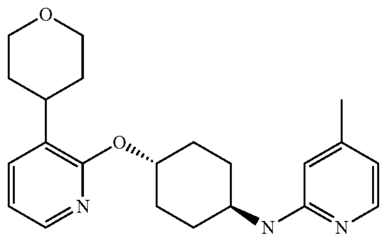 [SMILES: Cc1ccnc(N[C@H]2CC[C@H](Oc3ncccc3C3CCOCC3)CC2)c1] | (4-methyl-pyridin-2-yl)-{4-[3-(tetrahydro-pyran-4-yl)-pyridin-2-yloxy]-cyclohexyl}-amine | 368 | 0.150 |
| 7 | 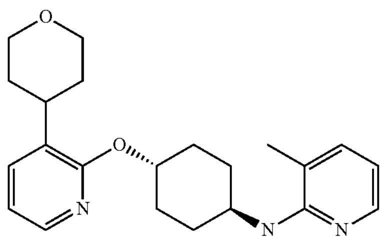 [SMILES: Cc1cccnc1N[C@H]1CC[C@H](Oc2ncccc2C2CCOCC2)CC1] | (3-methyl-pyridin-2-yl)-{4-[3-(tetrahydro-pyran-4-yl)-pyridin-2-yloxy]-cyclohexyl}-amine | 368 | 0.046 |
| 8 | 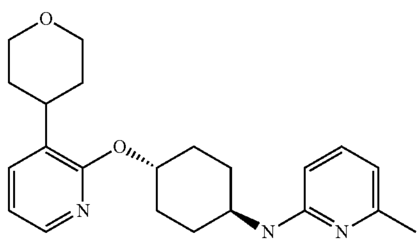 [SMILES: Cc1cccc(N[C@H]2CC[C@H](Oc3ncccc3C3CCOCC3)CC2)n1] | (6-methyl-pyridin-2-yl)-{4-[3-(tetrahydro-pyran-4-yl)-pyridin-2-yloxy]-cyclohexyl}-amine | 368 | 1.75 |
| 9 | 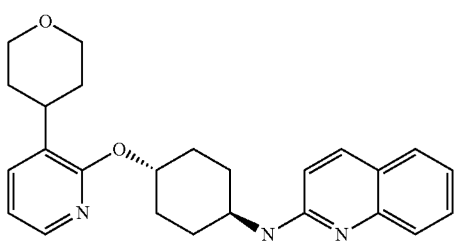 [SMILES: c1cnc(O[C@H]2CC[C@H](Nc3ccc4ccccc4n3)CC2)c(C2CCOCC2)c1] | Quinolin-2-yl-{4-[3-(tetrahydro-pyran-4-yl)-pyridin-2-yloxy]-cyclohexyl}-amine | 404 | 0.091 |
| 10 | 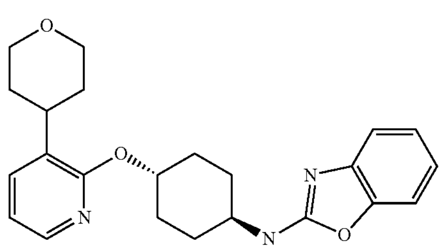 [SMILES: c1cnc(O[C@H]2CC[C@H](Nc3nc4ccccc4o3)CC2)c(C2CCOCC2)c1] | Benzooxazol-2-yl-{4-[3-(tetrahydro-pyran-4-yl)-pyridin-2-yloxy]-cyclohexyl}-amine | 394 | 0.012 |

TABLE 1A-continued

EXAMPLES 6-26 PREPARED ANALOGOUS TO SCHEMES 3-5.

| Example No. | Chemical Structure | Chemical Name | M + 1 | IC$_{50}$ (uM) |
|---|---|---|---|---|
| 11 | 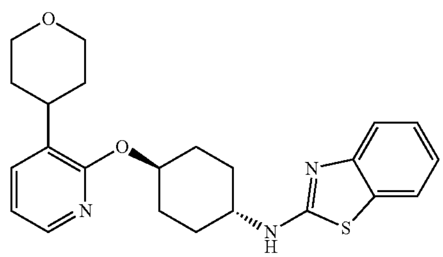 [SMILES: c1cnc(O[C@H]2CC[C@H](Nc3nc4ccccc4s3)CC2)c(C2CCOCC2)c1] | N-(trans-4-(3-(tetrahydro-2H-pyran-4-yl)pyridin-2-yloxy)cyclohexyl)benzo[d]thiazol-2-amine | 410.1 | 0.03252 |
| 12 | 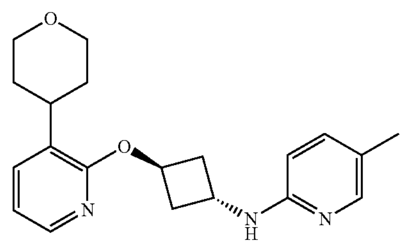 [SMILES: Cc1ccc(N[C@H]2C[C@H](Oc3ncccc3C3CCOCC3)C2)nc1] | 5-methyl-N-(trans-3-(3-(tetrahydro-2H-pyran-4-yl)pyridin-2-yloxy)cyclobutyl)pyridin-2-amine | 340.2 | 0.01763 |
| 13 | 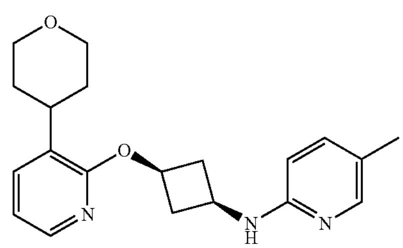 [SMILES: Cc1ccc(N[C@H]2C[C@@H](Oc3ncccc3C3CCOCC3)C2)nc1] | 5-methyl-N-(cis-3-(3-(tetrahydro-2H-pyran-4-yl)pyridin-2-yloxy)cyclobutyl)pyridin-2-amine | 340.2 | 0.008249 |
| 14 | 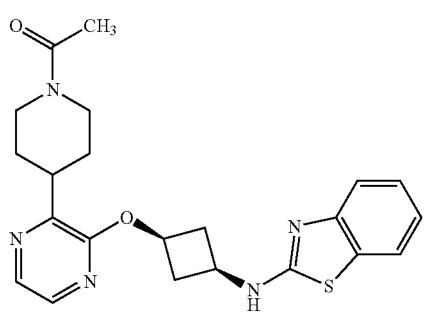 [SMILES: CC(=O)N1CCC(c2nccnc2O[C@H]2C[C@@H](Nc3nc4ccccc4s3)C2)CC1] | 1-(4-(3-(cis-3-(benzo[d]thiazol-2-ylamino)cyclobutoxy)pyrazin-2-yl)piperidin-1-yl)ethanone | 424.0 | 0.002766 |
| 15 | 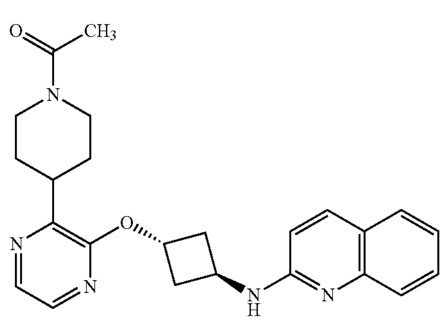 [SMILES: CC(=O)N1CCC(c2nccnc2O[C@H]2C[C@H](Nc3ccc4ccccc4n3)C2)CC1] | 1-(4-(3-(trans-3-(quinolin-2-ylamino)cyclobutoxy)pyrazin-2-yl)piperidin-1-yl)ethanone | 418.0 | 0.01582 |

TABLE 1A-continued

EXAMPLES 6-26 PREPARED ANALOGOUS TO SCHEMES 3-5.

| Example No. | Chemical Structure | Chemical Name | M + 1 | IC$_{50}$ (uM) |
|---|---|---|---|---|
| 16 | 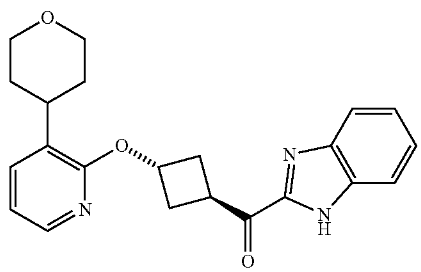 | (1H-benzo[d]imidazol-2-yl)(trans-3-(3-(tetrahydro-2H-pyran-4-yl)pyridin-2-yloxy)cyclobutyl)methanone | 378 | 0.007153 |
| 17 | 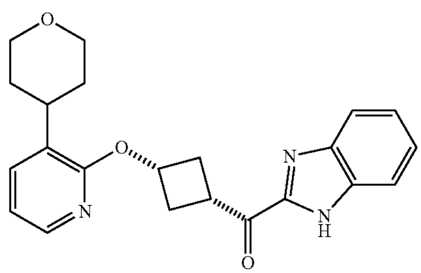 | (1H-benzo[d]imidazol-2-yl)(cis-3-(3-(tetrahydro-2H-pyran-4-yl)pyridin-2-yloxy)cyclobutyl)methanone | 378 | 0.000413 |
| 18 | 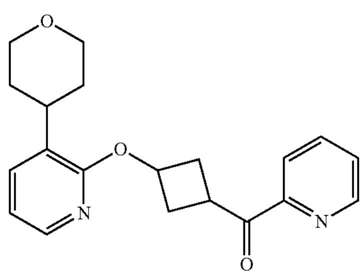 [SMILES: O=C(c1ccccn1)C1CC(Oc2ncccc2C2CCOCC2)C1] | pyridin-2-yl(3-(3-(tetrahydro-2H-pyran-4-yl)pyridin-2-yloxy)cyclobutyl)methanone | 339 | 0.2496 |
| 19 | 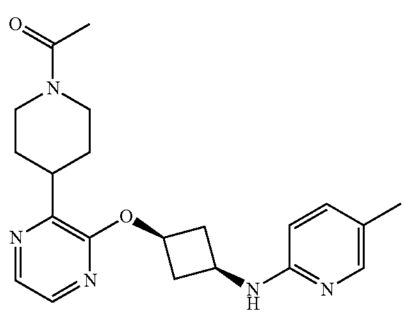 [SMILES: CC(=O)N1CCC(c2nccnc2O[C@H]2C[C@@H](Nc3ccc(C)cn3)C2)CC1] | 1-(4-(3-(cis-3-(5-methylpyridin-2-ylamino)cyclobutoxy)pyrazin-2-yl)piperidin-1-yl)ethanone | 382 | 0.06606 |
| 20 | 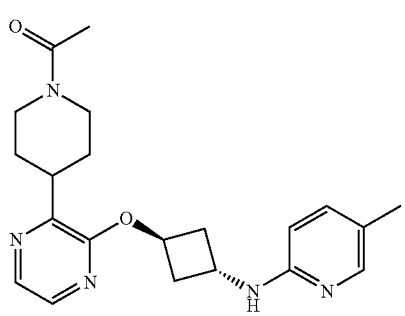 [SMILES: CC(=O)N1CCC(c2nccnc2O[C@H]2C[C@H](Nc3ccc(C)cn3)C2)CC1] | 1-(4-(3-(trans-3-(5-methylpyridin-2-ylamino)cyclobutoxy)pyrazin-2-yl)piperidin-1-yl)ethanone | 382 | 0.08455 |

TABLE 1A-continued

EXAMPLES 6-26 PREPARED ANALOGOUS TO SCHEMES 3-5.

| Example No. | Chemical Structure | Chemical Name | M + 1 | IC$_{50}$ (uM) |
|---|---|---|---|---|
| 21 | 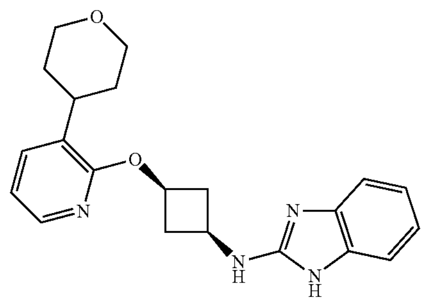 [SMILES: c1cnc(O[C@H]2C[C@@H](Nc3nc4ccccc4[nH]3)C2)c(C2CCOCC2)c1] | N-(cis-3-(3-(tetrahydro-2H-pyran-4-yl)pyridin-2-yloxy)cyclobutyl)-1H-benzo[d]imidazol-2-amine | 365 | 0.001529 |
| 22 | 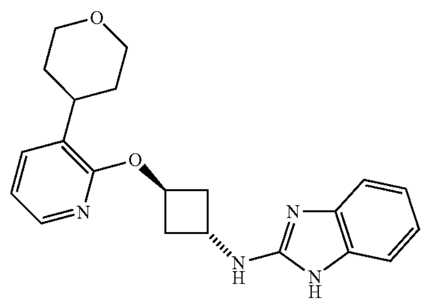 [SMILES: c1cnc(O[C@H]2C[C@H](Nc3nc4ccccc4[nH]3)C2)c(C2CCOCC2)c1] | N-(trans-3-(3-(tetrahydro-2H-pyran-4-yl)pyridin-2-yloxy)cyclobutyl)-1H-benzo[d]imidazol-2-amine | 365 | 0.002627 |
| 23 | 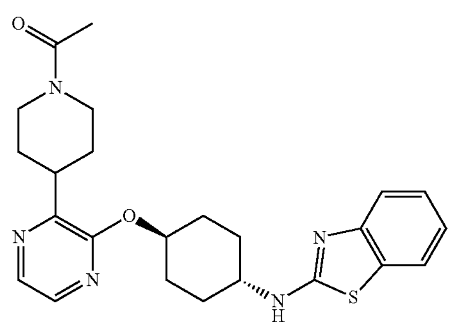 [SMILES: CC(=O)N1CCC(c2nccnc2O[C@H]2CC[C@H](Nc3nc4ccccc4s3)CC2)CC1] | 1-(4-(3-(trans-4-(benzo[d]thiazol-2-ylamino)cyclohexyloxy)pyrazin-2-yl)piperidin-1-yl)ethanone | 452.3 | 0.04551 |
| 24 | 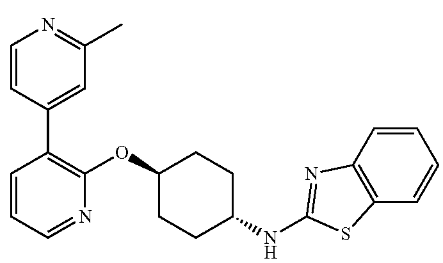 [SMILES: Cc1cc(-c2cccnc2O[C@H]2CC[C@H](Nc3nc4ccccc4s3)CC2)ccn1] | N-(trans-4-(2'-methyl-3,4'-bipyridin-2-yloxy)cyclohexyl)benzo[d]thiazol-2-amine | 417.2 | 0.01961 |
| 25 | 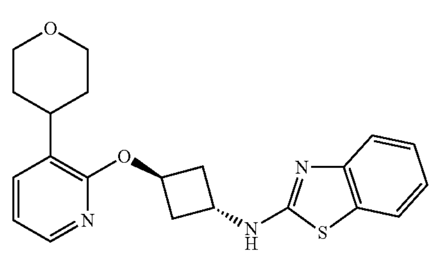 [SMILES: c1cnc(O[C@H]2C[C@H](Nc3nc4ccccc4s3)C2)c(C2CCOCC2)c1] | N-(trans-3-(3-(tetrahydro-2H-pyran-4-yl)pyridin-2-yloxy)cyclobutyl)benzo[d]thiazol-2-amine | 382.2 | 0.003195 |

TABLE 1A-continued

EXAMPLES 6-26 PREPARED ANALOGOUS TO SCHEMES 3-5.

| Example No. | Chemical Structure | Chemical Name | M + 1 | IC$_{50}$ (uM) |
|---|---|---|---|---|
| 26 | 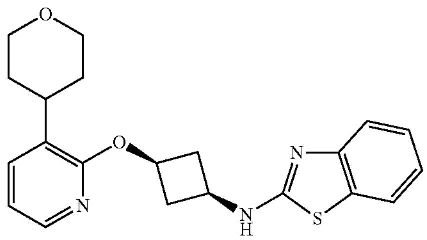 [SMILES: c1cnc(O[C@H]2C[C@@H](Nc3nc4ccccc4s3)C2)c(C2CCOCC2)c1] | N-(cis-3-(3-(tetrahydro-2H-pyran-4-yl)pyridin-2-yloxy)cyclobutyl)benzo[d]thiazol-2-amine | 382.2 | 0.000751 |

TABLE 1B

STARTING MATERIALS AND CONDITIONS USED IN PREPARATION AND NMR DATA OF EXAMPLES 6-26.

| Example No. | Scheme | Starting Material 1 | Starting Material 2 | Principle reagents and solvents |
|---|---|---|---|---|
| 6 | 3 | | | t-BuONa, DMSO |
| 7 | 3 | | | t-BuONa, DMSO |
| 8 | 3 | | | t-BuONa, DMSO |
| 9 | 3 | | | t-BuONa, DMSO |
| 10 | 3 | | | t-BuONa, DMSO |
| 11 | 3 | | | NaH, NMP, 60° C. |

TABLE 1B-continued

STARTING MATERIALS AND CONDITIONS USED IN PREPARATION AND NMR DATA OF EXAMPLES 6-26.

| Example No. | Scheme | Starting Material 1 | Starting Material 2 | Principle reagents and solvents |
|---|---|---|---|---|
| 12 | 5 | | | NaH, DMF |
| 13 | 5 | | | NaH, DMF |
| 14 | 5 | | | |
| 15 | 5 | | | |
| 16 | 4 | | | n-BuLi |

US 8,952,037 B2

97 98

TABLE 1B-continued

STARTING MATERIALS AND CONDITIONS USED IN PREPARATION AND NMR DATA OF EXAMPLES 6-26.

| Example No. | Scheme | Starting Material 1 | Starting Material 2 | Principle reagents and solvents |
|---|---|---|---|---|
| 17 | 4 | (tetrahydropyran-4-yl)pyridin-3-yl oxy cyclobutane N-methoxy-N-methyl carboxamide | 1-(methoxymethyl)-1H-benzimidazole | n-BuLi |
| 18 | 4 | (tetrahydropyran-4-yl)pyridin-3-yl oxy cyclobutane N-methoxy-N-methyl carboxamide | 2-bromopyridine | n-BuLi |
| 19 | 5 | trans-3-(5-methylpyridin-2-ylamino)cyclobutanol | 1-(4-(3-chloropyrazin-2-yl)piperidin-1-yl)ethanone | NaH, DMF |
| 20 | 5 | cis-3-(5-methylpyridin-2-ylamino)cyclobutanol | 1-(4-(3-chloropyrazin-2-yl)piperidin-1-yl)ethanone | NaH, DMF |
| 21 | 5 | 3-(1H-benzimidazol-2-ylamino)cyclobutanol | 2-fluoro-3-(tetrahydropyran-4-yl)pyridine | NaH, DMF |

TABLE 1B-continued

STARTING MATERIALS AND CONDITIONS USED IN PREPARATION AND NMR DATA OF EXAMPLES 6-26.

| Example No. | Scheme | Starting Material 1 | Starting Material 2 | Principle reagents and solvents |
|---|---|---|---|---|
| 22 | 5 | (HO-cyclobutyl-NH-benzimidazol-2-yl) | (2-fluoropyridin-3-yl)-tetrahydropyran | NaH, DMF |
| 23 | 3 | (trans-4-hydroxycyclohexyl-NH-benzothiazol-2-yl) | 1-acetyl-4-(3-chloropyrazin-2-yl)piperidine | NaH, DMF |
| 24 | 5 | (trans-4-hydroxycyclohexyl-NH-benzothiazol-2-yl) | 4-(2-fluoro-6-methylpyridin-3-yl)pyridine | NaH, DMF |
| 25 | 5 | (cis-3-hydroxycyclobutyl-NH-benzothiazol-2-yl) | 4-(2-fluoropyridin-3-yl)tetrahydropyran | NaH, DMF |
| 26 | 5 | (trans-3-hydroxycyclobutyl-NH-benzothiazol-2-yl) | 4-(2-fluoropyridin-3-yl)tetrahydropyran | NaH, DMF |

SCHEME 6

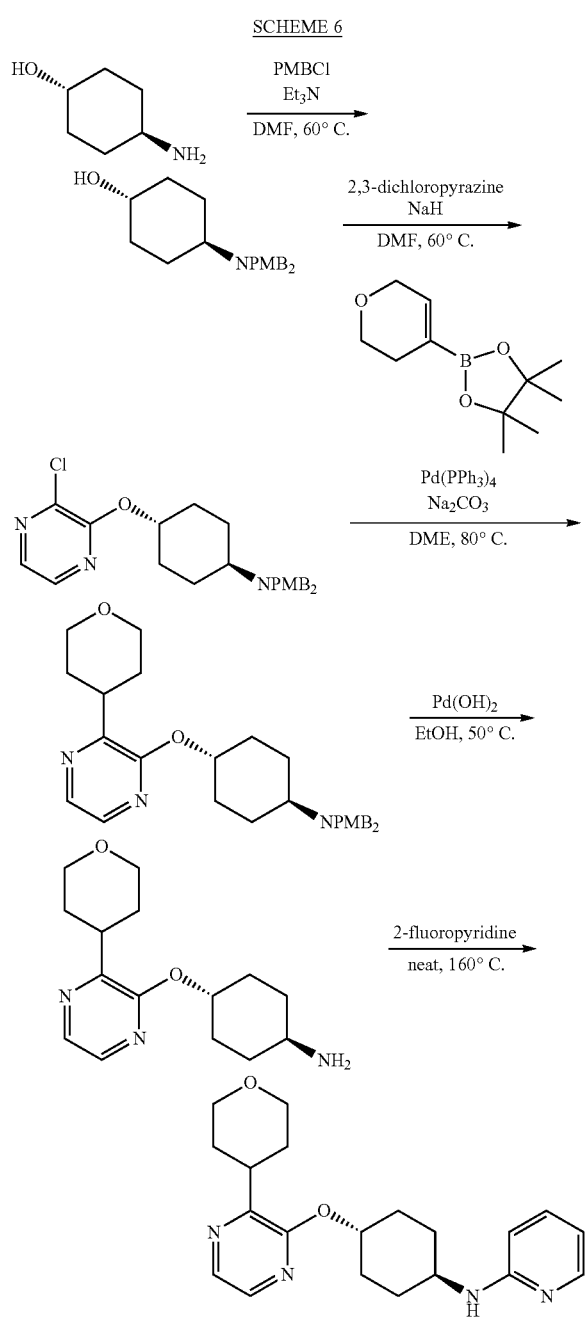

Example 27

N-(TRANS-4-(3-(TETRAHYDRO-2H-PYRAN-4-YL)PYRAZIN-2-YLOXY)CYCLOHEXYL)PYRIDIN-2-AMINE

Step 1. Trans-4-(BIS(4-METHOXYBENZYL)AMINO)CYCLOHEXANOL 1-(Chloromethyl)-4-methoxybenzene (0.28 mL, 2.00 mmol) was added to a solution of triethylamine (0.31 mL, 2.20 mmol) and trans-4-aminocyclohexanol (0.12 g, 1.00 mmol) in DMF (4 mL) under an argon atmosphere. The reaction mixture was stirred at 60° C. for 16 h. The mixture was diluted with water and extracted with EtOAc. The organic layer was separated, washed with water (2×), washed with saturated sodium chloride, dried over magnesium sulfate, filtered, and concentrated. The resulting crude oil was purified by silica gel chromatography to give trans-4-(bis(4-methoxybenzyl)amino)cyclohexanol as a white solid.

Step 2. Trans-4-(3-CHLOROPYRAZIN-2-YLOXY)-N,N-BIS(4-METHOXYBENZYL)CYCLOHEXANAMINE Sodium hydride (0.58 g, 14.5 mmol, 60% dispersion in mineral oil) was added to a solution of trans-4-(bis(4-methoxybenzyl)amino)cyclohexanol (4.30 g, 12.1 mmol) in DMF (50 mL). The mixture was stirred for 30 min at RT before 2,3-dichloropyrazine (1.89 mL, 12.7 mmol) was added dropwise via syringe. The reaction mixture was warmed to 60° C. and stirred overnight. The mixture was diluted with water and extracted with EtOAc (3×). The extracts were combined, washed with water (3×), washed with saturated sodium chloride, dried over magnesium sulfate, filtered, and concentrated. The resulting crude oil was purified by silica gel chromatography to give trans-4-(3-chloropyrazin-2-yloxy)-N,N-bis(4-methoxybenzyl)cyclohexanamine as a white solid.

Step 3. Trans-4-(3-(3,6-DIHYDRO-2H-PYRAN-4-YL)PYRAZIN-2-YLOXY)-N,N-BIS(4-METHOXYBENZYL)CYCLOHEXANAMINE trans-4-(3-Chloropyrazin-2-yloxy)-N,N-bis(4-methoxybenzyl)cyclohexanamine (0.810 g, 1.73 mmol), 2-(3,6-dihydro-2H-pyran-4-yl)-4,4,5,5-tetramethyl-1,3,2-dioxaborolane (0.455 g, 2.16 mmol), and tetrakis(triphenylphosphine)palladium(0) (0.100 g, 0.087 mmol) were mixed in DME (2 mL) under a nitrogen atmosphere. Sodium carbonate (2.60 mL, 5.19 mmol, 2 M in water) was added via syringe, and the reaction mixture was then heated to 80° C. and stirred for 5 h. The mixture was cooled to RT and partitioned between EtOAc and water. The layers were separated, and the aqueous layer was extracted with EtOAc (2×). The extracts were combined, dried over magnesium sulfate, filtered, and concentrated. The resulting crude product was purified by silica gel chromatography to give trans-4-(3-(3,6-dihydro-2H-pyran-4-yl)pyrazin-2-yloxy)-N,N-bis(4-methoxybenzyl)cyclohexanamine as a light yellow solid.

Step 4. Trans-4-(3-(TETRAHYDRO-2H-PYRAN-4-YL)PYRAZIN-2-YLOXY)CYCLOHEXANAMINE

Palladium hydroxide (0.040 g, 0.057 mmol, 20 weight % on carbon) was added to a stirred mixture of trans-4-(3-(3,6-dihydro-2H-pyran-4-yl)pyrazin-2-yloxy)-N,N-bis(4-methoxybenzyl)cyclohexanamine (0.40 g, 0.77 mmol) in ethanol (4 mL). The reaction mixture was placed under a hydrogen atmosphere (balloon) and stirred at 50° C. for 18 h. Additional palladium hydroxide (0.040 g) and methanol (1 mL) were added, and the reaction mixture was stirred at 50° C. for an additional 5 h. The reaction mixture was filtered, and the filtrate was concentrated. The resulting crude product was purified via silica gel chromatography to give trans-4-(3-(tetrahydro-2H-pyran-4-yl)pyrazin-2-yloxy)cyclohexanamine as a colorless oil.

Step 5. N-(TRANS-4-(3-(TETRAHYDRO-2H-PYRAN-4-YL)PYRAZIN-2-YLOXY)CYCLOHEXYL)PYRIDIN-2-AMINE trans-4-(3-(Tetrahydro-2H-pyran-4-yl)pyrazin-2-yloxy)cyclohexanamine (0.053 g, 0.19 mmol) and 2-fluoropyridine (0.033 mL, 0.38 mmol) were mixed in a microwave tube. The tube was sealed, and the mixture was stirred neat at 160° C. for 3 d. The crude mixture was purified via silica gel column chromatography to give N-(trans-4-(3-(tetrahydro-2H-pyran-4-yl)pyrazin-2-yloxy)cyclohexyl)pyridin-2-amine as a brown solid. [M+1] 355.2. IC$_{50}$ (uM): 2.665.

SCHEME 7A

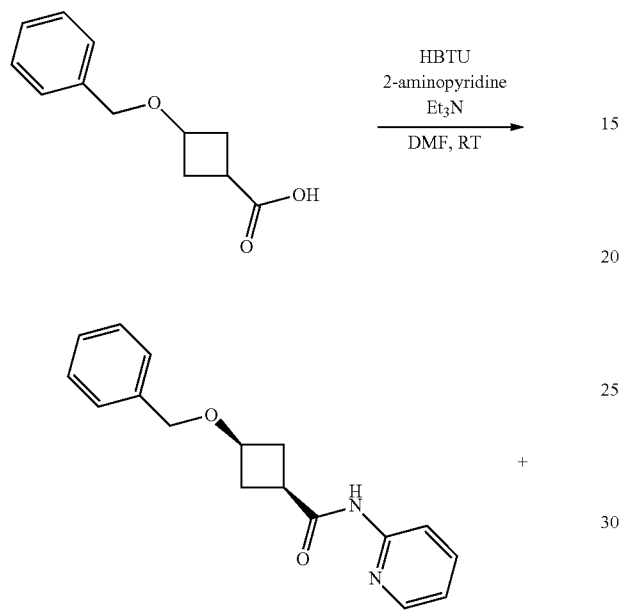

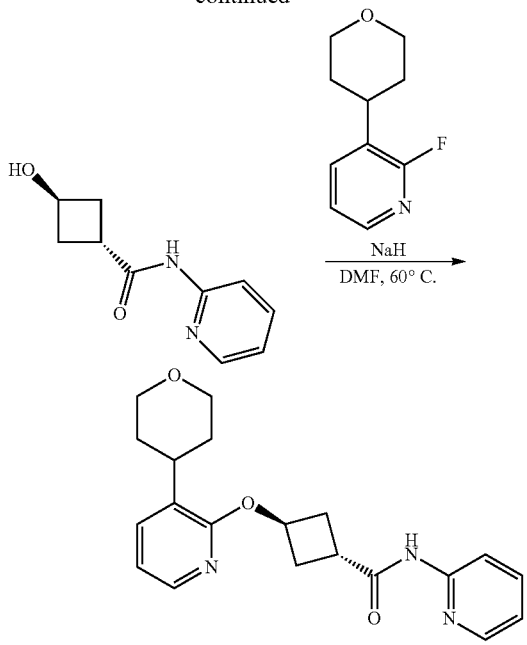

Example 28A

TRANS-N-(PYRIDIN-2-YL)-3-(3-(TETRAHYDRO-2H-PYRAN-4-YL)PYRIDIN-2-YLOXY)CYCLOBUTANECARBOXAMIDE

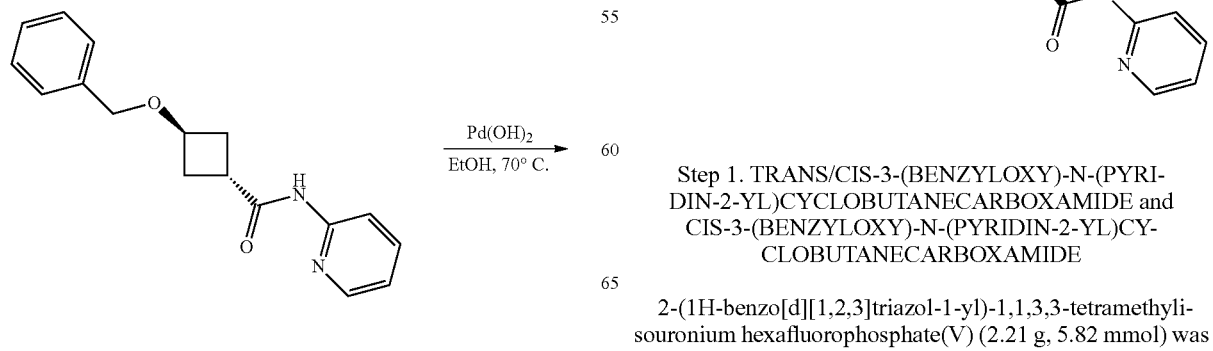

SCHEME 7B

Step 1. TRANS/CIS-3-(BENZYLOXY)-N-(PYRIDIN-2-YL)CYCLOBUTANECARBOXAMIDE and CIS-3-(BENZYLOXY)-N-(PYRIDIN-2-YL)CYCLOBUTANECARBOXAMIDE 2-(1H-benzo[d][1,2,3]triazol-1-yl)-1,1,3,3-tetramethylisouronium hexafluorophosphate(V) (2.21 g, 5.82 mmol) was added to a stirred mixture of 3-(benzyloxy)cyclobutanecarboxylic acid (0.80 g, 3.88 mmol), 2-aminopyridine (0.73 g, 7.76 mmol), and triethylamine (1.08 mL, 7.76 mmol) in DMF (15 mL). The reaction mixture was stirred at RT for 16 h. The reaction mixture was diluted with water and extracted with EtOAc. The organic extract was separated, washed with saturated sodium chloride, dried over magnesium sulfate, filtered, and concentrated. The resulting crude product was purified via silica gel chromatography to give the separated diastereomers trans-3-(benzyloxy)-N-(pyridin-2-yl)cyclobutanecarboxamide and cis-3-(benzyloxy)-N-(pyridin-2-yl)cyclobutanecarboxamide.

Step 2. Trans-3-HYDROXY-N-(PYRIDIN-2-YL)CYCLOBUTANECARBOXAMIDE trans-3-(benzyloxy)-N-(pyridin-2-yl)cyclobutanecarboxamide (0.394 g, 1.40 mmol) and palladium hydroxide (0.098 g, 0.14 mmol, 20 weight % on carbon) were mixed in ethanol (5 mL). The reaction mixture was placed under a hydrogen atmosphere (balloon) and stirred at 70° C. for 20 h. The reaction mixture was cooled to RT and filtered. The filtrate was concentrated, and the resulting crude product was purified via silica gel chromatography to give trans-3-hydroxy-N-(pyridin-2-yl)cyclobutanecarboxamide as an off white solid.

Step 3. TRANS-N-(PYRIDIN-2-YL)-3-(3-(TETRAHYDRO-2H-PYRAN-4-YL)PYRIDIN-2-YLOXY)CYCLOBUTANECARBOXAMIDE Sodium hydride (0.073 g, 1.8 mmol, 60% dispersion in mineral oil) was added to a stirred solution of trans-3-hydroxy-N-(pyridin-2-yl)cyclobutanecarboxamide (0.18 g, 0.92 mmol) in DMF (3.5 mL) under an argon atmosphere. The mixture was stirred at RT for 1 h. 2-fluoro-3-(tetrahydro-2H-pyran-4-yl)pyridine (0.17 g, 0.92 mmol) was added, and the reaction mixture was stirred at 60° C. for 18 h. The reaction mixture was diluted with EtOAc and washed with saturated ammonium chloride. The organic layer was separated, washed with saturated sodium chloride, dried over magnesium sulfate, filtered, and concentrated. The resulting crude product was purified via silica gel chromatography to give trans-N-(pyridin-2-yl)-3-(3-(tetrahydro-2H-pyran-4-yl)pyridin-2-yloxy)cyclobutanecarboxamide as a white solid. [M+1]=354.0. IC$_{50}$ (uM): 3.066.

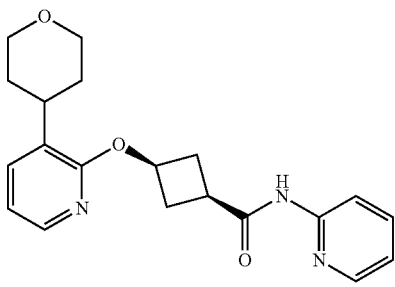 [SMILES: O=C(Nc1ccccn1)[C@H]1C[C@@H](Oc2ncccc2C2CCOCC2)C1]

Example 28B

CIS-N-(PYRIDIN-2-YL)-3-(3-(TETRAHYDRO-2H-PYRAN-4-YL)PYRIDIN-2-YLOXY)CYCLOBUTANECARBOXAMIDE

The cis isomer was prepared according to Scheme 7b by using the appropriate cis starting materials. [M+1]=354.2. IC$_{50}$ (UM): 3.671.

SCHEME 8

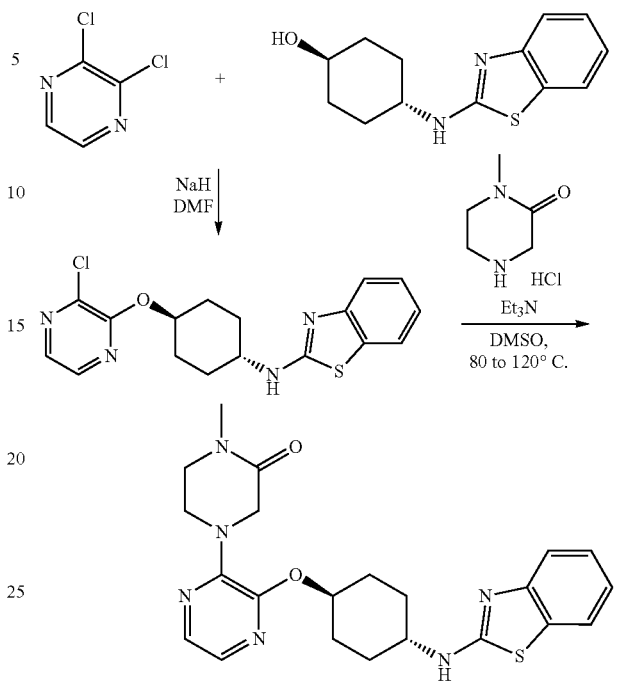

Example 29A 4-(3-(TRANS-4-(BENZO[D]THIAZOL-2-YLAMINO)CYCLOHEXYLOXY)PYRAZIN-2-YL)-1-METHYLPIPERAZIN-2-ONE Step 1. N-(TRANS-4-(3-CHLOROPYRAZIN-2-YLOXY)CYCLOHEXYL)BENZO[D]THIAZOL-2-AMINE Sodium hydride (60% dispersion, 0.41 g, 10.2 mmol) was added to a solution of trans-4-(benzo[d]thiazol-2-ylamino)cyclohexanol (as prepared according to Scheme 5) (1.10 g, 4.43 mmol) in DMF (20 mL) under argon. The mixture was stirred for 45 min and then 2,3-dichloropyrazine (0.66 g, 4.43 mmol) was added via syringe. This mixture was heated to 60° C. for 16 h, cooled to room temperature, then water was added slowly. The resulting suspension was filtered and the collected solid was purified by silica gel chromatography to give N-(trans-4-(3-chloropyrazin-2-yloxy)cyclohexyl)benzo[d]thiazol-2-amine (0.92 g, 2.54 mmol, 57% yield) as a white solid.

Step 2. 4-(3-(TRANS-4-(BENZO[D]THIAZOL-2-YLAMINO)CYCLOHEXYLOXY)PYRAZIN-2-YL)-1-METHYLPIPERAZIN-2-ONE N-(trans-4-(3-Chloropyrazin-2-yloxy)cyclohexyl)benzo[c/]thiazol-2-amine (0.080 g, 0.22 mmol), 1-methylpiperazin-2-one hydrochloride (0.10 g, 0.67 mmol), and triethylamine (0.093 mL, 0.67 mmol) were mixed in DMSO (2 mL) under an argon atmosphere. The reaction mixture was stirred at 80° C. for 24 h. The reaction mixture was then warmed to 120° C. and stirred for an additional 72 h. The reaction mixture was cooled to RT, diluted with water, and extracted with EtOAc (2×). The organic extracts were combined, washed with saturated sodium chloride, dried over magnesium sulfate, filtered, and concentrated. The resulting crude product was purified via silica gel chromatography to give 4-(3-(trans-4-(benzo[d]thiazol-2-ylamino)cyclohexyloxy)pyrazin-2-yl)-1-methylpiperazin-2-one as a light orange solid. [M+1] 439.2. IC$_{50}$ (uM): 0.5369.

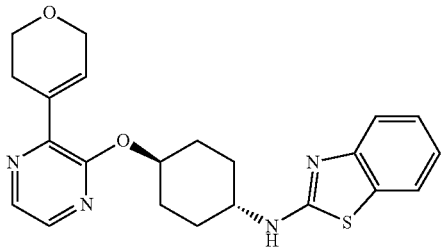 [SMILES: C1=C(c2nccnc2O[C@H]2CC[C@H](Nc3nc4ccccc4s3)CC2)CCOC1]

Example 29B

N-(TRANS-4-(3-(3,6-DIHYDRO-2H-PYRAN-4-YL)PYRAZIN-2-YLOXY)CYCLOHEXYL)BENZO[D]THIAZOL-2-AMINE

A mixture of 2-(3,6-dihydro-2H-pyran-4-yl)-4,4,5,5-tetramethyl-1,3,2-dioxaborolane (0.10 g, 0.49 mmol) and N-(trans-4-(3-chloropyrazin-2-yloxy)cyclohexyl)benzo[d]thiazol-2-amine (0.14 g, 0.39 mmol), prepared as in step 1 of example 9a, in 1,2-dimethoxyethane (2 mL) and aqueous sodium carbonate (2 M, 0.58 mL, 1.16 mmol) was placed under nitrogen atmosphere using 3 evacuation/backfill cycles. Tetrakis triphenylphosphine(palladium) (0.022 g, 0.019 mmol) was added and one more evacuation/backfill cycle was executed. The mixture was then heated to 80° C. After 4 h the mixture was cooled to RT and partitioned between ethyl acetate and water. The layers were separated and the aqueous layer was extracted with ethyl acetate twice. The combined extracts were dried over anhydrous magnesium sulfate, filtered, and concentrated in vacuo. The resulting oil was purified by silica gel chromatography to give N-(trans-4-(3-(3,6-dihydro-2H-pyran-4-yl)pyrazin-2-yloxy)cyclohexyl)benzo[d]thiazol-2-amine (0.13 g, 0.32 mmol, 83% yield). [M+1] 409.2. IC$_{50}$ (uM): 0.03702.

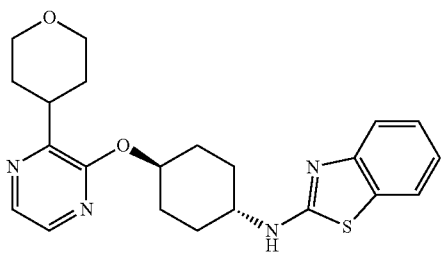 [SMILES: c1ccc2sc(N[C@H]3CC[C@H](Oc4nccnc4C4CCOCC4)CC3)nc2c1]

Example 29C

N-(TRANS-4-(3-(TETRAHYDRO-2H-PYRAN-4-YL)PYRAZIN-2-YLOXY)CYCLOHEXYL)BENZO[D]THIAZOL-2-AMINE

A mixture of N-(trans-4-(3-(3,6-dihydro-2H-pyran-4-yl)pyrazin-2-yloxy)cyclohexyl)benzo[d]thiazol-2-amine. As prepared in Example 30b, (0.22 g, 0.54 mmol), palladium hydroxide on carbon (20 wt % Pd dry basis, wet, Degussa type E101 NE/W) (0.60 g), and ammonium formate (0.51 g, 8.11 mmol) in methanol (3 mL) was heated to 65° C. for 12 h, then cooled to RT. The palladium was filtered off and the filtrate was concentrated in vacuo to give a white solid. This solid was partitioned between ethyl acetate and water, the layers were separated, and the organic layer was dried over anhydrous magnesium sulfate, filtered, and concentrated in vacuo to give an oil. The oil was then purified by silica gel chromatography to give N-(trans-4-(3-(tetrahydro-2H-pyran-4-yl)pyrazin-2-yloxy)cyclohexyl)benzo[d]thiazol-2-amine (0.030 g, 0.073 mmol, 14% yield) as a white solid. [M+1] 411.2. IC$_{50}$ (uM): 0.0635.

SCHEME 9

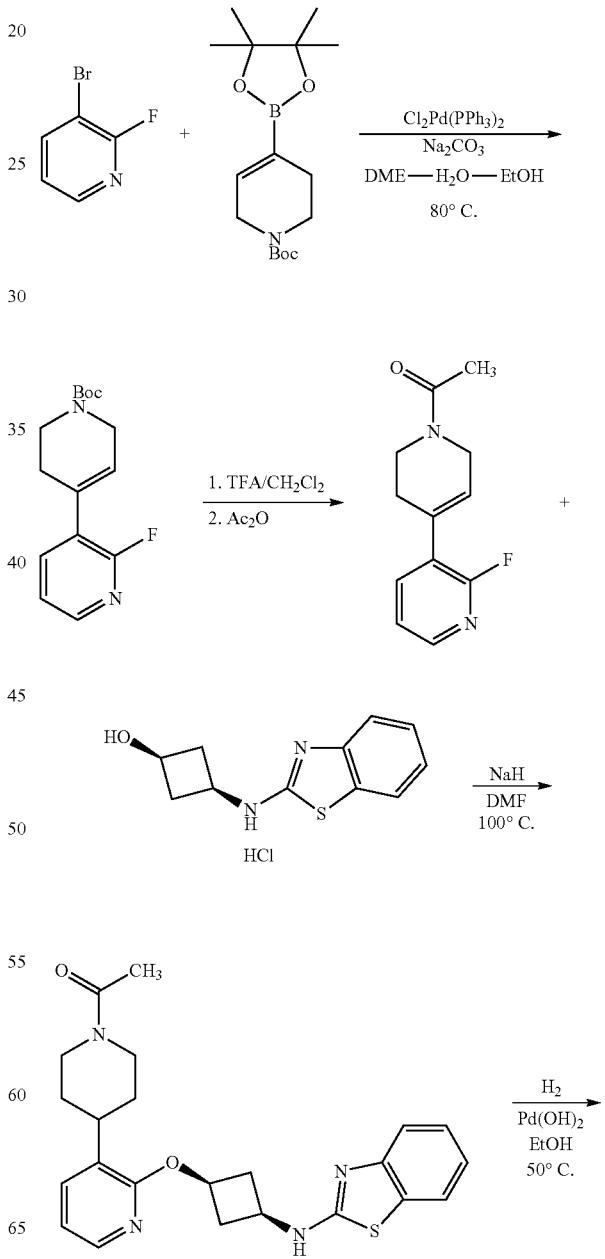

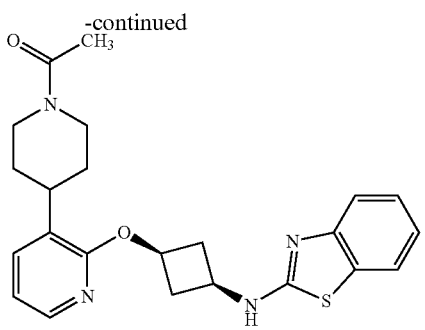

Example 30

1-(4-(2-(CIS-3-(BENZO[D]THIAZOL-2-YLAMINO)CYCLOBUTOXY)PYRIDIN-3-YL)PIPERIDIN-1-YL)ETHANONE

Step 1. TERT-BUTYL 4-(2-FLUOROPYRIDIN-3-YL)-5,6-DIHYDROPYRIDINE-1(2H)-CARBOXYLATE 3-Bromo-2-fluoropyridine (1.5 g, 8.5 mmol), tert-butyl 4-(4,4,5,5-tetramethyl-1,3,2-dioxaborolan-2-yl)-5,6-dihydropyridine-1(2H)-carboxylate (3.16 g, 10.2 mmol), trans-dichlorobis(triphenylphosphine)palladium (II) (0.48 g, 0.68 mmol), sodium carbonate (4.44 g, 41.9 mmol), and 6:1:1 DME-H$_2$O-EtOH (20 mL) were combined in a sealed tube and stirred at 80° C. for 18 h. The cooled reaction was diluted with CH$_2$Cl$_2$ and washed with aqueous saturated NaHCO$_3$ solution; the aqueous layer was back-washed with CH$_2$Cl$_2$ (1×). The combined organic extracts were dried (MgSO$_4$), filtered, and concentrated in vacuo. Flash column chromatography (10% to 40% EtOAc/Hexanes) gave tert-butyl 4-(2-fluoropyridin-3-yl)-5,6-dihydropyridine-1(2H)-carboxylate as a golden yellow oil. [M+1]=279.2.

Step 2. 1-(4-(2-FLUOROPYRIDIN-3-YL)-5,6-DIHYDROPYRIDIN-1(2H)—YL)ETHANONE

A solution of tert-butyl 4-(2-fluoropyridin-3-yl)-5,6-dihydropyridine-1(2H)-carboxylate (2.69 g, 9.67 mmol) in CH$_2$Cl$_2$ (8 mL) was added trifluoroacetic acid (7.45 mL, 97 mmol) and stirred at RT for 2 h. The reaction was concentrated in vacuo, and the residue was partitioned between CH$_2$Cl$_2$ and aqueous saturated NaHCO$_3$ solution. The organic layer was dried (MgSO$_4$), filtered, and concentrated in vacuo to give a golden yellow oil. A solution of the crude golden yellow oil in CH$_2$Cl$_2$ (10 mL) was cooled to 0° C. and added acetic anhydride (4.5 mL, 48.3 mmol). The reaction was gradually allowed to warm to RT and stirred for 16 h. The reaction was diluted with CH$_2$Cl$_2$ and washed with aqueous saturated NaHCO$_3$ solution; the aqueous layer was back-extracted with CH$_2$Cl$_2$ (1×). The organic extracts were combined, dried (MgSO$_4$), and concentrated in vacuo. Flash column chromatography (20% to 80% EtOAc/Hexanes) afforded 1-(4-(2-fluoropyridin-3-yl)-5,6-dihydropyridin-1(2H)-yl)ethanone as a colorless oil. [M+1]=221.1.

Step 3. 1-(4-(2-(CIS-3-(BENZO[D]THIAZOL-2-YLAMINO)CYCLOBUTOXY)PYRIDIN-3-YL)-5,6-DIHYDROPYRIDIN-1(2H)-YL)ETHANONE Sodium hydride, 60% dispersion in mineral oil (0.13 g, 3.18 mmol) was added to a solution of cis-3-(benzo[d]thiazol-2-ylamino)cyclobutanol hydrochloride (0.20 g, 0.795 mmol) in N,N-dimethylformamide (2.7 mL) under argon and the mixture was stirred for 30 min at RT. 1-(4-(2-Fluoropyridin-3-yl)-5,6-dihydropyridin-1(2H)-yl)ethanone (0.17 g, 0.79 mmol) was next added, and the resulting mixture was heated at 100° C. for 2 h. The cooled reaction was diluted with EtOAc and washed with water. The organic layer was dried (MgSO$_4$), filtered, and concentrated in vacuo. Flash column chromatography (20% to 80% EtOAc/Hexanes) afforded 1-(4-(2-(cis-3-(benzo[d]thiazol-2-ylamino)cyclobutoxy)pyridin-3-yl)-5,6-dihydropyridin-1(2H)-yl)ethanone as an off-white amorphous solid. [M+1]=421.0.

Step 4. 1-(4-(2-(CIS-3-(BENZ 0 [D]THIAZOL-2-YLAMINO)CYCLOBUTOXY)PYRIDIN-3-YL)PIPERIDIN-1-YL)ETHANONE A solution of 1-(4-(2-(cis-3-(benzo[d]thiazol-2-ylamino)cyclobutoxy)pyridin-3-yl)-5,6-dihydropyridin-1(2H)-yl)ethanone (0.12 g, 0.28 mmol) in ethanol (2 mL) was added palladium hydroxide, 20 wt. % Pd (dry basis) on carbon, wet, Degussa type E101 NE/W (0.039 g, 0.056 mmol) and hydrogenated (double-walled balloon pressure) at 50° C. for 3 days. The cooled reaction was filtered via a pad of Celite®, and the filtrate was concentrated in vacuo and purified via flash column chromatography (20% EtOAc/Hexanes to 100% EtOAc) to afford 1-(4-(2-(cis-3-(benzo[d]thiazol-2-ylamino)cyclobutoxy)pyridin-3-yl)piperidin-1-yl)ethanone as a white solid. [M+1]=423.0. IC$_{50}$ (uM): 0.001566.

SCHEME 10

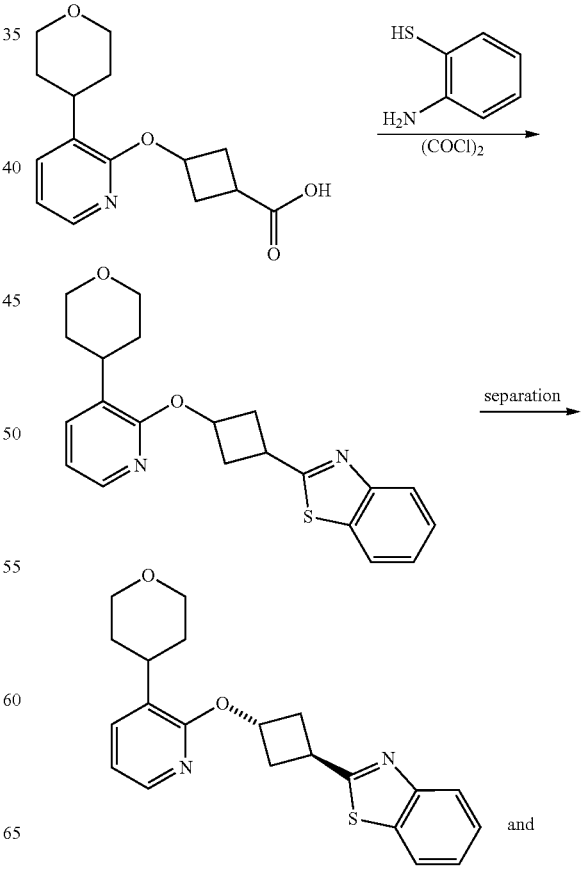

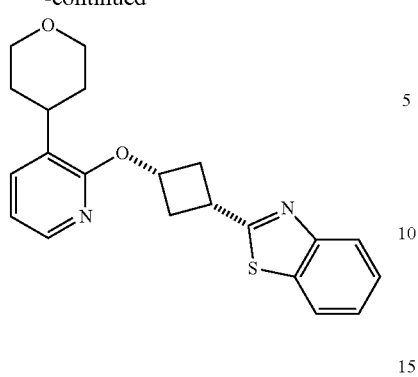

Examples 31A and 31B

TRANS and CIS 2-(-3-(3-(TETRAHYDRO-2H-PYRAN-4-YL)PYRIDIN-2-YLOXY)CYCLOBUTYL)BENZO[D]THIAZOLE To a solution of 3-(3-(tetrahydro-2H-pyran-4-yl)pyridin-2-yloxy)cyclobutanecarboxylic acid (prepared according to Scheme 4) (0.236 g, 0.851 mmol) in DCM (0.5 mL) at RT was added DMF (1 drop) and oxalyl dichloride (0.50 mL, 5.6 mmol). The reaction mixture was stirred at RT for 10 min and the solvent was removed under reduced pressure. The concentrate was dissolved in toluene (3 mL), cooled to 0° C., and 2-aminobenzenethiol (0.10 mL, 0.94 mmol) was added. The reaction mixture was warmed to RT and stirred for 2 h. The reaction was neutralized with saturated $NaHCO_3$ and diluted with EtOAc. The organic phase was washed with water (1×), brine (1×), dried over $MgSO_4$, filtered, and concentrated. Purification by flash column chromatography on silica gel (5% to 30% EtOAc in hexanes) followed by purification by flash column chromatography on silica gel (5% to 30% DCM in hexanes) gave 2-(trans-3-(3-(tetrahydro-2H-pyran-4-yl)pyridin-2-yloxy)cyclobutyl)benzo[d]thiazole (0.018 g, 0.049 mmol, 6% yield) and 2-(cis-3-(3-(tetrahydro-2H-pyran-4-yl)pyridin-2-yloxy)cyclobutyl)benzo[d]thiazole (0.029 g, 0.079 mmol, 9% yield) as colorless oils. [M+1]=367 each. $IC_{50}$ (uM): 0.01497 (trans) and 0.0633 (cis).

SCHEME 11A

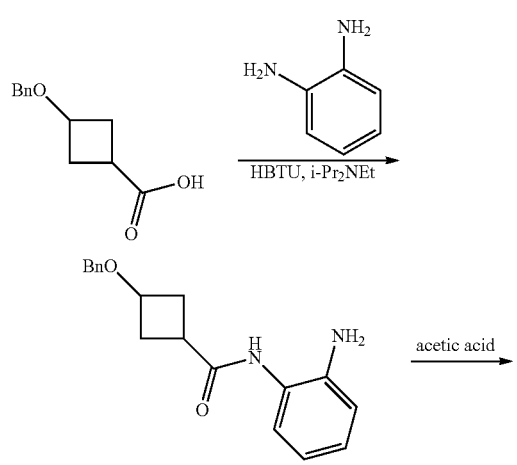

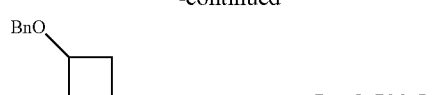

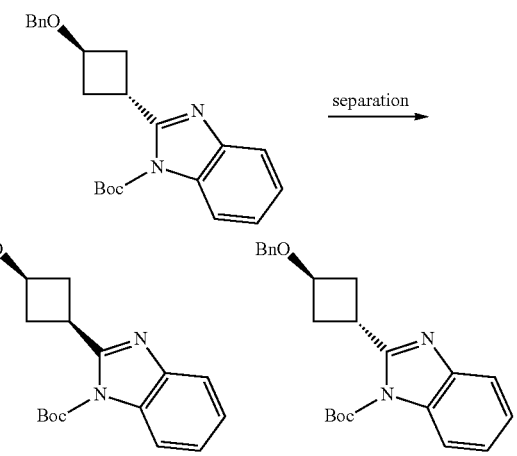

SCHEME 11B

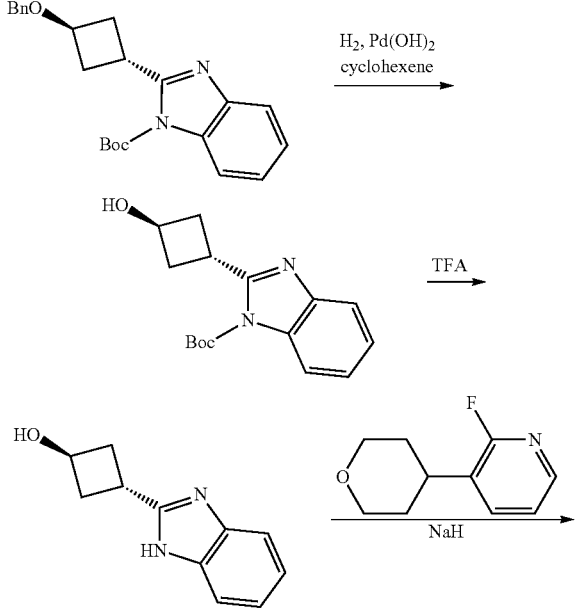

-continued

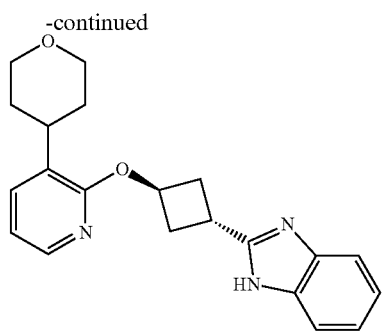

Example 32A 2-(TRANS-3-(3-(TETRAHYDRO-2H-PYRAN-4-YL)PYRIDIN-2-YLOXY)CYCLOBUTYL)-1H-BENZO[D]IMIDAZOLE Step 1. N-(2-AMINOPHENYL)-3-(BENZYLOXY)CYCLOBUTANECARBOXAMIDE HBTU (2.06 g, 5.44 mmol) was added to a solution of diisopropyl ethylamine (1.03 mL, 5.93 mmol), o-phenylenediamine (0.54 g, 4.95 mmol), and 3-(benzyloxy)cyclobutanecarboxylic acid (1.02 g, 4.95 mmol) in DMF (20 mL) under argon atmosphere at 0° C. The mixture was stirred overnight with gradual warming to RT, then poured into water. The resulting suspension was filtered and the solid was air-dried to give N-(2-aminophenyl)-3-(benzyloxy)cyclobutanecarboxamide (1.17 g, 3.95 mmol, 80% yield) as an off-white solid.

Step 2. 2-(3-(BENZYLOXY)CYCLOBUTYL)-1H-BENZO[D]IMIDAZOLE

A solution of N-(2-aminophenyl)-3-(benzyloxy)cyclobutanecarboxamide (1.78 g, 6.01 mmol) in acetic acid was heated to 100° C. for 1 h, then cooled to RT. The acetic acid was removed in vacuo and ethyl acetate was added to the resulting oil. The resulting suspension was filtered and the collected solid was air dried to give 2-(3-(Benzyloxy)cyclobutyl)-1H-benzo[d]imidazole. The filtrate was concentrated in vacuo to give another suspension, which was filtered, air dried, and added to the first crop of product to give a total of 0.96 g (3.43 mmol, 57% yield) of 2-(3-(Benzyloxy)cyclobutyl)-1H-benzo[d]imidazole as a white solid.

Step 3. TERT-BUTYL 2-(CIS-3-(BENZYLOXY)CYCLOBUTYL)-1H-BENZO[D]IMIDAZOLE-1-CARBOXYLATE AND TERT-BUTYL 2-(TRANS-3-(BENZYLOXY)CYCLOBUTYL)-1H-BENZO[D]IMIDAZOLE-1-CARBOXYLATE DMAP (0.020 g, 0.16 mmol) and di-tert-butyldicarbonate (0.83 g, 3.77 mmol) were added to a suspension of 2-(3-(benzyloxy)cyclobutyl)-1H-benzo[d]imidazole (0.96 g, 3.43 mmol) and triethylamine (1.20 mL, 8.58 mmol) in dichloromethane (15 mL) and the mixture was stirred for 16 h. Water was added, the resulting layers were separated, and the organic layer was dried over anhydrous magnesium sulfate, filtered, and concentrated in vacuo to give an oil. The oil was purified by silica gel chromatography to give tert-butyl 2-(cis-3-(benzyloxy)cyclobutyl)-1H-benzo[d]imidazole-1-carboxylate (0.43 g, 1.14 mmol, 33% yield) and tert-butyl 2-(trans-3-(benzyloxy)cyclobutyl)-1H-benzo[d]imidazole-1-carboxylate (0.47 g, 1.23 mmol, 36% yield).

Step 4. TERT-BUTYL 2-(TRANS-3-HYDROXYCYCLOBUTYL)-1H-BENZO[D]IMIDAZOLE-1-CARBOXYLATE A mixture of tert-butyl 2-(trans-3-(benzyloxy)cyclobutyl)-1H-benzo[d]imidazole-1-carboxylate (0.47 g, 1.23 mmol), cyclohexene (0.080 g, 0.91 mmol), and 20 wt % Pd (dry basis) on carbon, Degussa type E101 NE/W (2.45 g) in ethanol (5 mL) under argon was heated to 65° C. for 6 h, cooled to RT, and filtered through Celite®. The filtrate was concentrated in vacuo and the resulting oil was purified by silica gel chromatography to give tert-butyl 2-(trans-3-hydroxycyclobutyl)-1H-benzo[d]imidazole-1-carboxylate (0.31 g, 1.09 mmol, 88% yield) as a white solid.

Step 5. Trans-3-(1H-BENZO[D]IMIDAZOL-2-YL)CYCLOBUTANOL tert-Butyl 2-(trans-3-hydroxycyclobutyl)-1H-benzo[d]imidazole-1-carboxylate (0.31 g, 1.09 mmol) was stirred in a mixture of dichloromethane (5 mL) and TFA (5 mL) at RT for 4 h, then the mixture was concentrated in vacuo. The residue was partitioned between saturated aqueous sodium bicarbonate solution and 10:1 DCM/MeOH the layers were separated and the aqueous layer was extracted with 10:1 DCM/MeOH (3×). The combined extracts were dried over anhydrous magnesium sulfate, filtered, and concentrated in vacuo to give trans-3-(1H-benzo[d]imidazol-2-yl)cyclobutanol (0.11 g, 0.58 mmol, 54% yield) as a white solid.

Step 6. 2-(TRANS-3-(3-(TETRAHYDRO-2H-PYRAN-4-YL)PYRIDIN-2-YLOXY)CYCLOBUTYL)-1H-BENZO[D]IMIDAZOLE Sodium hydride (60% dispersion, 0.049 g, 1.2 mmol) was added to a solution of trans-3-(1H-benzo[d]imidazol-2-yl)cyclobutanol (0.11 g, 0.58 mmol) in DMF (1.5 mL) under argon and the mixture was stirred for 45 min at RT. 2-Fluoro-3-(tetrahydro-2H-pyran-4-yl)pyridine (0.11 g, 0.58 mmol) was added and the mixture was stirred for 16 h at 110° C. Ethyl acetate was added and the mixture was washed with water (2×), saturated aqueous sodium chloride (1×), dried over anhydrous magnesium sulfate, filtered, and concentrated in vacuo. The resulting oil was purified by silica gel chromatography to give 2-(trans-3-(3-(Tetrahydro-2H-pyran-4-yl)pyridin-2-yloxy)cyclobutyl)-1H-benzo[d]imidazole (37 mg, 0.11 mmol, 18% yield) as a white solid. [M+1]: 350.3. $IC_{50}$ (uM) 0.01041.

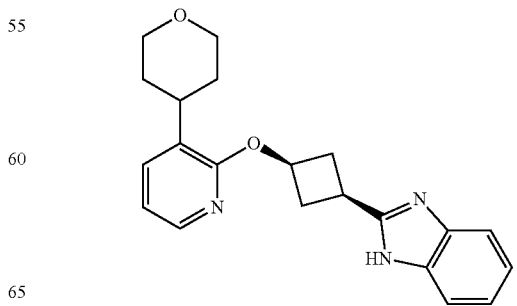

Example 32B

2-(CIS-3-(3-(TETRAHYDRO-2H-PYRAN-4-YL)PYRIDIN-2-YLOXY)CYCLOBUTYL)-1H-BENZO[D]IMIDAZOLE

The cis isomer was prepared according to scheme 12b by using the appropriate cis starting materials. [M+1]=350.2. IC$_{50}$ (uM): 0.2068.

SCHEME 12

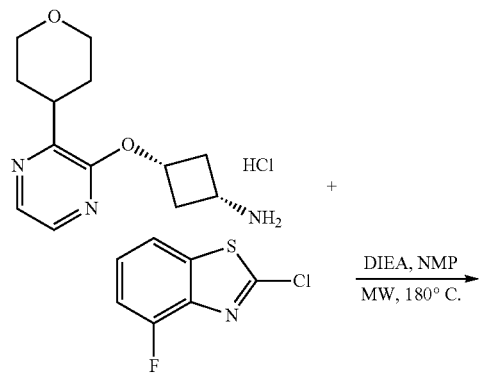

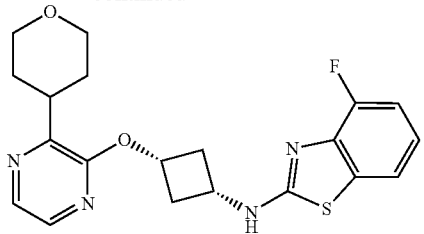

Example 33

4-FLUORO-N-((1S,3S)-3-((3-(TETRAHYDRO-2H-PYRAN-4-YL)PYRAZIN-2-YL)OXY)CYCLOBUTYL)BENZO[D]THIAZOL-2-AMINE

To a mixture of (1S,3S)-3-((3-(tetrahydro-2H-pyran-4-yl)pyrazin-2-yl)oxy)cyclobutanamine hydrochloride (see PREPARATION 5D, 200 mg, 0.8 mmol) in NMP (4 mL) was added 2-chloro-4-fluoro-benzothiazole (150 mg, 0.8 mmol) and DIEA (229 mg, 1.6 mmol), then heated to 180° C. for 2 h in microwave. The reaction mixture was diluted with water (10 mL), extracted with ethyl acetate (20 mL), washed with water and brine, dried over Na$_2$SO$_4$ and concentrated. The residue was purification by prep-HPLC to give the title compound (30 mg, yield 9%).

TABLE 2A

EXAMPLES 33-41 PREPARED ANALOGOUS TO SCHEME 12

| Ex. # | Structure | Chemical Name | M + 1 | IC$_{50}$ (uM) |
|---|---|---|---|---|
| 33 | 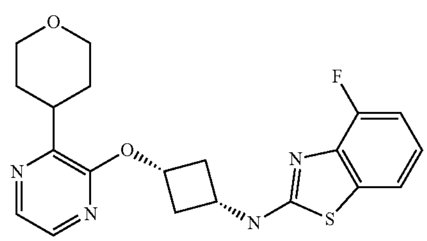 [SMILES: Fc1cccc2sc(N[C@H]3C[C@@H](Oc4nccnc4C4CCOCC4)C3)nc12] | 4-fluoro-N-((1S,3S)-3-((3-(tetrahydro-2H-pyran-4-yl)pyrazin-2-yl)oxy)cyclobutyl)benzo[d]thiazol-2-amine | 401 | 0.013 |
| 34 | 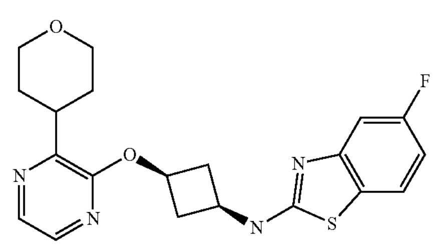 [SMILES: Fc1ccc2sc(N[C@H]3C[C@@H](Oc4nccnc4C4CCOCC4)C3)nc2c1] | 5-fluoro-N-((1S,3S)-3-((3-(tetrahydro-2H-pyran-4-yl)pyrazin-2-yl)oxy)cyclobutyl)benzo[d]thiazol-2-amine | 401 | 0.0183 |
| 35 | 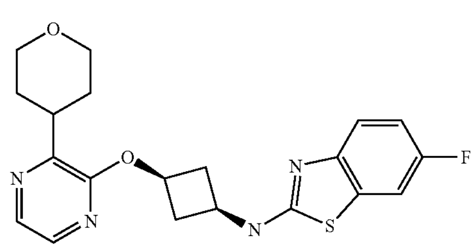 [SMILES: Fc1ccc2nc(N[C@H]3C[C@@H](Oc4nccnc4C4CCOCC4)C3)sc2c1] | 6-fluoro-N-((1S,3S)-3-((3-(tetrahydro-2H-pyran-4-yl)pyrazin-2-yl)oxy)cyclobutyl)benzo[d]thiazol-2-amine | 401 | 0.0151 |

TABLE 2A-continued

EXAMPLES 33-41 PREPARED ANALOGOUS TO SCHEME 12

| Ex. # | Structure | Chemical Name | M + 1 | IC$_{50}$ (uM) |
|---|---|---|---|---|
| 36 | 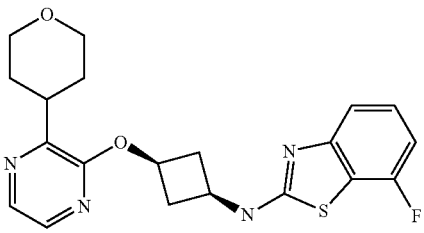 [SMILES: Fc1cccc2nc(N[C@H]3C[C@@H](Oc4nccnc4C4CCOCC4)C3)sc12] | 7-fluoro-N-((1S,3S)-3-((3-(tetrahydro-2H-pyran-4-yl)pyrazin-2-yl)oxy)cyclobutyl)benzo[d]thiazol-2-amine | 401 | 0.0271 |
| 37 | 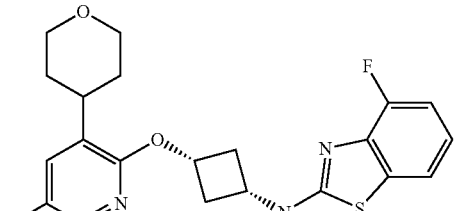 | 4-fluoro-N-((1S,3S)-3-((5-fluoro-3-(tetrahydro-2H-pyran-4-yl)pyridin-2-yl)oxy)cyclobutyl)benzo[d]thiazol-2-amine | 418 | 0.00543 |
| 38 | 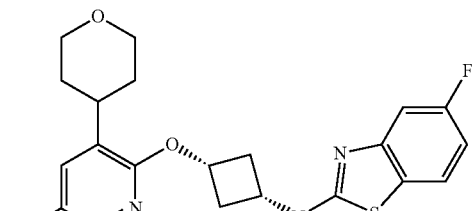 | 5-fluoro-N-((1S,3S)-3-((5-fluoro-3-(tetrahydro-2H-pyran-4-yl)pyridin-2-yl)oxy)cyclobutyl)benzo[d]thiazol-2-amine | 418 | 0.00349 |
| 39 | 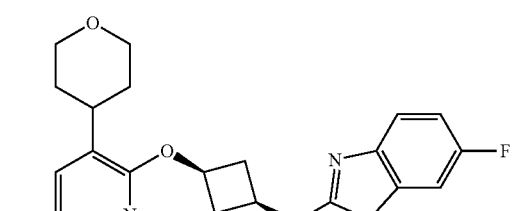 | 6-fluoro-N-((1S,3S)-3-((5-fluoro-3-(tetrahydro-2H-pyran-4-yl)pyridin-2-yl)oxy)cyclobutyl)benzo[d]thiazol-2-amine | 418 | 0.00144 |
| 40 | 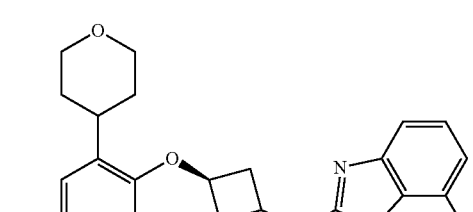 | 7-fluoro-N-((1S,3S)-3-((5-fluoro-3-(tetrahydro-2H-pyran-4-yl)pyridin-2-yl)oxy)cyclobutyl)benzo[d]thiazol-2-amine | 418 | 0.00245 |
| 41 | 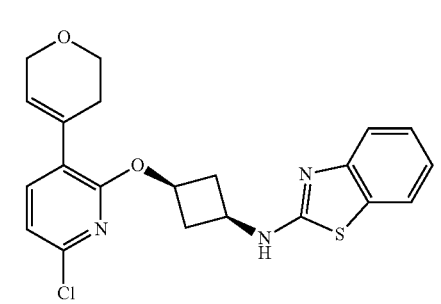 [SMILES: Clc1ccc(C2=CCOCC2)c(O[C@H]2C[C@@H](Nc3nc4ccccc4s3)C2)n1] | N-((1S,3S)-3-((6-chloro-3-(3,6-dihydro-2H-pyran-4-yl)pyridin-2-yl)oxy)cyclobutyl)benzo[d]thiazol-2-amine | 414 | 0.00355 |

TABLE 2B

PREPARATION AND NMR DATA OF EXAMPLES 33-41

| Ex.# | Starting Material (1) | Starting Material (2) | Reaction Condition | $^1$H NMR (CDCl$_3$, 400 MHz) δ (ppm) |
|---|---|---|---|---|
| 33 | (tetrahydropyran-pyrazine-cyclobutylamine HCl structure) (see Prep. 5D) | 4-fluoro-2-chlorobenzothiazole (similar to Preparation 6) | DIEA, NMP, MW 180° C. | 8.09 (s, 1H); 7.89-7.88 (d, J = 2.4 Hz, 1H); 7.51-7.48 (m, 1H); 7.35-7.33 (m, 1H); 7.24-7.15 (m, 1H); 5.07-5.00 (m, 1H); 4.10-4.06 (m, 2H); 3.67-3.56 (m, 3H); 3.30-3.17 (m, 3H); 2.47-2.41 (m, 2H); 2.05-1.90 (m, 2H); 1.77-1.74 (d, J = 13.2 Hz, 2H). |
| 34 | (tetrahydropyran-pyrazine-cyclobutylamine HCl structure) (see Prep. 5D) | 2-chloro-5-fluorobenzothiazole (see Prep. 6) | DIEA, NMP, MW 180° C. | 8.08-8.07 (d, J = 2.8 Hz, 1H); 7.87-7.86 (d, J = 2.8 Hz, 1H); 7.55-7.52 (m, 1H); 7.29-7.24 (m, 1H); 7.04-6.99 (m, 1H); 5.05-5.02 (m, 1H); 4.09-4.05 (m, 2H); 3.67-3.55 (m, 3H); 3.29-3.15 (m, 3H); 2.48-2.41 (m, 2H); 1.99-1.88 (m, 2H); 1.77-1.74 (m, 2H). |
| 35 | (tetrahydropyran-pyrazine-cyclobutylamine HCl structure) (see Prep. 5D) | 2-chloro-6-fluorobenzothiazole (similar to Preparation 6) | DIEA, NMP, MW 180° C. | 8.06-8.05 (d, J = 2.4 Hz, 1H); 7.86-7.85 (d, J = 2.8 Hz, 1H); 7.37-7.35 (m, 1H); 7.17-7.10 (m, 2H); 5.04-5.01 (m, 1H); 4.08-4.04 (m, 2H); 3.75-3.71 (m, 1H); 3.58-3.53 (m, 2H); 3.28-3.14 (m, 3H); 2.41-2.34 (m, 2H); 1.98-1.88 (m, 2H); 1.77-1.73 (m, 2H). |
| 36 | (tetrahydropyran-pyrazine-cyclobutylamine HCl structure) (see Prep. 5D) | 2-chloro-7-fluorobenzothiazole (similar to Preparation 6) | DIEA, NMP, MW 180° C. | 8.08-8.07 (d, J = 2.8 Hz, 1H); 7.87-7.86 (d, J = 2.8 Hz, 1H); 7.43-7.38 (m, 1H); 7.35-7.33 (d, J = 8 Hz, 1H); 7.02-6.98 (m, 1H); 5.08-5.01 (m, 1H); 4.08-4.05 (m, 2H); 3.72-3.55 (m, 3H); 3.29-3.17 (m, 3H); 2.48-2.41 (m, 2H); 1.98-1.88 (m, 4H). |
| 37 | (tetrahydropyran-fluoropyridine-cyclobutylamine HCl structure) (see Prep. 7D) | 2-chloro-7-fluorobenzothiazole (similar to Preparation 6) | DIEA, NMP, MW 180° C. | 7.77-7.76 (d, J = 2.8 Hz, 1H); 7.39-7.37 (m, 1H); 7.24-7.17 (m, 3H); 5.02-4.98 (m, 1H); 4.08-4.04 (m, 2H); 3.66-3.53 (m, 3H); 3.19-3.13 (m, 2H); 3.07-3.05 (m, 1H); 2.42-2.35 (m, 2H); 1.79-1.63 (m, 4H). |

TABLE 2B-continued

PREPARATION AND NMR DATA OF EXAMPLES 33-41

| Ex.# | Starting Material (1) | Starting Material (2) | Reaction Condition | $^1$H NMR (CDCl$_3$, 400 MHz) δ (ppm) |
|---|---|---|---|---|
| 38 | (see Prep. 7D) | (see Prep. 6) | DIEA, NMP, MW 180° C. | 7.77-7.76 (d, J = 2.8 Hz, 1 H); 7.53-7.49 (m, 1H); 7.26-7.18 (m, 2H); 6.97-6.93 (m, 1H); 5.02-4.98 (m, 1H); 4.07-4.04 (m, 2 H); 3.73-3.69 (m, 1H); 3.58-3.52 (m, 2H); 3.18-3.12 (m, 2H); 3.05-3.03 (m, 1H); 2.35-2.27 (m, 2 H); 1.78-1.60 (m, 4H). |
| 39 | (see Prep. 7D) | (similar to Preparation 6) | DIEA, NMP, MW 180° C. | 7.73-7.71 (m, 1H); 7.45-7.43 (m, 1H); 7.30-7.28 (d, J = 6.8 Hz, 1H); 7.21-7.08 (m, 2H); 4.99-4.93 (m, 1H); 4.03-4.00 (d, J = 11.6 Hz, 2H); 3.65-3.49 (m, 3H); 3.14-2.98 (m, 3H); 2.35-2.29 (m, 2H); 1.74-1.57 (m, 4H). |
| 40 | (see Prep. 7D) | (similar to Preparation 6) | DIEA, NMP, MW 180° C. | 7.73-7.72 (d, J = 3.2 Hz, 1H); 7.39-7.29 (m, 2H); 7.19-7.14 (m, 1H); 6.98-6.94 (m, 1H); 4.98-4.94 (m, 1H); 4.03-4.00 (m, 2H); 3.63-3.49 (m, 3H); 3.17-3.10 (m, 2H); 3.04-2.98 (m, 1H); 2.39-2.32 (m, 2H); 1.74-1.56 (m, 4H). |
| 41 | (see Prep. 7K) | (similar to Preparation 6) | DIEA, NMP, MW 180° C. | 7.61 (d, J = 8 Hz, 1H); 7.54 (d, J = 8 Hz, 1H); 7.45-7.40 (m, 2H); 7.30-7.25 (m, 1H); 6.89 (d, J = 7.6 Hz, 1H); 6.07-6.06 (m, 1H); 5.07-5.00 (m, 1H); 4.31-4.29 (m, 2H); 3.91-3.88 (m, 2H); 3.66-3.65 (m, 1H); 3.23-3.17 (m, 2H); 2.48-2.38 (m, 4H). |

Prep. = Preparation.

SCHEME 13

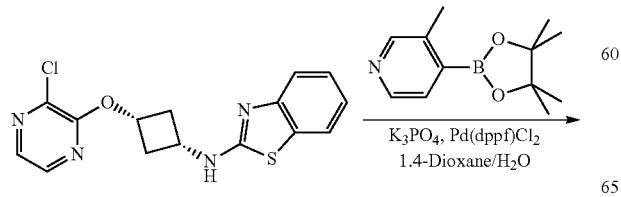

K$_3$PO$_4$, Pd(dppf)Cl$_2$
1,4-Dioxane/H$_2$O

-continued

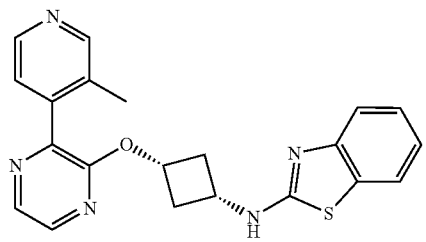

Example 42

N-((1S,3S)-3-((3-(3-METHYLPYRIDIN-4-YL)PYRAZIN-2-YL)OXY)CYCLOBUTYL)BENZO[D]THIAZOL-2-AMINE

To a mixture of N-((1S,3S)-3-((3-chloropyrazin-2-yl)oxy)cyclobutyl)benzo[d]thiazol-2-amine (see PREPARATION 5B; 150 mg, 0.6 mmol) in 1,4-Dioxane/H$_2$O (5:1) (12 mL) was added 3-methyl-4-(4,4,5,5-tetramethyl-[1,3,2]dioxaborolan-2-yl)-pyridine (197 mg, 0.9 mmol), K$_3$PO$_4$ (254 mg, 1.2 mmol) and Pd(dppf)Cl$_2$ (44 mg, 0.06 mmol), and then heated to reflux overnight. The reaction mixture was filtered and concentrated. The residue was purification by prep-HPLC to N-((1S,3S)-3-((3-(3-methylpyridin-4-yl)pyrazin-2-yl)oxy)cyclobutyl)benzo[d]thiazol-2-amine (70 mg, 0.18 mmol, yield 30%).

TABLE 3A

EXAMPLES 42-55 PREPARED ANALOGOUS TO SCHEME 13

| Ex. # | Structure | Chemical Name | M + 1 | IC$_{50}$ (uM) |
|---|---|---|---|---|
| 42 | 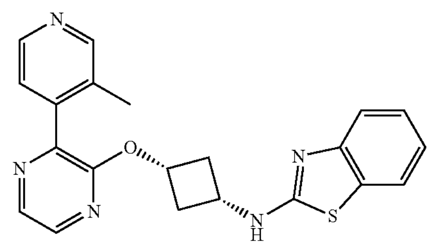 [SMILES: Cc1cnccc1-c1nccnc1O[C@H]1C[C@@H](Nc2nc3ccccc3s2)C1] | N-((1S,3S)-3-((3-(3-methylpyridin-4-yl)pyrazin-2-yl)oxy)cyclobutyl)benzo[d]thiazol-2-amine | 390 | 0.00423 |
| 43 | 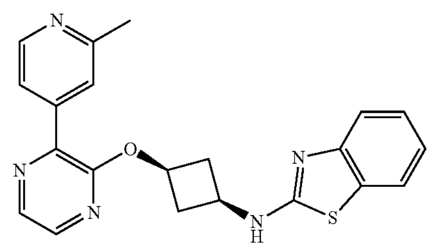 [SMILES: Cc1cc(-c2nccnc2O[C@H]2C[C@@H](Nc3nc4ccccc4s3)C2)ccn1] | N-((1S,3S)-3-((3-(2-methylpyridin-4-yl)pyrazin-2-yl)oxy)cyclobutyl)benzo[d]thiazol-2-amine | 390 | 0.0205 |
| 44 | 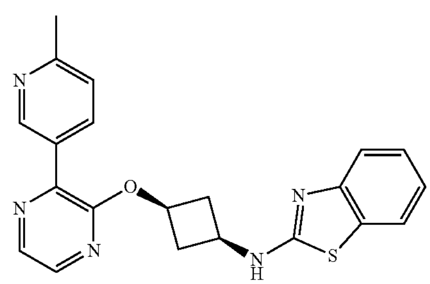 [SMILES: Cc1ccc(-c2nccnc2O[C@H]2C[C@@H](Nc3nc4ccccc4s3)C2)cn1] | N-((1S,3S)-3-((3-(6-methylpyridin-3-yl)pyrazin-2-yl)oxy)cyclobutyl)benzo[d]thiazol-2-amine | 390 | 0.00339 |
| 45 | 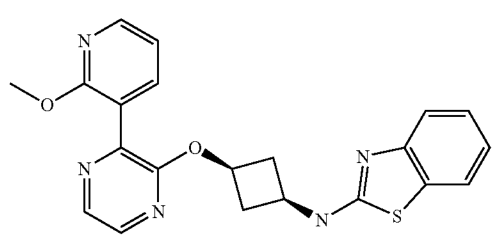 [SMILES: COc1ncccc1-c1nccnc1O[C@H]1C[C@@H](Nc2nc3ccccc3s2)C1] | N-((1S,3S)-3-((3-(2-methoxypyridin-3-yl)pyrazin-9-2-yl)oxy)cyclobutyl)benzo[d]thiazol-2-amine | 406 | 0.00411 |

TABLE 3A-continued

EXAMPLES 42-55 PREPARED ANALOGOUS TO SCHEME 13

| Ex. # | Structure | Chemical Name | M + 1 | IC$_{50}$ (uM) |
|---|---|---|---|---|
| 46 | 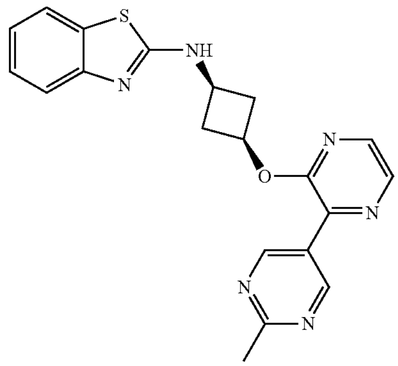 [SMILES: Cc1ncc(-c2nccnc2O[C@H]2C[C@@H](Nc3nc4ccccc4s3)C2)cn1] | N-((1S,3S)-3-((3-(2-methylpyrimidin-5-yl)pyrazin-2-yl)oxy)cyclobutyl)benzo[d]thiazol-2-amine | 391 | 0.00325 |
| 47 | 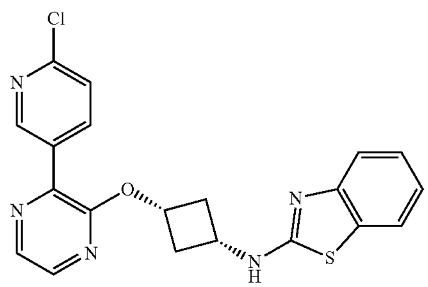 | N-((1S,3S)-3-((3-(6-chloropyridin-3-yl)pyrazin-2-yl)oxy)cyclobutyl)benzo[d]thiazol-2-amine | 410 | 0.00766 |
| 48 | 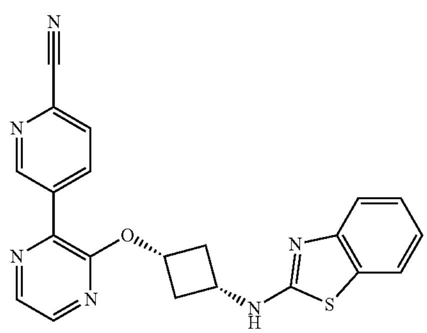 [SMILES: N#Cc1ccc(-c2nccnc2O[C@H]2C[C@@H](Nc3nc4ccccc4s3)C2)cn1] | 5-(3-((1S,3S)-3-(benzo[d]thiazol-2-ylamino)cyclobutoxy)pyrazin-2-yl)picolinonitrile | 401 | 0.0074 |
| 49 | 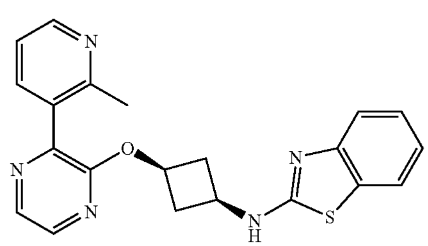 [SMILES: Cc1ncccc1-c1nccnc1O[C@H]1C[C@@H](Nc2nc3ccccc3s2)C1] | N-((1S,3S)-3-((3-(2-methylpyridin-3-yl)pyrazin-2-yl)oxy)cyclobutyl)benzo[d]thiazol-2-amine | 390 | 0.00194 |

TABLE 3A-continued

EXAMPLES 42-55 PREPARED ANALOGOUS TO SCHEME 13

| Ex. # | Structure | Chemical Name | M + 1 | IC$_{50}$ (uM) |
|---|---|---|---|---|
| 50 | 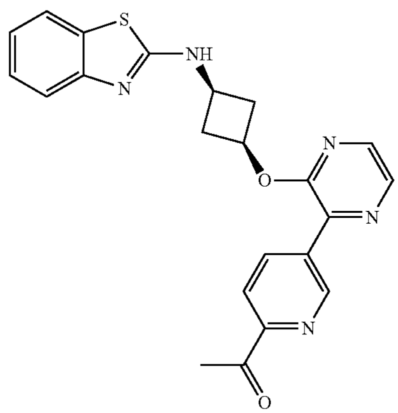 [SMILES: CC(=O)c1ccc(-c2nccnc2O[C@H]2C[C@@H](Nc3nc4ccccc4s3)C2)cn1] | 1-(5-(3-((1S,3S)-3-(benzo[d]thiazol-2-ylamino)cyclobutoxy)pyrazin-2-yl)pyridin-2-yl)ethanone | 418 | 0.00274 |
| 51 | 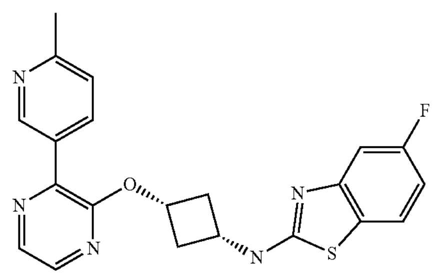 [SMILES: Cc1ccc(-c2nccnc2O[C@H]2C[C@@H](Nc3nc4cc(F)ccc4s3)C2)cn1] | 5-fluoro-N-((1S,3S)-3-((3-(6-methylpyridin-3-yl)pyrazin-2-yl)oxy)cyclobutyl)benzo[d]thiazol-2-amine | 408 | 0.0197 |
| 52 | 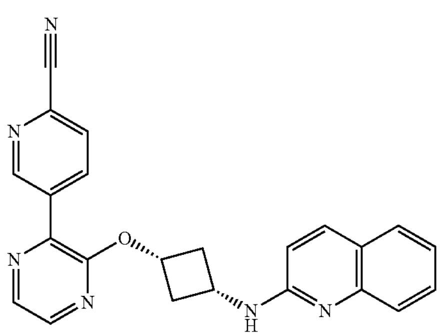 [SMILES: N#Cc1ccc(-c2nccnc2O[C@H]2C[C@@H](Nc3ccc4ccccc4n3)C2)cn1] | 5-(3-((1S,3S)-3-(quinolin-2-ylamino)cyclobutoxy)pyrazin-2-yl)picolinonitrile | 395 | 0.00835 |
| 53 | 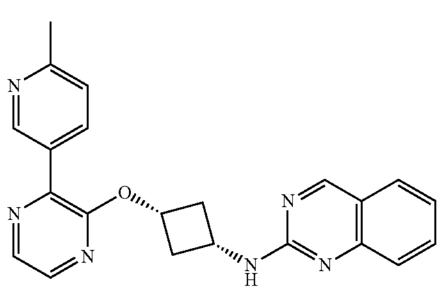 [SMILES: Cc1ccc(-c2nccnc2O[C@H]2C[C@@H](Nc3ncc4ccccc4n3)C2)cn1] | N-((1S,3S)-3-((3-(6-methylpyridin-3-yl)pyrazin-2-yl)oxy)cyclobutyl)quinazolin-2-amine | 385 | 0.00243 |

TABLE 3A-continued

EXAMPLES 42-55 PREPARED ANALOGOUS TO SCHEME 13

| Ex. # | Structure | Chemical Name | M + 1 | IC$_{50}$ (uM) |
|---|---|---|---|---|
| 54 | 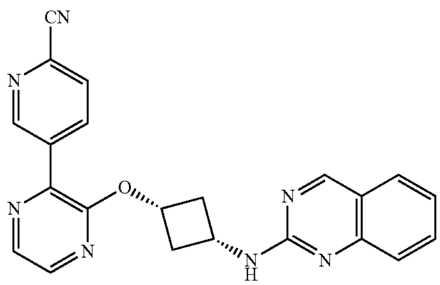 [SMILES: N#Cc1ccc(-c2nccnc2O[C@H]2C[C@@H](Nc3ncc4ccccc4n3)C2)cn1] | 5-(3-((1S,3S)-3-(quinazolin-2-ylamino)cyclobutoxy)pyrazin-2-yl)picolinonitrile | 396 | 0.00771 |
| 55 | 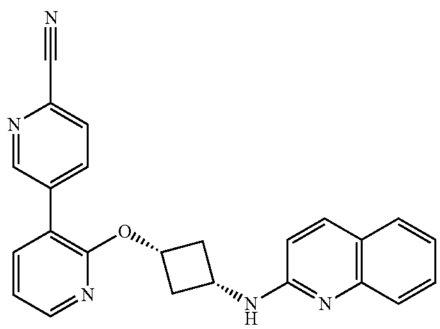 [SMILES: N#Cc1ccc(-c2cccnc2O[C@H]2C[C@@H](Nc3ccc4ccccc4n3)C2)cn1] | 2'-((1S,3S)-3-(quinolin-2-ylamino)cyclobutoxy)-[3,3'-bipyridine]-6-carbonitrile | 394 | 0.00129 |

TABLE 3B

PREPARATION AND NMR DATA OF EXAMPLES 42-55

| Ex. # | Starting Material (1) | Starting Material (2) | Reaction Condition | $^1$H NMR (CDCl$_3$, 400 MHz) δ (ppm) |
|---|---|---|---|---|
| 42 | (see Preparation 5B) | | Pd(dppf)Cl$_2$, K$_3$PO$_4$, Dioxane/H$_2$O | 8.77 (s, 1H); 8.72-8.70 (d, J = 5.6 Hz, 1H); 8.37-8.36 (d, J = 2.8 Hz, 2H); 8.26-8.25 (d, J = 2.8 Hz, 1H); 7.95-7.94 (d, J = 6 Hz, 1H); 7.60-7.58 (d, J = 7.6 Hz, 1H); 7.51-7.49 (d, J = 8 Hz, 1H); 7.43-7.40 (m, 1H); 7.29-7.24 (m, 1H); 5.13-5.06 (m, 1H); 3.72 (s, 1H); 3.23-3.17 (m, 2H); 2.50 (s, 3H); 2.45-2.36 (m, 2H). |
| 43 | (see Preparation 5B) | | Pd(dppf)Cl$_2$, K$_3$PO$_4$, Dioxane/H$_2$O | 8.75-8.73 (d, J = 6.4 Hz, 1H); 8.64-8.63 (d, J = 7.2 Hz, 2H); 8.45-8.44 (d, J = 2.4 Hz, 1H); 8.37-8.36 (d, J = 2.4 Hz, 1H); 7.75-7.73 (d, J = 8 Hz, 1H); 7.51-7.49 (d, J = 8.4 Hz, 1H); 7.46-7.42 (m, 1H); 7.30-7.26 (m, 1H); 5.32-5.26 (m, 1H); 4.15-4.11 (m, 1H); 3.31-3.24 (m, 2H); 2.85 (s, 3H); 2.53-2.45 (m, 2H). |

TABLE 3B-continued

PREPARATION AND NMR DATA OF EXAMPLES 42-55

| Ex. # | Starting Material (1) | Starting Material (2) | Reaction Condition | $^1$H NMR (CDCl$_3$, 400 MHz) δ (ppm) |
|---|---|---|---|---|
| 44 | (see Preparation 5B) | | Pd(dppf)Cl$_2$, K$_3$PO$_4$, Dioxane/H$_2$O | 9.23-9.22 (d, J = 1.6 Hz, 1H); 8.27-8.22 (m, 2H); 8.01-8.00 (d, J = 2.4 Hz, 1H); 7.54-7.48 (m, 2H); 7.24-7.14 (m, 2H); 7.04-7.00 (m, 1H); 5.12-5.06 (m, 1H); 4.07-3.99 (m, 1H); 3.20-3.13 (m, 2H); 2.61 (s, 3H); 2.23-2.16 (m, 2H). |
| 45 | (see Preparation 5B) | | Pd(dppf)Cl$_2$, K$_3$PO$_4$, Dioxane/H$_2$O | 8.25-8.21 (m, 2H); 8.07-8.06 (d, J = 2.8 Hz, 2H); 7.71-7.69 (m, 1H); 7.57-7.55 (d, J = 8 Hz, 1H); 7.51-7.49 (d, J = 8 Hz, 1H); 7.27-7.23 (m, 1H); 7.09-7.05 (m, 1H); 7.01-6.98 (m, 1H); 5.10-5.03 (m, 1H); 3.99-3.96 (m, 1H); 3.93 (s, 3H); 3.16-3.09 (m, 2H); 2.11-2.04 (m, 2H). |
| 46 | (see Preparation 5B) | | Pd(dppf)Cl$_2$, K$_3$PO$_4$, Dioxane/H$_2$O | 8.33-8.21 (m, 1H); 8.02-8.01 (m, 1H); 7.80-7.78 (d, J = 7.6 Hz, 1H); 7.55-7.48 (m, 2H); 7.37-7.33 (m, 1H); 5.27-5.23 (m, 1H); 4.16-4.12 (m, 1H); 3.32-3.25 (m, 2H); 2.76 (s, 3H); 2.52-2.41 (m, 2H). |
| 47 | (see Preparation 5B) | | Pd(dppf)Cl$_2$, K$_3$PO$_4$, Dioxane/H$_2$O | 9.11 (d, J = 2.4 Hz, 1H); 8.42-8.39 (m, 1H); 8.30-8.29 (m, 1H); 8.08-8.07 (m, 1H); 7.62 (d, J = 8 Hz, 1H); 7.56 (d, J = 8 Hz, 1H); 7.47-7.43 (m, 2H); 7.31-7.26 (m, 1H); 5.16-5.09 (m, 1H); 3.77-3.72 (m, 1H); 3.28-3.21 (m, 2H); 2.61-2.47 (m, 2H). |
| 48 | (see Preparation 5B) | | Pd(dppf)Cl$_2$, K$_3$PO$_4$, Dioxane/H$_2$O | 9.41 (s, 1H); 8.60-8.58 (m, 1H); 8.34 (d, J = 2.4 Hz, 1H); 8.13 (d, J = 2.4 Hz, 1H); 7.80-7.78 (m, 1H); 7.61 (d, J = 8 Hz, 1H); 7.53 (d, J = 8 Hz, 1H); 7.45-7.41 (m, 1H); 7.30-7.24 (m, 1H); 5.16-5.12 (m, 1H); 3.75-3.71 (m, 1H); 3.28-3.21 (m, 2H); 2.53-2.46 (m, 2H). |
| 49 | (see Preparation 5B) | | Pd(dppf)Cl$_2$, K$_3$PO$_4$, Dioxane/H$_2$O | 8.85 (d, J = 5.6 Hz, 1H); 8.73 (d, J = 8 Hz, 1H); 8.42 (s, 1H); 8.37 (s, 1H); 8.06-8.03 (m, 1H); 7.78 (d, J = 7.6 Hz, 1H); 7.54-7.46 (m, 2H); 7.36-7.32 (m, 1H); 5.24-5.20 (m, 1H); 4.13-4.09 (m, 1H); 3.28-3.21 (m, 2H); 2.77 (s, 3H); 2.43-2.36 (m, 2H). |

TABLE 3B-continued

PREPARATION AND NMR DATA OF EXAMPLES 42-55

| Ex. # | Starting Material (1) | Starting Material (2) | Reaction Condition | $^1$H NMR (CDCl$_3$, 400 MHz) δ (ppm) |
|---|---|---|---|---|
| 50 | 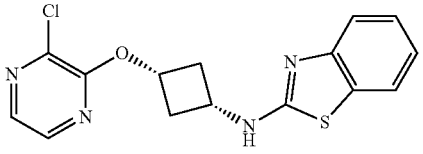<br>(see Preparation 5B) | 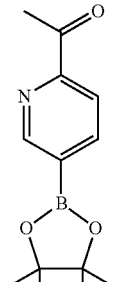<br>(see Prep. 9) | Pd(dppf)Cl$_2$, K$_3$PO$_4$, Dioxane/H$_2$O | 9.41 (s, 1H); 8.55-8.53 (m, 1H); 8.35-8.34 (m, 1H); 8.16-8.12 (m, 2H); 7.63-7.56 (m, 2H); 7.46-7.42 (m, 1H); 7.29-7.27 (m, 1H); 5.20-5.12 (m, 1H); 3.82-3.75 (m, 1H); 3.29-3.24 (m, 3H); 2.78 (s, 3H); 2.53-2.46 (m, 2H). |
| 51 | 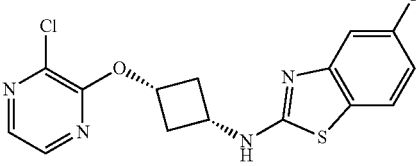<br>(see Preparation 5I) | 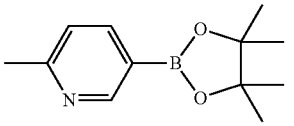 | Pd(dppf)Cl$_2$, K$_3$PO$_4$, 1,4-Dioxane | (CD$_3$OD) 9.47 (s, 1H); 9.27-9.25 (m, 1H); 8.42 (s, 1H); 8.32 (s, 1H); 8.05-8.02 (m, 1H); 7.71-7.68 (m, 1H); 7.25-7.22 (m, 1H); 7.04-6.99 (m, 1H); 5.32-5.25 (m, 1H); 4.21-4.13 (m, 1H); 3.28-3.24 (m, 2H); 2.88 (s, 3H); 2.48-2.41 (m, 2H). |
| 52 | 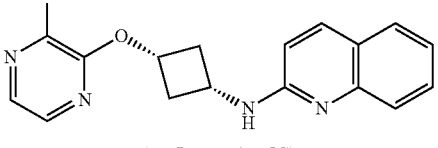<br>(see Preparation 5G) | 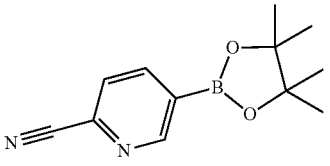 [SMILES: CC1(C)OB(c2ccc(C#N)nc2)OC1(C)C] | Pd(dppf)Cl$_2$, K$_3$PO$_4$, Dioxane/H$_2$O | 9.45 (s, 1H); 8.67-8.64 (m, 1H); 8.34-8.33 (d, J = 2.8 Hz, 1H); 8.20-8.14 (m, 2H); 7.82-7.69 (m, 4H); 7.45-7.41 (m, 1H); 6.84-6.81 (d, J = 9.2 Hz, 1H); 5.20-5.16 (m, 1H); 3.96 (s, 1H); 3.24-3.21 (m, 2H); 2.51-2.46 (m, 2H). |
| 53 | 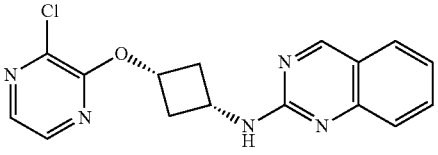<br>(see Preparation 5G) | 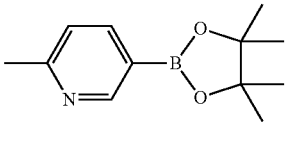 | Pd(dppf)Cl$_2$, K$_3$PO$_4$, Dioxane/H$_2$O | (d$_6$-DMSO) 9.12-9.08 (m, 2H); 8.35-8.20 (m, 3H); 7.80-7.61 (m, 3H); 7.48-7.37 (m, 2H); 7.23-7.19 (m, 1H); 5.12-5.04 (m, 1H); 4.33-4.27 (m, 1H); 2.98-2.91 (m, 2H); 2.53 (s, 3H); 2.27-2.20 (m, 2H). |
| 54 | 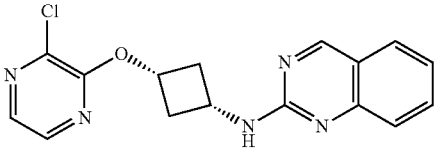<br>(see Preparation 5G) | 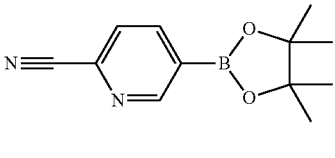 [SMILES: CC1(C)OB(c2ccc(C#N)nc2)OC1(C)C] | Pd(dppf)Cl$_2$, K$_3$PO$_4$, Dioxane/H$_2$O | (d$_6$-DMSO) 9.40 (s, 1H); 9.12 (s, 1H); 8.68-8.66 (m, 1H); 8.45-8.36 (m, 2H); 8.21-8.19 (m, 1H); 7.81-7.68 (m, 3H); 7.48-7.45 (m, 1H); 7.26-7.22 (m, 1H); 5.15-5.12 (m, 1H); 4.36-4.32 (m, 1H); 2.99-2.96 (m, 2H); 2.31-2.25 (m, 2H). |

TABLE 3B-continued

PREPARATION AND NMR DATA OF EXAMPLES 42-55

| Ex. # | Starting Material (1) | Starting Material (2) | Reaction Condition | $^1$H NMR (CDCl$_3$, 400 MHz) δ (ppm) |
|---|---|---|---|---|
| 55 | (see Preparation 7G) | | Pd(dppf)Cl$_2$, K$_3$PO$_4$, Dioxane/H$_2$O | (CD$_3$OD) 8.91-8.90 (m, 1H); 8.23-8.20 (m, 3H); 7.91 (d, J = 8.4 Hz, 1H); 7.87-7.82 (m, 3H); 7.78-7.74 (m, 1H); 7.51-7.47 (m, 1H); 7.14-7.12 (m, 1H); 7.00 (s, 1H); 5.23-5.20 (m, 1H); 4.29-4.27 (m, 1H); 3.24-3.22 (m, 2H); 2.33-2.26 (m, 2H). |

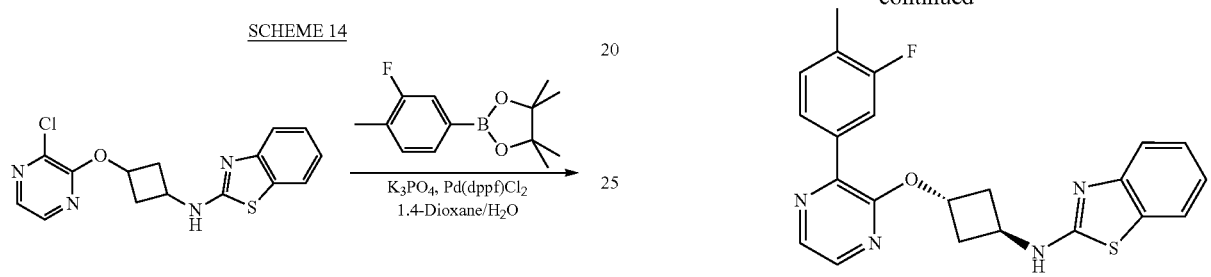

SCHEME 14

Examples 56 and 57

N-((1S,3S)-3-((3-(3-FLUORO-4-METHYLPHENYL)PYRAZIN-2-YL)OXY)CYCLOBUTYL)BENZO[D]THIAZOL-2-AMINE and N-((1R,3R)-3-((3-(3-FLUORO-4-METHYLPHENYL)PYRAZIN-2-YL)OXY)CYCLOBUTYL)BENZO[D]THIAZOL-2-AMINE To a mixture of N-(3-((3-chloropyrazin-2-yl)oxy)cyclobutyl)benzo[d]thiazol-2-amine (see PREPARATION 5C, 150 mg, 0.6 mmol) in 1,4-Dioxane/water (5:1) (12 mL) was added 2-(3-Fluoro-4-methyl-phenyl)-4,4,5,5-tetramethyl-[1,3,2]dioxaborolane (212 mg, 0.9 mmol), K$_3$PO$_4$ (254 mg, 1.2 mmol) and Pd(dppf)Cl$_2$ (44 mg, 0.06 mmol). The mixture was heated to reflux overnight. The reaction mixture was filtered and concentrated. The residue was purification by prep-HPLC to give Examples 56 and 57.

TABLE 4A

EXAMPLES 56-59 PREPARED ANALOGOUS TO SCHEME 14

| Ex.# | Structure | Chemical Name | M + 1 | IC$_{50}$ (uM) |
|---|---|---|---|---|
| 56 | 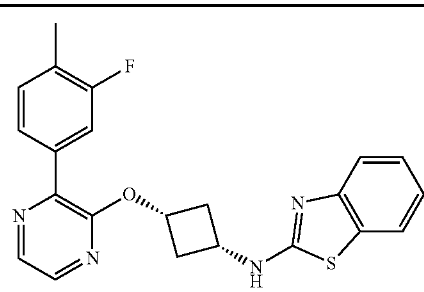 | N-((1S,3S)-3-((3-(3-fluoro-4-methylphenyl)pyrazin-2-yl)oxy)cyclobutyl)benzo[d]thiazol-2-amine | 407 | 0.0362 |

TABLE 4A-continued

EXAMPLES 56-59 PREPARED ANALOGOUS TO SCHEME 14

| Ex.# | Structure | Chemical Name | M + 1 | IC$_{50}$ (uM) |
|---|---|---|---|---|
| 57 | 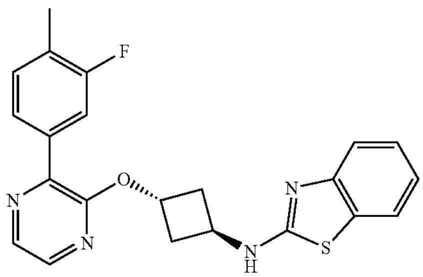 [SMILES: Cc1ccc(-c2nccnc2O[C@H]2C[C@H](Nc3nc4ccccc4s3)C2)cc1F] | N-((1R,3R)-3-((3-(3-fluoro-4-methylphenyl)pyrazin-2-yl)oxy)cyclobutyl)benzo[d]thiazol-2-amine | 407 | 0.0444 |
| 58 | 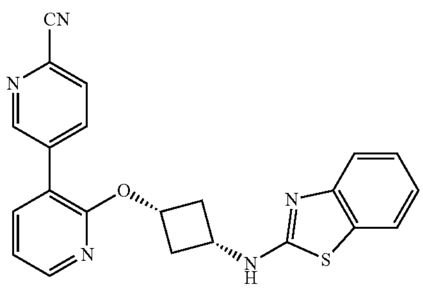 [SMILES: N#Cc1ccc(-c2cccnc2O[C@H]2C[C@@H](Nc3nc4ccccc4s3)C2)cn1] | 2'-((1S,3S)-3-(benzo[d]thiazol-2-ylamino)cyclobutoxy)-[3,3'-bipyridine]-6-carbonitrile | 400 | 0.00056 |
| 59 | 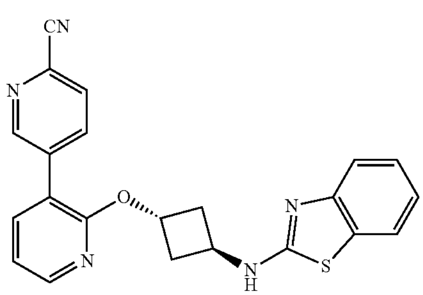 [SMILES: N#Cc1ccc(-c2cccnc2O[C@H]2C[C@H](Nc3nc4ccccc4s3)C2)cn1] | 2'-((1R,3R)-3-(benzo[d]thiazol-2-ylamino)cyclobutoxy)-[3,3'-bipyridine]-6-carbonitrile | 400 | 0.00297 |

TABLE 4B

PREPARATION AND NMR DATA OF EXAMPLES 56-59

| Ex.# | Starting Material (1) | Starting Material (2) | Reaction Condition | $^1$H NMR (CDCl$_3$, 400 MHz) δ (ppm) |
|---|---|---|---|---|
| 56 | 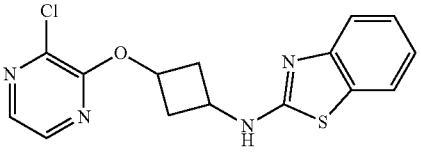<br>(see Preparation 5C) | 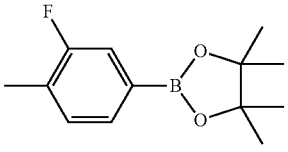 | K3PO4, Pd(dppf)Cl$_2$ 1,4-Dioxane/ H2O | 8.19-8.18 (m, 1H); 7.94-7.93 (d, J = 2.4 Hz, 1H); 7.74-7.67 (m, 2H); 7.54-7.49 (m, 2H); 7.41-7.37 (m, 1H); 7.23-7.19 (m, 2H); 5.08-5.01 (m, 1H); 3.66-3.60 (m, 1H); 3.20-3.14 (m, 2H); 2.49-2.42 (m, 2H); 2.27 (s, 3H). |
| 57 | 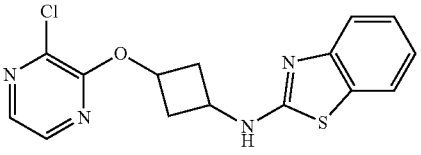<br>(see Preparation 5C) | 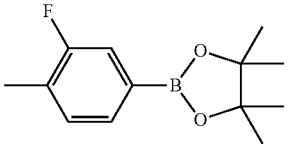 | K3PO4, Pd(dppf)Cl$_2$ 1,4-Dioxane/ H2O | 8.25-8.24 (d, J = 2 Hz, 1H); 8.03-8.02 (d, J = 2 Hz, 1H); 7.82-7.78 (m, 2H); 7.62-7.55 (m, 2H); 7.47-7.43 (m, 1H); 7.31-7.26 (m, 2H); 5.55 (s, 1H); 4.16 (s, 1H); 2.90-2.77 (m, 4H); 2.35 (s, 3H). |
| 58 | 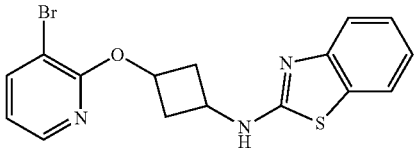<br>(see Preparation 7E) | 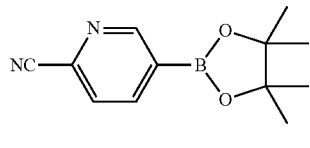 [SMILES: CC1(C)OB(c2ccc(C#N)nc2)OC1(C)C] | Pd(dppf)Cl$_2$, K$_3$PO$_4$ dioxane/ H$_2$O | (CD$_3$OD) 8.95-8.94 (m, 1H); 8.23-8.20 (m, 2H); 7.92-7.90 (m, 1H); 7.85-7.83 (m, 1H); 7.57-7.56 (m, 1H); 7.55-7.54 (m, 1H); 7.43-7.41 (m, 1H); 7.26-7.22 (m, 1H); 7.12-7.02 (m, 1H); 5.13 (s, 1H); 4.10 (s, 1H); 3.12-3.09 (m, 2H); 2.14-2.10 (m, 2H). |
| 59 | 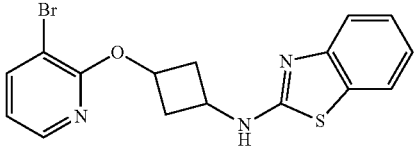<br>(see Preparation 7E) | 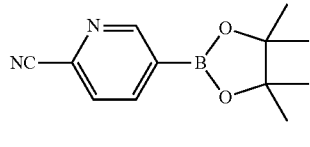 | Pd(dppf)Cl$_2$, K$_3$PO$_4$ dioxane/ H$_2$O | (CD$_3$OD) 9.01 (s, 1H); 8.30-8.21 (m, 2H); 7.97-7.95 (m, 1H); 7.90-7.88 (m, 1H); 7.79-7.77 (m, 1H); 7.51-7.48 (m, 2H); 7.37-7.33 (m, 1H); 7.17-7.14 (m, 1H); 5.56-5.53 (m, 1H); 4.47-4.44 (m, 1H); 2.77-2.74 (m, 4H). |

SCHEME 15

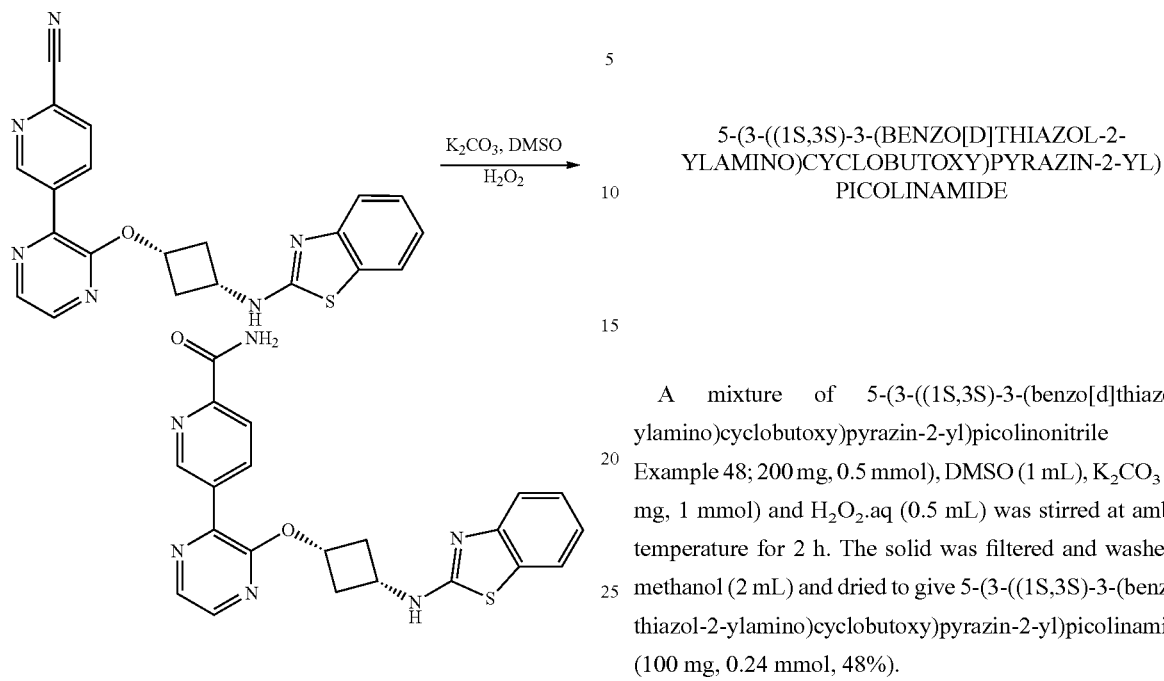

Example 60

5-(3-((1S,3S)-3-(BENZO[D]THIAZOL-2-YLAMINO)CYCLOBUTOXY)PYRAZIN-2-YL)PICOLINAMIDE

A mixture of 5-(3-((1S,3S)-3-(benzo[d]thiazol-2-ylamino)cyclobutoxy)pyrazin-2-yl)picolinonitrile (see Example 48; 200 mg, 0.5 mmol), DMSO (1 mL), $K_2CO_3$ (138 mg, 1 mmol) and $H_2O_2$.aq (0.5 mL) was stirred at ambient temperature for 2 h. The solid was filtered and washed by methanol (2 mL) and dried to give 5-(3-((1S,3S)-3-(benzo[d]thiazol-2-ylamino)cyclobutoxy)pyrazin-2-yl)picolinamide (100 mg, 0.24 mmol, 48%).

TABLE 5A

EXAMPLES 60-63 PREPARED ANALOGOUS TO SCHEME 15

| Ex. # | Structure | Chemical Name | M + 1 | IC$_{50}$ (uM) |
|---|---|---|---|---|
| 60 | 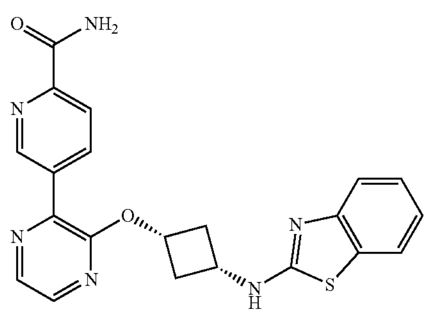 [SMILES: NC(=O)c1ccc(-c2nccnc2O[C@H]2C[C@@H](Nc3nc4ccccc4s3)C2)cn1] | 5-(3-((1S,3S)-3-(benzo[d]thiazol-2-ylamino)cyclobutoxy)pyrazin-2-yl)picolinamide | 419 | 0.00296 |
| 61 | 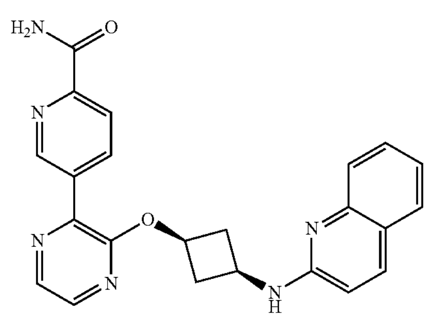 [SMILES: NC(=O)c1ccc(-c2nccnc2O[C@H]2C[C@@H](Nc3ccc4ccccc4n3)C2)cn1] | 5-(3-((1S,3S)-3-(quinolin-2-ylamino)cyclobutoxy)pyrazin-2-yl)picolinamide | 413 | 0.0038 |

TABLE 5A-continued

EXAMPLES 60-63 PREPARED ANALOGOUS TO SCHEME 15

| Ex. # | Structure | Chemical Name | M + 1 | IC$_{50}$ (uM) |
|---|---|---|---|---|
| 62 | 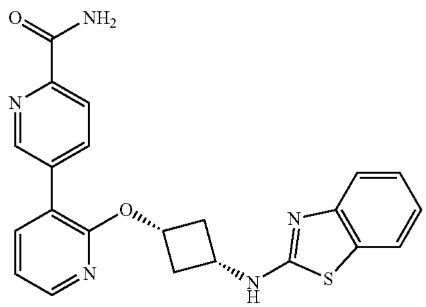 [SMILES: NC(=O)c1ccc(-c2cccnc2O[C@H]2C[C@@H](Nc3nc4ccccc4s3)C2)cn1] | 2'-((1S,3S)-3-(benzo[d]thiazol-2-ylamino)cyclobutoxy)-[3,3'-bipyridine]-6-carboxamide | 418 | 0.000129 |
| 63 | 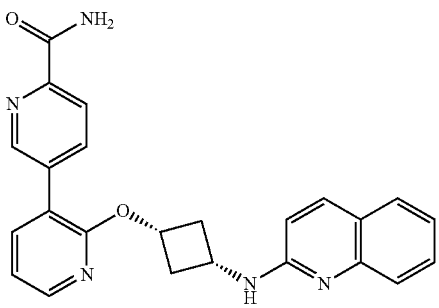 [SMILES: NC(=O)c1ccc(-c2cccnc2O[C@H]2C[C@@H](Nc3ccc4ccccc4n3)C2)cn1] | 2'-((1S,3S)-3-(quinolin-2-ylamino)cyclobutoxy)-[3,3'-bipyridine]-6-carboxamide | 412 | 0.00026 |

TABLE 5B

PREPARATION AND NMR DATA OF EXAMPLES 60-63

| Ex. # | Starting Material (1) | Reaction Condition | $^1$H NMR (d-DMSO, 400 MHz) δ (ppm) |
|---|---|---|---|
| 60 | | K$_2$CO$_3$, DMSO, H$_2$O$_2$ | 9.28-9.27 (m. 1H); 8.59-8.57 (m, 1H); 8.41 (d, J = 2.8 Hz, 1H); 8.34 (d, J = 7.2 Hz, 1H); 8.29 (d, J = 2.4 Hz, 1H); 8.19 (s, 1H); 8.16-8.14 (m, 1H); 7.65-7.64 (m, 2H); 7.38-7.36 (m, 1H); 7.22-7.18 (m, 1H); 7.02-6.98 (m, 1H); 5.13-5.10 (m, 1H); 4.16-4.10 (m, 1H); 3.05-2.98 (m, 2H); 2.23-2.16 (m, 2H). |
| 61 | | K$_2$CO$_3$, DMSO, H$_2$O$_2$ | 9.28 (s, 1H); 8.59-8.57 (m, 1H); 8.39-8.15 (m, 4H); 7.83 (d, J = 9.0 Hz, 1H); 7.72 (s, 1H); 7.58 (d, J = 7.9 Hz, 1H); 7.49-7.34 (m, 3H); 7.12 (t, J = 7.0 Hz, 1H); 6.69 (d, J = 8.8 Hz, 1H); 5.20-5.10 (m, 1H); 4.40-4.30 (m, 1H); 3.07-2.96 (m, 2H); 2.21-2.09 (m, 2H). |

(see Example 52)

TABLE 5B-continued

PREPARATION AND NMR DATA OF EXAMPLES 60-63

| Ex. # | Starting Material (1) | Reaction Condition | ¹H NMR (d-DMSO, 400 MHz) δ (ppm) |
|---|---|---|---|
| 62 | (see Example 58) | $K_2CO_3$, DMSO, $H_2O_2$ | 8.87-8.86 (m, 1H); 8.30-8.08 (m, 5H); 7.94-7.91 (m, 1H); 7.66-7.64 (m, 2H); 7.37-7.35 (m, 1H); 7.21-7.13 (m, 2H); 7.01-6.97 (m, 1H); 5.08-5.02 (m, 1H); 4.08-4.01 (m, 1H); 2.99-2.92 (m, 2H); 2.10-2.03 (m, 2H). |
| 63 | (see Example 55) | $K_2CO_3$, DMSO, $H_2O_2$ | 8.88-8.87 (m, 1H); 8.19-8.09 (m, 4H), 7.94-7.91 (m, 1H); 7.83-7.81 (m, 1H); 7.66 (brs, 1H); 7.59-7.57 (m, 1H); 7.48-7.45 (m, 2H); 7.30-7.29 (m, 1H); 7.16-7.14 (m, 2H); 6.68-6.66 (m, 1H); 5.13-5.11 (m, 1H); 4.34-4.30 (m, 1H); 2.98-2.94 (m, 2H), 2.06-2.01 (m, 2H). |

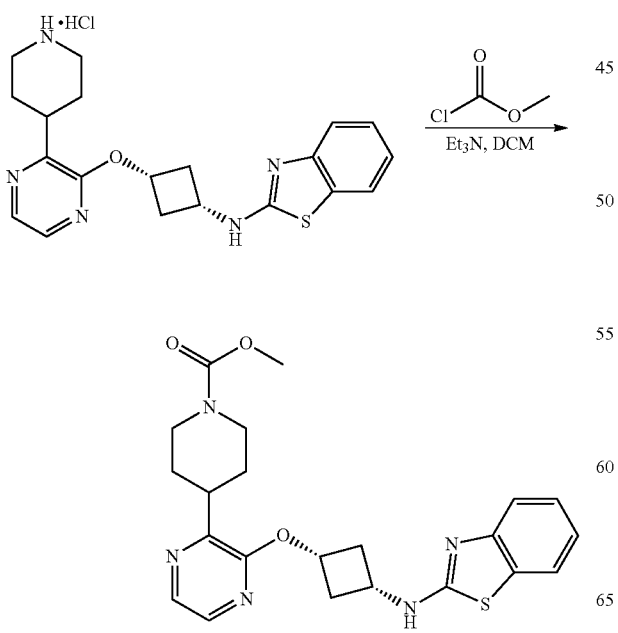

SCHEME 16

Example 64

METHYL 4-(3-((1S,3S)-3-(BENZO[D]THIAZOL-2-YLAMINO)CYCLOBUTOXY)PYRAZIN-2-YL)PIPERIDINE-1-CARBOXYLATE

To a solution of N-((1S,3S)-3-((3-(piperidin-4-yl)pyrazin-2-yl)oxy)cyclobutyl)benzo[d]thiazol-2-amine hydrochloride (see PREPARATION 5E; 381 mg, 1 mmol) in dry DCM (10 mL) was added Et₃N (1 mL). The reaction mixture was cooled to 0° C. with an ice bath, and methyl chloroformate (188 mg, 2 mmol) was added dropwise. After 1 hour, the reaction mixture was warmed to room temperature, and stirred overnight. Then the reaction mixture was washed with brine, dried over $Na_2SO_4$, filtered, and concentrated under vacuum to give the crude product. The residue was purified by prep-HPLC to give methyl 4-(3-((1S,3S)-3-(benzo[d]thiazol-2-ylamino)cyclobutoxy)pyrazin-2-yl)piperidine-1-carboxylate (307 mg, 0.7 mmol, 70% yield).

TABLE 6A

EXAMPLES 64-72 PREPARED ANALOGOUS TO SCHEME 16

| Ex. # | Structure | Chemical Name | M + 1 | IC$_{50}$ (uM) |
|---|---|---|---|---|
| 64 | 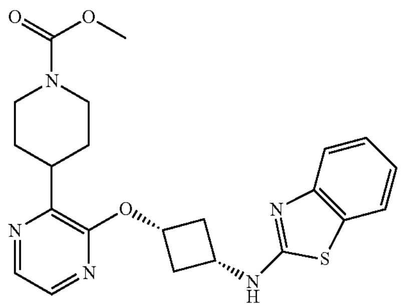 [SMILES: COC(=O)N1CCC(c2nccnc2O[C@H]2C[C@@H](Nc3nc4ccccc4s3)C2)CC1] | 4-(3-((1S,3S)-3-(benzo[d]thiazol-2-ylamino)cyclobutoxy)pyrazin-2-yl)piperidine-1-carboxylate | 440 | 0.00424 |
| 65 | 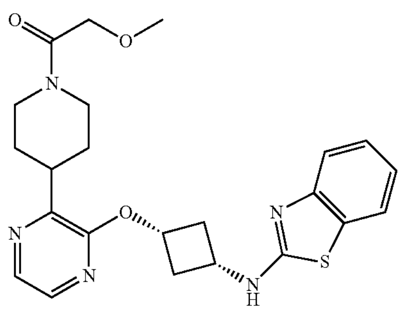 [SMILES: COCC(=O)N1CCC(c2nccnc2O[C@H]2C[C@@H](Nc3nc4ccccc4s3)C2)CC1] | 1-(4-(3-((1S,3S)-3-(benzo[d]thiazol-2-ylamino)cyclobutoxy)pyrazin-2-yl)piperidin-1-yl)-2-methoxyethanone | 454 | 0.00657 |
| 66 | 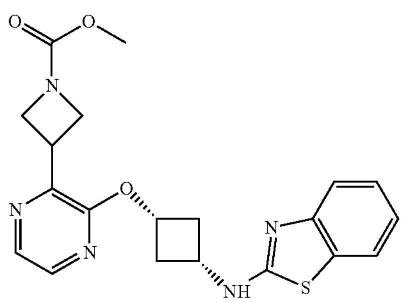 [SMILES: COC(=O)N1CC(c2nccnc2O[C@H]2C[C@@H](Nc3nc4ccccc4s3)C2)C1] | methyl 3-(3-((1S,3S)-3-(benzo[d]thiazol-2-ylamino)cyclobutoxy)pyrazin-2-yl)azetidine-1-carboxylate | 412 | 0.0175 |
| 67 | 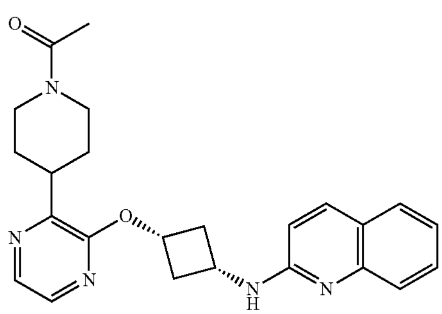 [SMILES: CC(=O)N1CCC(c2nccnc2O[C@H]2C[C@@H](Nc3ccc4ccccc4n3)C2)CC1] | 1-(4-(3-((1S,3S)-3-(quinolin-2-ylamino)cyclobutoxy)pyrazin-2-yl)piperidin-1-yl)ethanone | 418 | 0.00493 |
| 68 | 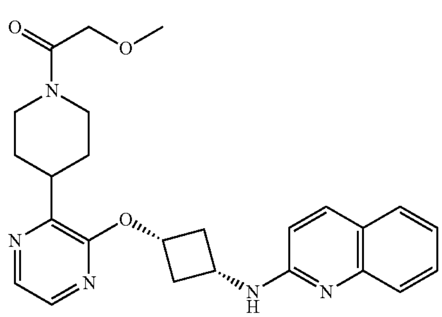 [SMILES: COCC(=O)N1CCC(c2nccnc2O[C@H]2C[C@@H](Nc3ccc4ccccc4n3)C2)CC1] | 2-methoxy-1-(4-(3-((1S,3S)-3-(quinolin-2-ylamino)cyclobutoxy)pyrazin-2-yl)piperidin-1-yl)ethanone | 448 | 0.00506 |

TABLE 6A-continued

EXAMPLES 64-72 PREPARED ANALOGOUS TO SCHEME 16

| Ex. # | Structure | Chemical Name | M + 1 | IC$_{50}$ (uM) |
|---|---|---|---|---|
| 69 | 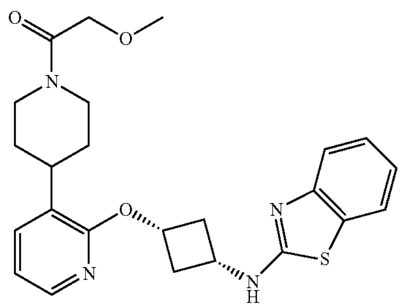 [SMILES: COCC(=O)N1CCC(c2cccnc2O[C@H]2C[C@@H](Nc3nc4ccccc4s3)C2)CC1] | 1-(4-(2-((1S,3S)-3-(benzo[d]thiazol-2-ylamino)cyclobutoxy)pyridin-3-yl)piperidin-1-yl)-2-methoxyethanone | 453 | 0.00129 |
| 70 | 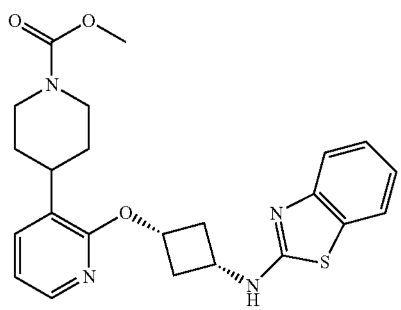 [SMILES: COC(=O)N1CCC(c2cccnc2O[C@H]2C[C@@H](Nc3nc4ccccc4s3)C2)CC1] | methyl 4-(2-((1S,3S)-3-(benzo[d]thiazol-2-ylamino)cyclobutoxy)pyridin-3-yl)piperidine-1-carboxylate | 439 | 0.00318 |
| 71 | 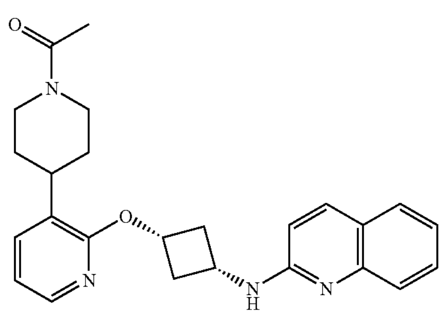 [SMILES: CC(=O)N1CCC(c2cccnc2O[C@H]2C[C@@H](Nc3ccc4ccccc4n3)C2)CC1] | 1-(4-(2-((1S,3S)-3-(quinolin-2-ylamino)cyclobutoxy)pyridin-3-yl)piperidin-1-yl)ethanone | 417 | 0.00132 |
| 72 | 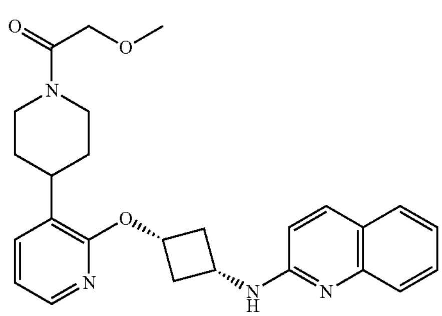 [SMILES: COCC(=O)N1CCC(c2cccnc2O[C@H]2C[C@@H](Nc3ccc4ccccc4n3)C2)CC1] | 2-methoxy-1-(4-(2-((1S,3S)-3-(quinolin-2-ylamino)cyclobutoxy)pyridin-3-yl)piperidin-1-yl)ethanone | 447 | 0.000948 |

TABLE 6B

PREPARATION AND NMR DATA OF EXAMPLES 64-72

| Ex.# | Starting Material (1) | Starting Material (2) | Reaction Condition | $^1$H NMR (CD$_3$OD, 400 MHz) δ (ppm) |
|---|---|---|---|---|
| 64 | (see Preparation 5E) | | Et$_3$N, DCM | 7.98-7.97 (d, J = 2.8 Hz, 1H); 7.83-7.82 (d, J = 2.8 Hz, 1H); 7.52 (d, J = 7.6 Hz, 1H); 7.47 (d, J = 7.6 Hz, 1H); 7.22-7.20 (m, 1H); 7.07-7.01 (m, 1H); 4.99-4.92 (m, 1H); 4.35-4.10 (br, 2H); 3.99-3.91 (m, 1H); 3.64 (s, 3H); 3.20-3.08 (m, 3H); 2.91-2.80 (m, 2H), 2.17-2.04 (m, 2H); 1.82-1.73 (m, 4H). |
| 65 | (see Preparation 5E) | | Et$_3$N, DCM | 8.06 (d, J = 2.8 Hz, 1H); 7.98-7.97 (m, 1H); 7.79 (d, J = 8.0 Hz, 1H); 7.55-7.48 (m, 2H); 7.37-7.33 (m, 1H); 5.14-5.10 (m, 1H); 4.59 (d, J = 13.6 Hz, 1H); 4.22-4.08 (m, 3H); 3.98 (d, J = 15.2 Hz, 1H); 3.40-3.34 (m, 4H); 3.27-3.19 (m, 3H); 2.83 (d, J = 2.4 Hz, 1H); 2.42-2.40 (m, 2H); 1.93-1.90 (m, 2H); 1.82-1.75 (m, 2H). |
| 66 | (see Preparation 5F) | | Et$_3$N, DCM | 8.09-8.08 (d, J = 2.4 Hz, 1H); 7.89-7.88 (d, J = 2.8 Hz, 1H); 7.57-7.50 (m, 2H); 7.42-7.38 (m, 1H); 7.26-7.20 (m, 1H); 4.99-4.95 (m, 1H); 4.30-4.20 (m, 4H); 4.10-4.06 (m, 1H); 3.66-3.54 (m, 4H); 3.16-3.09 (m, 2H); 2.41-2.34 (m, 2H). |
| 67 | (see Preparation 5H) | | Et$_3$N, DCM | 8.28-8.21 (s, 1H); 8.08-8.07 (d, J = 2.8 Hz, 1H); 7.99-7.96 (m, 1H); 7.95-7.83 (m, 2H); 7.81-7.75 (m, 1H); 7.54-7.50 (m, 1H); 7.12-7.01 (s, 1H); 5.18-5.14 (m, 1H); 4.63-4.60 (m, 1H); 4.31 (s, 1H); 4.07-4.03 (d, J = 13.6 Hz, 1H); 3.38-3.33 (m, 1H); 3.27-3.24 (m, 3H); 2.83-2.76 (m, 1H); 2.41-2.34 (m, 2H); 2.13 (s, 3H); 1.96-1.83 (m, 3H); 1.74-1.68 (m, 1H). |
| 68 | (see Preparation 5H) | | Et$_3$N, DCM | 8.25 (s, 1H); 8.05 (s, 1H); 7.97 (s, 1H); 7.86-7.77 (m, 3H); 7.50 (s, 1H); 7.03 (s, 1H); 5.14 (s, 1H); 4.59-4.56 (d, J = 11.6 Hz, 1H); 4.27-4.16 (m, 3H); 3.99-3.96 (m, 1H); 3.39 (s, 4H); 3.23 (s, 3H); 2.85-2.79 (m, 1H); 2.36 (s, 2H); 1.89-1.69 (m, 4H). |

TABLE 6B-continued

PREPARATION AND NMR DATA OF EXAMPLES 64-72

| Ex.# | Starting Material (1) | Starting Material (2) | Reaction Condition | $^1$H NMR (CD$_3$OD, 400 MHz) δ (ppm) |
|---|---|---|---|---|
| 69 | (see Preparation 7J) | | Et$_3$N, DCM | 7.87-7.86 (m, 1H); 7.50-7.49 (m, 1H); 7.48-7.42 (m, 1H); 7.35-7.33 (m, 1H); 7.18-7.14 (m, 1H); 6.98-6.94 (m, 1H); 6.83-6.80 (m, 1H); 4.98-4.96 (m, 1H); 4.58-4.56 (m, 1H); 4.12-4.10 (m, 2H); 4.07-4.06 (m, 1H); 4.02-4.01 (m, 1H); 3.31 (s, 3H); 3.05-2.99 (m, 4H); 2.62-2.60 (m, 1H); 2.08-2.01 (m, 2H); 1.82 (d, J = 13.2 Hz, 2H); 1.58-1.53 (m, 2H). |
| 70 | (see Preparation 7J) | | Et$_3$N, DCM | 7.97-7.95 (m, 1H); 7.81-7.79 (m, 1H); 7.55-7.51 (m, 3H); 7.49-7.34 (m, 1H); 6.94-6.91 (m, 1H); 5.13-5.09 (m, 1H); 4.25 (d, J = 12.8 Hz, 2H); 4.09-4.08 (m, 1H); 3.69 (s, 3H); 3.23-3.20 (m, 2H); 3.02 (s, 3H); 2.35-2.30 (m, 2H); 1.84 (d, J = 12.4 Hz, 2H); 1.64-1.60 (m, 2H). |
| 71 | (see Preparation 7G) | | Et3N, DCM | 8.16 (d, J = 9.2 Hz, 1H); 8.03 (d, J = 4 Hz, 1H); 7.79 (d, J = 8.4 Hz, 1H); 7.71-7.68 (m, 2H); 7.48-7.46 (m, 2H); 6.97-6.94 (m, 1H); 6.83 (d, J = 9.2 Hz, 1H); 5.20-5.16 (m, 1H); 4.79 (d, J = 12 Hz, 1H); 3.94 (s, 2H); 3.32-3.10 (m, 4H); 2.78-2.72 (m, 1H); 2.42 (d, J = 8.4 Hz, 2H); 2.19 (s, 3H); 2.07-1.86 (m, 2H); 1.63-1.51 (m, 2H). |
| 72 | (see Preparation 7G) | | Et$_3$N, DCM | 8.26-8.24 (m, 1H); 7.97-7.96 (m, 1H); 7.87-7.80 (m, 2H); 7.78-7.76 (m, 1H); 7.55-7.50 (m, 2H); 7.01-6.99 (m, 1H); 6.94-6.91 (m, 1H); 5.15-5.12 (m, 1H); 4.65-4.62 (m, 1H); 4.25-4.11 (m, 3H); 3.97-3.95 (m, 1H); 3.39 (s, 3H); 3.25-3.09 (m, 4H); 2.74-2.73 (m, 1H); 2.33-2.26 (m, 2H); 1.91-1.87 (m, 2H); 1.72-1.62 (m, 2H). |

SCHEME 17

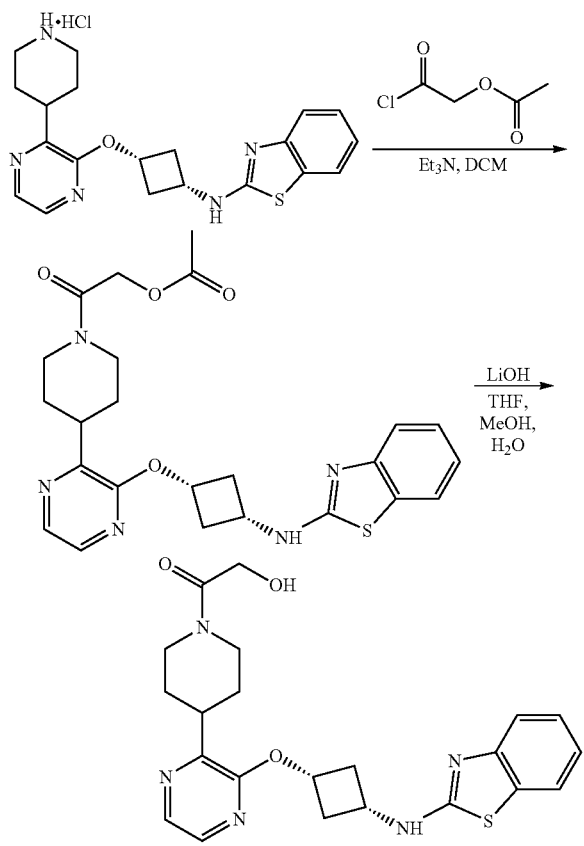

Example 73

1-(4-(3-((1S,3S)-3-(BENZO[D]THIAZOL-2-YLAMINO)CYCLOBUTOXY)PYRAZIN-2-YL)PIPERIDIN-1-YL)-2-HYDROXYETHANONE

Step 1. 2-(4-(3-((1S,3S)-3-(BENZO[D]THIAZOL-2-YLAMINO)CYCLOBUTOXY)PYRAZIN-2-YL)PIPERIDIN-1-YL)-2-OXOETHYL ACETATE To a solution of N-((1S,3S)-3-((3-(piperidin-4-yl)pyrazin-2-yl)oxy)cyclobutyl)benzo[d]thiazol-2-amine hydrochloride (see PREPARATION 5E; 381 mg, 1 mmol) in dry DCM (10 mL) was added Et₃N (1 mL). The reaction mixture was cooled to 0° C. with an ice bath, and 2-chloro-2-oxoethyl acetate (272 mg, 2 mmol) was added dropwise to the reaction mixture, 1 hour later, the reaction mixture was warmed to room temperature, and stirred overnight. Then the reaction mixture was washed with brine, dried over Na₂SO₄, filtered, and concentrated under vacuum to give the crude product (337 mg, 0.7 mmol, 70% yield). ESI-MS (M+1): 482 calc. for $C_{24}H_{27}N_5O_4S$ 481.

Step 2. 1-(4-(3-((1S,3S)-3-(BENZO[D]THIAZOL-2-YLAMINO)CYCLOBUTOXY)PYRAZIN-2-YL)PIPERIDIN-1-YL)-2-HYDROXYETHANONE A solution of 2-(4-(3-((1S,3S)-3-(benzo[d]thiazol-2-ylamino)cyclobutoxy)pyrazin-2-yl)piperidin-1-yl)-2-oxoethyl acetate (240 mg, 0.5 mmol) and LiOH (24 mg, 1.0 mmol) in THF/MeOH/H₂O (3:3:1) (21 mL) was stirred at RT for 1 hour. Then the reaction mixture was filtered and concentrated under vacuum to give the crude product. The crude product was purified by prep-HPLC to give 1-(4-(3-((1S,3S)-3-(benzo[d]thiazol-2-ylamino)cyclobutoxy)pyrazin-2-yl)piperidin-1-yl)-2-hydroxyethanone (175 mg, 0.8 mmol, 80% yield). M+1: 440. PDE10 IC$_{50}$ (uM): 0.00481. ¹H NMR (CD₃OD, 400 MHz) δ (ppm):
8.06 (d, J=2.8 Hz, 1H); 7.97 (d, J=2.8 Hz, 1H); 7.78 (d, J=7.6 Hz, 1H); 7.54-7.46 (m, 2H); 7.35-7.31 (m, 1H); 5.13-5.10 (m, 1H); 4.61-4.57 (m, 1H); 4.26-4.15 (m, 2H); 4.10-4.09 (m, 1H); 3.85 (d, J=13.6 Hz, 1H); 3.37-3.32 (m, 1H); 3.26-3.19 (m, 3H); 2.86 (d, J=2 Hz, 1H); 2.39-2.33 (m, 2H); 1.94-1.70 (m, 4H).

SCHEME 18

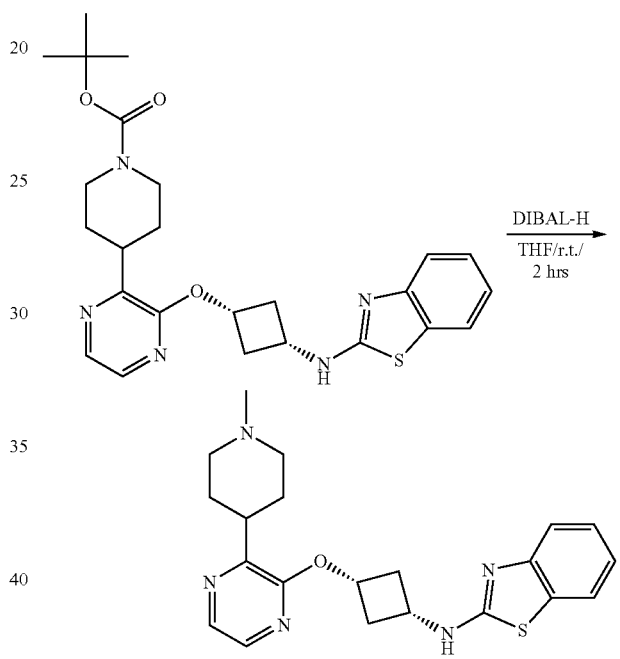

Example 74

N-((1S,3S)-3-((3-(1-METHYLPIPERIDIN-4-YL)PYRAZIN-2-YL)OXY)CYCLOBUTYL)BENZO[D]THIAZOL-2-AMINE

To the solution of tert-butyl 4-(3-((1S,3S)-3-(benzo[d]thiazol-2-ylamino)cyclobutoxy)pyrazin-2-yl)piperidine-1-carboxylate (see PREPARATION 5E, step 2; 482 mg, 1 mmol) in THF (10 ml) was added the diisobutylaluminum hydride (DIBAL-H) (1N in toluene) (1 ml). The mixture was stirred at RT for 2 h and quenched by water (1 ml). Reaction mixture was concentrated and the residue was purified by silica gel chromatography to give N-((1S,3S)-3-((3-(1-methylpiperidin-4-yl)pyrazin-2-yl)oxy)cyclobutyl)benzo[d]thiazol-2-amine. M+1: 396. PDE10 IC$_{50}$ (uM): 0.0498. ¹H NMR (CDCl₃, 400 MHz) δ (ppm):
8.05-7.97 (m, 2H); 7.59-7.53 (m, 2H); 7.30-7.23 (m, 1H); 7.10-7.06 (m, 1H); 5.27-5.24 (m, 1H); 4.24-4.20 (m, 1H); 3.51-3.42 (m, 3H); 3.21-3.04 (m, 3H); 2.84-2.52 (m, 6H); 2.49-2.31 (m, 2H); 2.14-2.01 (m, 2H).

SCHEME 19

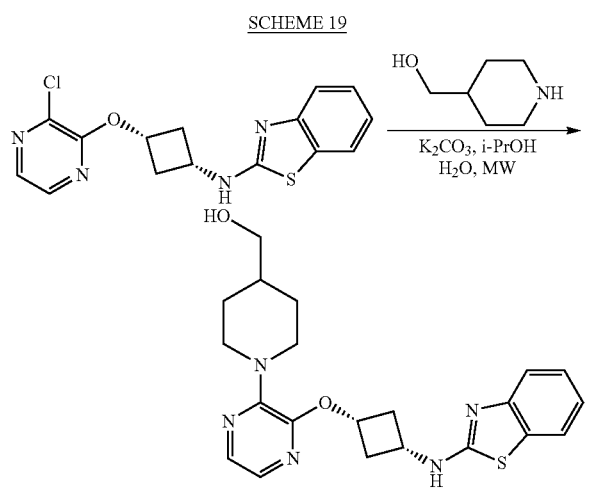
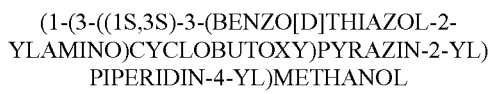

Example 75

(1-(3-((1S,3S)-3-(BENZO[D]THIAZOL-2-YLAMINO)CYCLOBUTOXY)PYRAZIN-2-YL)PIPERIDIN-4-YL)METHANOL

To a mixture of N-((1S,3S)-3-((3-chloropyrazin-2-yl)oxy)cyclobutyl)benzo[d]thiazol-2-amine (see PREPARATION 5B; 332 mg, 1 mmol) and piperidin-4-yl-methanol (115 mg, 1 mmol) and $K_2CO_3$ (276 mg, 2 mmol) was added isopropyl alcohol (i-PrOH) (2 mL) and water (0.5 mL). The solution was heated to 160° C. under microwave for 5 h. Then the mixture was diluted with water (20 mL) and extracted with EtOAc (2×30 mL). The combined organic extracts were washed with water (10 mL) and brine (10 mL), dried over $Na_2SO_4$, and filtered. The filtrate was evaporated in vacuo and the residue was purified by prep-HPLC to give (1-(3-((1S,3S)-3-(benzo[d]thiazol-2-ylamino)cyclobutoxy)pyrazin-2-yl)piperidin-4-yl)methanol. (111 mg, 0.27 mmol, 27% yield).

TABLE 7A

EXAMPLES 75-90 PREPARED ANALOGOUS TO SCHEME 19

| Ex.# | Structure | Chemical Name | ESI-MS (M + 1) | $IC_{50}$ (uM) |
|---|---|---|---|---|
| 75 | 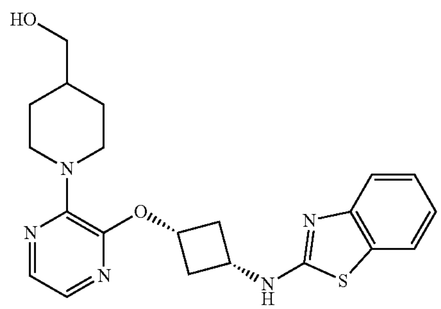 [SMILES: OCC1CCN(c2nccnc2O[C@H]2C[C@@H](Nc3nc4ccccc4s3)C2)CC1] | (1-(3-((1S,3S)-3-(benzo[d]thiazol-2-ylamino)cyclobutoxy)pyrazin-2-yl)piperidin-4-yl)methanol | 412 | 0.00316 |
| 76 | 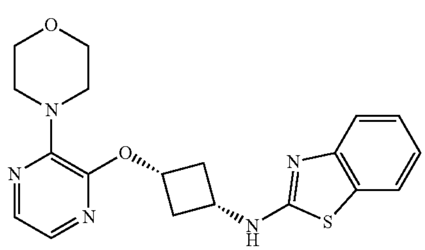 [SMILES: c1ccc2sc(N[C@H]3C[C@@H](Oc4nccnc4N4CCOCC4)C3)nc2c1] | N-((1S,3S)-3-((3-morpholinopyrazin-2-yl)oxy)cyclobutyl)benzo[d]thiazol-2-amine | 384 | 0.0224 |
| 77 | | N-((1S,3S)-3-((3-(3-methylpyrrolidin-1-yl)pyrazin-2-yl)oxy)cyclobutyl)benzo[d]thiazol-2-amine | 382 | 0.00692 | racemic mixtures

TABLE 7A-continued

EXAMPLES 75-90 PREPARED ANALOGOUS TO SCHEME 19

| Ex.# | Structure | Chemical Name | ESI-MS (M + 1) | IC$_{50}$ (uM) |
|---|---|---|---|---|
| 78 | racemic mixtures | 1-(3-((1S,3S)-3-(benzo[d]thiazol-2-ylamino)cyclobutoxy)pyrazin-2-yl)pyrrolidine-3-carbonitrile | 393 | 0.00107 |
| 79 | racemic mixtures | N-((1S,3S)-3-((3-(3-methylpiperidin-1-yl)pyrazin-2-yl)oxy)cyclobutyl)benzo[d]thiazol-2-amine | 396 | 0.0294 |
| 80 | racemic mixtures | (1-(3-((1S,3S)-3-(benzo[d]thiazol-2-ylamino)cyclobutoxy)pyrazin-2-yl)piperidin-3-yl)methanol | 412 | 0.00362 |
| 81 | 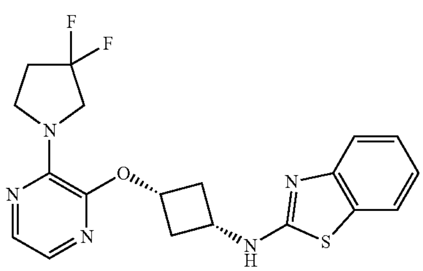 [SMILES: FC1(F)CCN(c2nccnc2O[C@H]2C[C@@H](Nc3nc4ccccc4s3)C2)C1] | N-((1S,3S)-3-((3-(3,3-difluoropyrrolidin-1-yl)pyrazin-2-yl)oxy)cyclobutyl)benzo[d]thiazol-2-amine | 404 | 0.0111 |
| 82 | 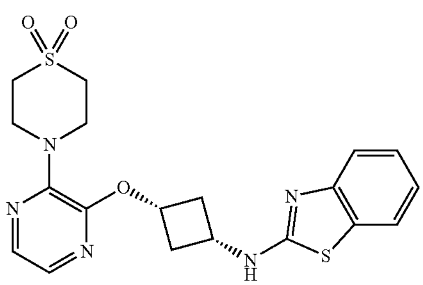 [SMILES: O=S1(=O)CCN(c2nccnc2O[C@H]2C[C@@H](Nc3nc4ccccc4s3)C2)CC1] | 4-(3-((1S,3S)-3-(benzo[d]thiazol-2-ylamino)cyclobutoxy)pyrazin-2-yl)thiomorpholine 1,1-dioxide | 432 | 0.0185 |

TABLE 7A-continued

EXAMPLES 75-90 PREPARED ANALOGOUS TO SCHEME 19

| Ex.# | Structure | Chemical Name | ESI-MS (M + 1) | IC$_{50}$ (uM) |
|---|---|---|---|---|
| 83 | 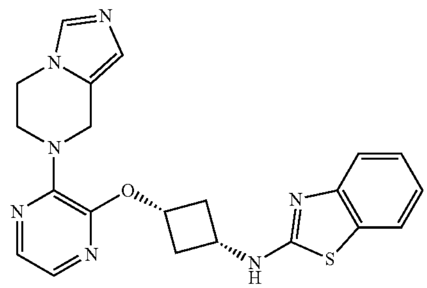 [SMILES: c1ccc2sc(N[C@H]3C[C@@H](Oc4nccnc4N4CCn5cncc5C4)C3)nc2c1] | N-((1S,3S)-3-((3-(5,6-dihydroimidazo[1,5-a]pyrazin-7(8H)-yl)pyrazin-2-yl)oxy)cyclobutyl)benzo[d]thiazol-2-amine | 420 | 0.00699 |
| 84 | single R enantiomer | (R)-1-(3-((1S,3S)-3-(benzo[d]thiazol-2-ylamino)cyclobutoxy)pyrazin-2-yl)pyrrolidin-3-ol | 384 | 0.0142 |
| 85 | single S enantiomer | (S)-1-(3-((1S,3R)-3-(benzo[d]thiazol-2-ylamino)cyclobutoxy)pyrazin-2-yl)pyrrolidin-3-ol | 384 | 0.0175 |
| 86 | 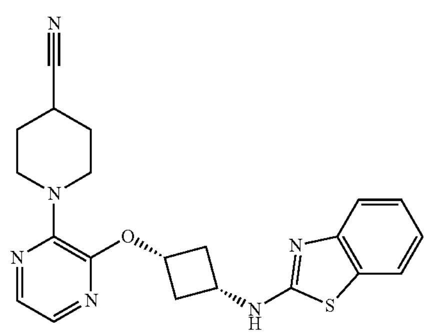 [SMILES: N#CC1CCN(c2nccnc2O[C@H]2C[C@@H](Nc3nc4ccccc4s3)C2)CC1] | 1-(3-((1S,3S)-3-(benzo[d]thiazol-2-ylamino)cyclobutoxy)pyrazin-2-yl)piperidine-4-carbonitrile | 407 | 0.00231 |
| 87 | 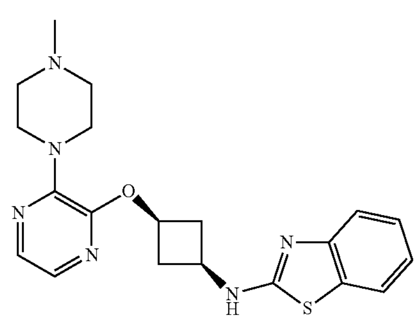 [SMILES: CN1CCN(c2nccnc2O[C@H]2C[C@@H](Nc3nc4ccccc4s3)C2)CC1] | N-((1S,3S)-3-((3-(4-methylpiperazin-1-yl)pyrazin-2-yl)oxy)cyclobutyl)benzo[d]thiazol-2-amine | 397 | 0.122 |

TABLE 7A-continued

EXAMPLES 75-90 PREPARED ANALOGOUS TO SCHEME 19

| Ex.# | Structure | Chemical Name | ESI-MS (M + 1) | IC$_{50}$ (uM) |
|---|---|---|---|---|
| 88 | 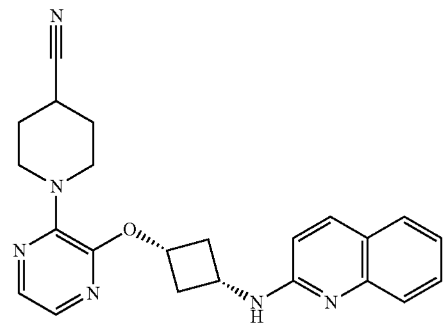 [SMILES: N#CC1CCN(c2nccnc2O[C@H]2C[C@@H](Nc3ccc4ccccc4n3)C2)CC1] | 1-(3-((1S,3S)-3-(quinolin-2-ylamino)cyclobutoxy)pyrazin-2-yl)piperidine-4-carbonitrile | 401 | 0.00226 |
| 89 | 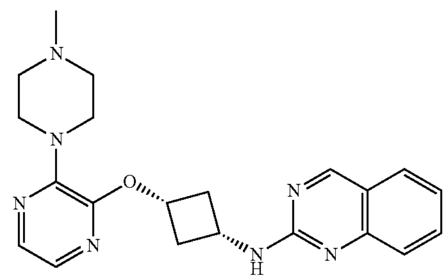 [SMILES: CN1CCN(c2nccnc2O[C@H]2C[C@@H](Nc3ncc4ccccc4n3)C2)CC1] | N-((1S,3S)-3-((3-(4-methylpiperazin-1-yl)pyrazin-2-yl)oxy)cyclobutyl)quinazolin-2-amine | 392 | 0.316 |
| 90 | 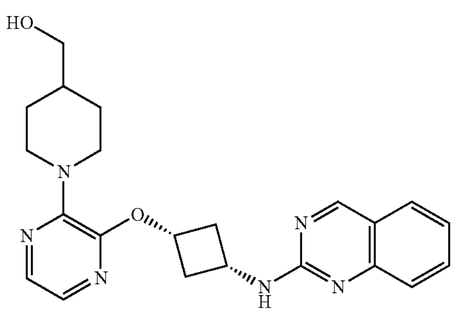 [SMILES: OCC1CCN(c2nccnc2O[C@H]2C[C@@H](Nc3ncc4ccccc4n3)C2)CC1] | (1-(3-((1S,3S)-3-(quinazolin-2-ylamino)cyclobutoxy)pyrazin-2-yl)piperidin-4-yl)methanol | 407 | 0.01089 |

TABLE 7B

PREPARATION AND NMR DATA OF EXAMPLES 75-90

| Ex. # | Starting Material (1) | Starting Material (2) | Reaction Condition | $^1$H NMR (CDCl$_3$, 400 MHz) δ (ppm) |
|---|---|---|---|---|
| 75 | (see Preparation 5B) | | K$_2$CO$_3$ iPrOH, H$_2$O, MW 160° C. | 7.70-7.69 (d, J = 2.8 Hz, 1H); 7.59-7.53 (m, 2H); 7.47-7.46 (d, J = 3.2 Hz, 1H); 7.32-7.24 (m, 1H); 7.12-7.08 (m, 1H); 5.04-5.00 (m, 1H); 4.20-4.17 (d, J = 12.8 Hz, 2H); 4.00-3.97 (m, 1H); 3.55-3.53 (d, J = 6 Hz, 2H); 3.22-3.15 (m, 2H); 2.83-2.76 (m, 2H); 2.20-2.15 (m, 2H); 1.83-1.71 (m, 3H); 1.44-1.34 (m, 2H). |

TABLE 7B-continued

PREPARATION AND NMR DATA OF EXAMPLES 75-90

| Ex. # | Starting Material (1) | Starting Material (2) | Reaction Condition | $^1$H NMR (CDCl$_3$, 400 MHz) δ (ppm) |
|---|---|---|---|---|
| 76 | (see Preparation 5B) | morpholine | Et$_3$N DMSO, MW 140° C. | 7.67 (d, J = 2.8 Hz, 1H); 7.53 (d, J = 5.6 Hz, 1H); 7.49-7.47 (m, 2H); 7.24-7.19 (m, 1H); 7.05-7.01 (m, 1H); 5.00-4.93 (m, 1H); 4.02-3.85 (m, 1H); 3.78-3.76 (m, 4H); 3.46-3.43 (m, 4H); 3.17-3.10 (m, 2H); 2.16-2.09 (m, 2H). |
| 77 | (see Preparation 5B) | 3-methylpyrrolidine | Et$_3$N DMSO, MW 140° C. | 7.75-7.73 (m, 1H), 7.51 (d, J = 8.0 Hz, 1H), 7.46-7.41 (m, 1H), 7.34 (s, 2H), 7.30-7.26 (m, 1H), 5.13-5.07 (m, 1H), 4.13-3.98 (m, 3H), 3.88-3.81 (m, 1H), 3.40-3.35 (m, 1H), 3.24-3.17 (m, 2H), 2.45-2.35 (m, 3H), 2.35-2.26 (m, 1H), 2.70-1.65 (m, 1H), 1.15 (J = 6.8 Hz, 3H). |
| 78 | (see Preparation 5B) | 3-cyanopyrrolidine | Et$_3$N DMSO, MW 140° C. | 7.80 (d, J = 8.0 Hz, 1H), 7.55-7.51 (m, 3H), 7.39 (d, J = 3.2 Hz, 2H), 5.12-5.08 (m, 1H), 4.15-4.09 (m, 2H), 4.08-4.00 (m, 1H), 4.00-3.90 (m, 1H), 3.89-3.80 (m, 1H), 3.50-3.40 (m, 1H), 3.25-3.22 (m, 2H), 2.45-2.39 (m, 3H), 2.35-2.26 (m, 1H). |
| 79 | (see Preparation 5B) | 3-methylpiperidine | Et$_3$N DMSO, MW 140° C. | 7.65-7.56 (m, 3H); 7.45-7.46 (m, 2H); 7.29 (m, 1H); 5.07 (m, 1H); 4.22-4.21 (m, 1H); 4.13-4.11 (m, 1H); 3.71-3.69 (m, 1H); 3.21-3.19 (m, 2H); 3.06-3.03 (m, 1H); 2.74-2.70 (m, 1H); 2.48-2.50 (m, 2H); 1.84-1.81 (m, 3H); 1.71-1.70 (m, 1H); 1.23-1.14 (m, 1H); 0.95 (d, J = 5.6 Hz, 3H). |
| 80 | (see Preparation 5B) | 3-(hydroxymethyl)piperidine | Et$_3$N DMSO, MW 140° C. | 7.79 (d, J = 8.0 Hz, 1H), 7.68-7.60 (m, 1H), 7.55-7.47 (m, 3H), 7.37-7.32 (m, 1H), 5.16-5.08 (m, 1H), 4.41-4.25 (m, 1H), 4.14-4.02 (m, 2H), 3.55-3.51 (m, 1H), 3.46-3.41 (m, 1H), 3.26-3.19 (m, 2H), 3.04-2.97 (m, 1H), 2.91-2.76 (m, 1H), 2.44-2.31 (m, 2H), 1.90-1.78 (m, 3H), 1.74-1.63 (m, 1H), 1.45-1.23 (m, 1H). |
| 81 | (see Preparation 5B) | 3,3-difluoropyrrolidine | Et$_3$N DMSO, MW 140° C. | 7.66 (d, J = 2.8 Hz, 1H); 7.62 (d, J = 7.6 Hz, 1H); 7.56 (d, J = 8.0 Hz, 1H); 7.39 (d, J = 2.8 Hz, 1H); 7.29-7.25 (m, 1H); 7.11-7.08 (m, 1H); 5.01-4.98 (m, 1H); 4.04-3.92 (m, 3H); 3.89-3.86 (m, 2H); 3.22-3.16 (m, 2H); 2.43-2.36 (m, 2H); 2.24-2.17 (m, 2H). |

TABLE 7B-continued

PREPARATION AND NMR DATA OF EXAMPLES 75-90

| Ex. # | Starting Material (1) | Starting Material (2) | Reaction Condition | $^1$H NMR (CDCl$_3$, 400 MHz) δ (ppm) |
|---|---|---|---|---|
| 82 | (see Preparation 5B) | thiomorpholine 1,1-dioxide | DIEA, NMP, MW 200° C. | 7.78-7.77 (m, 2H); 7.62-7.61 (m, 1H); 7.49-7.48 (m, 2H); 7.35-7.31 (m, 1H); 5.10-5.07(m, 1H); 4.35-4.31 (m, 1H); 4.12-4.09 (m, 4H); 3.96-3.92 (m, 1H); 3.14-3.11 (m, 6H); 2.37 (s, 1H). |
| 83 | (see Preparation 5B) | 4,5,6,7-tetrahydroimidazo[1,5-a]pyrazine | DIEA, NMP, MW 200° C. | 8.67 (s, 1H), 7.80-7.64 (m, 1H), 7.66-7.64 (m, 2H), 7.59-7.57 (m, 1H), 7.51-7.46 (m, 1H), 7.35-7.31 (m, 1H), 7.26 (s, 1H), 5.20-5.16 (m, 1H), 4.84 (s, 2H), 4.48-4.45 (m, 2H), 4.13-4.10 (m, 2H), 3.78-3.77 (m, 1H), 3.33-3.26 (m, 2H), 2.56-2.49 (m, 2H). |
| 84 | (see Preparation 5B) | (R)-3-hydroxypyrrolidine | Et$_3$N DMSO, MW 140° C. | 7.57 (d, J = 8.0 Hz, 1H); 7.51 (d, J = 8.4 Hz, 1H); 7.42 (t, J = 7.6 Hz, 1H); 7.36 (d, J = 4.0 Hz, 1H); 7.28-7.24 (m, 2H); 5.08-5.01 (m, 1H); 4.59 (s, 1H); 4.13-4.03 (m, 3H); 3.98-3.95 (m, 1H); 3.72 (br, 1H); 3.22-3.16 (m, 2H); 2.51-2.43 (m, 2H); 2.13-2.10 (m, 1H); 2.07-1.99 (m, 1H). |
| 85 | (see Preparation 5B) | (S)-3-hydroxypyrrolidine | Et$_3$N DMSO, MW 140° C. | 7.57 (d, J = 8.0 Hz, 1H); 7.51 (d, J = 8.4 Hz, 1H); 7.44-7.41 (m, 1H); 7.37-7.36 (m, 1H); 7.28-7.24 (m, 2H); 5.08-5.01 (m, 1H); 4.59 (s, 1H); 4.13-4.03 (m, 3H); 3.98-3.95 (m, 1H); 3.72 (br, 1H); 3.22-3.16 (m, 2H); 2.51-2.43 (m, 2H); 2.13-2.11 (m, 1H); 2.07-1.99 (m, 1H). |
| 86 | (see Preparation 5B) | 4-cyanopiperidine | Et$_3$N DMSO, MW 150° C. | 7.64 (d, J = 2.8 Hz, 1 H); 7.53-7.51 (m, 1 H); 7.49-7.47 (m, 2 H); 7.19-7.15 (m, 1 H); 7.02-6.98 (m, 1 H); 4.96-4.93 (m, 1 H); 3.89 (s, 1 H); 3.70-3.65 (m, 2 H); 3.28-3.24 (m, 2 H); 3.22-3.10 (m, 2 H); 2.74-2.72 (m, 1 H); 2.16-2.10 (m, 2 H); 1.91-1.82 (m, 4 H). |
| 87 | (see Preparation 5B) | 1-methylpiperazine | Neat, MW 150° C. | 7.75 (d, J = 2.8 Hz, 1 H); 7.63-7.55 (m, 3 H); 7.32 (t, J = 7.8 Hz, 1 H); 7.12 (t, J = 7.8 Hz, 1 H); 5.89 (br, 1 H); 5.10-5.02 (m, 1 H); 4.11-4.02 (m, 1 H); 3.73 (br, 4 H); 3.27-3.17 (m, 2 H); 2.79 (br, 4 H); 2.52 (s, 3 H); 2.25-2.16 (m, 2 H). |

TABLE 7B-continued

PREPARATION AND NMR DATA OF EXAMPLES 75-90

| Ex. # | Starting Material (1) | Starting Material (2) | Reaction Condition | $^1$H NMR (CDCl$_3$, 400 MHz) δ (ppm) |
|---|---|---|---|---|
| 88 | (see Preparation 5G) | | Et$_3$N DMSO, MW 150° C. | 8.17 (d, J = 9.2 Hz, 1 H); 7.72-7.68 (m, 4 H); 7.51 (d, J = 2.8 Hz, 1 H); 7.41-7.38 (m, 1 H); 6.82 (d, J = 9.2 Hz, 1 H); 5.09-5.05 (m, 1 H); 3.93-3.92 (m, 1 H); 3.82-3.78 (m, 2 H); 3.49-3.44 (m, 2 H); 3.18 (s, 2 H); 2.88-2.86 (m, 1 H); 2.43-2.42 (m, 2 H); 2.04-2.03 (m, 2 H); 1.96-1.95 (m, 2 H). |
| 89 | (see Preparation 5J) | | NMP, MW 180° C. | 8.99 (s, 1H); 7.74-7.22 (m, 1H); 7.70-7.68 (m, 2H); 7.68-7.66 (m, 1H); 7.62-7.60 (m, 1H); 7.29-7.24 (m, 1H); 5.55-5.53 (m, 1H); 5.11-5.04 (m, 1H); 4.48-4.38 (m, 1H); 3.64-3.54 (m, 4H); 3.23-3.17 (m, 2H); 2.63-2.61 (m, 4H); 2.39 (s, 3H); 2.19-2.12 (m, 2H). |
| 90 | (see Preparation 5J) | | NMP, MW 180° C. | 8.91 (s, 1H); 7.64-7.63 (m, 1H); 7.62-7.60 (m, 2H); 7.59-7.51 (m, 1H); 7.44-7.43 (m, 1H); 7.18-7.16 (m, 1H); 5.36-5.34 (m, 1H); 5.01-4.98 (m, 1H); 4.36-4.14 (m, 2H); 3.50-3.49 (m, 2H); 3.15-3.08 (m, 2H); 2.78-2.72 (m, 2H); 2.10-2.03 (m, 2H); 1.98-1.51 (m, 3H); 1.39-1.33 (m, 2H). |

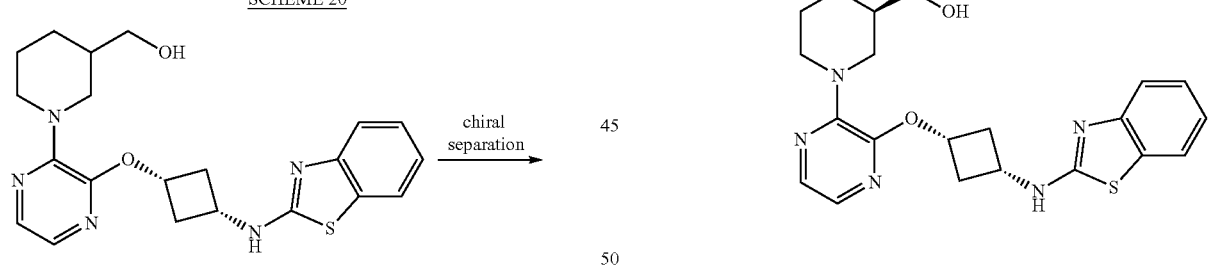

SCHEME 20

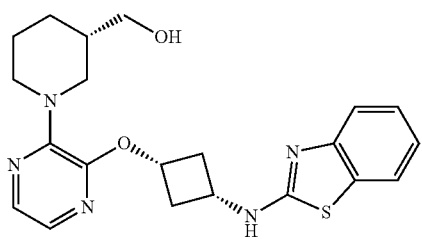 [SMILES: OCC1CCCN(c2nccnc2O[C@H]2C[C@@H](Nc3nc4ccccc4s3)C2)C1]

Examples 91 and 92: ((S)-1-(3-((1S,3R)-3-(BENZO[D]THIAZOL-2-YLAMINO)CYCLOBUTOXY)PYRAZIN-2-YL)PIPERIDIN-3-YL)METHANOL and ((R)-1-(3-((1S,3S)-3-(BENZO[D]THIAZOL-2-YLAMINO)CYCLOBUTOXY)PYRAZIN-2-YL)PIPERIDIN-3-YL)METHANOL Racemic mixture (1-(3-((1S,3S)-3-(benzo[d]thiazol-2-ylamino)cyclobutoxy)pyrazin-2-yl)piperidin-3-yl)methanol, made according to Example 80, (0.054 g, 0.13 mmol) was separated by chiral prep-HPLC (Column: Chiralcel OD-H 250*30 mm, 5u; Mobile phase: 85% hexane in EtOH (0.05% diethyl amine); Flow rate: 30 mL/minute) to give examples 91 and 92 as separated enantiomers. ESI-MS (M+1): 412 calc. for C$_{21}$H$_{25}$N$_5$O$_2$S 411

TABLE 8A

EXAMPLES 91-96 PREPARED ANALOGOUS TO SCHEME 20

| Ex. # | Structure | Chemical Name | ESI-MS (M + 1) | IC$_{50}$ (uM) |
|---|---|---|---|---|
| 91 and 92 | 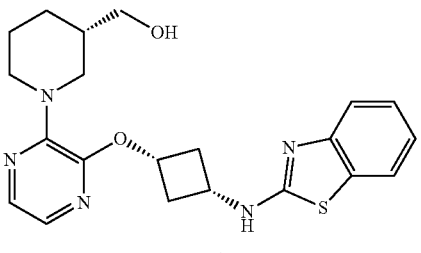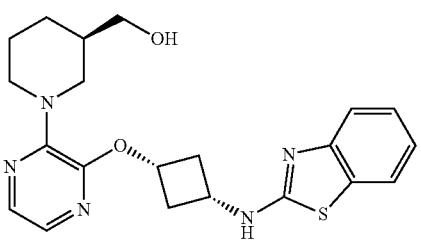 as separated enantiomers | ((S)-1-(3-((1S,3R)-3-(benzo[d]thiazol-2-ylamino)cyclobutoxy)pyrazin-2-yl)piperidin-3-yl)methanol and ((R)-1-(3-((1S,3S)-3-(benzo[d]thiazol-2-ylamino)cyclobutoxy)pyrazin-2-yl)piperidin-3-yl)methanol | 412 | 0.026 and 0.00281 |
| 93 and 94 | 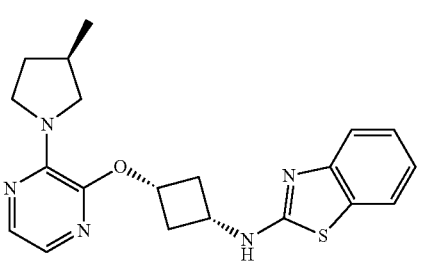 [SMILES: CC1CCN(c2nccnc2O[C@H]2C[C@@H](Nc3nc4ccccc4s3)C2)C1]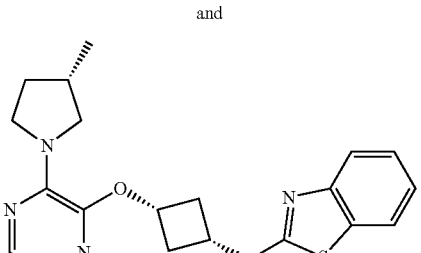 and As separated single enantiomer | N-((1S,3S)-3-((3-((R)-3-methylpyrrolidin-1-yl)pyrazin-2-yl)oxy)cyclobutyl)benzo[d]thiazol-2-amine and N-((1R,3S)-3-((3-((S)-3-methylpyrrolidin-1-yl)pyrazin-2-yl)oxy)cyclobutyl)benzo[d]thiazol-2-amine | 382 | 0.00324 and 0.00802 |

TABLE 8A-continued

EXAMPLES 91-96 PREPARED ANALOGOUS TO SCHEME 20

| Ex. # | Structure | Chemical Name | ESI-MS (M + 1) | IC$_{50}$ (uM) |
|---|---|---|---|---|
| 95 and 96 | 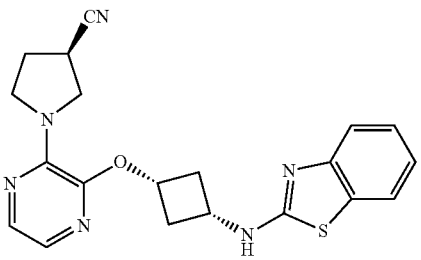 and 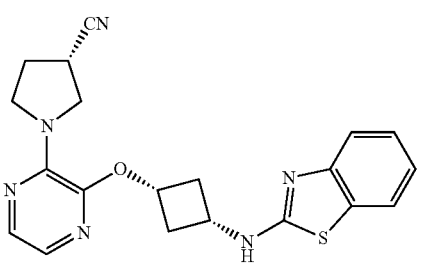 [SMILES: N#CC1CCN(c2nccnc2O[C@H]2C[C@@H](Nc3nc4ccccc4s3)C2)C1] As separated single enantiomer | (R)-1-(3-((1S,3S)-3-(benzo[d]thiazol-2-ylamino)cyclobutoxy)pyrazin-2-yl)pyrrolidine-3-carbonitrile and (S)-1-(3-((1S,3R)-3-(benzo[d]thiazol-2-ylamino)cyclobutoxy)pyrazin-2-yl)pyrrolidine-3-carbonitrile | 393 | 0.000728 and 0.00527 |

Note:
The absolute stereospecificity of each enantiomer was not determined in the examples below and therefore the IC$_{50}$ and NMR data reported herein can be for either enantiomer.

TABLE 8B

PREPARATION AND NMR DATA OF EXAMPLES 91-96, AS SEPARATED SINGLE ENANTIOMER.

| Ex. # | Starting Material (1) | Separation Condition | $^1$H NMR (CDCl$_3$, 400 MHz) δ (ppm) |
|---|---|---|---|
| 91 and 92 | 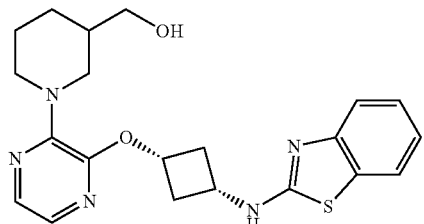 | Column: Chiralcel OD-H 250*30 mm, 5 u; Mobile phase: 85% hexane in EtOH (0.05% diethyl amine); Flow rate: 30 mL/minute | 7.62 (d, J = 2.8 Hz, 1H); 7.53 (d, J = 8.1 Hz, 1H); 7.50 (d, J = 8.1 Hz, 1H); 7.49 (d, J = 2.8 Hz, 1H); 7.25-7.20 (m, 1H); 7.04-7.00 (m, 1H); 5.95 (br, 1H); 5.08-5.05 (m, 1H); 3.99-3.95 (m, 2H); 3.60-3.49 (m, 3H); 3.17-3.06 (m, 3H); 2.98-2.93 (m, 1H); 2.31-2.10 (m, 2H); 1.95 (br, 1H); 1.80-1.58 (m, 2H); 1.27-1.25 (m, 1H); and 7.67 (d, J = 2.8 Hz, 1H); 7.57 (d, J = 8.2 Hz, 1H); 7.51 (d, J = 8.4 Hz, 1H); 7.45-7.44 (m, 1H); 7.29-7.27 (m, 1H); 7.09-7.05 (m, 1H); 6.58 (brs, 1H); 5.13-5.10 (m, 1H); 4.07-4.0 (m, 2H); 3.78-3.74 (m, 2H); 3.65-3.53 (m, 2H); 3.21-3.14 (m, 3H); 3.05-3.00 (m, 1H); 2.27-2.23 (m, 2H); 1.97-1.96 (m, 1H); 1.77-1.65 (m, 2H); 1.31-1.25 (m, 1H). |

TABLE 8B-continued

PREPARATION AND NMR DATA OF EXAMPLES 91-96, AS SEPARATED SINGLE ENANTIOMER.

| Ex. # | Starting Material (1) | Separation Condition | $^1$H NMR (CDCl$_3$, 400 MHz) δ (ppm) |
|---|---|---|---|
| 93 and 94 | | Column: ChiralPak AD-H, 250 × 30 mmI.D; Mobile phase: A for SF CO$_2$ and B for Ethanol (0.2%DEA); Gradient: B 40%; Flow rate: 40 mL/min | 7.54-7.47 (m, 3H); 7.25-7.16 (m, 2H); 7.05-7.01 (m, 1H); 5.49-5.47 (m, 1H); 4.93-4.90 (m, 1H); 3.96-3.92 (m, 1H); 3.81-3.63 (m, 2H); 3.63-3.58 (m, 1H); 3.18-3.10 (m, 3H); 2.24-2.22 (m, 1H); 2.10-1.97 (m, 3H); 1.50-1.47 (m, 1H); 1.41 (d, J = 6.4 Hz, 3H); and 7.60-7.58 (m, 2H); 7.57 (d, J = 12.0 Hz, 1H); 7.30-7.22 (m, 2H); 7.11-7.07 (m, 1H); 5.59 (br, 1H); 4.99-4.96 (m, 1H); 4.01-3.98 (m, 1H); 3.87-3.71 (m, 2H); 3.69-3.66 (m, 1H); 3.24-3.14 (m, 3H); 2.31-2.26 (m, 1H); 2.18-2.09 (m, 2H); 2.07-2.03 (m, 1H); 1.58-1.51 (m, 1H); |
| 95 and 96 | | Column: ChiralPak AD-H, 250 × 30 mmI.D; Mobile phase: A for SF CO$_2$ and B for Ethanol (0.2% DEA); Gradient: B 40%; Flow rate: 40 mL/min | 7.57 (d, J = 2.8 Hz, 1H); 7.53 (d, J = 7.6 Hz, 1H); 7.48 (d, J = 8.4 Hz, 1H); 7.30 (d, J = 3.2 Hz, 1H); 7.23-7.21 (m, 1H); 7.03-7.01 (m, 1H); 5.54 (brs, 1H); 4.97-4.90 (m, 1H); 3.99-3.83 (m, 4H); 3.77-3.71 (m, 1H); 3.16-3.08 (m, 3H); 2.30-2.20 (m, 2H); 2.11-2.07 (m, 2H); and 7.63 (d, J = 2.8 Hz, 1H); 7.60 (d, J = 0.4 Hz, 1H); 7.58 (d, J = 0.8 Hz, 1H); 7.54 (d, J = 8.4 Hz, 1H); 7.29-7.27 (m, 1H); 7.10-7.08 (m, 1H); 5.52 (s, 1H); 5.02-4.98 (m, 1H); 4.06-3.88 (m, 4H); 3.83-3.77 (m, 1H); 3.22-3.14 (m, 3H); 2.35-2.28 (m, 2H); 2.18-2.11 (m, 2H). |

SCHEME 21

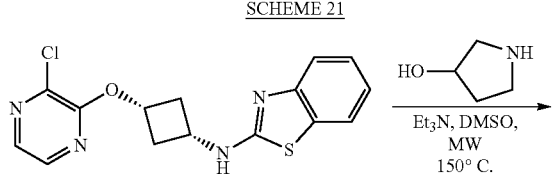

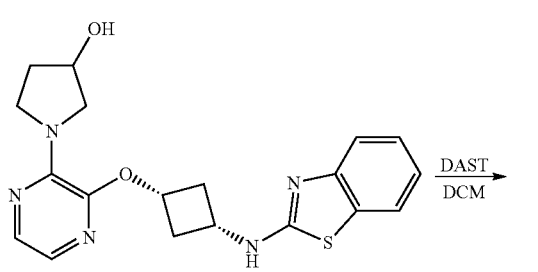

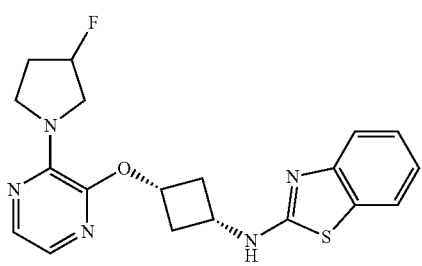

Example 97

N-((1S,3S)-3-((3-(3-FLUOROPYRROLIDIN-1-YL)PYRAZIN-2-YL)OXY)CYCLOBUTYL)BENZO[D]THIAZOL-2-AMINE as Racemic Mixture Step 1. 1-(3-((1S,3S)-3-(BENZO[D]THIAZOL-2-YLAMINO)CYCLOBUTOXY)PYRAZIN-2-YL)PYRROLIDIN-3-OL as Racemic Mixture To a mixture of N-((1S,3S)-3-((3-chloropyrazin-2-yl)oxy)cyclobutyl)benzo[d]thiazol-2-amine (see PREPARATION 5B; 0.083 g, 0.25 mmol) and pyrrolidin-3-ol (0.022 g, 0.25 mmol) was added triethylamine (0.05 g, 0.50 mmol) and DMSO (3 mL). The solution was heated to 150° C. in microwave for 3 h. Then the mixture was diluted with water (10 mL) and extracted with EtOAc (2×20 mL). The combined organic extracts were washed with water (10 mL) and brine (10 mL), dried over Na$_2$SO$_4$ and filtered. The filtrate was evaporated in vacuo and the residue was purified by reverse phase prep-HPLC (10% to 80% water/MeCN) to give racemic mixture 1-(3-((1S,3S)-3-(benzo[d]thiazol-2-ylamino)cyclobutoxy)pyrazin-2-yl)pyrrolidin-3-ol (0.050 g, 0.13 mmol, 54% yield) as white solid. ESI-MS (M+1): 384 calc. for C$_{19}$H$_{21}$N$_5$O$_2$S 383.

Step 2. N-((1S,3S)-3-((3-(3-FLUOROPYRROLIDIN-1-YL)PYRAZIN-2-YL)OXY)CYCLOBUTYL)BENZO[D]THIAZOL-2-AMINE as Racemic Mixture In a 50 mL flask, 1-(3-((1S,3S)-3-(benzo[d]thiazol-2-ylamino)cyclobutoxy)pyrazin-2-yl)pyrrolidin-3-ol (0.050 g, 0.13 mmol) was dissolved in anhyd DCM (15 mL). The solution was cooled to −10° C. under nitrogen atmosphere and diethylaminosulfur trifluoride (DAST, purchased from Alfa Aesar™) (0.26 g, 0.10 mmol) was added dropwise. The reaction mixture was allowed to warm to r.t and stirred for 2 h. The mixture was poured into cold water (10 mL). The separated aqueous phase was extracted twice with DCM (20 mL), and the combined organic phases were dried over $MgSO_4$. After filtration, the solvent was evaporated in vacuo, and the concentrate was purified by flash chromatography on silica gel (20% to 45% EtOAc in petroleum ether) to give racemic mixture N-((1S,3S)-3-((3-(3-fluoropyrrolidin-1-yl)pyrazin-2-yl)oxy)cyclobutyl)benzo[d]thiazol-2-amine (0.039 g, 0.10 mmol, 75% yield) as a white solid. PDE10 $IC_{50}$ (uM): 0.00335. M+1: 386. $^1$H NMR ($CDCl_3$, 400 MHz) δ (ppm):

7.54-7.45 (m, 3H); 7.21-7.15 (m, 1H); 7.01-6.89 (m, 2H); 5.25-5.12 (m, 1H); 4.92-4.88 (m, 1H); 393-3.72 (m, 5H); 3.10-3.07 (m, 2H); 2.24-1.89 (m, 4H).

SCHEME 22

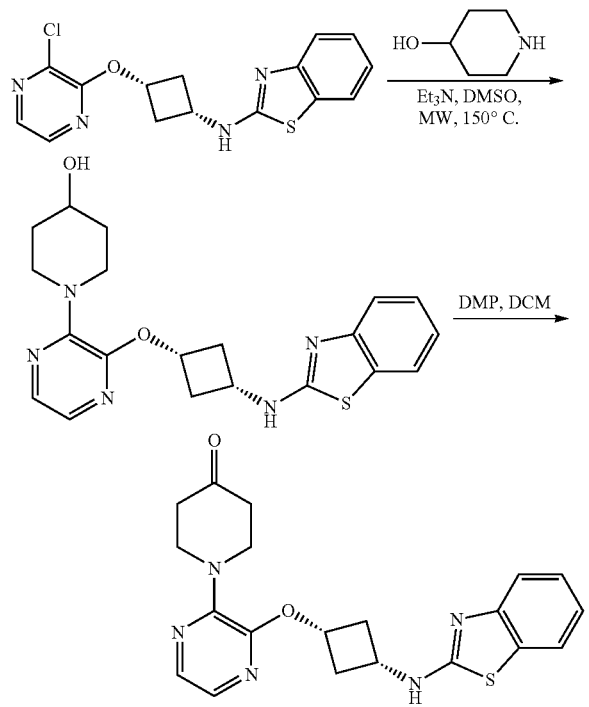

Example 98

1-(3-((1S,3S)-3-(BENZO[D]THIAZOL-2-YLAMINO)CYCLOBUTOXY)PYRAZIN-2-YL)PIPERIDIN-4-ONE

Step 1: 1-(3-((1S,3S)-3-(BENZO[D]THIAZOL-2-YLAMINO)CYCLOBUTOXY)PYRAZIN-2-YL) PIPERIDIN-4-0 L as Racemic Mixture To a mixture of N-((1S,3S)-3-((3-chloropyrazin-2-yl)oxy)cyclobutyl)benzo[d]thiazol-2-amine (see PREPARATION 5B; 332 mg, 1.0 mmol) and piperidin-4-ol (101 mg, 1.0 mmol) and $Et_3N$ (202 mg, 2.0 mmol) was added DMSO (2 mL). The solution was heated to 150° C. under microwave for 2 h. Then the mixture was diluted with water (10 mL) and extracted with EtOAc (2×30 mL). The combined organic extracts were washed with water (10 mL) and brine (10 mL), dried over $Na_2SO_4$, and filtered. The filtrate was evaporated in vacuo and the residue was purified by flash column chromatography on silica gel (20% to 60% EtOAc in petroleum ether) to give the title product (311 mg, 0.80 mmol, 80% yield). ESI-MS (M+1): 398 calc. for $C_{20}H_{23}N_5O_2S$ 397.

Step 2: 1-(3-((1S,3S)-3-(BENZO[D]THIAZOL-2-YLAMINO)CYCLOBUTOXY)PYRAZIN-2-YL) PIPERIDIN-4-ONE The 1-(3-((1S,3S)-3-(benzo[d]thiazol-2-ylamino)cyclobutoxy)pyrazin-2-yl)piperidin-4-ol (397 mg, 1 mmol) was dissolved in anhydrous $CH_2Cl_2$ (10 mL), treated with Dess-Martin periodinane (DMP) (800 mg, 2 mmol, 2.0 equiv) and stirred at RT until complete conversion. The organic layer was washed with an aq solution of $NaHCO_3/Na_2S_2O_3$ (3×10 mL)), dried over $Na_2SO_4$, filtered and evaporated. The resulting residue was purified by prep-HPLC to give 1-(3-((1S,3S)-3-(benzo[d]thiazol-2-ylamino)cyclobutoxy)pyrazin-2-yl)piperidin-4-one (288 mg, 0.73 mmol, 73% yield). PDE10 $IC_{50}$ (uM): 0.0211. M+1: 396. $^1$H NMR ($CDCl_3$, 400 MHz) δ (ppm):

7.74-7.73 (d, J=3.2 Hz, 1H); 7.61-7.59 (d, J=7.6 Hz, 1H); 7.54-7.52 (m, 2H); 7.46-7.41 (m, 1H); 7.30-7.24 (m, 1H); 5.10-5.02 (m, 1H); 3.89-3.87 (m, 4H); 3.71-3.67 (m, 1H); 3.25-3.18 (m, 2H); 2.62-2.55 (m, 4H); 2.49-2.42 (m, 2H).

SCHEME 23

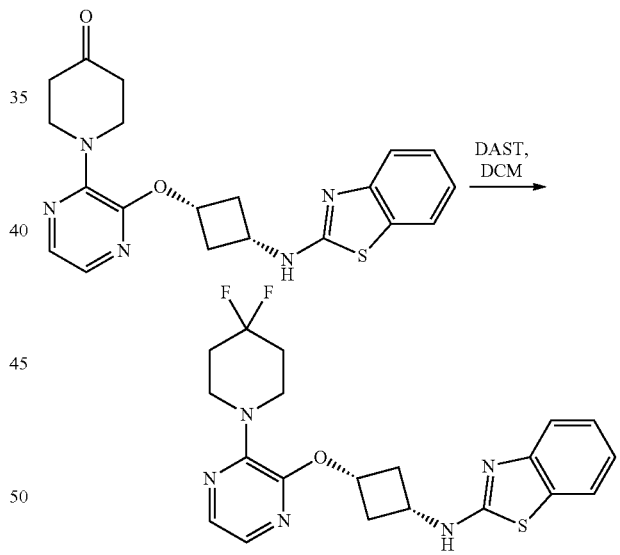

Example 99

N-((1S,3S)-3-((3-(4,4-DIFLUOROPIPERIDIN-1-YL)PYRAZIN-2-YL)OXY)CYCLOBUTYL)BENZO[D]THIAZOL-2-AMINE

In a 50 mL flask, 1-(3-((1S,3S)-3-(benzo[d]thiazol-2-ylamino)cyclobutoxy)pyrazin-2-yl)piperidin-4-one (0.10 g, 0.25 mmol) was dissolved in anhydrous DCM (15 mL). The solution was cooled to −10° C. under nitrogen atmosphere and diethylaminosulfur trifluoride (DAST, purchased from Alfa Aesar™) (0.78 g, 0.30 mmol) was added dropwise. The reaction mixture was allowed to warm to RT and stirred for 2 h. The mixture was poured into cold water (10 mL). The separated aqueous phase was extracted twice with DCM (20 mL), and the combined organic phases were dried over MgSO$_4$. After filtration, the solvent was evaporated in vacuo, and the residue was purified by flash chromatography on silica gel (20% to 45% EtOAc in petroleum ether) to give N-((1S,3S)-3-((3-(4,4-difluoropiperidin-1-yl)pyrazin-2-yl)oxy)cyclobutyl)benzo[d]thiazol-2-amine (0.050 g, 0.12 mmol, 49% yield) as a white solid. PDE10 IC$_{50}$ (uM): 0.0177. M+1: 418. $^1$H NMR: (CD$_3$OD, 400 MHz) δ (ppm):

7.78-7.75 (m, 1H), 7.72 (d, J=2.8 Hz, 1H), 7.56 (d, J=2.8 Hz, 1H), 7.54-7.51 (m, 1H), 7.49-7.45 (m, 1H), 7.34-7.29 (m, 1H), 5.13-5.09 (m, 1H), 4.16-4.09 (m, 1H), 3.67-3.65 (m, 4H), 3.24-3.20 (m, 2H), 2.35-2.31 (m, 2H), 2.09-2.02 (m, 4H).

SCHEME 24

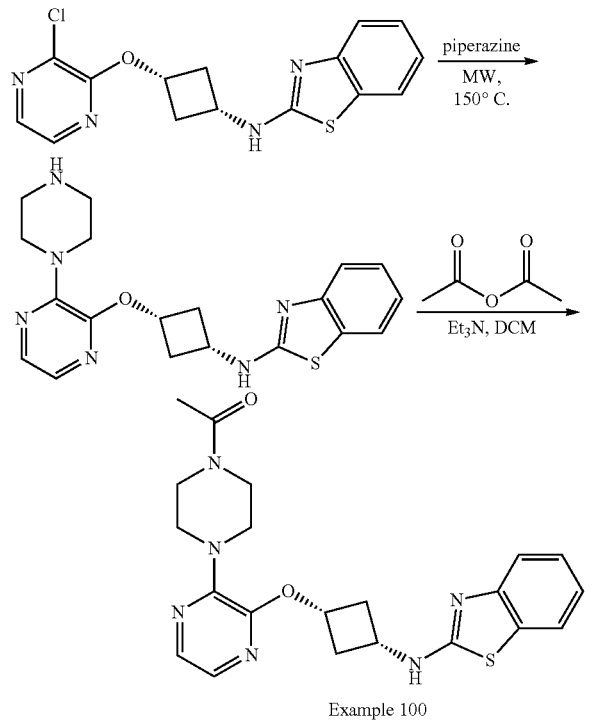

Example 100

Example 100

1-(4-(3-((1S,3S)-3-(BENZO[D]THIAZOL-2-YLAMINO)CYCLOBUTOXY)PYRAZIN-2-YL)PIPERAZIN-1-YL)ETHANONE

Step 1. N-((1S,3S)-3-((3-(PIPERAZIN-1-YL)PYRAZIN-2-YL)OXY)CYCLOBUTYL)BENZO[D]THIAZOL-2-AMINE A solution of N-((1S,3S)-3-((3-chloropyrazin-2-yl)oxy)cyclobutyl)benzo[d]thiazol-2-amine (see PREPARATION 5B; 332 mg, 1 mmol) and piperazine (860 mg, 10 mmol) was heated to 150° C. in microwave for 2 hrs. Then the mixture was diluted with water (10 mL) and extracted with EtOAc (2×30 mL). The combined organic extracts were washed with water (10 mL) and brine (10 mL), dried over Na$_2$SO$_4$, and filtered. The filtrate was evaporated in vacuo and the residue was purified by flash column chromatography on silica gel (20% to 60% EtOAc in petroleum ether) to give the title product (115 mg, 0.3 mmol, 30% yield). ESI-MS (M+1): 383 calc. for C$_{19}$H$_{22}$N$_6$OS 382.

Step 2. 1-(4-(3-((1S,3S)-3-(BENZO[D]THIAZOL-2-YLAMINO)CYCLOBUTOXY)PYRAZIN-2-YL)PIPERAZIN-1-YL)ETHANONE To a solution of N-((1S,3S)-3-((3-(piperazin-1-yl)pyrazin-2-yl)oxy)cyclobutyl)benzo[d]thiazol-2-amine (382 mg, 1 mmol) in dry DCM (10 mL) was added Et$_3$N (1 mL). The reaction mixture was cooled to 0° C. with an ice bath, and acetic anhydride (204 mg, 2 mmol) was added dropped to the reaction mixture. After 1 hour, the reaction mixture was warmed to room temperature, and stirred overnight. Then the reaction mixture was washed with brine, dried over Na$_2$SO$_4$, filtered, and concentrated under vacuum to give the crude product. The crude product was purified by prep-HPLC to give 1-(4-(3-((1S,3S)-3-(benzo[d]thiazol-2-ylamino)cyclobutoxy)pyrazin-2-yl)piperazin-1-yl)ethanone (297 mg, 0.7 mmol, 70% yield).

TABLE 9A

EXAMPLES 101-102 PREPARED ANALOGOUS TO SCHEME 24

| Ex. # | Structure | Chemical Name | M + 1 | IC$_{50}$ (uM) |
|---|---|---|---|---|
| 100 | 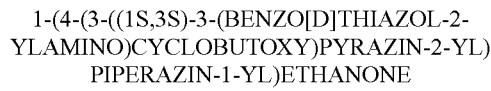 | 1-(4-(3-((1S,3S)-3-(benzo[d]thiazol-2-ylamino)cyclobutoxy)pyrazin-2-yl)piperazin-1-yl)ethanone | 425 | 0.00926 |

TABLE 9A-continued

EXAMPLES 101-102 PREPARED ANALOGOUS TO SCHEME 24

| Ex. # | Structure | Chemical Name | M + 1 | IC$_{50}$ (uM) |
|---|---|---|---|---|
| 101 | 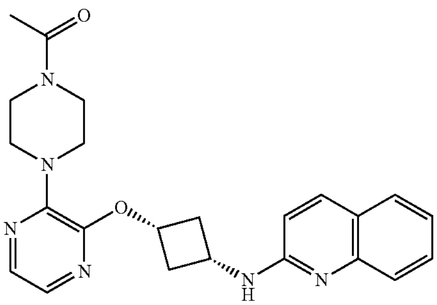 [SMILES: CC(=O)N1CCN(c2nccnc2O[C@H]2C[C@@H](Nc3ccc4ccccc4n3)C2)CC1] | 1-(4-(3-((1S,3S)-3-(quinolin-2-ylamino)cyclobutoxy)pyrazin-2-yl)piperazin-1-yl)ethanone | 419 | 0.0237 |

TABLE 9B

PREPARATION AND NMR DATA OF EXAMPLES 100-101

| Ex. # | Starting Material (1) | Starting Material (2) | Reaction Condition | $^1$H NMR (CDCl$_3$, 400 MHz) δ (ppm) |
|---|---|---|---|---|
| 100 | | | Et$_3$N, DCM | 7.71-7.70 (d, J = 2.8 Hz, 1H); 7.60-7.58 (d, J = 8 Hz, 1H); 7.52-7.49 (m, 2H); 7.43-7.39 (m, 1H); 7.28-7.24 (m, 1H); 5.09-5.02 (m, 1H); 3.75-3.74 (d, J = 5.2 Hz, 3H); 3.70 (s, 4H); 3.61-3.60 (d, J = 5.2 Hz, 2H); 3.24-3.17 (m, 2H); 2.47-2.40 (m, 2H); 2.15 (s, 3H). |
| 101 | | | Et$_3$N, DCM | (CD$_3$OD) 8.26 (s, 1 H); 7.85 (d, J = 8.0 Hz, 2 H); 7.79-7.75 (m, 1 H); 7.72 (d, J = 2.8 Hz, 1 H); 7.56 (d, J = 2.8 Hz, 1 H); 7.53-7.48 (m, 1 H); 7.03 (s, 1 H); 5.16-5.12 (m, 1 H); 3.70-3.64 (m, 4 H); 3.57-3.50 (m, 5 H); 3.25-3.23 (m, 2 H); 2.40-2.33 (m, 2 H); 2.12 (s, 3 H). |

SCHEME 25

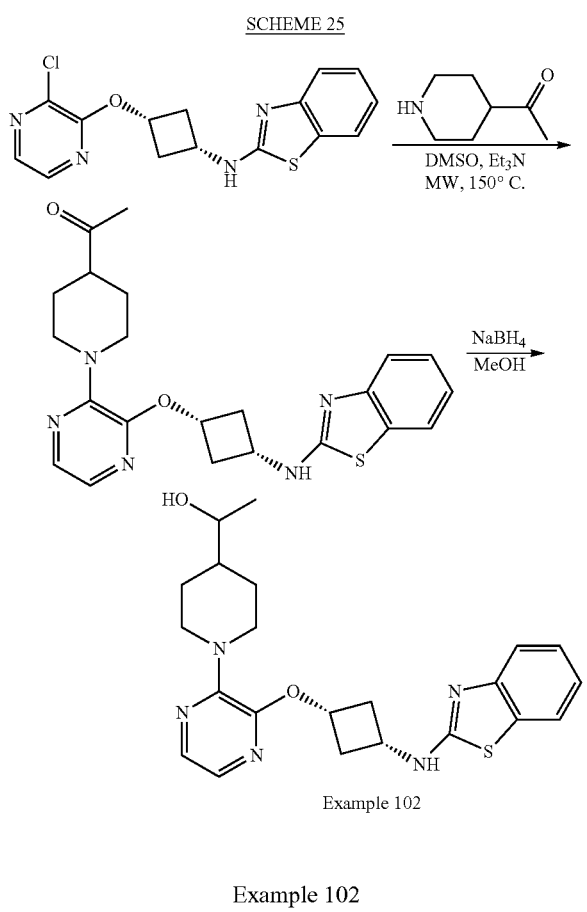

Example 102

Example 102

1-(1-(3-((1S,3S)-3-(BENZO[D]THIAZOL-2-YLAMINO)CYCLOBUTOXY)PYRAZIN-2-YL)PIPERIDIN-4-YL)ETHANOL

Step 1. 1-(1-(3-((1S,3S)-3-(BENZO[D]THIAZOL-2-YLAMINO)CYCLOBUTOXY)PYRAZIN-2-YL)PIPERIDIN-4-YL)ETHANONE To a mixture of N-((1S,3S)-3-((3-chloropyrazin-2-yl)oxy)cyclobutyl)benzo[d]thiazol-2-amine (see PREPARATION 5B; 332 mg, 1 mmol) and 1-(piperidin-4-yl)ethanone (127 mg, 1 mmol) and Et$_3$N (202 mg, 2 mmol) was added DMSO (2 mL). The solution was heated to 150° C. under microwave for 3 h. Then the mixture was concentrated and extracted with EtOAc (2×30 mL). The combined organic extracts were washed with water (10 mL) and brine (10 mL), dried over Na$_2$SO$_4$, and filtered. The filtrate was evaporated in vacuo and the residue was purified by flash column chromatography on silica gel (20% to 60% EtOAc in petroleum ether) to give the title product (127 mg, 0.3 mmol, 30% yield). ESI-MS (M+1): 424 calc. for C$_{22}$H$_{25}$N$_5$O$_2$S 423.

Step 2. 1-(1-(3-((1S,3S)-3-(BENZO[D]THIAZOL-2-YLAMINO)CYCLOBUTOXY)PYRAZIN-2-YL)PIPERIDIN-4-YL)ETHANOL as Racemic Mixture 1-(1-(3-((1S,3S)-3-(benzo[d]thiazol-2-ylamino)cyclobutoxy)pyrazin-2-yl)piperidin-4-yl)ethanone (423 mg, 1 mmol) was dissolved in 20 ml of methanol. This solution was cooled down to 0° C. using an ice bath and sodium tetraborohydride (76 mg, 2 mmol) was added by portions. The reaction mixture was stirred for 4 h at ambient temperature, and then saturated aqueous solution of ammonium chloride (10 mL) was added. The methanol was evaporated under vacuum and then the reaction mixture was diluted in ethyl acetate. The organic layer was separated from the aqueous layer. The aqueous layer was extracted one more time with ethyl acetate. The organic layers were combined and dried over magnesium sulphate, followed by concentration under reduced pressure. The residue was purified by column chromatography on silica gel to give racemic mixture 1-(1-(3-((1S,3S)-3-(benzo[d]thiazol-2-ylamino)cyclobutoxy)pyrazin-2-yl)piperidin-4-yl)ethanol as racemix mixture (298 mg, 0.7 mmol, 70% yield). PDE10 IC$_{50}$ (uM): 0.0108. M+1: 426. $^1$H NMR (CDCl$_3$, 400 MHz) δ (ppm):

7.63-7.62 (d, J=3.2 Hz, 1H); 7.57-7.56 (m, 1H); 7.47-7.46 (d, J=3.2 Hz, 1H); 7.43-7.40 (m, 1H); 7.25-7.21 (m, 1H); 7.06-7.01 (m, 1H); 5.04-5.00 (m, 1H); 4.23-4.19 (m, 2H); 4.12-4.08 (m, 1H); 3.52-3.49 (m, 1H); 3.12-3.09 (m, 2H); 2.74-2.72 (m, 2H); 2.17-2.14 (m, 2H); 1.89-1.81 (m, 1H); 1.71-1.60 (m, 1H); 1.44-1.39 (m, 3H); 1.16-1.14 (d, J=6 Hz, 3H).

SCHEME 26

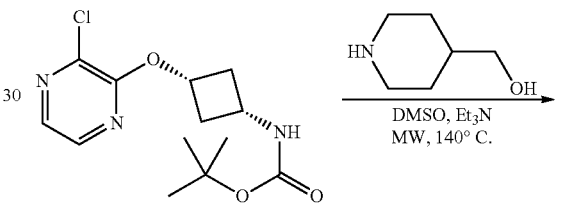

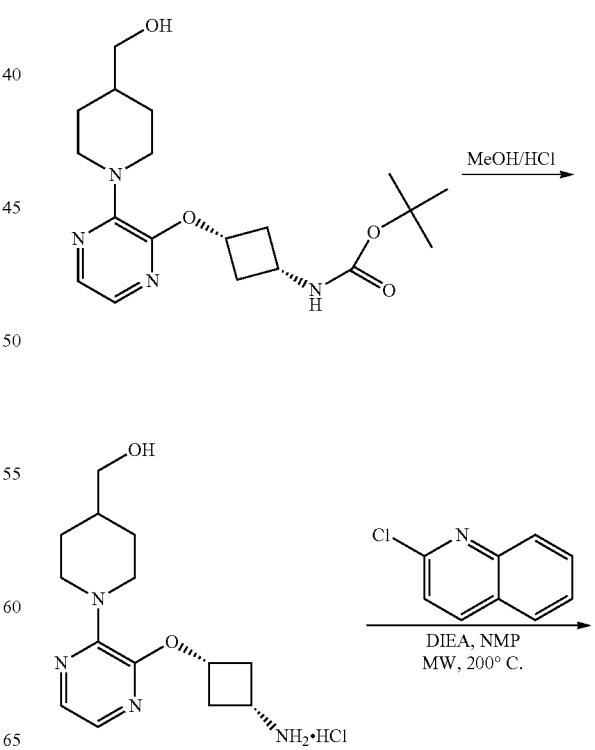

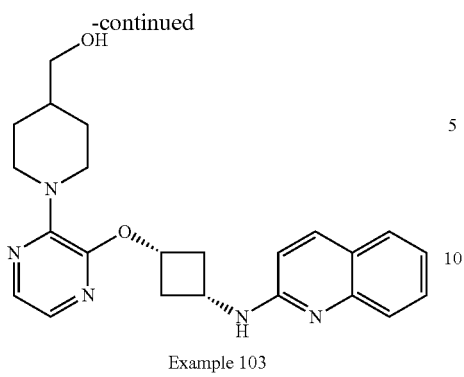

Example 103

Example 103

(1-(3-((1S,3S)-3-(QUINOLIN-2-YLAMINO)CYCLOBUTOXY)PYRAZIN-2-YL)PIPERIDIN-4-YL)METHANOL

Step 1. TERT-BUTYL ((1S,3S)-3-((3-(4-(HYDROXYMETHYL)PIPERIDIN-1-YL)PYRAZIN-2-YL)OXY)CYCLOBUTYL)CARBAMATE To a mixture of tert-butyl ((1S,3S)-3-((3-chloropyrazin-2-yl)oxy)cyclobutyl)carbamate (see PREPARATION 5A, step 1; 299 mg, 1 mmol) and piperidin-4-yl-methanol (115 mg, 1 mmol) and Et$_3$N (202 mg, 2 mmol) was added DMSO (6 mL). The solution was heated to 140° C. under microwave for 3 h. Then the mixture was concentrated and extracted with EtOAc (2×30 mL). The combined organic extracts were washed with water (10 mL) and brine (10 mL), dried over Na$_2$SO$_4$, and filtered. The filtrate was evaporated in vacuo and the residue was purified by flash column chromatography on silica gel (20% to 60% EtOAc in petroleum ether) to give tert-butyl ((1S,3S)-3-((3-(4-(hydroxymethyl)piperidin-1-yl)pyrazin-2-yl)oxy)cyclobutyl)carbamate (113 mg, 0.3 mmol, 30% yield). ESI-MS (M+1): 379 calc. for C$_{19}$H$_{30}$N$_4$O$_4$ 378.

Step 2. (1-(3-((1S,3S)-3-AMINOCYCLOBUTOXY)PYRAZIN-2-YL)PIPERIDIN-4-YL)METHANOL HYDROCHLORIDE To tert-butyl ((1S,3S)-3-((3-(4-(hydroxymethyl)piperidin-1-yl)pyrazin-2-yl)oxy)cyclobutyl)carbamate (378 mg, 1 mmol) was added 4 M HCl in MeOH (100 mL). The solution was stirred at RT for 2 h. The solvent was removed under reduced pressure to give (1-(3-((1S,3S)-3-aminocyclobutoxy)pyrazin-2-yl)piperidin-4-yl)methanol hydrochloride (299 mg, 0.95 mmol, yield 95%). ESI-MS (M+1): 279 calc. for C$_{14}$H$_{22}$N$_4$O$_2$ 278.

Step 3. (1-(3-((1S,3S)-3-(QUINOLIN-2-YLAMINO)CYCLOBUTOXY)PYRAZIN-2-YL)PIPERIDIN-4-YL)METHANOL A mixture of (1-(3-((1S,3S)-3-aminocyclobutoxy)pyrazin-2-yl)piperidin-4-yl)methanol hydrochloride (278 g, 1 mmol), 2-chloro-quinoline (163 mg, 1 mmol) and DIEA (286 mg, 2 mmol) in NMP (12 mL) was heated to 200° C. for 2 h in microwave. The reaction mixture was diluted with water, extracted with EtOAc (40 mL), washed with brine and dried over Na$_2$SO$_4$. The organic layers were concentrated and purified by column chromatography on silica gel to give (1-(3-((1S,3S)-3-(quinolin-2-ylamino)cyclobutoxy)pyrazin-2-yl)piperidin-4-yl)methanol (182 mg, 0.45 mmol, 45%).

TABLE 10A

EXAMPLES 103-104 PREPARED ANALOGOUS TO SCHEME 26

| Ex. # | Structure | Chemical Name | M + 1 | IC$_{50}$ (uM) |
|---|---|---|---|---|
| 103 | 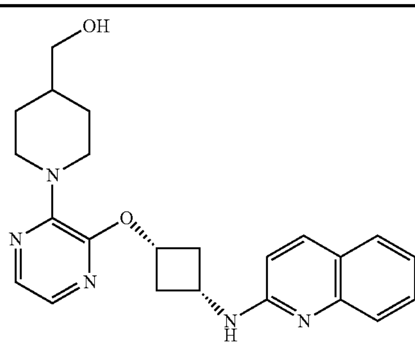 | (1-(3-((1S,3S)-3-(quinolin-2-ylamino)cyclobutoxy)pyrazin-2-yl)piperidin-4-yl)methanol | 406 | Not yet taken |
| 104 | 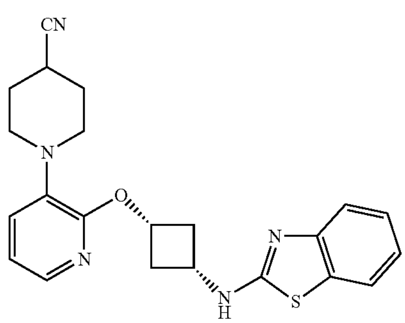 [SMILES: N#CC1CCN(c2cccnc2O[C@H]2C[C@@H](Nc3nc4ccccc4s3)C2)CC1] | 1-(2-((1S,3S)-3-(benzo[d]thiazol-2-ylamino)cyclobutoxy)pyridin-3-yl)piperidine-4-carbonitrile | 406 | 0.00125 |

TABLE 10B
PREPARATION AND NMR DATA OF EXAMPLES 103-104
| Ex. # | Starting Material (1) | Starting Material (2) | Reaction Condition | $^1$H NMR (CD$_3$OD, 400 MHz) δ (ppm) |
|---|---|---|---|---|
| 103 | (See Preparation 5A) | 2-chloroquinoline | DIEA, NMP, MW | 7.79 (d, J = 8.8 Hz, 1 H); 7.62-7.53 (m, 3 H); 7.48-7.43 (m, 2 H); 7.16-7.12 (m, 1 H); 6.70-6.68 (d, J = 8.8 Hz, 1 H); 5.05-5.01 (m, 1 H); 4.31 (s, 1 H); 4.19-4.16 (d, J = 13.2 Hz, 2 H); 3.41 (d, J = 6.4 Hz, 2 H); 3.11-3.07 (m, 2 H); 2.79-2.73 (m, 2 H); 2.13-2.06 (m, 2 H); 1.79-1.75 (m, 2 H); 1.62-1.60 (m, 1 H); 1.33-1.29 (m, 2 H). |
| 104 | (See Preparation 7L) | 2-chlorobenzothiazole | DIEA, NMP, MW | (CDCl$_3$) 7.81-7.79 (m, 1H); 7.64-7.56 (m, 2H); 7.34-7.30 (m, 1H); 7.14-7.10 (m, 2H); 6.89-6.86 (m, 1H); 5.50 (br, 1H); 5.13-5.06 (m, 1H); 4.07-4.03 (m, 1H); 3.31-3.20 (m, 4H); 3.06-3.00 (m, 2H); 2.88-2.83 (m, 1H); 2.21-2.05 (m, 6H). |
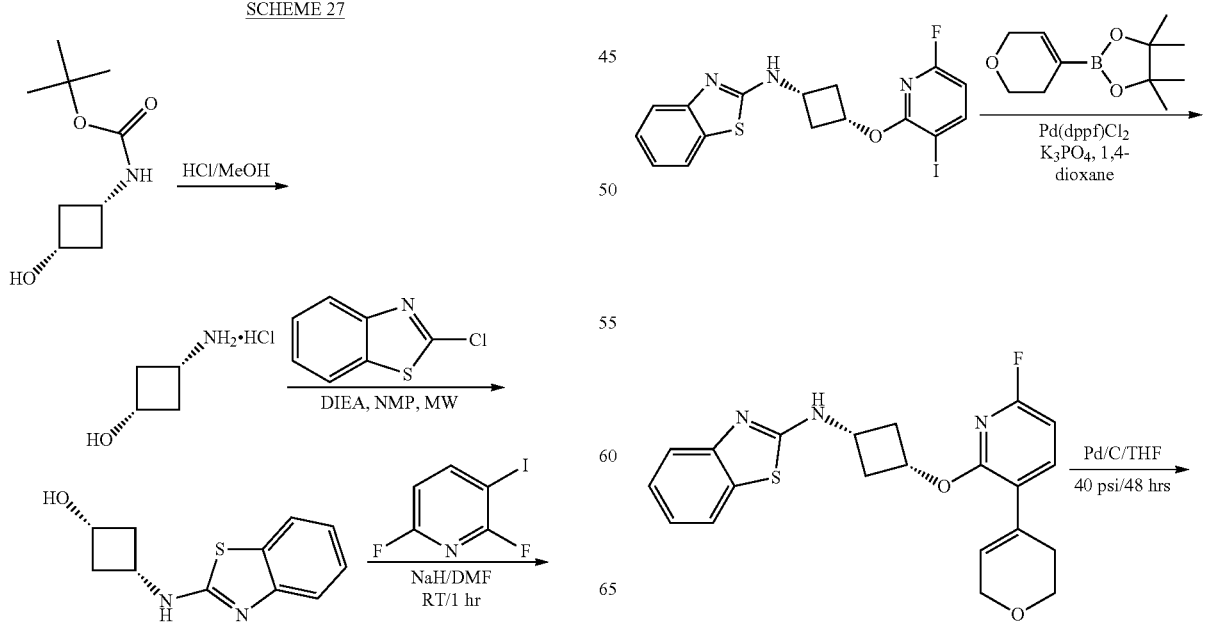
SCHEME 27

189
-continued

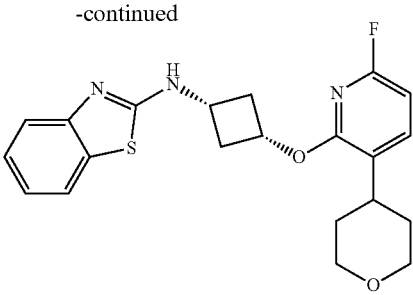

Ex. 105

Example 105

N-((1S,3S)-3-((6-FLUORO-3-(TETRAHYDRO-2H-PYRAN-4-YL)PYRIDIN-2-YL)OXY)CYCLOBUTYL)BENZO[D]THIAZOL-2-AMINE

Step 1. (1S,3S)-3-AMINOCYCLOBUTANOL HYDROCHLORIDE

The mixture of tert-butyl ((1S,3S)-3-hydroxycyclobutyl)carbamate (see PREPARATION 4A; 187 mg, 1 mmol, 1.0 eqv) in HCl/MeOH 4 N (15 ml) was stirred at room temperature for 4 hours. Reaction mixture was concentrated to give (1S,3S)-3-aminocyclobutanol hydrochloride. (120 mg, 0.98 mmol, 98% yield) ESI-MS (M+1): 88 calc. for $C_4H_9NO$ 87.

Step 2. (1S,3S)-3-(BENZO[D]THIAZOL-2-YLAMINO)CYCLOBUTANOL

A mixture of (1S,3S)-3-aminocyclobutanol hydrochloride (120 mg, 0.98 mmol, 1.0 eqv), 2-chloro-benzothiazole (purchased from ALDRICH™) (169 mg, 1 mmol, 1.02 eqv) and DIEA (286 mg, 2 mmol, 2.04 eqv) in NMP (2 mL) was heated to 180° C. for 2 hours in microwave. To the reaction mixture was added water, and the residue was extracted with EtOAc (30 mL). The combined organic layer was washed with brine and dried over $Na_2SO_4$. The organic layers were concentrated and purified by column chromatography on silica gel to give (1S,3S)-3-(benzo[d]thiazol-2-ylamino)cyclobutanol (160 mg, 0.72 mmol, yield 73%). ESI-MS (M+1): 221 calc. for $C_{11}H_{12}N_2OS$ 221.

190

Step 3. N-((1S,3S)-3-((6-FLUORO-3-IODOPYRIDIN-2-YL)OXY)CYCLOBUTYL)BENZO[D]THIAZOL-2-AMINE To the mixture of (1S,3S)-3-(benzo[d]thiazol-2-ylamino)cyclobutanol (160 mg, 0.72 mmol, 1.0 eqv), 2,6-difluoro-3-iodopyridine (see PREPARATION 8; 374 mg, 1.44 mmol, 2.0 eqv) and DMF (2 ml) was added sodium hydride 60% (29 mg, 0.72 mmol, 1.0 eqv) at 0° C. The mixture was stirred at room temperature for 1 hour. The mixture was poured into water (50 ml) and extracted with ethyl acetate. The organic layer was dried and concentrated. The residue was purified by silica gel chromatography to give N-((1S,3S)-3-((6-fluoro-3-iodopyridin-2-yl)oxy)cyclobutyl)benzo[d]thiazol-2-amine (105 mg, 0.22 mmol, 31% yield). ESI-MS (M+1): 442 calc. for $C_{16}H_{13}FIN_3OS$ 441.

Step 4. N-((1S,3S)-3-((3-(3,6-DIHYDRO-2H-PYRAN-4-YL)-6-FLUOROPYRIDIN-2-YL)OXY)CYCLOBUTYL)BENZO[D]THIAZOL-2-AMINE The mixture of N-((1S,3S)-3-((6-fluoro-3-iodopyridin-2-yl)oxy)cyclobutyl)benzo[d]thiazol-2-amine (100 mg, 0.22 mmol, 1.0 eqv), 2-(3,6-dihydro-2H-pyran-4-yl)-4,4,5,5-tetramethyl-1,3,2-dioxaborolane (70 mg, 0.33 mmol, 1.5 eqv) $K_3PO_4$ (212 mg, 1 mmol, 5 eqv) and Pd(dppf)Cl$_2$ (50 mg) in 1,4-dioxane (3 ml) was stirred at 80° C. overnight. The mixture was cool down to room temperature and concentrated. The residue was purified by silica gel chromatography to give N-((1S,3S)-3-((3-(3,6-dihydro-2H-pyran-4-yl)-6-fluoropyridin-2-yl)oxy)cyclobutyl)benzo[d]thiazol-2-amine (80 mg, 0.2 mmol, 90% yield) ESI-MS (M+1): 398 calc. for $C_{21}H_{20}FN_3O_2S$ 398.

Step 5. N-((1S,3S)-3-((6-FLUORO-3-(TETRAHYDRO-2H-PYRAN-4-YL)PYRIDIN-2-YL)OXY)CYCLOBUTYL)BENZO[D]THIAZOL-2-AMINE The mixture of N-((1S,3S)-3-((3-(3,6-dihydro-2-pyran-4-yl)-6-fluoropyridin-2-yl)oxy)cyclobutyl)benzo[d]thiazol-2-amine (80 mg, 0.2 mmol, 1 eqv) Pd/C 10% wet (0.3 g) in THF (10 ml) was stirred at 40 psi for 48 hours under $H_2$. The reaction mixture was filtered and concentrated to give N-((1S,3S)-3-((6-fluoro-3-(tetrahydro-2H-pyran-4-yl)pyridin-2-yl)oxy)cyclobutyl)benzo[d]thiazol-2-amine (60 mg, 0.15 mmol, 75% yield). PDE10 IC$_{50}$ (uM): 0.000758. $^1$H NMR (CD$_3$OD, 400 MHz) δ (ppm): 7.79-7.77 (m, 1H); 7.73-7.68 (m, 1H); 7.56-7.47 (m, 2H); 7.35-7.32 (m, 1H); 6.58-6.55 (m, 1H); 5.09-5.03 (m, 1H); 4.14-4.04 (m, 3H); 3.61-3.55 (m, 2H); 3.27-3.05 (m, 3H); 2.35-2.28 (m, 2H); 1.83-1.77 (m, 4H).

SCHEME 28

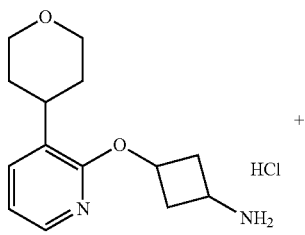

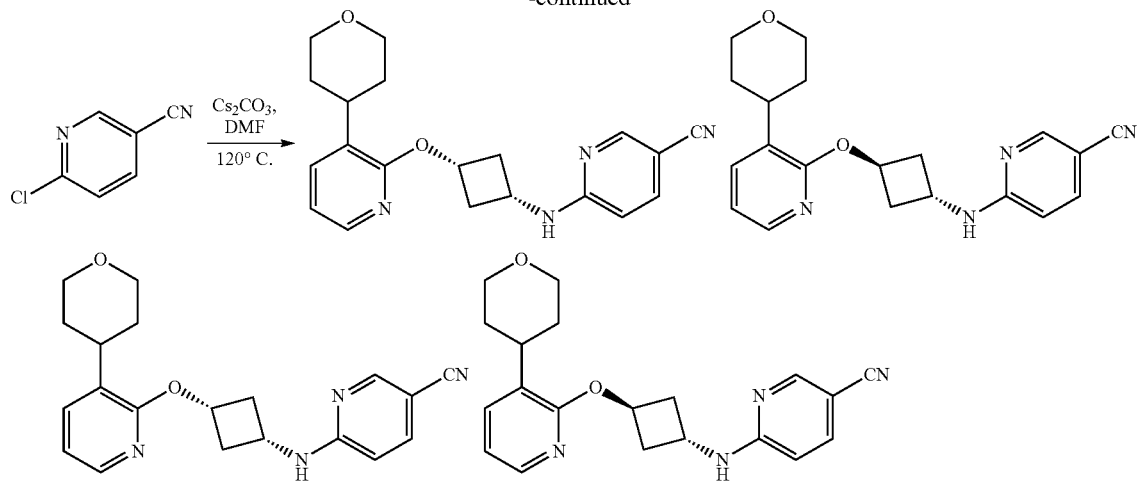

Example 106 and Example 107

6-(((1R,3R)-3-((3-(TETRAHYDRO-2H-PYRAN-4-YL)PYRIDIN-2-YL)OXY)CYCLOBUTYL)AMINO)NICOTINONITRILE and 6-(((1S,3S)-3-((3-(TETRAHYDRO-2H-PYRAN-4-YL)PYRIDIN-2-YL)OXY)CYCLOBUTYL)AMINO) NICOTINONITRILE To a mixture of $Cs_2CO_3$ (652 mg, 2 mmol) and 3-((3-(tetrahydro-2H-pyran-4-yl)pyridin-2-yl)oxy)cyclobutan-amine hydrochloride (see PREPARATION 7C; 248 mg, 1 mmol) was added DMF (20 mL) and 6-chloro-nicotinonitrile (138 mg, 1 mmol). The reaction mixture was heated to 120° C. for 10 hours. The mixture was diluted with water (60 mL) and extracted with EtOAc (2×50 mL). The combined organic extracts were washed with water (60 mL) and brine (60 mL), dried over $Na_2SO_4$ and filtered. The filtrate was evaporated in vacuo and the residue was purified by prep-HPLC to give examples 105 (175 mg, 0.5 mmol, 50% yield) and 106 (55 mg, 0.156 mmol, 39% yield) as a pair of separated stereoisomers.

TABLE 11A

EXAMPLES 106-111 PREPARED ANALOGOUS TO SCHEME 28.

| Ex. # | Structure | Chemical Name | M + 1 | $IC_{50}$ (uM) |
|---|---|---|---|---|
| 106 and 107* | (structure shown) | 6-(((1S,3S)-3-((3-(tetrahydro-2H-pyran-4-yl)pyridin-2-yl)oxy)cyclobutyl)amino)nicotinonitrile and 6-(((1R,3R)-3-((3-(tetrahydro-2H-pyran-4-yl)pyridin-2-yl)oxy)cyclobutyl)amino)nicotinonitrile; respectively. | 351 | 0.59 and 0.865, respectively |

TABLE 11A-continued

EXAMPLES 106-111 PREPARED ANALOGOUS TO SCHEME 28.

| Ex. # | Structure | Chemical Name | M + 1 | IC$_{50}$ (uM) |
|---|---|---|---|---|
| 108 and 109* | | N-((1R,3R)-3-((3-(tetrahydro-2H-pyran-4-yl)pyridin-2-yl)oxy)cyclobutyl)-5-(trifluoromethyl)pyridin-2-amine and N-((1S,3S)-3-((3-(tetrahydro-2H-pyran-4-yl)pyridin-2-yl)oxy)cyclobutyl)-5-(trifluoromethyl)pyridin-2-amine; respectively. | 394 | 0.436 and 0.106; 0.59 and 0.865, respectively |
| 110 and 111* | | 5-chloro-N-((1S,3S)-3-((3-(tetrahydro-2H-pyran-4-yl)pyridin-2-yl)oxy)cyclobutyl)pyridin-2-amine and 5-chloro-N-((1R,3R)-3-((3-(tetrahydro-2H-pyran-4-yl)pyridin-2-yl)oxy)cyclobutyl)pyridin-2-amine; respectively. | 360 | 0.0262 and 0.0837; 0.59 and 0.865, respectively |

*as a pair of separated stereoisomers having the same mass.

TABLE 11B

PREPARATION AND NMR OF EXAMPLES 106-111

| Ex. # | Starting Materials (1) and (2) | Reaction Condition | $^1$H NMR (CDCl$_3$, 400 MHz) δ (ppm) |
|---|---|---|---|
| 106 and 107 | 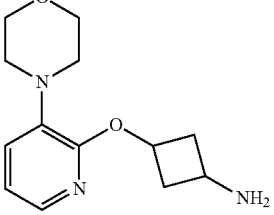 | Cs$_2$CO$_3$, DMF 120° C. | 8.25 (s, 1H); 7.97-7.96 (d, J = 5.2 Hz, 1H); 7.72-7.70 (d, J = 9.2 Hz, 1H); 7.44-7.43 (d, J = 7.2 Hz, 1H); 6.89-6.86 (m, 1H); 6.52-6.50 (m, 1H); 5.12-5.08 (m, 1H); 4.08-4.06 (d, J = 11.2 Hz, 2H); 3.89 (s, 1H); 3.59-3.53 (m, 2H); 3.15-3.12 (m, 2H); 3.11-3.01 (m, 1H); 2.22-2.16 (m, 2H); 1.77-1.72 (m, 4H) and 8.35-8.34 (d, J = 0.8 Hz, 1H); 7.98-7.96 (m, 1H); 7.65-7.63 (d, J = 7.6 Hz, 1H); 7.45-7.43 (m, 1H); 6.89-6.85 (m, 1H); 6.42-6.36 (m, 1H); 5.47-5.44 (m, 1H); 4.35 (s, 1H); 4.11-4.06 (m, 2H); 3.61-3.55 (m, 2H); 3.11-3.03 (m, 1H); 2.70-2.64 (m, 2H); 2.57-2.51 (m, 2H); 1.79-1.75 (m, 4H); respectively. |
| 108 and 109 | 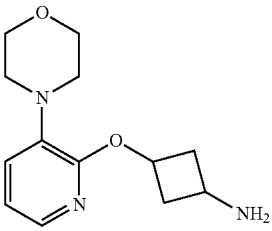 | Cs$_2$CO$_3$, DMF 120° C. | 8.22 (s, 1H); 7.94-7.92 (m, 1H); 7.83-7.80 (m, 1H); 7.58-7.56 (m, 1H); 6.94-6.91 (m, 1H); 6.86-6.83 (d, J = 9.2 Hz, 1H); 5.42 (s, 1H); 4.46 (s, 1H); 4.08-4.04 (m, 2H); 3.63-3.56 (m, 2H); 3.13 (s, 1H); 2.66-2.58 (m, 4H); 1.83-1.77 (m, 4H) and 8.23-8.22 (d, J = 0.8 Hz, 1H); 7.96-7.94 (m, 1H); 7.81-7.78 (m, 1H); 7.56-7.53 (m, 1H); 6.94-6.90 (m, 1H); 6.81-6.79 (d, J = 9.2 Hz, 1H); 5.10-5.06 (m, 1H); 4.09-4.02 (m, 3H); 3.59-3.53 (m, 2H); 3.12-3.07 (m, 3H); 2.16-2.13 (m, 2H); 1.81-1.75 (m, 4H) ; respectively. |
| 110 and 111 | 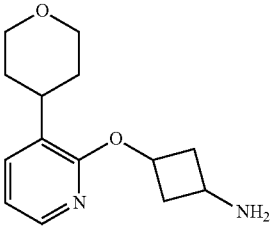 | t-BuONa, DMF | (CD$_3$OD,) 7.94-7.93 (d, J = 4.8 Hz, 1H); 7.89-7.88 (d, J = 2 Hz, 1H); 7.53-7.51 (m, 1H); 7.40-7.37 (m, 1H); 6.91-6.88 (m, 1H); 6.48-6.46 (d, J = 8.8 Hz, 1H); 5.05-5.01 (m, 1H); 4.04-3.96 (m, 3H); 3.59-3.52 (m, 2H); 3.07-3.01 (m, 3H); 2.05-1.99 (m, 2H); 1.79-1.75 (m, 4H) and (CD$_3$OD) 7.94-7.93 (d, J = 4.8 Hz, 1H); 7.89-7.88 (d, J = 2 Hz, 1H); 7.53-7.51 (m, 1H); 7.40-7.37 (m, 1H); 6.91-6.88 (m, 1H); 6.48-6.46 (d, J = 8.8 Hz, 1H); 5.05-5.01 (m, 1H); 4.04-3.96 (m, 3H); 3.59-3.52 (m, 2H); 3.07-3.01 (m, 3H); 2.05-1.99 (m, 2H); 1.79-1.75 (m, 4H); respectively. |

SCHEME 29

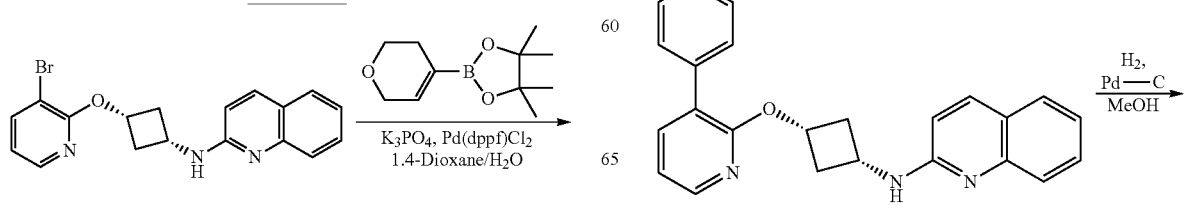

-continued

-continued

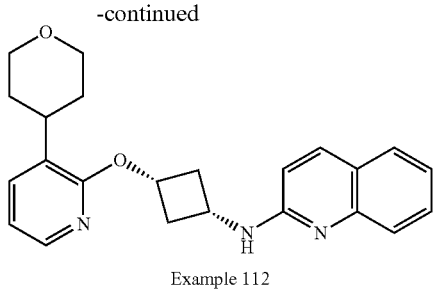

Example 112

Example 112

N-((1S,3S)-3-((3-(TETRAHYDRO-2H-PYRAN-4-YL)PYRIDIN-2-YL)OXY)CYCLOBUTYL)QUINOLIN-2-AMINE

Step 1. N-((1S,3S)-3-((3-(3,6-DIHYDRO-2H-PYRAN-4-YL)PYRIDIN-2-YL)OXY)CYCLOBUTYL)QUINOLIN-2-AMINE To the mixture of N-((1S,3S)-3-((3-bromopyridin-2-yl)oxy)cyclobutyl)quinolin-2-amine (see PREPARATION 7G; 370 mg, 1 mmol, 1.0 eqv), 2-(3,6-dihydro-2H-pyran-4-yl)-4,4,5,5-tetramethyl-1,3,2-dioxaborolane (315 mg, 1.5 mmol, 1.5 eqv) and $NaCO_3$ (212 mg, 2 mmol) in 1,4-dioxane (60 mL) and $H_2O$ (6 mL) was added $Pd(dppf)Cl_2$ (36.6 mg, 0.05 mmol). The reaction mixture was stirred at 110° C. under $N_2$ overnight. The reaction mixture was filtered through CELITE® and washed with $CH_2Cl_2$. The organic layer was concentrated and the crude product was purified by silica gel column to give N-((1S,3S)-3-((3-(3,6-dihydro-2H-pyran-4-yl)pyridin-2-yl)oxy)cyclobutyl)quinolin-2-amine (188 mg, 0.52 mmol, yield 52%). ESI-MS (M+1): 374 calc. for $C_{23}H_{23}N_3O_2$ 373.

Step 2. N-((1S,3S)-3-((3-(TETRAHYDRO-2H-PYRAN-4-YL)PYRIDIN-2-YL)OXY)CYCLOBUTYL)QUINOLIN-2-AMINE A mixture of N-((1S,3S)-3-((3-(3,6-dihydro-2H-pyran-4-yl)pyridin-2-yl)oxy)cyclobutyl)quinolin-2-amine (373 mg, 1 mmol) and wet Pd—C (50%, 200 mg) in MeOH (100 mL) was stirred under $H_2$ (40 psi) at 30° C. overnight then the reaction mixture was filtered through CELITE® and washed with MeOH (100 mL). The filtrate was concentrated to give N-((1S,3S)-3-((3-(tetrahydro-2H-pyran-4-yl)pyridin-2-yl)oxy)cyclobutyl)quinolin-2-amine (336 mg, 0.9 mmol, yield 90%).

TABLE 12A

EXAMPLES 112-113 PREPARED ANALOGOUS TO SCHEME 29

| Ex. # | Structure | Chemical Name | M + 1 | $IC_{50}$ (uM) |
|---|---|---|---|---|
| 112 | 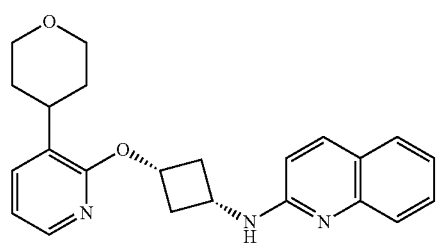 [SMILES: c1cnc(O[C@H]2C[C@@H](Nc3ccc4ccccc4n3)C2)c(C2CCOCC2)c1] | N-((1S,3S)-3-((3-(tetrahydro-2H-pyran-4-yl)pyridin-2-yl)oxy)cyclobutyl)quinolin-2-amine | 376 | 0.0015 |
| 113 | 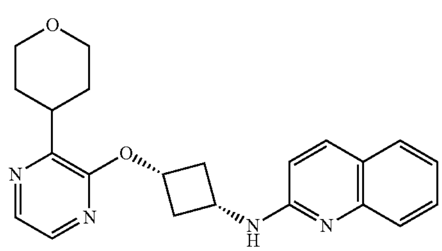 [SMILES: c1ccc2nc(N[C@H]3C[C@@H](Oc4nccnc4C4CCOCC4)C3)ccc2c1] | N-((1S,3S)-3-((3-(tetrahydro-2H-pyran-4-yl)pyrazin-2-yl)oxy)cyclobutyl)quinolin-2-amine | 377 | 0.0075 |

TABLE 12B
PREPARATION AND NMR OF EXAMPLES 112-113
| Ex. # | Starting Material (1) | Reaction Condition | ¹H NMR (CDCl₃, 400 MHz) δ (ppm) |
|---|---|---|---|
| 112 | (see Preparation 7G) | H₂, Pd/C, MeOH | 8.13 (d, J = 8.0 Hz, 1 H); 7.97-7.95 (m, 1 H); 7.78 (d, J = 8.0 Hz, 1 H); 7.68-7.64 (m, 2 H); 7.47-7.44 (m, 1 H); 7.40-7.36 (m, 1 H); 6.90-6.88 (m, 1 H); 6.87-6.78 (m, 1 H); 5.13-5.10 (m, 1 H); 4.07-4.03 (m, 2 H); 3.88-3.85 (m, 1 H); 3.60-3.53 (m, 2 H); 3.17-3.08 (m, 3 H); 2.41 (d, J = 12.0 Hz, 2 H); 1.77-1.67 (m, 4 H). |
| 113 | (see Preparation 5G) | H₂, Pd/C, MeOH | (CD₃OD) 8.35-8.24 (m, 1H); 8.08 (s, 1H); 7.98 (s, 1H); 7.88-7.80 (m, 3H); 7.53 (s, 1H); 7.28-6.99 (m, 1H); 5.16 (s, 1H); 4.30-4.29 (m, 1H); 4.05 (d, J = 7.2 Hz, 2H); 3.60-3.55 (m, 2H); 3.26-3.22 (m, 3H); 2.39 (d, J = 12 Hz, 2H); 1.94 (d, J = 12 Hz, 2H); 1.79 (s, 2H). |
SCHEME 30
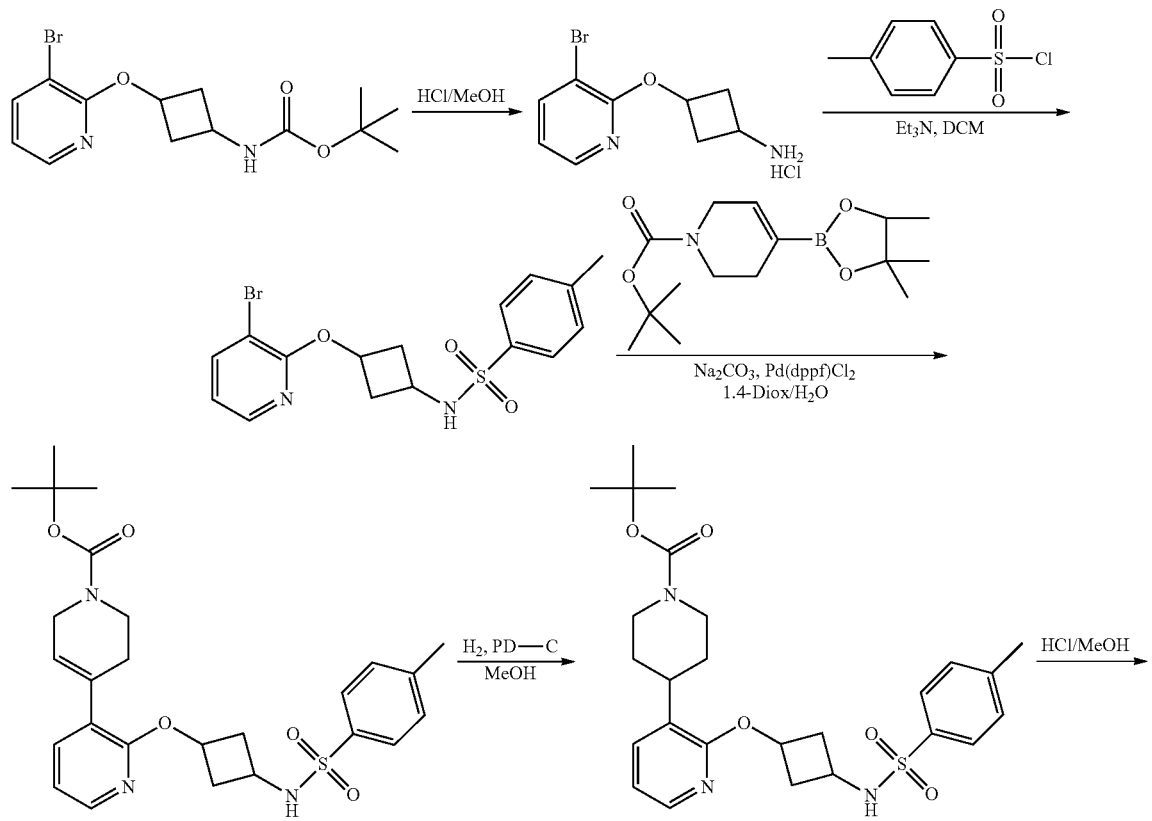

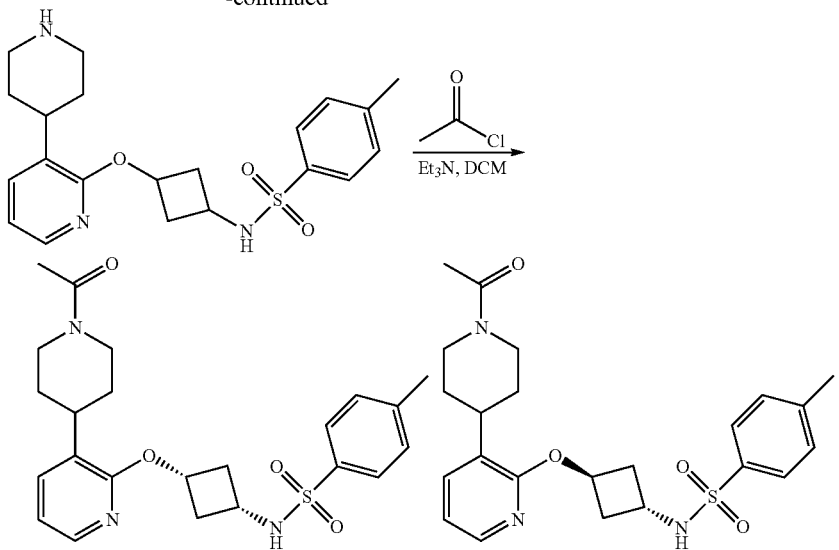

Examples 114 and 115

Examples 114 and 115

N-((1S,3S)-3-((3-(1-ACETYLPIPERIDIN-4-YL)PYRIDIN-2-YL)OXY)CYCLOBUTYL)-4-METHYLBENZENESULFONAMIDE and N-((1R,3R)-3-((3-(1-ACETYLPIPERIDIN-4-YL)PYRIDIN-2-YL)OXY)CYCLOBUTYL)-4-METHYLBENZENESULFONAMIDE

STEP 1: 3-((3-BROMOPYRIDIN-2-YL)OXY)CYCLOBUTANAMINE HYDROCHLORIDE

To a solution of tert-butyl (3-((3-bromopyridin-2-yl)oxy)cyclobutyl)carbamate (see PREPARATION 7B; 342 mg, 1 mmol) was added 4 M HCl in MeOH (50 mL). The solution was stirred at room temperature for 2 hours. The solvent was removed under reduced pressure to give 3-((3-bromopyridin-2-yl)oxy)cyclobutanamine hydrochloride (223 mg, 0.95 mmol, yield 95%). ESI-MS (M+1): 243 calc. for $C_9H_{11}BrN_2O$ 242.

Step 2. N-(3-((3-BROMOPYRIDIN-2-YL)OXY)CYCLOBUTYL)-4-METHYLBENZENESULFONAMIDE To a solution of 3-((3-bromopyridin-2-yl)oxy)cyclobutanamine hydrochloride (243 mg, 1 mmol) in dry DCM (10 mL) was added $Et_3N$ (1 mL). The reaction mixture was cooled to 0° C. with an ice bath, and p-toluenesulfonyl chloride (380 mg, 2 mmol) was added dropwise. After 1 hour, the reaction mixture was warmed to room temperature, and stirred overnight. Then the reaction mixture was washed with brine, dried over $Na_2SO_4$, filtered, and concentrated under vacuum to give the crude product. The crude product was purified by flash chromatography on silica gel (20% to 45% EtOAc in petroleum ether) to give N-(3-((3-bromopyridin-2-yl)oxy)cyclobutyl)-4-methylbenzenesulfonamide (318 mg, 0.8 mmol, yield 80%). ESI-MS (M+1): 397 calc. for $C_{16}H_{17}BrN_2O_3S$ 396.

Step 3. TERT-BUTYL 2-(3-(4-METHYLPHENYLSULFONAMIDO)CYCLOBUTOXY)-5',6'-DIHYDRO-[3,4'-BIPYRIDINE]-1'(2'H)-CARBOXYLATE To a solution of N-(3-((3-bromopyridin-2-yl)oxy)cyclobutyl)-4-methylbenzenesulfonamide (397 mg, 1 mmol), tert-butyl 4-(4,4,5,5-tetramethyl-1,3,2-dioxaborolan-2-yl)-5,6-dihydropyridine-1(2H)-carboxylate (335 mg, 1.1 mmol) and $NaCO_3$ (212 mg, 2 mmol) in 1,4-dioxane (60 mL) and $H_2O$ (6 mL) was added $Pd(dppf)Cl_2$ (36.6 mg, 0.05 mmol). The reaction mixture was stirred at 110° C. under $N_2$ overnight. The reaction mixture was filtered through CELITE® and washed with $CH_2Cl_2$. The organic layer was concentrated and the crude product was purified by silica gel column to give tert-butyl 2-(3-(4-methylphenylsulfonamido)cyclobutoxy)-5',6'-dihydro-[3,4'-bipyridine]-1'(2'H)-carboxylate (351 mg, 0.7 mmol, yield 70%). ESI-MS (M+1): 500 calc. for $C_{26}H_{33}N_3O_5S$ 499.

Step 4. TERT-BUTYL 4-(2-(3-(4-METHYLPHENYLSULFONAMIDO)CYCLOBUTOXY)PYRIDIN-3-YL)PIPERIDINE-1-CARBOXYLATE A mixture of tert-butyl 2-(3-(4-methylphenylsulfonamido)cyclobutoxy)-5',6'-dihydro-[3,4'-bipyridine]-1'(2'H)-carboxylate (499 mg, 1 mmol) and wet Pd—C (50%, 1.0 g) in MeOH (50 mL) was stirred under $H_2$ (40 psi) at 30° C. overnight then the reaction mixture was filtered through CELITE® and washed with MeOH. The filtrate was concentrated to give tert-butyl 4-(2-(3-(4-methylphenylsulfonamido)cyclobutoxy)pyridin-3-yl)piperidine-1-carboxylate (476 mg, 0.95 mmol, yield 95%). ESI-MS (M+1): 502 calc. for $C_{26}H_{35}N_3O_5S$ 501.

Step 5. 4-METHYL-N-(3-((3-(PIPERIDIN-4-YL)PYRIDIN-2-YL)OXY)CYCLOBUTYL)BENZENESULFONAMIDE HYDROCHLORIDE To tert-butyl 4-(2-(3-(4-methylphenylsulfonamido)cyclobutoxy)pyridin-3-yl)piperidine-1-carboxylate (501 mg, 1 mmol) was added 4 M HCl in MeOH (100 mL). The solution was stirred at room temperature for 2 hours. The solvent was removed under reduced pressure to give 4-methyl-N-(3-((3-(piperidin-4-yl)pyridin-2-yl)oxy)cyclobutyl)benzenesulfonamide hydrochloride (381 mg, 0.95 mmol, yield 95%). ESI-MS (M+1): 402 calc. for $C_{21}H_{27}N_3O_3S$ 401.

Step 6. N-((1S,3S)-3-((3-(1-ACETYLPIPERIDIN-4-YL)PYRIDIN-2-YL)OXY)CYCLOBUTYL)-4-METHYLBENZENESULFONAMIDE AND N-((1R,3R)-3-((3-(1-ACETYLPIPERIDIN-4-YL)PYRIDIN-2-YL)OXY)CYCLOBUTYL)-4-METHYLBENZENESULFONAMIDE To a solution of 4-methyl-N-(3-((3-(piperidin-4-yl)pyridin-2-yl)oxy)cyclobutyl)benzenesulfonamide hydrochloride (401 mg, 1 mmol) in dry $CH_2Cl_2$ (10 mL) was added $Et_3N$ (1 mL). The reaction mixture was cooled to 0° C. with an ice bath, and acetyl chloride (156 mg, 2 mmol) was added dropwise. After 1 hour, the reaction mixture was warmed to room temperature, and stirred overnight. Then the reaction mixture was washed with brine, dried over $Na_2SO_4$, filtered, and concentrated under vacuum to give the crude product. The crude product was purified by chiral-prep-HPLC (Column: Chiralcel OD-H 250*30 mm, 5u; Mobile phase: 80% hexane in EtOH (0.05% diethyl amine); Flow rate: 30 mL/minute) to give examples 114 and 115.

Example 114

N-((1S,3S)-3-((3-(1-acetylpiperidin-4-yl)pyridin-2-yl)oxy)cyclobutyl)-4-methylbenzenesulfonamide PDE10 $IC_{50}$ (uM): 12.4. M+1: 444. $^1$H NMR ($CD_3OD$, 400 MHz) δ (ppm): 7.89-7.87 (m, 1H); 7.74-7.72 (m, 2H); 7.50-7.48 (m, 1H); 7.37-7.35 (d, J=8 Hz, 2H); 6.89-6.87 (m, 1H); 4.87-4.78 (m, 1H); 4.70-4.60 (m, 1H); 4.02-3.99 (m, 1H); 3.50-3.46 (m, 1H); 3.30-3.29 (m, 1H); 3.10-2.96 (m, 1H); 2.67-2.61 (m, 3H); 2.41 (s, 3H); 2.11 (s, 3H); 1.90-1.79 (m, 4H); 1.65-1.51 (m, 2H).

Example 115

N-((1R,3R)-3-((3-(1-acetylpiperidin-4-yl)pyridin-2-yl)oxy)cyclobutyl)-4-methylbenzenesulfonamide PDE10 $IC_{50}$ (uM): 0.916. M+1: 444. $^1$H NMR ($CD_3OD$, 400 MHz) δ (ppm): 7.90-7.88 (m, 1H); 7.73-7.70 (m, 2H); 7.54-7.52 (m, 1H); 7.37-7.35 (m, 2H); 6.92-6.89 (m, 1H); 5.20-5.18 (m, 1H); 3.96-3.93 (m, 2H); 3.23-3.22 (d, J=2.4 Hz, 2H); 3.01 (s, 1H); 2.71-2.70 (d, J=2.8 Hz, 1H); 2.41 (s, 3H); 2.31-2.26 (m, 4H); 2.13 (s, 3H); 1.86-1.80 (m, 2H); 1.66-1.53 (m, 2H).

SCHEME 31

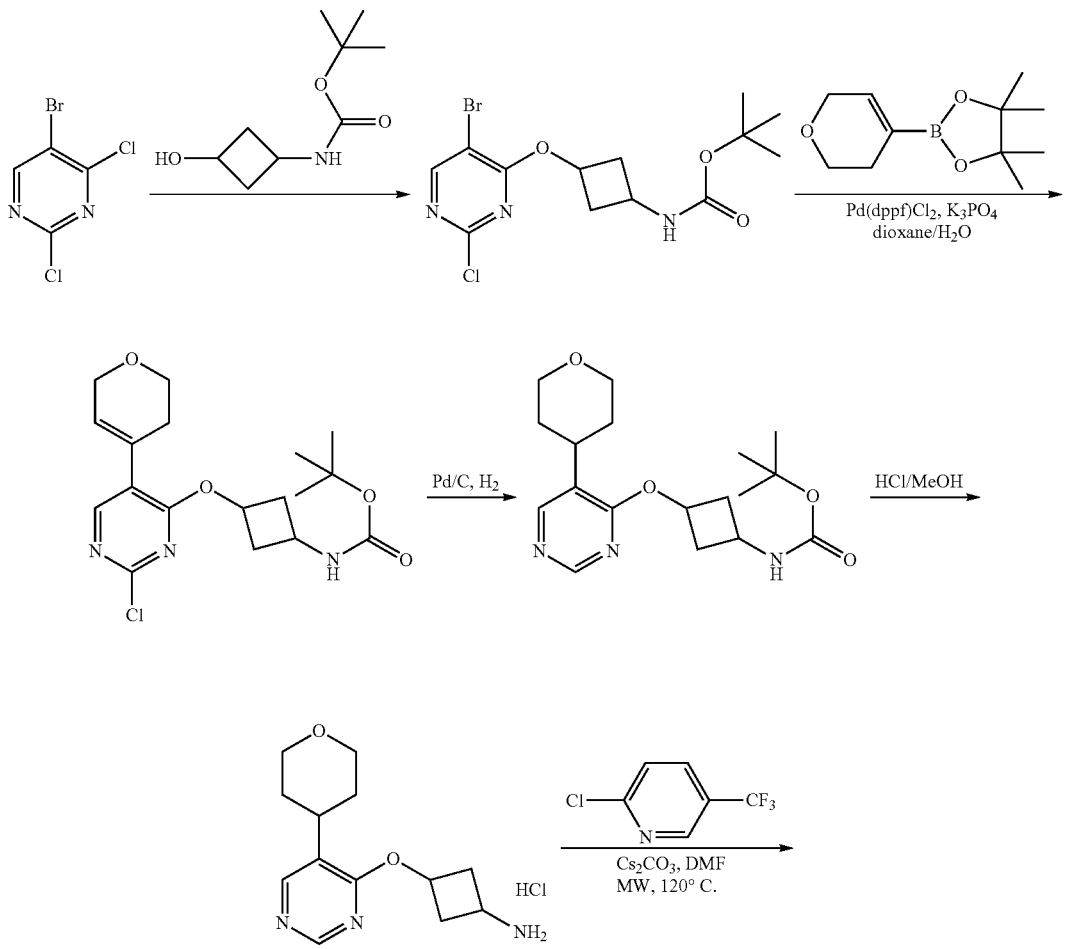

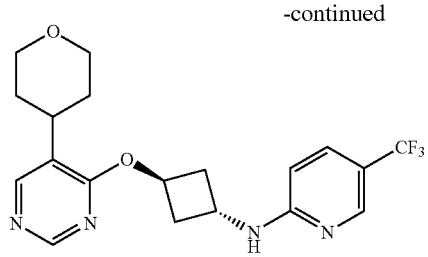
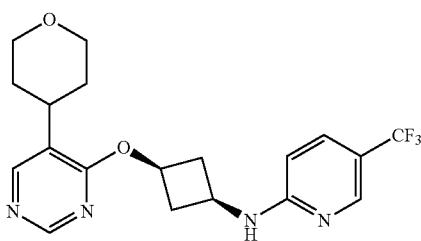

Examples 116 and 117

Examples 116 and 117

N-((1R,3R)-3-((5-(TETRAHYDRO-2H-PYRAN-4-YL)PYRIMIDIN-4-YL)OXY)CYCLOBUTYL)-5-(TRIFLUOROMETHYL)PYRIDIN-2-AMINE and N-((1S,3S)-3-((5-(TETRAHYDRO-2H-PYRAN-4-YL)PYRIMIDIN-4-YL)OXY)CYCLOBUTYL)-5-(TRIFLUOROMETHYL)PYRIDIN-2-AMINE

Step 1. [3-(5-BROMO-2-CHLORO-PYRIMIDIN-4-YLOXY)-CYCLOBUTYL]-CARBAMIC ACID TERT-BUTYL ESTER To a solution of (3-hydroxy-cyclobutyl)-carbamic acid tert-butyl ester (2.5 g, 13.3 mmol) in THF (40 mL) were added $Cs_2CO_3$ (8.6 g, 26.6 mmol) and 5-bromo-2,4-dichloropyrimidine (3 g, 13.3 mmol). The reaction mixture was heated at reflux overnight. The reaction mixture was filtered and concentrated, diluted with EtOAc and water. The aqueous phase was extracted with EtOAc (3×100 mL) and the combined organic extracts were washed with brine (60 mL), dried over $MgSO_4$, filtered, and concentrated. Purification by flash column chromatography on silica gel to give the product (4.75 g, 12.6 mmol, yield: 95%). ESI-MS (M+1): 378 calc. for $C_{13}H_{17}BrClN_3O_3$ 377.

Step 2. {3-[2-CHLORO-5-(3,6-DIHYDRO-2H-PYRAN-4-YL)-PYRIMIDIN-4-YLOXY]-CYCLOBUTYL}-CARBAMIC ACID TERT-BUTYL ESTER To a solution of [3-(5-bromo-2-chloro-pyrimidin-4-yloxy)-cyclobutyl]-carbamic acid tert-butyl ester (5.1 g, 13.3 mmol) in dioxane (80 mL) was treated with $Na_2CO_3$ (2.8 g, 26.6 mmol) in 15 mL of $H_2O$ as a solution, followed by additional of 4-(4,4,5,5-tetramethyl-[1,3,2]dioxaborolan-2-yl)-3,6-dihydro-2H-pyran (3.3 g 16.0 mmol) and Pd(dppf)$Cl_2$ (974 mg, 1.33 mmol). The resulting mixture was heated at refluxing overnight under $N_2$ atmosphere. TLC showed that most of the staring materials were consumed completely. The solution was filtered, and the filter was concentrated. And the residue was purified by silica gel chromatography to give the product (2.2 g, 5.76 mmol, 43%). ESI-MS (M+1): 382 calc. for $C_{18}H_{24}ClN_3O_4$ 381.

Step 3. {3-[5-(TETRAHYDRO-PYRAN-4-YL)-PYRIMIDIN-4-YLOXY]-CYCLOBUTYL}-CARBAMIC ACID TERT-BUTYL ESTER To a solution of {3-[2-chloro-5-(3,6-dihydro-2H-pyran-4-yl)-pyrimidin-4-yloxy]-cyclobutyl}-carbamic acid tert-butyl ester (2.2 g, 5.76 mmol) in MeOH (40 mL) was added Pd/C (1.0 g). The reaction solution was stirred at room temperature overnight under $H_2$ atmosphere. LCMS showed that the staring material was consumed completely. The mixture was filtered and concentrated to give the product (1.2 g, 3.44 mmol, yield: 60%). ESI-MS (M+1): 350 calc. for $C_{18}H_{27}N_3O_4$ 349.

Step 4. 3-[5-(TETRAHYDRO-PYRAN-4-YL)-PYRIMIDIN-4-YLOXY]-CYCLOBUTYLAMINE

The mixture of {3-[5-(tetrahydro-pyran-4-yl)-pyrimidin-4-yloxy]-cyclobutyl}-carbamic acid tert-butyl ester (1.2 g, 3.21 mmol) in HCl/MeOH (20 mL) was stirred at room temperature for 1 hour. Then it was concentrated to give 3-[5-(tetrahydro-pyran-4-yl)-pyrimidin-4-yloxy]-cyclobutylamine (916 mg, 3.21 mmol, yield: 93%) which was used in the next step without further purification. ESI-MS (M+1): 250 calc. for $C_{13}H_{19}N_3O_2$ 249.

Step 5. N-((1R,3R)-3-((5-(TETRAHYDRO-2H-PYRAN-4-YL)PYRIMIDIN-4-YL)OXY)CYCLOBUTYL)-5-(TRIFLUOROMETHYL)PYRIDIN-2-AMINE AND N-((1S,3S)-3-((5-(TETRAHYDRO-2H-PYRAN-4-YL)PYRIMIDIN-4-YL)OXY)CYCLOBUTYL)-5-(TRIFLUOROMETHYL)PYRIDIN-2-AMINE To a solution of 3-[5-(tetrahydro-pyran-4-yl)-pyrimidin-4-yloxy]-cyclobutylamine (916 mg, 3.21 mmol) in DMF (20 mL) were added $Cs_2CO_3$ (2.1 g, 6.42 mmol) and 2-chloro-5-trifluoromethyl-pyridine (697 mg, 3.85 mmol). The mixture was heated at 120° C. for 2 hours. The reaction mixture was concentrated, diluted with EtOAc and water. The aqueous layer was extracted with EtOAc (3×) and the combined organic extracts were washed with brine (1×), dried over $MgSO_4$, filtered, and concentrated. Purification by flash column chromatography on silica gel, and followed by supercritical fluid chromatography (SFC) to give the products.

Example 116

N-((1R,3R)-3-((5-(tetrahydro-2H-pyran-4-yl)pyrimidin-4-yl)oxy)cyclobutyl)-5-(trifluoromethyl)pyridin-2-amine PDE10 $IC_{50}$ (uM): 0.959. M+1: 395. $^1$H NMR ($CD_3OD$, 400 MHz) δ (ppm): 8.47 (s, 1H), 8.24 (s, 1H), 8.12-8.11 (m, 1H), 7.51 (dd, J=8.8 Hz, 2.4 Hz, 1H), 6.49 (d, J=9.2 Hz, 1H), 5.48-5.40 (m, 1H), 4.64-4.60 (m, 1H), 3.99-3.95 (m, 2H), 3.54-3.47 (m, 2H), 3.03-2.96 (m, 1H), 2.59-2.52 (m, 2H), 2.47-2.41 (m, 2H), 1.82-1.71 (m, 4H).

Example 117

N-((1S,3S)-3-((5-(tetrahydro-2H-pyran-4-yl)pyrimidin-4-yl)oxy)cyclobutyl)-5-(trifluoromethyl)pyridin-2-amine PDE10 $IC_{50}$ (uM): 0.321. M+1: 395. $^1$H NMR ($CD_3OD$, 400 MHz) δ (ppm): 8.60 (s, 1H), 8.35 (s, 1H), 8.22-8.21 (m, 1H), 7.59 (d, J=9.2 Hz, 1H), 6.58 (d, J=8.8 Hz, 1H), 5.20-5.16 (m, 1H), 4.20-4.10 (m, 1H), 4.06-4.02 (m, 2H), 3.59-3.52 (m, 2H), 3.12-3.03 (m, 3H), 2.16-2.09 (m, 2H), 1.90-1.76 (m, 4H).

The following Examples 118-127 can be prepared according to the above schemes and preparations from starting materials available to those skilled in the art.

TABLE 13

EXAMPLES 118-127

| Ex. # | Structure | Chemical Name |
|---|---|---|
| 118 | 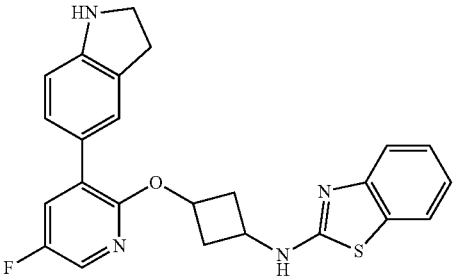 [SMILES: Fc1cnc(OC2CC(Nc3nc4ccccc4s3)C2)c(-c2ccc3c(c2)CCN3)c1] | N-(3-((5-fluoro-3-(indolin-5-yl)pyridin-2-yl)oxy)cyclobutyl)benzo[d]thiazol-2-amine |
| 119 | 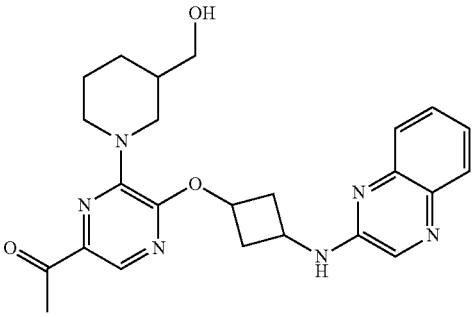 [SMILES: CC(=O)c1cnc(OC2CC(Nc3cnc4ccccc4n3)C2)c(N2CCCC(CO)C2)n1] | 1-(6-(3-(hydroxymethyl)piperidin-1-yl)-5-(3-(quinoxalin-2-ylamino)cyclobutoxy)pyrazin-2-yl)ethanone |
| 120 | 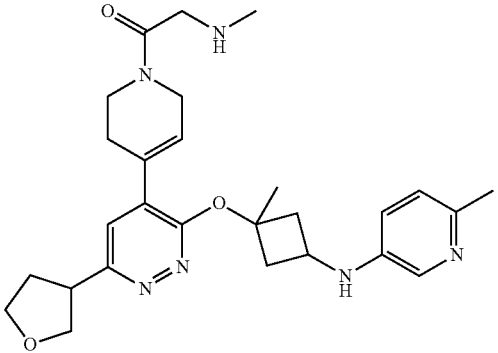 [SMILES: CNCC(=O)N1CC=C(c2cc(C3CCOC3)nnc2OC2(C)CC(Nc3ccc(C)nc3)C2)CC1] | 1-(4-(3-(1-methyl-3-((5-methylpyridin-2-yl)amino)cyclobutoxy)-6-(tetrahydrofuran-3-yl)pyridazin-4-yl)-5,6-dihydropyridin-1(2H)-yl)-2-(methylamino)ethanone |
| 121 | 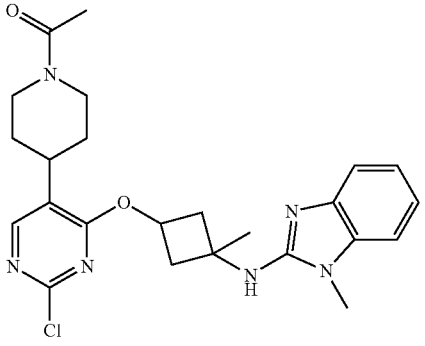 [SMILES: CC(=O)N1CCC(c2cnc(Cl)nc2OC2CC(C)(Nc3nc4ccccc4n3C)C2)CC1] | 1-(4-(2-chloro-4-(3-methyl-3-((1-methyl-1H-benzo[d]imidazol-2-yl)amino)cyclobutoxy)pyrimidin-5-yl)piperidin-1-yl)ethanone |

TABLE 13-continued

EXAMPLES 118-127

| Ex. # | Structure | Chemical Name |
|---|---|---|
| 122 | 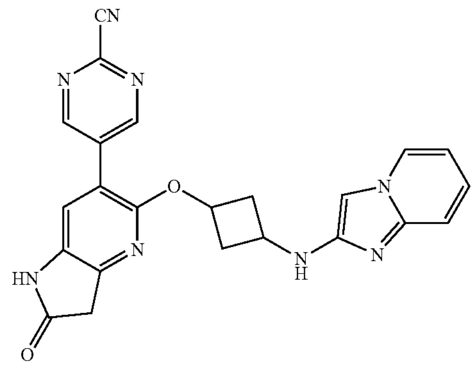 [SMILES: N#Cc1ncc(-c2cc3c(nc2OC2CC(Nc4cn5ccccc5n4)C2)CC(=O)N3)cn1] | 5-(5-(3-(imidazo[1,2-a]pyridin-2-ylamino)cyclobutoxy)-2-oxo-2,3-dihydro-1H-pyrrolo[3,2-b]pyridin-6-yl)pyrimidine-2-carbonitrile |
| 123 | 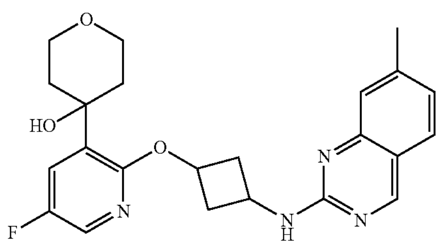 [SMILES: Cc1ccc2cnc(NC3CC(Oc4ncc(F)cc4C4(O)CCOCC4)C3)nc2c1] | 4-(5-fluoro-2-(3-((7-methylquinazolin-2-yl)amino)cyclobutoxy)pyridin-3-yl)tetrahydro-2H-pyran-4-ol |
| 124 | 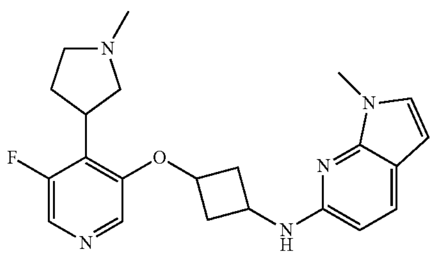 [SMILES: CN1CCC(c2c(F)cncc2OC2CC(Nc3ccc4ccn(C)c4n3)C2)C1] | N-(3-((5-fluoro-4-(1-methylpyrrolidin-3-yl)pyridin-3-yl)oxy)cyclobutyl)-1-methyl-1H-pyrrolo[2,3-b]pyridin-6-amine |
| 125 | 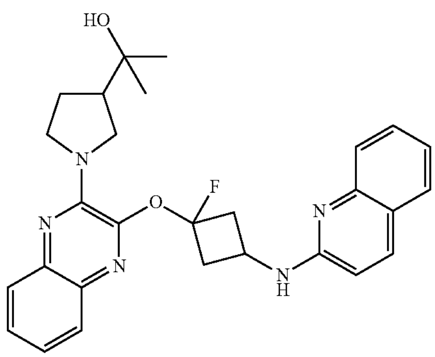 [SMILES: CC(C)(O)C1CCN(c2nc3ccccc3nc2OC2(F)CC(Nc3ccc4ccccc4n3)C2)C1] | 2-(1-(3-(1-fluoro-3-(quinolin-2-ylamino)cyclobutoxy)quinoxalin-2-yl)pyrrolidin-3-yl)propan-2-ol |
| 126 | 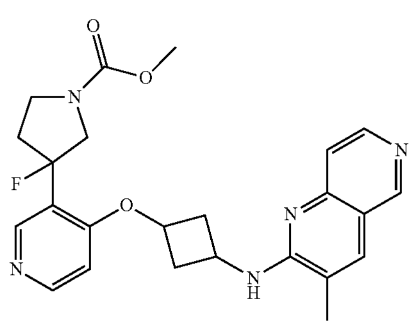 [SMILES: COC(=O)N1CCC(F)(c2cnccc2OC2CC(Nc3nc4ccncc4cc3C)C2)C1] | methyl 3-fluoro-3-(4-(3-((3-methyl-1,6-naphthyridin-2-yl)amino)cyclobutoxy)pyridin-3-yl)pyrrolidine-1-carboxylate |

TABLE 13-continued

EXAMPLES 118-127

| Ex. # | Structure | Chemical Name |
|---|---|---|
| 127 | 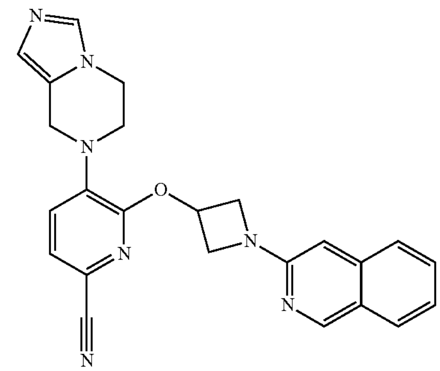 [SMILES: N#Cc1ccc(N2CCn3cncc3C2)c(OC2CN(c3cc4ccccc4cn3)C2)n1] | 5-(5,6-dihydroimidazo[1,5-a]pyrazin-7(8H)-yl)-6-((1-(isoquinolin-3-yl)azetidin-3-yl)oxy)picolinonitrile |

Biological Examples

The above PDE10 $IC_{50}$ data were obtained by using the following assays.

Example A

MPDE10A7 Enzyme Activity and Inhibition

Enzyme Activity. An IMAP TR-FRET assay was used to analyze the enzyme activity (Molecular Devices Corp., Sunnyvale Calif.). 5 µL, of serial diluted PDE10A (BPS Bioscience, San Diego, Calif.) or tissue homogenate was incubated with equal volumes of diluted fluorescein labeled cAMP or cGMP for 60 min in 384-well polystyrene assay plates (Corning, Corning, N.Y.) at room temperature. After incubation, the reaction was stopped by adding 60 µL, of diluted binding reagents and was incubated for 3 hours to overnight at room temperature. The plates were read on an Envision (Perkin Elmer, Waltham, Mass.) for time resolved fluorescence resonance energy transfer. The data were analyzed with GraphPad Prism (La Jolla, Calif.).

Enzyme Inhibition. To check the inhibition profile, 5 µL, of serial diluted compounds were incubated with 5 µL, of diluted PDE10 enzyme (BPS Bioscience, San Diego, Calif.) or tissue homogenate in a 384-well polystyrene assay plate (Corning, Corning, N.Y.) for 30 min at room temperature. After incubation, 10 µL, of diluted fluorescein labeled cAMP or cGMP substrate were added and incubated for 60 min at room temperature. The reaction was stopped by adding 60 µL of diluted binding reagents and plates were read on an Envision (Perkin Elmer, Waltham, Mass.) for time resolved fluorescence resonance energy transfer. The data were analyzed with GraphPad Prism (La Jolla, Calif.).

Example B

Apomorphine Induced Deficits in Prepulse Inhibition of the Startle Response in Rats, an In Vivo Test for Antipsychotic Activity The thought disorders that are characteristic of schizophrenia may result from an inability to filter, or gate, sensorimotor information. The ability to gate sensorimotor information can be tested in many animals as well as in humans. A test that is commonly used is the reversal of apomorphine-induced deficits in the prepulse inhibition of the startle response. The startle response is a reflex to a sudden intense stimulus such as a burst of noise. In this example, rats can be exposed to a sudden burst of noise, at a level of 120 db for 40 msec, e.g., the reflex activity of the rats can be measured. The reflex of the rats to the burst of noise may be attenuated by preceding the startle stimulus with a stimulus of lower intensity, at 3 db to 12 db above background (65 db), which attenuates the startle reflex by 20% to 80%.

The prepulse inhibition of the startle reflex, described above, may be attenuated by drugs that affect receptor signaling pathways in the CNS. One commonly used drug is the dopamine receptor agonist apomorphine. Administration of apomorphine reduces the inhibition of the startle reflex produced by the prepulse. Antipsychotic drugs such as haloperidol prevents apomorphine from reducing the prepulse inhibition of the startle reflex. This assay can be used to test the antipsychotic efficacy of PDE10 inhibitors, as they reduce the apomorphine-induced deficit in the prepulse inhibition of startle.

Example C

Conditioned Avoidance Responding (Car) in Rats, an In Vivo Test for Antipsychotic Activity Conditioned avoidance responding (CAR) occurs, for instance, when an animal learns that a tone and light predict the onset of a mild foot shock. The subject learns that when the tone and light are on, it must leave the chamber and enter a safe area. All known antipsychotic drugs reduce this avoidance response at doses which do not cause sedation. Examining the ability of test compounds to suppress the conditioned avoidance has been widely used for close to fifty years to screen for drugs with useful antipsychotic properties.

In this example, an animal can be placed in a two-chambered shuttle box and presented with a neutral conditioned stimulus (CS) consisting of a light and tone, followed by an aversive unconditioned stimulus (US) consisting of a mild foot shock through a floor grid in the shuttle box chamber. The animal can be free to escape the US by running from one chamber to the other, where the grid is not electrified. After several presentations of the CS-US pair, the animal typically learns to leave the chamber during the presentation of the CS and avoid the US altogether. Animals treated with clinically-relevant doses of antipsychotic drugs have a suppression of their rate of avoidances in the presence of the CS even though their escape response to the shock itself is unaffected.

Specifically, conditioned avoidance training can be conducted using a shuttle box (Med Associates, St. Albans, Vt.). The shuttle box is typically divided into 2 equal compartments that each contain a light source, a speaker that emits an 85 dB tone when activated and an electrified grid that can deliver a scrambled foot shock. Sessions can consist of 20 trials per day (intertrial interval of 25-40 sec) during which a 10 sec illumination and a concurrent 10 sec tone signals the subsequent delivery of a 0.5 mA shock applied for a maximum of 10 sec. Active avoidance, defined as the crossing into the opposite compartment during the 10 sec conditioning stimuli (light and tone) prevents the delivery of the shock. Crossing over to the other compartment after the delivery of the shock terminates shock delivery and may be recorded as an escape response. If an animal does not leave the conditioning chamber during the delivery of the shock it is recorded as an escape failure. Training can be continued daily until the avoidance of 16 or more shocks out of 20 trials (80% avoidance) on 2 consecutive days is achieved. After this criterion is reached the rats may be given one day of pharmacological testing. On test day, rats can be randomly assigned to experimental groups, weighed and injected intraperitoneally (i.p.) (1 cc tuberculin syringe, 26⅜ gauge needle) or per os (p.o.) (18 gauge feeding needle) with either control or compound solutions. Compounds can be injected at 1.0 ml/kg for i.p. and 10 mL/kg for p.o. administration. Compounds can be administered either acutely or chronically. For testing, each rat may be placed in the shuttle box, and given 20 trials with the same parameters as described above for training trials. The number of avoidances, escapes, and escape failures can be recorded.

Example D

PCP-Induced Hyperactivity (PCP-LMA)

Equipment Used: 4×8 home cage photobeam activity system (PAS) frame from San Diego Instruments. Open PAS program and prepare an experimental session using the following variables:
Multiphase experiment
300 sec/interval (5 min)
12 intervals (1 h)
Individual on screen switches.
Start recording after first beam break.
End session after end of interval.
Cage Preparation:
Techniplast™ rat cage with filter top, but no wire lid. Place ~400 mL bedding and one food pellet in cage and place 250 mL techniplast water bottle in holder on filter top. Place the prepped cage in the PAS frame. Make sure bedding or pellet doesn't block the photobeams.
Animal Preparation:
Mark rats and record their weights. Bring rats to testing room.
Phase I: Habituation
Start the experiment session. Place the rat in the enclosure. The computer should start recording when it detects the rat breaking the beam. The computer will record for 1 h. During the habituation phase, prepare risperidone (positive control): Measure out risperidone, calculate final volume at 1 mg/mL concentration and add 1% glacial acetic acid of the final volume to dissolve risperidone. When risperidone is dissolved, add saline to final volume to make a concentration of 1 mg/mL. Fill syringes (3 mL syringes with 23 g ½ needle or oral gavage needle) with Amgen compound solution (5 mL/kg) or risperidone (1 mL syringe with 23 g½ needle) control (1 mL/kg) s.c.

Phase II: Compound Pre-Treatment
Make sure Phase I has ended. Remove rat from enclosure, start the next phase using on-screen individual switch, administer compound p.o or i.p. and control s.c. and place rat back in the enclosure. The computer should start recording when it detects the rat breaking the beam. The computer will record for 1 h.
During phase II, prepare pcp: Dissolve pcp in saline to a concentration of mg/mL.
Fill syringes (1 mL syringes with 26 g⅜ needle) with pcp solution (1 mL/kg).
Phase III: PCP Administration.
Make sure phase II is ended. Remove rat from enclosure, start the next phase using on-screen individual switch, administer pcp s.c. and place rat back in the enclosure. The computer will record for 1 h.
Clean-Up:
End-session to terminate experiment and so that computer will compile data. Export raw data to excel file for data analysis. Euthanize rats and take necessary tissue/sample for PK.
Data Generation:
Export raw data to excel file for data analysis. Total time of movement is recorded as the number of photobeam breaks by the computer. Total time of movement (seconds) is combined into 5 minute bins and averaged for each treatment group for an N of 7-10 animals. Data are analyzed for statistical significance using a two-way ANOVA followed by a Bonferroni's post-hoc test for multiple comparisons.

The foregoing is merely illustrative of the invention and is not intended to limit the invention to the disclosed compounds. Variations and changes which are obvious to one skilled in the art are intended to be within the scope and nature of the invention which are defined in the appended claims. All patents, patent applications, and other publications recited herein are hereby incorporated by reference in their entirety.

What is claimed is:

1. A compound of formula I:

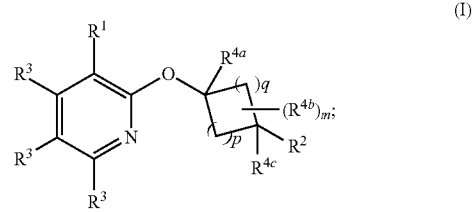

a stereoisomer, or a pharmaceutically-acceptable salt thereof,
m is 1, 2, 3, or 4;
each of p and q is independently 1;
the ring containing p and q is in cis or trans configuration;
$R^1$ is $C_{0-4}$alk-$L^1$;
$R^2$ is —C(=O)$R^5$;
$R^3$ is H, F, Cl, Br, CN, OH, O$C_{1-4}$alk, $C_{1-4}$alk, or $C_{1-4}$haloalk;
$R^{4a}$ is H, $C_{1-4}$alk, or $C_{1-4}$haloalk;
each $R^{4b}$ and $R^{4c}$ is independently H, F, Cl, Br, CN, OH, O$C_{1-4}$alk, $C_{1-4}$alk, or $C_{1-4}$haloalk;
$R^5$ is $C_{0-8}$alk-$L^3$;
$R^a$ is independently H or $R^b$;

$R^b$ is independently phenyl, benzyl, or $C_{1-6}$alk, wherein said phenyl, benzyl, and $C_{1-6}$alk are being substituted by 0, 1, 2 or 3 substituents selected from halo, $C_{1-4}$alk, $C_{1-3}$haloalk, —OH, —$OC_{1-4}$alk, —$NH_2$, —$NHC_{1-4}$alk, —$OC(=O)C_{1-4}$alk, or —$N(C_{1-4}alk)C_{1-4}$alk; and $L^1$ is cyclobutyl, cyclohexyl, cyclopentyl, cycloheptyl, phenyl, dihydropyranyl, or tetrahydropyranyl, and $L^3$ is benzimidazolyl, wherein each of $L^1$ and $L^3$ is independently substituted by 0, 1, 2 or 3 $R^8$ groups which are F, Cl, Br, $C_{1-6}$alk, $C_{1-4}$haloalk, —$OR^a$, —$OC_{1-4}$haloalk, CN, —$C(=O)R^b$, —$C(=O)OR^a$, —$C(=O)NR^aR^a$, —$C(=NR^a)NR^aR^a$, —$OC(=O)R^b$, —$OC(=O)NR^aR^a$, —$OC_{2-6}alkNR^aR^a$, —$OC_{2-6}alkOR^a$, —$SR^a$, —$S(=O)R^b$, —$S(=O)_2R^b$, —$S(=O)_2NR^aR^a$, —$NR^aR^a$, —$N(R^a)C(=O)R^b$, —$N(R^a)C(=O)OR^b$, —$N(R^a)C(=O)NR^aR^a$, —$N(R^a)C(=NR^a)NR^aR^a$, —$N(R^a)S(=O)_2R^b$, —$N(R^a)S(=O)_2NR^aR^a$, —$NR^aC_{2-6}alkNR^aR^a$, —$NR^aC_{2-6}alkOR^a$, —$C_{1-6}alkNR^aR^a$, —$C_{1-6}$ $alkOR^a$, —$C_{1-6}$ $alkN(R^a)C(=O)R^b$, —$C_{1-6}$ $alkOC(=O)R^b$, —$C_{1-6}$ $alkC(=O)NR^aR^a$, —$C_{1-6}$ $alkC(=O)OR^a$ or oxo.

2. The compound as in claim 1 wherein m is 1.

3. The compound as in claim 1 wherein the group

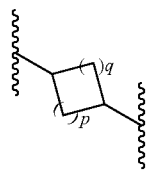

is in cis configuration.

4. The compound as in claim 1 wherein the group

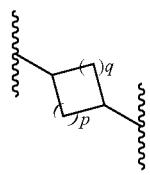

is in trans configuration.

5. The compound as in claim 1 wherein $R^1$ is $C_{0-4}alk-L^1$; wherein said $L^1$ is cyclobutyl, cyclohexyl, cyclopentyl, cycloheptyl, phenyl, dihydropyranyl, or tetrahydropyranyl, all of which are substituted by 0, 1, 2 or 3 $R^8$ groups selected from F, Cl, Br, $C_{1-6}$alk, $C_{1-4}$haloalk, —$OR^a$, —$OC_{1-4}$haloalk, CN, —$C(=O)R^b$, —$C(=O)OR^a$, —$NR^aR^a$, —$C(=O)NR^aR^a$, —$SR^a$, and —$C_{1-6}alkOR^a$.

6. The compound as in claim 1 wherein $R^1$ is $C_{1-4}alk-L^1$; wherein said $L^1$ is tetrahydropyranyl or dihydropyranyl each of which is substituted by 0, 1, 2 or 3 $R^8$ groups selected from F, Cl, Br, $C_{1-6}$alk, $C_{1-4}$haloalk, —$OR^a$, —$OC_{1-4}$haloalk, CN, —$C(=O)R^b$, —$C(=O)OR^a$, —$NR^aR^a$, —$C(=O)NR^aR^a$, —$SR^a$, and —$C_{1-6}alkOR^a$.

7. The compound as in claim 1 wherein $R^1$ is:

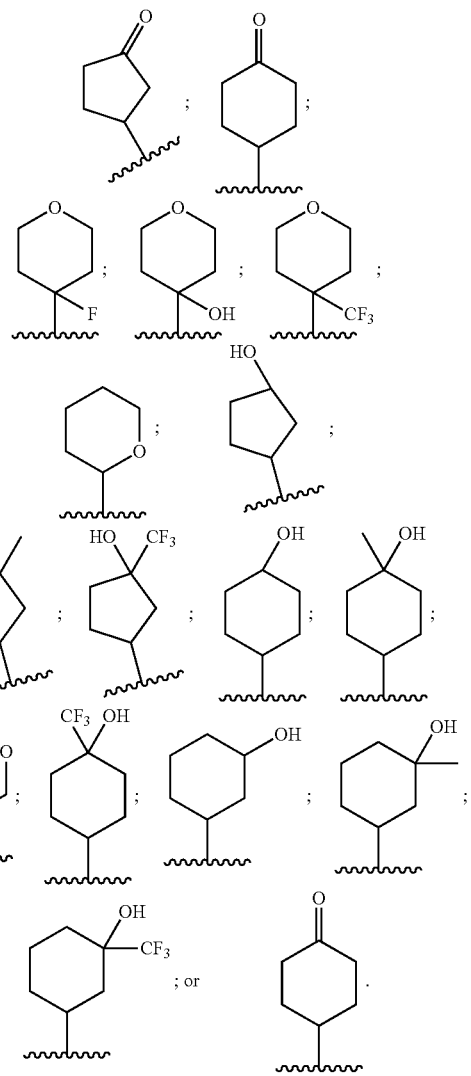

8. The compound as in claim 1 wherein $R^3$ is H, F, Cl, $C_{1-4}$alk, or $C_{1-4}$haloalk.

9. The compound as in claim 1 wherein $R^{4a}$ is H.

10. The compound as in claim 1 wherein each of $R^{4a}$, $R^{4b}$, and $R^{4c}$ is H.

11. The compound as in claim 1 wherein Ra is H or $C_{1-6}$alk substituted by 0 or 1 —OH, —$OC_{1-4}$alk, —$OC(=O)C_{1-4}$alk, or —$N(C_{1-4}alk)C_{1-4}$alk.

12. A pharmaceutical composition comprising a compound as in claim 1 and a pharmaceutically acceptable excipient thereof.

13. The compound of claim 1, which is selected from:
(1H-benzo[d]imidazol-2-yl)(trans-3-(3-(tetrahydro-2H-pyran-4-yl)pyridin-2-yloxy)cyclobutyl)methanone; and
(1H-benzo[d]imidazol-2-yl)(cis-3-(3-(tetrahydro-2H-pyran-4-yl)pyridin-2-yloxy)cyclobutyl)methanone; or a pharmaceutically acceptable salt thereof.

* * * * *